US009873890B2

(12) United States Patent
Alam et al.

(10) Patent No.: US 9,873,890 B2
(45) Date of Patent: Jan. 23, 2018

(54) NUCLEIC ACID MOLECULES ENCODING ENZYMES THAT CONFER DISEASE RESISTANCE IN JUTE

(75) Inventors: Maqsudul Alam, Honolulu, HI (US); Haseena Khan, Dhaka (BD); Mahboob Zaman, Dhaka (BD); Mohammed K. Uddin, Dhaka (BD); Mohammed S. Haque, Dhaka (BD); Mohammed S. Islam, Dhaka (BD); Muhammad S. Azam, Dhaka (BD); Niaz Mahmood, Dhaka (BD)

(73) Assignee: Bangladesh Jute Research Institute, Dhaka (BD)

( * ) Notice: Subject to any disclaimer, the term of this patent is extended or adjusted under 35 U.S.C. 154(b) by 978 days.

(21) Appl. No.: 14/128,897

(22) PCT Filed: Jun. 8, 2012

(86) PCT No.: PCT/US2012/041467
§ 371 (c)(1),
(2), (4) Date: Apr. 2, 2014

(87) PCT Pub. No.: WO2012/177418
PCT Pub. Date: Dec. 27, 2012

(65) Prior Publication Data
US 2014/0317778 A1 Oct. 23, 2014

Related U.S. Application Data

(60) Provisional application No. 61/500,407, filed on Jun. 23, 2011.

(51) Int. Cl.
| | |
|---|---|
| *C12N 15/82* | (2006.01) |
| *C07K 14/415* | (2006.01) |
| *C07K 16/16* | (2006.01) |
| *C07K 16/40* | (2006.01) |
| *C12N 9/12* | (2006.01) |

(52) U.S. Cl.
CPC ........ *C12N 15/8279* (2013.01); *C07K 14/415* (2013.01); *C07K 16/16* (2013.01); *C07K 16/40* (2013.01); *C12N 9/1205* (2013.01)

(58) Field of Classification Search
None
See application file for complete search history.

(56) References Cited

U.S. PATENT DOCUMENTS

| | | |
|---|---|---|
| 2004/0123343 A1 | 6/2004 | La Rosa et al. |
| 2006/0174379 A1 | 8/2006 | Haigler et al. |

FOREIGN PATENT DOCUMENTS

| | | | |
|---|---|---|---|
| WO | WO 2009091518 A2 * | 7/2009 | ........ C07K 14/415 |
| WO | WO-2010/023310 A2 | 3/2010 | |

OTHER PUBLICATIONS

Friedberg (Automated protein function prediction—the genomic challenge. Brief. Bioinformatics. 7:225-242, 2006).*
Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Mir et al (A preliminary genetic analysis of fibre traits and the use of new genomic SSRs for genetic diversity in jute. Euphytica 161:413-427, 2008).*
McHale et al (Plant NBS-LRR proteins: adaptable guards. Genome Biology, 7:212.1-212.11, Apr. 2006).*
Alam, M.M. et al., "A Putative Leucine-Rich Repeat Receptor-Like Kinase of Jute Involved in Stress Response," Plant Mol Biol Rep 28:394-402 (2010).
Islam, A.S. et al., "Preliminary Progress in Jute (*Corchorus* species) Genome Analysis," Plant Tissue Clut. & Biotech, 15(2):145-156 (2005).
Mahmood, N. et al., "Differentially Expressed Transcripts of Wild and Cultivated Jute (*Corchorus* spp.) Varieties Upon Fungal (*Macrophomina phaseolina*) Infection," Annals of Biological Research, 1(3):120-127 (2010).
Sharmin, S. et al., "Identification of a Novel Dehydration Responsive Transcript from Tossa Jute (*Corcohrus olitorius* L.)," Journal of Cell and Molecular Biology, 9(1):21-29 (2011).
Supplementary Partial European Search Report for EP 12 80 1816 dated Feb. 13, 2015.
Islam, M.S. et al., "Regeneration and Genetic Transformation of Tossa Jute (*Corchorus olitorlus* L.," Australian Journal of Crop Science, 3(5):287-293 (2009).
Chattopadhyay et al., "Development of a transgenic hairy root system in jute (*C. capsularis*) with gusA reporter gene through Agrobacterium rhizogenes mediated co-transformation," Plant Cell Report, 30:485-493 (2010).
Chomczynski et al., "Single-step method of RNA isolation by acid guanidinium thiocyanate-phenol-chloroform extraction," Anal Biochem, 162(1): 156-159 (1987).
GenBank Accession No. AY600403.1.
Hossain et al., "Confirmation of Agrobacterium Mediated Gene Transfer in Jute by Histochemical GUS asssay," The Journal of Experimental Biology, 1(2):73-77 (2010).
Sajib et al., "Tissue culture independent transformation for Corchorus olitorius," Plant Cell Tiss Org, 95(3): 333-340 (2008).
Sarkar et al., "Nitric oxide production by necrotrophic pathogen Macrophomina phaseolina and the host plant in charcoal rot disease of jute: complexity of the interplay between necrotroph-host plant interactions," PLoS One, 10(9): e107348 (2014).

\* cited by examiner

*Primary Examiner* — Medina A Ibrahim
*Assistant Examiner* — Wayne Zhong
(74) *Attorney, Agent, or Firm* — Foley Hoag LLP

(57) ABSTRACT

The invention further relates to vectors, host cells, seeds, and plants comprising such a nucleic acid molecule. One aspect of the invention is an isolated antibody or antigen binding fragment thereof that specifically binds to a polypeptide molecule of the present invention. One aspect of the invention is a plane or plant cell transfected by a vector of the present invention. One aspect of the invention relates to isolated nucleic acid molecules and fragments thereof encoding enzymes or proteins involved in disease resistance in jute.

13 Claims, 19 Drawing Sheets

Figure 1a

```
Ptc TIR-NBS-LRR GI:224127726    ELHLSGCSKLKEFP-EIEGNKKCLRKLCLDQTSIEELPPSIQYLVCLISLSIKDCKRLSG 775
Mtr TIR-NBS-LRR GI:224127726    KLILSGSSKFKFLP--EPGEKMENLSMLALEGTDIRKLPLSLGRLVGLTNLNLKDCKSLVC 759
Col TIR-NBS-LRR1                TWILSSGCNLERLPDQIDGSMECLVELYLDGTGIRHLFSLTSHLSGLVLNLKDCRNLAS 754
Col TIR-NBS-LRR2                TLILSSGCSNLERLPDQIDGKMECLVELRLSG-TGVGHLSGAIGHLSGAVLNLKDCRNLAS 761
                                 **.*::: :* ::   : *  * *: *.: .*.  :  * ** *.*:,*:.* .

Ptc TIR-NBS-LRR GI:224127726    LPSSINGLKSIKTLHLSGCSELEKLPENFGQLECLNRLDVSFTAIREPPVSIFSLKNLKY 835
Mtr TIR-NBS-LRR GI: 87162908    LPDTIHGLKSLIFLDISGCSKLACKLPGRLKEIKCLSEIFANDFAIDRLFSSIFYLDSLKV 819
Col TIR-NBS-LRR1                LPSNIHGLKRLKIFDLSGCSKLEILPRSLQQVRSLREIDLSRTAIRQPPSFIFQFKNLKH 814
Col TIR-NBS-LRR2                LPSSINGLKCLKTLNLSGCSNLFHPPENLQQLFSIREIDLSGTAITKPPSFIFQFKNLNH 821
                                **.,*:**: *  : ***** :*:. :::.*:** . *** : *  ** :.:**

Ptc TIR-NBS-LRR GI:224127726    LSFHGCAESSRSTTNIWQRLMFFLMPGKP-ANSTSLVLP-SLSGLSSLTRLGLSNCNLGEG 894
Mtr TIR-NBS-LRR GI: 87162908    LSFAGCQGPS--TTSMNWFLPFNLMFGSQPASNGFRLPSSVNGLFSLSYLNLSYCNLSEE 877
Col TIR-NBS-LRR1                LSFRGCKGPLS-KLRFNLPSLFKVMQSRSLNSMALMLP-PLSGLSSLTNLDISYCNLGEE 872
Col TIR-NBS-LRR2                LSFHGCKAFPT-KLQPNQPSLG------CPNCMALTLP-PLSGLSSLTQLNISYCNLYEG 870
                                *** **  .      .    . :  **  .: **,**  *,:*  ***  **

Ptc TIR-NBS-LRR GI:224127726    AVPNDTGYLSSLRQLNLSRNKFVSLPISIDQLSGLQSIRMEDCKMLQSLPELPSNLEEFR 954
Mtr TIR-NBS-LRR GI: 87162908    SFPNYFHHLSBLKSLDLTGNNFVIIPSSISKLSRLRFLCLNWCQKLQLLPELPLTMTQLN 937
Col TIR-NBS-LRR1                AIPSDVYRLSSLKKLNLCGNNFISLPANLERLSNLKCLVLTHCMELKSLPEFLTSIASSC 932
Col TIR-NBS-LRR2                AIPSDICSLSSLKRLDLRGNNFFSLPANLERLSNLDYLGLTDCMELKSLPEFLTTSPLVPI 933
                                :.*. .    ****: *:* *:,:..:** * :*: *.* ***:  .

Ptc TIR-NBS-LRR GI:224127726    VNGCTSLEKMQFS-RKLCQLNYL--RYLFINCWRLSESDCWNNMFPTLLRKCFQGPPNLI 1011
Mtr TIR-NBS-LRR GI: 87162908    ASNCDSLDTMKFNPAKLCSL--------FASPRKLS--------YVQELYKRFEDRCLPT 981
Col TIR-NBS-LRR1                NIIGRHSVLLSANATVRNSVSCA--SIWLTNCFRLSEN----TDIVTLLKKHLKASANSR 986
Col TIR-NBS-LRR2                SNDCSFPVGLFANARACNSMDWAPASIWLTNCYRLAEN----TNVLTLLKKHLKVFAKAF 989
                                 :   .   .:    : ,. :*:      *  *::

Ptc TIR-NBS-LRR GI:224127726    ESFSVILPGSEIPTWFSHQSEGSSVSVQTPPHSHENDEWLGYAVCASLG------YPDFP 1065
Mtr TIR-NBS-LRR GI: 87162908    TRFDMLIPGDEIPSWFVPQRSVSWAAKVHIP-NNFPQDEWVGFALCFLV------SYADP 1034
Col TIR-NBS-LRR1                Q-LNIVLPGSEIPEWFSNQPDGCSIKIPLPYQILNDSQCIGVAFCCVFVNAIEHRRKAFI 1045
Col TIR-NBS-LRR2                ETLDLILPGSQIPDWFSHQSNESSIKIPLPHHLQSNSKWIGVAFCCVFVDVVGIDCKAFV 1049
                                 : .::**:** **  *  . .:   * : ::: :* *.*     :

Ptc TIR-NBS-LRR GI:224127726    PKVFRSPMQCFFNGDGNESESIYVLKPCEILSDHLWFLYFPSRFKR------------- 1112
Mtr TIR-NBS-LRR GI: 87162908    PELCKHETDCYLFASNGKKLITTRSLPFMCPCYPHLYILLYMSIDEFRDEILKDDYW---- 1090
Col TIR-NBS-LRR1                HGRKSQNVDNHVLCITNGCSSVTKDHLLLGYWSRDYFYSITSLEERCGETEQLSSL---- 1101
Col TIR-NBS-LRR2                HGRMSHDINGYGLYFGKG--SSVTKDHLWLRYWSRNKLYS-FALDDKCGETGHPQSLKCPV 1107
                                ::   .             .       .

Ptc TIR-NBS-LRR GI:224127726    -------FDRHVRFRFEDNCSQT-KVIKCGVRLVYQQDVEELNRMT---------NLYENS 1156
Mtr TIR-NBS-LRR GI: 87162908    -------SESGIESVLKCYCCQSLQVVSCGGRLVCKQDVEDWSKMS---------HFNES- 1134
Col TIR-NBS-LRR1                --ESDELEVVVEVDSDEMLSSKPTIKKCGIHYVYKKDVESMEQIKEHHILQIGNTTIEDI 1159
Col TIR-NBS-LRR2                DQESDEFEVAVEVELSRSRFKKVKKCGVRLVYERDLQELEQL-----LQICNSICADE 1162
                                :  :. .                 . .** ::* ::*:::: .::

Ptc TIR-NBS-LRR GI:224127726    TFEGVDECFQESGGALVKRLGHTKDVGEASGSVSSDEQFPTKKLKQI--------- 1203 (SEQ ID NO:39)
Mtr TIR-NBS-LRR GI: 87162908    -------------------------------------------------- (SEQ ID NO:40)
Col TIR-NBS-LRR1                PQPQNGDESEIGKGALVKRKRNFYEKSESDKIBERPQPKRLQQFLKCIMRKEL-1212 (SEQ ID NO:2)
Col TIR-NBS-LRR2                SK--TDEVP-------VKRKRNIYE--EEAELSESDSFRCPERFLRYIMQKKEHN 1206 (SEQ ID NO:4)
```

Figure 1b

```
Col TIR-NBS-LRR3                        ------------------------------------------------------------
Stu nematode res-like protein gi37781360 ------------------------------------------------------------
Ptc TIR-NBS-LRR gi224126307             MASSSMQKAASSSYSPPQWKYDVFLSFRGKDTRNNFTSHLYSNLEQRGIDVYMDDRGLER  60

Col TIR-NBS-LRR3                        ------------------------------------------------------------
Stu nematode res-like protein gi37781360 ------------------------------------------------------------
Ptc TIR-NBS-LRR gi224126307             GKTIEPALWQAIEDSRFSIVVFSRDYASSPWCLDELVKIVQCMKEMGHTVLPVFYLVDPS 120

Col TIR-NBS-LRR3                        ------------------------------------------------------------
Stu nematode res-like protein gi37781360 ------------------------------------------------------------
Ptc TIR-NBS-LRR gi224126307             EVADQKGNYKKAFIEHKEKHSGNLDKVKCWSDCLSTVANLSGKDVRNPDESQSIKKIVEY 180

Col TIR-NBS-LRR3                        ------------------------------------------------------------
Stu nematode res-like protein gi37781360 ------------------------------------------------------------
Ptc TIR-NBS-LRR gi224126307             IQCKLSFTLPTISKNLVGIDSRLKVLNEYIDEQANDTLFIGICGMGGMGKTTVARVLYDR 240

Col TIR-NBS-LRR3                        ------------------------------------------------------------
Stu nematode res-like protein gi37781360 ------------------------------------------------------------
Ptc TIR-NBS-LRR gi224126307             IRWQFGGSCFLANVREVFAEKDGLCRLQEQLLSEISMELPTARDSSRRIDLIKRRLRLKK 300

Col TIR-NBS-LRR3                        ------------------------------------------------------------
Stu nematode res-like protein gi37781360 ------------------------------------------------------------
Ptc TIR-NBS-LRR gi224126307             VLLILDDVDDEEQLQMLAAEHGTFGPGSRIYITSRNKEVLDSHGVTRIYEADKLNDKDAL 360

Col TIR-NBS-LRR3                        ------------------------------------------------------------
Stu nematode res-like protein gi37781360 ------------------------------------------------------------
Ptc TIR-NBS-LRR gi224126307             MLFSWKAFKRDQPAEDLSELSKQVVGYANGLPLALEVIGSFLHKRGLREWKSAIDRMNDI 420

Col TIR-NBS-LRR3                        ------------------------------------------------------------
Stu nematode res-like protein gi37781360 ------------------------------------------------------------
Ptc TIR-NBS-LRR gi224126307             PDRKIIDVLRISFDGLHELEKKIFLDIACFLKGMKKDRITRLLDSCGFHADIGMQALISK 480

Col TIR-NBS-LRR3                        ------------------------------------------------------------
Stu nematode res-like protein gi37781360 ------------------------------------------------------------
Ptc TIR-NBS-LRR gi224126307             SLIRVSRDEIRMHKLLQKMGEEIVRCESPEEPGRRSRLCTYKDVCDALKDSTGKIESIFV 540

Col TIR-NBS-LRR3                        ------------------------------------------------------------
Stu nematode res-like protein gi37781360 ------------------------------------------------------------
Ptc TIR-NBS-LRR gi224126307             DLPKAKEAPWNMTAFSKMTKLRLLKIHNVDLSEGPEYLSNELRFLEWHAYPSKSLPACFR 600

Col TIR-NBS-LRR3                        ------------------------------------------------------------
Stu nematode res-like protein gi37781360 -------------------------------------------------HEAGVIERIAE  11
Ptc TIR-NBS-LRR gi224126307             LQDLVELYMSCSSIEQLWCGCKLLTCLLHVSAFMRRLCTSSNVCNTSTFDESQSIKKIAE 660

Col TIR-NBS-LRR3                        ------------------------------------------------------------
Stu nematode res-like protein gi37781360 DIMARLGSQRHASNVGNLVGMELHMHQVYKMLGVGSGGVRFLGILGMSGVGKTTLARVIY  71
Ptc TIR-NBS-LRR gi224126307             YIQCKLSFTLQTISKN-LVGIDSRLKVLNEYIDEQATDTLFIGICGMGGMGKTTVARVMY 719

Col TIR-NBS-LRR3                        ------------------------------------------------------------
Stu nematode res-like protein gi37781360 DNIRSQFQGTCFLHEVRDRSA-KQGLERLQEILLSEILVVFKLRINDLFEGANMQFQRLR 130
Ptc TIR-NBS-LRR gi224126307             DEIRWQFQGSCFLANVREVFAEKDGRCRLQEQLLSEISMELPTAR-DSSRRIDLIKRRLR 778

Col TIR-NBS-LRR3                        ------------------------------------------------------------
Stu nematode res-like protein gi37781360 YKKVLVLVLDDVDHIDQLDTLAGEREWFGDGSRIIITTKDKHLLVKYETEKIYPMGTLDKY 190
Ptc TIR-NBS-LRR gi224126307             LKKVLLILDDVDDEEQLQMLAAEHGSFGPGSRIYITSRNKEVLDSHGVTRIYEADKLNDK 838

Col TIR-NBS-LRR3                        ------------------------------------------------------------
Stu nematode res-like protein gi37781360 ESLQLFEQHAFEKNHPTKEFEDLSAQVIEHTGGLPVALEVLGSFLYGRGLDEWLSEVERL 250
Ptc TIR-NBS-LRR gi224126307             DALMLFSWKAFKRDQPAEDLSELSKQVVGYANGLPLALEVIGSFLHKRGLREWKSAIDRM 898

Col TIR-NBS-LRR3                        ------------------------------------------------------------
Stu nematode res-like protein gi37781360 KQIPQNETLEKLEPSFIGLNNNIEQKIFLDIACFFSGKKKDSVTRILESFHFSPVTGIKVL 310
Ptc TIR-NBS-LRR gi224126307             NDIPDRKIIDVLRISFDGLHELEKKIFLDIACFLKGMKKDRIARLLDSCGFHADIGMQAL 958

Col TIR-NBS-LRR3                        ------------------------------------------------------------
Stu nematode res-like protein gi37781360 MENCLITILQGRIATHQLIQDMGWHIVRREASYNPRICSRLKKREDICPVLEPNLATDKI 370
Ptc TIR-NBS-LRR gi224126307             IEKSLISVSRDEIRMHNLLQKMGEEIVRCESPEEPGRRSRLCTYKDVCTALED--STEKI
1016

Col TIR-NBS-LRR3                        ------------------------------------------------------------
Stu nematode res-like protein gi37781360 EGISLHLTMEEEVNFGGKAFMQMPSLRFLKFRNAYVCQGPEPLPDELRWLDWHGYPSKSL 430
Ptc TIR-NBS-LRR gi224126307             QSIPLDLPKAKEAQWNMTAFSKMTKLRLLKIHNVDLSEGPEYLSKELRFLEWHAYPSKSL
1076

Col TIR-NBS-LRR3                        ------------------------------------------------------------
Stu nematode res-like protein gi37781360 PNSFKGDQLVSLTLEKSRIIQLWKYSKDLGKLKYMNLSHSQKLIRTPDFSVMPNLERLVL 490
Ptc TIR-NBS-LRR gi224126307             PACFRPDELVELYMSCSSIEQLWCGCKILVNLEIINLGNSLYLINTPDFTGIPNLESLIL
1136

Col TIR-NBS-LRR3                        ------------------------------------------------------------
Stu nematode res-like protein gi37781360 EECKSLVEINFSIGDLGKLVLENLKMCRNLKTLFKRIRLEKLETLVLSGCSKLRTFPEIE 550
Ptc TIR-NBS-LRR gi224126307             EGCASLSEVHPSFGRHKKLQLVNLVNCYSLRILPSNLEMESLEVCTLSSCSKLDKFPDIV
1196
```

Figure 2a

```
Col TIR-NBS-LRR3                                  --------------------------------------------ASLPSSIHELKCLKTIDLSG  20
Stu nematode res-like protein gi37781360          EKMNCLABLYLGATALSELSASVENLSGVGVINLCYCKHLESLPSSIFELKCLKTLDVSG    610
Ptc TIR-NBS-LRR gi224126507                       GNINCLHELRLDKTATAKLSSSFHCLAGLVLLSMNNCKNLESIPSSIRGLKSLKGLDVSD
1256
                                                  *:*:***  **:**  **:*:

Col TIR-NBS-LRR3                                  CSKLENLPESLQQVESLEELDLSGTAITTKPPSFIFQLKNLKHLSFRGCKGTVSKSRPNLL   80
Stu nematode res-like protein gi37781360          CSKLKNLPDDLGLLVGLEEFHCIHTAIQTIPSSISLLKNLKHLSLRGCNALSS--------  663
Ptc TIR-NBS-LRR gi224126507                       CSELKNIPENLGEVESLEEFDASGTSIRQPPTSFFLLKNLKVLSFKGCKRIAV--------
1309
                                                  **:*:*:*:.*    : .**:. : *:*    *:   *****  **:;**:

Col TIR-NBS-LRR3                                  SLFKVMQRGGGSVNSVALTLFPLSGLTCLTKLDISYCNLGEGAYPSDICHLSGLRDLNLS  140
Stu nematode res-like protein gi37781360          ---QVSSSSHG-QKSVGVNFQNLSGLCSLIMEDLSDCNISDGGILSNLGFLPSLAGLILL  719
Ptc TIR-NBS-LRR gi224126507                       --------------NLTDQILPSLSGLCSLEELDLCACNLGEGAVPEDIGCLSSLRSLNLS
1356
                                                  :  .   :   ****  .*  **:. **::*:.  .:.   *.**  .* .*.

Col TIR-NBS-LRR3                                  GNTPFSSLPAN-LDGLSNLERIRLRHCTELKSLPEI LRST-----YHSVGVFANAAIHNSR  194
Stu nematode res-like protein gi37781360          GNNFSNIPAASISRLTPLETLALAGCRRLESLPELPPSIKEIYADECTSLMSIDQLTKYS  779
Ptc TIR-NBS-LRR gi224126507                       RNNFISLPKS-INQLSRLEKLALKDCVMLESLPEVPLKVQKVKLDGCLKLKEIPDPIKLC
1413
                                                  *.* .:*   :.:*:.**  :   *   *:*****:.       .  .*

Col TIR-NBS-LRR3                                  DWACIFLP--NCYRIAEN---PNIVPLKKNLKVGLYIS-------P----PNQLTQRNL   238 (SEQ ID NO:6)
Stu nematode res-like protein gi37781360          MLEEVSFI--KCHQLVTNKQEASMVDSLLKQMHEGLYLNCSFSMYIPCVEIPEWFTYKNS  837
Ptc TIR-NBS-LRR gi224126507                       SLKRSEFKCLNCWELYMHNGQNMMGLNMLEKYLQGSSPRPGFGIAVPGNEIPGWSTHQSK
1475
                                                  :  :*  .:      .:      : ::  *           *   *  :* :.

Col TIR-NBS-LRR3                                  ------------------------------------------------------------
Stu nematode res-like protein gi37781360          GTFSTSVALPKNWYTPT----FRGTATCVVFDMMTP-FTLNKPNSDFPFSPFNVKCSKFTQ  893
Ptc TIR-NBS-LRR gi224126507                       E-SSIRVQMPSNYLDGDDNGWDGFAACAAFSTYELKERSNESSSELELSFHSYDQGVKVE
1534

Col TIR-NBS-LRR3                                  ------------------------------------------------------------
Stu nematode res-like protein gi37781360          GLVMWFSFIGHDGLWHRFRTCLSSIGSEKPVG---------------LGNTFLAQVPLD   937
Ptc TIR-NBS-LRR gi224126507                       NCCVRMVNSQHLIVASKEAASSYTPSWQSPTCHLIIASKEAASSYIDSLANSSSYSQWMH
1594

Col TIR-NBS-LRR3                                  ------------------------------------------------------------
Stu nematode res-like protein gi37781360          RFWRLECDNYIFNDFIQLEVGVCDN----------------YHSDVVVKGLGVRLVYR   979
Ptc TIR-NBS-LRR gi224126507                       DVFPSFRGKHNSMNFTHLHYALFQRGIIRYKRQIKYLKKIESSLVSDIKESGLSYIIFAR
1654

Col TIR-NBS-LRR3                                  ------------------------------
Stu nematode res-like protein gi37781360          N-----------------------------------                          980
Ptc TIR-NBS-LRR gi224126507                       DYVSTLGFGGFVKIDEFMKKMKSDTVFPVSTVSYRVEQSRVDEQTESYTIVFLKDEEDFS
1714

Col TIR-NBS-LRR3                                  ------------------------------
Stu nematode res-like protein gi37781360          ----------------------------(SEQ ID NO:41)
Ptc TIR-NBS-LRR gi224126507                       EDKEKVQRWMDILTEVAISSGSESSKR 1741 (SEQ ID NO:42)
```

Figure 2b

```
ColNBS-LRR              MAEAAVSFVLERLADILEEIDFQTNVRNEVVRLQDELKRMRCFLRDADAK  50
PtcNBS-LRR gi224075299  MAEAAVSFVLERLADLFDELEFHTDVHKEVERLQDELRRIRCFLRDADAK  50
                        ***************::*:.*:*:*;;** ******;*:***********

ColNBS-LRR              QDDDDRVRNWVSDIRNVAYDAEDLIDTFILRIDAVQKKNS---IKKYASV  97
PtcNBS-LRR gi224075299  QDEDERVRNWV3DIRDVAYDAEDLIDRFIMMNDPLKKKKKNHFIKKCTSY 100
                        **:*:;******** :********** **:. *..:**:.  *** :*

ColNBS-LRR              FKDWKRRSKIANELIAIQRRILDVSQSREKYGIKNIGEGISTAKERLRKQ 147
PtcNBS-LRR gi224075299  VKGWKQRSKIAEDLMAIRSRLQDISASRETYCIQNVGEGTTAAGETLRKL 150
                        .*.**:*****::*;:*:**: *: *;* ***.***:*;*** ::* * ***

ColNBS-LRR              RRSSPRGEEKDIVGLEDDIAKLVTQLVDAEDQWHAISVVGMGGICKTTLA 197
PtcNBS-LRR gi224075299  RRSSPRDEERDIVGLEDDTAKLVDHLLQMGDHWSAVSIVGMGGIGKTTLG 200
                        ******.**:*****:** ****.:*:. *;* *;*;*:***********.

ColNBS-LRR              KKVYNHADIQARFPTRAWVYVSQEYSIRDIFQAIIKQVASTGRNLEKLRE 247
PtcNBS-LRR gi224075299  IKIYNHSAVRARFFSRAWICVSQEFSARDILQRVIRQIASPRERLEALTD 250
                        *:***. ::****;***: ****:* ***:*  :*:*;**,..** *  :

ColNBS-LRR              EELEETLYEHLRKKRYLVVLDDVWSIEAWNSLSEAFPDSSSNGSRVMLTT 297
PtcNBS-LRR gi224075299  EELEDLVYENLRRKRYLVVLDDIWSTNAWDCLKKAFPVDRSNGSRLLLTT 300
                        ****:: **:***:********:**  **:.*.:***. ;*****::***

ColNBS-LRR              RNKSIALKADARSVPYDLHFMNEENGWMLFCKKAFIQSADSHRSPRLEEI 347
PtcNBS-LRR gi224075299  RNKNVALHVDPQTTPYDLGFLSKQNSWELFCKKTFIDGRDTSCSPILEEI 350
                        ***:.**:.*  :.*****.* .::* ::****:**:. *:*.**:****

ColNBS-LRR              GKEIVEKCAGLPLAIIVMGGLLSTKRSLAEWKRVLSNMSSFFAQDPNGVS 397
PtcNBS-LRR gi224075299  GREIVERCAGLPLAIIVIGGLLSRKKRLNEWERILNNMDSHFARHPNGVA 400
                        *:****;************: *****..** *;  **;*:*..*.*:**.;

ColNBS-LRR              AILALSYNDLPYYLKSCFLHLGQFPEDQPIPTHKLFRLWIAEGLIPQQGE 447
PtcNBS-LRR gi224075299  AILALSYNDLPYYLKSCFLYLGLFPEDCTIQAHKLFRLWVAEGLIPHQEL 450
                        *******************:**.****  *.:*******:*****:*:

ColNBS-LRR              RVEDVAEDYLNELIERNMVQVAKWSVNEPVKQCRLHDLLRDLSISKAKAE 497
PtcNBS-LRR gi224075299  RGEDVAEDYLNELIERNMVQMEGMSVNGRVKQCRLHDLLRDLSISKAKTE 500
                        * :*************;****:   ***  *********:********;*

ColNBS-LRR              SFHEIQGSQSLEPSARSRRHAIYSTFHWPQCKYSNPQLRTLLLFRVDHNQ 547
PtcNBS-LRR gi224075299  NFLQIPGNENIPSLTRCRRHPIYSDSHLSCVERLSPHLRSLLFFRVVS-R 549
                        .*. :*  *.: :  .:* .*** :**  *.   . :.*:*.**;:***

ColNBS-LRR              SQVNYYIN-DPY---KMEGSDLDYISKNFKLLRVLELEGIPCATIPSIIG 593
PtcNBS-LRR gi224075299  VRYRYFIGRNVYGFCELSGAKFDYITRNFLLRILELESISCSSIPSTIG 599
                        : .*:*. : *  ::.:.*;:.***;;**.***;*****;*:;*** **

ColNBS-LRR              LLIHLKYLGLKETNLQELSSAIGSLRSLQTLDIAANLHLLTIPNVIWKLK 643
PtcNBS-LRR gi224075299  ELIHLSYLGLKETNIRVLPSTLGSLCNLQTLDIAGNLHLRIIPDVICNMK 649
                        ****.*******;: *.*;*** ******.****   ::***;*:  :*

ColNBS-LRR              RLRHLYMCGHKYGGPLRIDTLQHLQALSEINVQRWMQNDPANLTSLR--- 690
PtcNBS-LRR gi224075299  NLRHLYMCGHS-GGHLRIDTLKHLQTLTEIDVSRWKQNNTADLVSLRKLG 698
                        ,********* ** ****** :*****::** :*.*;*;:**:* ***

ColNBS-LRR              --------------------------TEEADFPSLTQLSALQNLVKLH 712
PtcNBS-LRR gi224075299  IRGNLCSDTIKIFDSISALLQLRSLYLRAEGAEFPSLVQLGSLRSLIKLH 748
                                                  ;*  *;****,**,  ,*:***

ColNBS-LRR              MRGTIRQLPNSEEFPPNLCQLTLEHTHLQQDSVGILEKLPRLLILRLKAR 762
PtcNBS-LRR gi224075299  LRGGISQLPSQQDFPPNLSQLTLEHTQLEQESIEILEKLPKLSILRFKAE 798
                        ;** *  ***..::;*****,*********,*:*:*: *******;*;***.

ColNBS-LRR              SYDGEKMKISVSGFPQLDVLELVSLESLEELNLEEGAMLRLRSFRIIKCE 812
PtcNBS-LRR gi224075299  SYSKEKLTISADGFPQLDFLEFNSLESLHEFNIEENAVPRLESFLIVNCK 848
                        **, **:.**,;******;**.:**;*:*****;*:;.;**,***;:*:;

ColNBS-LRR              KLKMLPEGMKTLTGLRELDIELMPKSFVDRIRGEDPYKVQHVPSILFV 860 (SEQ ID NO:8)
PtcNBS-LRR gi224075299  GLRMLPEEMRFVATLHKLVIEEMPKVFVDRLGGEDLHKVQHIPLIKFI 896 (SEQ ID NO:43)
                        ;*:****  *: .::;**  **.:****:.**** :***:*  * *:
```

Figure 3

```
Col CC-NBS-LRR1              MEFVVGIVSSIFTPAVQLIISPIKNKIKYISNHENNVQTLKNQVESLKDERKRVQHSVDA 60
Ptc CC-NBS-LRR gi224111284   MEFVISIVATVA----ELLVVPIKRQIGYYLDCNTNIQNLKNEVEKLTDAKTRVNHSIEE 56
                             ****:.**::      :*:.***.:* *: : :.*:*.***:**.*.* :.**:**::

Col CC-NBS-LRR1              ARQNGEEIEDDVKKWQKTVDQKIADEVEKVIADEEKAKKKCFVGLCPNLWARYKHSVKAE 120
Ptc CC-NBS-LRR gi224111284   ARRNGEEIEVDVENWLTSVNGVIGGGGGVVVDE---SSKKCFMGLCPDLKLRYRLGKAAK 113
                             **:******.**:;* .:*: *.. *: : :.****:****:* **:. . *:

Col CC-NBS-LRR1              EKGKVVAKLLEQCKFDKVSYRPAPQCASVIAAFVKGFEEFKSREVLLKGIMEALNDDKIN 180
Ptc CC-NBS-LRR gi224111284   KELTVVVNLQEKGKFDRVSYRAAPSGIGP----VKDYEAFESRNSVLNDIVDALKDCDVN 169
                             ::.**:.:* *:****:****.**.*.*       **.:* **:* ::*.*::**:* .:*

Col CC-NBS-LRR1              TMGVHGMGGVGKTMLVKEVARQYKEGRLFDYVVMAKVTQTVDVKTIQNDIAELLGLRFDE 240
Ptc CC-NBS-LRR gi224111284   MVGVYGMGGVGKTTLAKKVAEQVKEGRLFDKVVLAVVSHTPDIRRIQGEIADGLGLKLNA 229
                             ::**:********.*.*:**.********** **;* *::* *:: **.:**: ***:::

Col CC-NBS-LRR1              QSIVRRADRLRERLKRETKVLVVLDDVWERLDLEEVGIPVADEHKGCKILLTSRDLNVLS 300
Ptc CC-NBS-LRR gi224111284   ETDKGRADQLCEGLKNVTRVLVILDDIWKELKLEDVGIPSGSDHEGCKILMTSRNKNVLS 289
                             ::    ***:* * **: *:***:***:*;.*.**:**** ..:*:*****:***:****

Col CC-NBS-LRR1              NGMNSEKNFVVGLLTEEETWNLFKKKAGYVVESSDIKPTAIEVAKKCAKLPIAIATVAGA 360
Ptc CC-NBS-LRR gi224111284   REMGANRNFQVQVLPVREAWNFFEKMVGVPVKNPSVQPVAAEVAKRCAGLPILLATVARA 349
                             . *.:::**. :*:. .*:**.*:** .*. .*:..::.* ****.*** ****.* *

Col CC-NBS-LRR1              LRNKEAFHWKDALCQLQKPSTVNLKGVATTVHSAYKLSYDFLESEEVKFTFLLC-CLLGR 419
Ptc CC-NBS-LRR gi224111284   LKNEDLYAWKDALKQLTR---FDKDEIDNQVYSCLELSYKALRGDEIKSLFLLCGQFLTY 406
                             *:*::: ****** ** :*:***.*.:*::***.*.****   :*

Col CC-NBS-LRR1              NGLIEDLLKYVIGMRLFQG-ITIEETRNRVLTVVSNLKASCLLLDSYNNEEKFDIHDVVWD 478
Ptc CC-NBS-LRR gi224111284   DSSISDLLKYAIGLDLFKGRSTLEEARNRLRTLVDELKAGCLLLEGDKDGRVNMHDVVQS 466
                             :. *.*****.**: **:* *:**:***: *:.:****.*****:. :: :...****

Col CC-NBS-LRR1              VALLIASRDHMFVLRDGEELKDWPTQEMKENCSAINFRCPRIMTELPDEMEGLPRL-SLL 537
Ptc CC-NBS-LRR gi224111284   FAFSVASRDHHVLIVAD--EFKEWPTSDVLQQYTAISLPY-PKIPDLPAILECPNLNSFI 523
                             .*: :*****:*:::  *  *:*:***. ::  **.:    *   * .:** :* .* *::

Col CC-NBS-LRR1              RLDNVGALEIPANFFRRMERLDVLHFTRMHFSSLPVSISLLTNLHTLCLSDCALQDITIV 597
Ptc CC-NBS-LRR gi224111284   LLNKDPSLQIPDNFFREMKELKVLDLTRVNLSPLPSSLQFLENLQTLCLDGCVLEDISIV 583
                             *::  :*:** ****.*.*:*.*:*.:.**.::.** *:.** **:***:.***.*:**

Col CC-NBS-LRR1              GKLKNLEILSLARSVIEALPEETAQLTRLRLLDLSHCSKLQLIPPNVLSSLSKLEELYLY 657
Ptc CC-NBS-LRR gi224111284   GELKLKVLSLISSDIVCLPREIGKLTRLLLLDLSNCERLEVISPNVLSSLTRLEELYMG 643
                             *:**:*:*** .  *  * .**.* .:**** *****.*:*;:;*,*******::****:

Col CC-NBS-LRR1              NSFVQWEGEVHSSGRRNASLDELKHLSHLPTLYVHIPNAEIVPKDL--FIERLERFSILI 715
Ptc CC-NBS-LRR gi224111284   NSFVRWETEGSSSQRNNACLSELKRLSNLITLHMQITDADNMLKDLSFLFQKLERFRIFI 703
                             ****:** * **.*.**.*.***::** **;:*  **::.*:* ***.*::****.*;*

Col CC-NBS-LRR1              SDERPWYSEFEYSRTLKLKIYTSIYLDHAVRMLLKKTEDLHLYQLKGIKNVLDELIDGVE 775
Ptc CC-NBS-LRR gi224111284   GDGWDWSVKYATSRTLKLKLNTVIQLEEWVNTLLKSTEELKQELKGVKSILND-LDGED 762
                             * *  *  :: ******* * *. *. *** ****.*:*:*** *;**** .:;; :*:  :

Col CC-NBS-LRR1              LPELKNLHIRNGSEVQYIMRKKIECAQLKSMTLEGLPKLISFWFEDKRCSTSHEERATSS 835
Ptc CC-NBS-LRR gi224111284   FPRLKHLHVQNCFGVQYIIN---------------------------------------- 782
                             :*::**:**:;*   ****:.

Col CC-NBS-LRR1              NPLPLFNKQLVFPCLESLRLSSINAERIWHSPLSENCTFAANLKSLTVEGCGELEHLLSP 895
Ptc CC-NBS-LRR gi224111284   ----------------SIRMGPR------------------------------------ 789
                                             *:*:..

Col CC-NBS-LRR1              SVARSLVQLTHFEVARCQRLREIISTEEIEDESVAICFPQLNSLEIRSLQNLANFCAGNY 955
Ptc CC-NBS-LRR gi224111284   -----------------------------------TAFLNLDSLFLENLDNLEKICHG-- 812
                                                                .* :*:*** ..:*:** ::* *

Col CC-NBS-LRR1              NIEFPALKVLEVNGCPVLKEFIRVNKSEFHVPALFNEKVALPSLERMEFSYLKNVKMIFD 1015
Ptc CC-NBS-LRR gi224111284   ------------------------------------------------------------

Col CC-NBS-LRR1              FQLLAGSFCKLKAMSVYHCDALLTIFSSNIFGAFQSLENLDVYRCNSLEMIFEVGGLNIR 1075
Ptc CC-NBS-LRR gi224111284   -QLMAESLGKLRILKVES------------------------------------------ 829
                              **:* *: **: :.*

Col CC-NBS-LRR1              EPHVVHSQLPSLYISSLPALKHVWNKDPQGILSFQNLHTVDLSFCRNLKSLFPVSVAKHL 1135
Ptc CC-NBS-LRR gi224111284   ------------------------------------------CHRLKNLFSVSMARRL 845
                                                                         *:.**.**.**:*:*

Col CC-NBS-LRR1              QQLENLRLCNSAVEEIVFSEEGLEEPIG----PEFAQLSSLVLYNLRELKCFYRGQHTIVW 1192
Ptc CC-NBS-LRR gi224111284   VRLEEITIIDCRIMEEVVAEESENDTADGEPIEFAQLRRLTLQCLPQFTSFHSNRR---- 901
                             :**:: :.. * *.** ,::,  .  :***** .*.*  * :::.*. :::
```

Figure 4a

```
Col CC-NBS-LRR1           AMLKELETDHSTLLKIVGSNSQHLGIQEMNSNDPPECTTGQPLFSTEKVIPILEELHLRL 1252
Ptc CC-NBS-LRR gi224111284 ---QKLLASDVRSKEIVAGN--------------ELGTSMSLFNTKILFPNLEDLKLSS 943
                             :**  :..    :**..*           *  *. .**.*:  ::* **:*:*

Col CC-NBS-LRR1           TNPDDISKICDGHFLQRFCNLESLELSSSEGDDAQILFDAVTLPRIKTLILSSCNFLKHI 1312
Ptc CC-NBS-LRR gi224111284 IK----------------------------------------------------VEKT 949
                           :                                                        ::*

Col CC-NBS-LRR1           WEKKDSELGHILQKLEILEVNECGDLTSFGPSSASFQNLTTLEVTYCNMMINLATPSVVQ 1372
Ptc CC-NBS-LRR gi224111284 WHDQP----------------------AVQPPCVKNLASMVVESCSNLNYLLTSSMVE 985
                           *..:                        . .....:*^::: * *. : * *.*:*:

Col CC-NBS-LRR1           NLVQLTTMRIAYCRGMAEIVANEG-GEATPTYEINFSKLQSLELNRLHRLTSFSPGNYTI 1431
Ptc CC-NBS-LRR gi224111284 SLAQLERLEICNCESMEEIVVPEGIGEGEMMSKMLFPKLHLLELSGLPKLTRFCTSN--- 1042
                           .*.**  :.*. *,.* ***. ** **..   :: *.**:  ***. *  :** *...*

Col CC-NBS-LRR1           NFPSLQELMRVKESHNDRKGRWAGDLNTTIQLLYSVNVVEGYHGICNIKLSDTSPELMEI 1491
Ptc CC-NBS-LRR gi224111284 ------------------------------------------------------------

Col CC-NBS-LRR1           WNGRNPHEIVDLKFLGRVEFCNCSSLKYIFTLSRLLSLKHLSYLVVKECSTLREVVMEQE 1551
Ptc CC-NBS-LRR gi224111284 ------------------------------------------------------------

Col CC-NBS-LRR1           IEEEATTDNFIFPNLRYIKIESCSSLRCFYLGSGALEIPRLEIIEITDCPKMTTFASSFP 1611
Ptc CC-NBS-LRR gi224111284 ------------------LLECBSLKVLMVGN---------------CPELKEFTS--- 1065
                                             : .* **: : :*.                **:;. * *

Col CC-NBS-LRR1           RDEEKEISADGSEKRVGHCDLNIEPFFSDKVALPSLERLRIKGMGKCRKIWQDQLTVNSF 1671
Ptc CC-NBS-LRR gi224111284 ------IPSSADVFVMSKPDNTKSAFFDDKVAFPDLEVFLIFEMDNLKAIWHNELHSDSF 1119
                                 *.:...   ::.:  *  . .**.*****:*.**  * *  .:: : **:;:* :**

Col CC-NBS-LRR1           CELKYILVESCEKLSNIFPFNMMERLEKLEELQIVNCDSLEEIFEPEALTNNQSHGVATT 1731
Ptc CC-NBS-LRR gi224111284 CELKILHVGHGKNLLNIFPSSMLGRLHNLENLYINDCDSVEEIFDLQVLIN--------- 1170
                           ****  : *    ::* ****  .*: **.:**:*  * :***:****: :.* *

Col CC-NBS-LRR1           ESIVEETMAKFVFPSATYLRLENLPNLKCFYSRTHATEWPSLKKMKVLDCQNVQIFASEC 1791
Ptc CC-NBS-LRR gi224111284 ---VEQRLA--------------------------------------------------- 1176
                              **: :*

Col CC-NBS-LRR1           PAFGETQGASTEINISNQPPLFRVNEVTFPILEELKLKPDDTWHGQVLSTECFSKLKVLE 1851
Ptc CC-NBS-LRR gi224111284 ------------------------------------------------------------

Col CC-NBS-LRR1           LICIPEKATDLACCFIQSLPNLEKLLVKDSSFCQIFQFEGLSDDDQRHAALTRLSELRLS 1911
Ptc CC-NBS-LRR gi224111284 ---------------------------------------DTATQLRVVRLR-------- 1188
                                                                  : *:*  :**

Col CC-NBS-LRR1           KLPSLTHLWTEEFQPCAAFSNLKLLEVLECVKLKTLVPSLVSFNNLTTLKVSGCHCLTNL 1971
Ptc CC-NBS-LRR gi224111284 NLPHLKHVWNRDFQ-----------------------GILSFHNLCTVHVRGCPGLRSL 1224
                           :**.*.*:*..: *                         .::*:*:** *::* ** ** .*

Col CC-NBS-LRR1           VTCSIATSLMQLKRMSITDCNMIEEIIACDADEIQG----AIVFSQLRYLKLSCLPSLAS 2027
Ptc CC-NBS-LRR gi224111284 FPASIALNLLQLEELLIENCG-VEEIVAKDEGLEEGPSSFRFSFPKVTYLHLVEVPELKR 1283
                           ...***..*.:**:.:  * :*.   :***.:* *       : *.:: **;*  :*.*

Col CC-NBS-LRR1           FCLGNQSFDFPTLQKLIVHECPKLEIFCQGDLTTPKLQQVLLPEYEYEYYDAEEYEDEYD 2087
Ptc CC-NBS-LRR gi224111284 FYPGVHVSEWPRLKKFWVYHCKKIEIFPS---------------EIKCSHEPCWEDHVD 1327
                           * *  ::*  :;* *;:*  *;;* *;*** .              *  : .   :**. *

Col CC-NBS-LRR1           AEEYEENSMWEGDLKSTIRKLFEEMAEDEDEDEDEDDDEEHEDEDEDEDDDEEHEDEDED 2147
Ptc CC-NBS-LRR gi224111284 IEGQQP--------LLSFRKV--------------------------------------- 1340
                            *  :           ::**:

Col CC-NBS-LRR1           EDDDG 2152(SEQ ID NO:10)
Ptc CC-NBS-LRR gi224111284 -----(SEQ ID NO:44)
```

Figure 4b

```
Col CC-NBS-LRR3              ----------------------------------------------------------
Ptc CC-NBS-LRR gi224132258   ---MAIQEIFLAAPLCMLFTRLISPEFLKFARREGIWKKADKWRGMLLKVQEVLDDAEEKQ  58
Ptc CC-NBS-LRR gi224059584   MALVIGDAILSATISHIINQLASLELLKFARRGKIHSDIKKLBANLHMIHAVLDDAEEKQ  60
Col CC-NBS-LRR2              ----------------------------------------------------------

Col CC-NBS-LRR3              ----------------------------------------------------------
Ptc CC-NBS-LRR gi224132258   LTEEKAVKIWLSDLRDLAYDVEDLLDEFATESLRRELMAAEEASTSKVRRIVSTTLSFIKI 118
Ptc CC-NBS-LRR gi224059584   MGSHAVKIWLDQIRELAYDMEDLLDG-----VFSELKEEQRASSSKAKSAIPGFLSS--F 113
Col CC-NBS-LRR2              ----------------------------------------------------------

Col CC-NBS-LRR3              ----------------------------------------------------------
Ptc CC-NBS-LRR gi224132258   SASATKFNPKMRSEMKFVSSELDGMAKQRIEIGLFKMSGGERTSTDVWQKPPSAEVPNRP 178
Ptc CC-NBS-LRR gi224059584   YPFGNLLLTYKEDSKIKRTTARFQEIAQKKDNLELRENGSGGVLKSKSLKRLPSTSLVDLS 173
Col CC-NBS-LRR2              ----------------------------------------------------------

Col CC-NBS-LRR3              ----------------------------------------------------------
Ptc CC-NBS-LRR gi224132258   VIYGRDCSKKKVIDLLLTEEANBGDTNFHVVPIVGMSGICKFTLAQHVFQDELVKEWFST 238
Ptc CC-NBS-LRR gi224059584   YVSGRDEKEEILRLLFSDEG-CDEYGIGVIPIVGMGGVGKTTLAQLVYNDETVDKFFDL 232
Col CC-NBS-LRR2              ----------------------------------------------------------

Col CC-NBS-LRR3              ----------------------------------------------------------
Ptc CC-NBS-LRR gi224132258   KAWACVSEDFDVMRISKAILESVTPHPCDFKEYNQVQVKLREALAGKKFLLVLDDVWNKN 298
Ptc CC-NBS-LRR gi224059584   KVWCCVSEDFCVVRVTRTILEAVSG-SYDAKDLNLLQLRLREREKLAGKKKFLIVLDDVWNEN 291
Col CC-NBS-LRR2              ----------------------------------------------------------

Col CC-NBS-LRR3              ----------------------------------------------------------
Ptc CC-NBS-LRR gi224132258   YGLWVALKPPEAAGAPGSKILLTTEDADVALRVGPTEYHCLKPLSDQDCWSVFVKHAFFN 358
Ptc CC-NBS-LRR gi224059584   YDDWTVLRRPFQVTSPGSRIILTTRNQBVALMMSAFPCYLLKELSFEDSLSLFAKHALGR 351
Col CC-NBS-LRR2              ----------------------------------------------------------

Col CC-NBS-LRR3              ----------------------------------------------------------
Ptc CC-NBS-LRR gi224132258   RELGAQTNLQSVCERIVTKCKGLPLAARTLSGLLRTKQREDEWEDILNSKIWDLSDSQSD 418
Ptc CC-NBS-LRR gi224059584   SNFSELPDLQEIGCKIVQRCGGLPLAVKTLSGLLRTKPYVDEWESVLNSKMWDISEHKGG 411
Col CC-NBS-LRR2              ----------------------------------------------------------

Col CC-NBS-LRR3              ----------------------------------------------------------
Ptc CC-NBS-LRR gi224132258   ILPVLRLSYYHLPSHLKSCFTYSALIPKDFEFEEKDLVLLWMAEGLVPQQVQNKQMEDMG 478
Ptc CC-NBS-LRR gi224059584   IVPALRLSYYRLPSHLKQLFVFCSILPKDYSFYKDELVLLWMAQCFLPDACGCKKRMEDFY 471
Col CC-NBS-LRR2              ----------------------------------------------------------

Col CC-NBS-LRR3              ----------------------------------------------------------
Ptc CC-NBS-LRR gi224132258   AEYFRDLVSRSIFQVANCDESRFVMHDLVSDLAQWAASGDICFQLGXDLNAIRQFKVSKRA 538
Ptc CC-NBS-LRR gi224059584   SCFN-ELLSRSFFCRSSSNEQRYLMHHLISDLAQSIAGETCVNLNDKLENNKVFFDPEKT 530
Col CC-NBS-LRR2              ----------------------------------------------------------

Col CC-NBS-LRR3              ----------------------------------------------------------
Ptc CC-NBS-LRR gi224132258   RBSSYIR-GWDGIRKFEVVHTPKRLFCFLPLPSLLG--HNTGYLTSHVPFDLLPELEFLR 595
Ptc CC-NBS-LRR gi224059584   RHMSFTRRTYSVLQRFKDLGKLKRLRPFIALRLYSSPWAAYCYLSNNVLHSALSKLRRLR 590
Col CC-NBS-LRR2              ---------------------MKTPQLLCLMDEENELPSNLEYVEISDCS---  29

Col CC-NBS-LRR3              ------------------------------------------------------MP  2
Ptc CC-NBS-LRR gi224132258   VLSLSGYCIDTLPNSIGDLKHLRFLNLSFSAIRNLPQSVCSLYNLQTLLLKCCCLLECLP 655
Ptc CC-NBS-LRR gi224059584   VLSLSGGYCIFELPNSIGDLKQLRYLNFSQTKIKRLPESVSTLINLQTLKLG-CRKLNKLP 649
Col CC-NBS-LRR2              -------NLAKLPNGLQKRLSGLKDLSVKWCPKLMSFPNAELPSTLKTLSILGCESLSSLP  82
                                                                                 :*

Col CC-NBS-LRR3              SNPFG--------------------ALINLQLLSDFVVGKDRGYQIRELQDLSNLKG  38
Ptc CC-NBS-LRR gi224132258   SKLGSLINLRHLDITSASSIKAMPMGISKLYTNLQTLSDFVLGKDKGSRLSSLVNLKSLRG 715
Ptc CC-NBS-LRR gi224059584   QGTGNLIULCHLDITDTDNLFEMPSWMGNLIGLQKLSKFTVGKKEGCGIEELRGLQNLEG 709
Col CC-NBS-LRR2              KGLVH----------------NGSSSIGRUNLDNLETLGCPSLRLFSIGELPT 119
                                                         :.   ..:    .  *     :     . *

Col CC-NBS-LRR3              SLYISGLENVVETEDASKAKIHDKSGLDKLVLDWKSGMKFNRDFENIREDVEQKVLDLLE  98
Ptc CC-NBS-LRR gi224132258   TLCITGLENVIDAREAMEANKDINNLEVLLLEWSPRTDNSR-----NEKVDKDVLDDLR 779
Ptc CC-NBS-LRR gi224059584   RLSIMALHNVIDARHAVHANLRGKHNLDELELEWSKSDIKDE------DRQHQMLVLDSLQ 764
Col CC-NBS-LRR2              CLKQLDIWDCMQLKCIPERLLENSQSLEFIRIGNCKNLKTLPQCLYRFDYLIELHVNQCP 179
                                .  : ::   .  :  . .*:  :    : :  . :

Col CC-NBS-LRR3              PSK--QLKKLVIMHYRGLMLAKWVGNSSLCN----LESLQLINCTNCLSLPSLGELPLLK 152
Ptc CC-NBS-LRR gi224132258   PHG--KVKELTINCYAGLTFPPWVGNPSFSS-----IPFLALENCTKCTSLPPLGLLPSLK 824
Ptc CC-NBS-LRR gi224059584   PHT--NLKELKISFYGGTEFPGWVGHPGFSR-----IVHLRLSCCRKCTVLPFLGRLPLLR 818
Col CC-NBS-LRR2              SLESFPERGLFIRNLNIVLISNCVNLKSLPNRMRHYLTSLQYLTLFGCPSVESFPEEEFTI 239
                                  *  *   ::  *:  *:..     *:        *    :  :

Col CC-NBS-LRR3              NVVIRKLSISSVGVEFSLGEK-TMEPFRALELLQFED---------------------- 188
Ptc CC-NBS-LRR gi224132258   NLSIVSLTAVRKVGPEFYGQG-CSKPFFVLSTLLFKNMQEWEBWMIL-------------- 870
Ptc CC-NBS-LRR gi224059584   DLCIQGLLAVETVGHEFYGDCSSVKPFPSLKTLIFEDMQBWKSWSAVGVDGEAEEQFPSL 878
Col CC-NBS-LRR2              PTTLVHLRVQSLPNLEYLSKG--LQDLVFLESLDVWNCPKLQYLPKDGLPSMLCLLQIRN 297
                                :   *  .  .*:..     : :  *:

Col CC-NBS-LRR3              --------------------------------------------------(SEQ ID
NO:14)
Ptc CC-NBS-LRR gi224132258   VGLVLTNSLS--------------------------- 880(SEQ
ID NO:45)
Ptc CC-NBS-LRR gi224059584   SELTLWNCPKLLGRFPSCLPSCVKITIAKCPMLVDSDEKLPVLGELKLEECDEVKPKCMF 938
Col CC-NBS-LRR2              CPLLEKECLYEK--------------------------- 309(SEQ
ID NO:12)
```

Figure 5a

```
Col CC-NBS-LRR3
Ptc CC-NBS-LRR gi224132258
Ptc CC-NBS-LRR gi224059584    HNSSLIFLKLGSMSRLTYLKGQLLQSLGALKVLMISDFPKLTSLWQKGTGLENFSHPQFV  998
Col CC-NBS-LRR2

Col CC-NBS-LRR3
Ptc CC-NBS-LRR gi224132258
Ptc CC-NBS-LRR gi224059584    SLTEIGMPSTHKSGKLSGCDKLDLLFIHTVEMLLSLEDLCTESCPNLVSIPEAGLLSSLR 1058
Col CC-NBS-LRR2

Col CC-NBS-LRR3
Ptc CC-NBS-LRR gi224132258
Ptc CC-NBS-LRR gi224059584    HLVLRDCKALRSLPDGMSNCPLEDLEIEECPSLECFPGRMLPATLFGLKIRYCTELKSLP 1118
Col CC-NBS-LRR2

Col CC-NBS-LRR3
Ptc CC-NBS-LRR gi224132258
Ptc CC-NBS-LRR gi224059584    EDLMHNKNGPGTLCHFEHLETIGCPSLKSFPDGKLPYFLKTLKIWDCSQLKPLSEMMLHD 1178
Col CC-NBS-LRR2

Col CC-NBS-LRR3
Ptc CC-NBS-LRR gi224132258
Ptc CC-NBS-LRR gi224059584    DMSLEYLAISDCRALSSFPECLSSFEHLSELNLSNCSALKLFPGVGFPPANLRTLTTYNC 1238
Col CC-NBS-LRR2

Col CC-NBS-LRR3
Ptc CC-NBS-LRR gi224132258
Ptc CC-NBS-LRR gi224059584    KNLKSLFNEMRKLTSLQELTICSCPALKSFPNGDMPPHLTSLEIWDCDNLGCLSEWNLQ  1298
Col CC-NBS-LRR2

Col CC-NBS-LRR3
Ptc CC-NBS-LRR gi224132258
Ptc CC-NBS-LRR gi224059584    SLTCLRDFSIAGGCFSHTVSFPDEKCLLPTNLTSVWIGRLPNLESLSMQLQSLAYLEELE 1358
Col CC-NBS-LRR2

Col CC-NBS-LRR3
Ptc CC-NBS-LRR gi224132258
Ptc CC-NBS-LRR gi224059584    TVDCPKLKSLPRGCLPHALGRFSTRDCPLMTQRCSKLKGVYWPLTSHIPCVRIDDGNDM  1417(SEQ
ID NO:46)
Col CC-NBS-LRR2
```

Figure 5b

```
Col NBS               MDPLQAVAAATQIISSMVGAVGALEQASRNLDEAPKRIRSLEEFVCDLENLAQRIRQKHA 60
Ptc NBS GI: 224058687 MEALQVISSATQIISSMVGAVSALDQASRNLDEAPKRIRSLEEFVYDLENLTRGIRQKHV 60
                     *:**::::*********:**:*****************:*****::*****:*.*****.

Col NBS               NKLHNAQLDYQLQSLHALIERLRPNIRKARTVVSKSKIFNLAKVFWNSMAGDPLGKLTVL 120
Ptc NBS GI: 224058687 YKLHNPQLDHQIQSLNALIERLRPNITKARRIVSRSRIKNLAKVVSSMACDPLSKLINT 120
                     ****:****:****:*********:***::**:*:**:***** ::***.***.**:.

Col NBS               IKDDLNWWLDTQMLAQNVEKVLESTAQDTPVRLKIKTDQGYPTSSKCIFVKELLEQEDTH 180
Ptc NBS GI: 224058687 IRDDLNWWLESQRLTQHVQKVIESTAQDVPVRLKIKIEQGWPLSSKCHFVRNLLEQEDSH 180
                     *:*******::*:* ::*:**:*******.******::** *:**** **::******:*

Col NBS               RVILIVGLSGIGKSCLARQVASDPPKKFAGGALELGFGQWCSRAACNGSKVEYQKRLARK 240
Ptc NBS GI: 224058687 RVILIVGLSGIGKSCLARQVASNPPTKFVGGAVELGFGQWCSRNACNGNKEDYQRRLARK 240
                     **********************:**.**.***:**********.:****.*: **:*****

Col NBS               ISKFLVQIGFWKKIKEENSGDLDYVCYLLQSALYGKSILVLLDDVWEQDIVQRFAKLYDN 300
Ptc NBS GI: 224058687 ISNFLVQIGFWKKIKDENSGDLEYVCCILQEALYGKSIVILLDDVWEQDIVERFAKLYDN 300
                     **:************:******:*** :**.*******::**********:********

Col NBS               NCKYLVTTRNEAVHEITEAEKVELSKEDIREISKGILLYHSLLSEEELPGIAESLLERCG 360
Ptc NBS GI: 224058687 DCKYLVTTRNEAVCEITEAEKVELSKEDTREISKAILQYHSLLGMEELPGIAETLLERCG 360
                     :************ ************** *****.** *****. ********:******

Col NBS               HHPLTVAVMGKALRKEVRAEKWEKAITNLSTFATCAPGPVSYVNEKDAEDTLTIFGSFEF 420
Ptc NBS GI: 224058687 HHPLTVAVMGKALRKEVRAEKWEKATTNLSIFATCAPGPVSYVNEKEAESTLTIFGSFEF 420
                     *************************:****:**************:**.**********

Col NBS               SLEAMPVDSKRLFIALASLSWAEPVPEACIEAIWSCIGQESLFSLIVCKLVEGSLLMKVD 480
Ptc NBS GI: 224058687 SLEAMPRDSKRLFIALASLSWAEPVPEACLEAVWSVIGDESLFPLIVCKLVEGSLLIKTD 480
                     ****** **********************:**:** **:****.***********:*.*

Col NBS               MDPLYQVHDMVSLYLDSKTTDSIEMLLHRSKPEETAFICPWLLIFGKENVKKIVEERMKL 540
Ptc NBS GI: 224058687 MDPLYLVHDMVSLYLASKADDSTEILLNEYSPDETAFICFWLLIFGKENVKKIAEERMEF 540
                     ***** ********* **::** *:*:.. **:****** ************: ****::

Col NBS               FFDILDEKQVVITLESSIEALMASKSISELEASPASFSRILGPKITDYVSTNSQSMIAVS 600
Ptc NBS GI: 224058687 LFNVLEGKQVVTTLEALIHALMASKSMSELEVSREKFSRILGPRIADLISTDSLSLIAVI 600
                     :*::*: ****** **: * ******:****.* .********:*: ::**:* *:***

Col NBS               AEAIIIFSKTDYCNYFPSLETDSTVLKEASMLEDCED-PVIQTNILTILAKIAEFGSPE 659
Ptc NBS GI: 224058687 TEAITNIFSKSDYCNYFPSLETTGAINRLATTLEYCEENPITQIHILIVLAKLAEFGSPG 660
                     :**   *****:*********** .::::**  **:**::* *:*** :***:******

Col NBS               IVDKVLQSIPFNQVADLLSPNAKDWHESMFTILMSLTKAGKGSKAVERMFAFQIDKNLINL 719
Ptc NBS GI: 224058687 TVDKVLDSIPFNQLADLLSSSAEKWHESMFTVLNSLTKACKSNAVERMFASGIEKKLIKL 720
                     *****:***********.. **:********:*:******.:*.*******: *:::**:*

Col NBS               IESESELVQHHAIVTLKAFYELAGPSLNSSLRPANLDLLFWQVRLRLERFVMPDRNIPLS 779
Ptc NBS GI: 224058687 LENGGEVLQHHAIVTLKGFYEVARTFENVSLQFSNLNLLPWQVRHRLETFVLSDRTVPHS 780
                     :*. .* :************.***: . .  *:*:****:*** *** **:.**.:*:*

Col NBS               PKPQTFEDLIHKMLDNDNKQVLEAMQDLVPIIEKAGDPGFRQMIVQSPLIRRLSELLQHG 839
Ptc NBS GI: 224058687 PKPLSFEDLVYKVLDGNKRQVLQAMQDLIPIIEKSADSHVREMILHSPLVNRLSELLQSR 840
                     *** :****::*:**.:::***:****:******:.*. .::*:::***:.*******.

Col NBS               HTEQNSIRSESAFLLMKLAYSGGEPCINKFLEFDVIPELVKMMQCNTAELQDSAYTALHQ 899
Ptc NBS GI: 224058687 HSEHNSIRSESAFLMMKLAFSGGEPCIKKFLDHDIVPELVKMMQCNVVELQDSAYTALHQ 900
                     *:*:********** ****:*******:***::*:***********..***********

Col NBS               MLFGNGGVLVLSKIPKMCLIDKIPYALESKSAKTREVLLHFVPDIVELGSKACLEKMLSL 959
Ptc NBS GI: 224058687 MLFSNGGILVLNNIFETGFVDRMVQSVDSKSIKTQEVNVHCILDLVELGNKSCLEQMLSL 960
                     ***.***:***.:*::  :*: : ::: ****:**:**::* :.*:****.*:***:***

Col NBS               QVVEKLTKLEKSGGGSGEIVIGFLRAMDKCKHLTVAERKVMKQQVVRKVRASLKGHKFEF 1019
Ptc NBS GI: 224058687 QVVEKLVKLEKNTGGSGETIVGFLRGMDKCKHLSMMERRVIRKQQVVRKIRACLKGHKFET 1020
                     ******.****..*.**** :.****.*******:: **:*::****** **.*******

Col NBS               RILAAVEAFLSGGSRGASGSGSGRNRK 1046 (SEQ ID NO:16)
Ptc NBS GI: 224058687 QILASVDACVSEGSKGSS----SRYRK 1043 (SEQ ID NO:47)
                     :***:*:*  * **:*:*    .* **
```

Figure 6

```
Col LRR1          ----------------------------------------------------------
Rco LRR gi: 255546155  ----------MEVIGPLIGILCSTCDNMARKISYVINVNRKVHSLTTLLEELKYKRDDIQ  50
Col LRR-TM-PK     MGRADFTTTTPKLLLLLVFIAMLWLSTFGFAAATPLLHSEEVKALKAIGKKMGKKDWDFG  60
Ath LRR gi:42561789  ------MIYLHRIYFIIVLFTLIFHGRLGFSDNN-KLHEAEVRALKEIGKKLGKKDWDFN  53

Col LRR1          ----------------------------------------------------------
Rco LRR gi: 255546155  RQVDCAELKGLICTCQVQGWLERVKDVETKASLITGVLGQR--------------------  91
Col LRR-TM-PK     VDPCSGKGKWIEGDEET-GFASKVTCNCSFN--NNTTCHVV--------------------  98
Ath LRR gi:42561789  KDPCSGEGTWIVTTYTTKGFESNITCDCSFLPQNSSCHVIRIALKSQNLTGIVPPEFSKL  113

Col LRR1          ----------------------------------------------------------
Rco LRR gi: 255546155  -----KQCFMCCVANSCTRYKLSKRVSELQMEINELIGKGAFDAVIADGLVSETVQEMPI  146
Col LRR-TM-PK     ----TMDLSPNYFTGSIPKEWATMKLDMLSFMGNRLSGPFPKVLTNITSLTNLSIEGNNF  154
Ath LRR gi:42561789  RHLKVLDLSRNSLTGSIPKEWASMRLEDLSFMGNRLSGPFPKVLTRLTMLRNLSLEGNQF  173

Col LRR1          ----------------------------------------------------------
Rco LRR gi: 255546155  RPSVG--LNMMVEKVQQFLAEDEVGIIGIYGMGGIGKTTLLKSINNKFLTKSHEFEVVIW  204
Col LRR-TM-PK     SGPIPFEIGKLINLQKLVLSSNALSGELPAELAKLVNLTDIRFSDNNFSGKIPDFISNWK  214
Ath LRR gi:42561789  SGPIPPDIGQLVHLEKLHLPSNAFTGPLTEKLGLLKNLTDMRISDNNFTGPIPDFISNWT  233

Col LRR1          -----EFVVSKIQQSIVARLG----------------------------LPWEENDS    24
Rco LRR gi: 255546155  AVVSKDFIVDNIQQAVGARLG----------------------------LSWEECEG   233
Col LRR-TM-PK     QIQKLQFQGCSLEGPIPSSISTLTSLSDLRISDLKGKGSPFPLLRNHDSLKTLILRNCKI  274
Ath LRR gi:42561789  RILKLQMHGCGLDGPIPSSISSLTSLTDLRISDLGGKPSSFPPLKNLESIKTLILRKCKI  293
                       :   :   .:  : .              *   .: .

Col LRR1          YELQTSKIHNVLKNKRFLLLLDDVWEGIDLSEIGIPLPDEENKCKLIFTTRSMDVCTDMD   84
Rco LRR gi: 255546155  REQRVWKIYRVMKSKKFLLLLDDVWEGIDLQQIGIPLPNKENKCKVIFTTRSLDVCSDLD  293
Col LRR-TM-PK     HGEIPEYIGDMKKLKTLDLSYNNLTGEIPSSFYKLTKADFLYLTRNQLTGSGVPEWILERN  334
Ath LRR gi:42561789  IGPIPKYIGDLKKLKTLDLSFNLLSGEIPSSFENMKKADFIYLTGNKLTGGVPNYFVERN  353
                      :  * *  :  *    ::    ::  .:     :*        .:

Col LRR1          AHRKLKVEFLDEEKSWRLFCEKVGRMEILE------------------------SPPVRTYA  122
Rco LRR gi: 255546155  AHRKLKVEILGNEDSWKLFCDKMAGREILE------------------------WESIRPYA  331
Col LRR-TM-PK     KNADISFNNFTWDTSSP-IECPRGSVNLVESYSTPTNKLSVHSCLKQNFPCSASTSQHK   393
Ath LRR gi:42561789  KNVDVSFNNFTDESSIPSHDCNRVTSNLVESFALG-NKSHKGSTCFLQRMPCVHPKRYHL  412
                   : :..: :   *       :::*                  :

Col LRR1          ETIVRKCGGLPLALITVGRAMANKETEEEWKYAIELLNKSPSELRG--MEDVFTLLKFSY  180
Rco LRR gi: 255546155  ETIVRKCGGLPLALITIGKAMANKETEEEWRYAVEILNRYPSEIRG--MEDVFTLLKFSY  389
Col LRR-TM-PK     YSLHINCCGGQELNVNGDAKYEADMEPRGASMFYLGHN--WALSSTGNFMDNDIDADDYIV  451
Ath LRR gi:42561789  YKLYINCGGGEVKVDKEITYQADDEPKGASMYVLGANKRWALSSTGNFMDNDDDADEYTV  472
                       :***    ::         *: *.  ..        *   * . .      .

Col LRR1          DNLDSETTKMCFLYCSLFPAS-CSIEKQQLVEYWIGEG-------------FLDSSNAHNK  227
Rco LRR gi: 255546155  DNLETDTLRSCFLYCALYPED-YSIDKEQLIEYWIGEG-------------FLDS-NVHNK  435
Col LRR-TM-PK     TNTSALS-NVSAATHELYTTARVSPLSLTYYGLCLGNGNYTVNLHFAEIIYINDRPSFYSL  510
Ath LRR gi:42561789  QNTSRLSVNASSPSFGLYRTARVSPLSLTYYGICLGNGNYTVNLHFAEIIFTDDNTLYSL  532
                     *        : .        :*:*          :    :..  :

Col LRR1          GFAAIGSLKVACLLETGD----EETQVKMNDVIRSFALWIASE---------SGVNKGNLLV  276
Rco LRR gi: 255546155  GHAIIGSLKVACLLIATE----EKTQVKMHDVRSFALWIATE--------CGLNKGLILV  484
Col LRR-TM-PK     GKRIFDVYIQGELVLKDFNIQDEAGGTGKPIVKNFTAVVTRNTLKIHLYWAGRGTTGIPA  570
Ath LRR gi:42561789  GKRLFDIYVQDQLVIKNFNIQEAARGSGKPIIKSFLVNVTDHTLKIGLRWAGKGTTGIPI  592
                   *   :.     .*: ..       : ::::  ::       ..     *..

Col LRR1          EASLG--LIEAPGVENWEEAKRISLLDNGITVLEQVPICPNLLTLLLQWNNGLNRIAANFF  335
Rco LRR gi: 255546155  EASMG--LTAVPDAERWNGAQPRVSLMDNGITTLAEVPDCPNLLTLLLQYNSGLSRIPDTYF  543
Col LRR-TM-PK     RGMYGPLISAISVVSNFEPPTVVGKKNYLIIAAGAASAAILIVLMVLGIIWREGWLGGKI  630
Ath LRR gi:42561789  RGVYGPMISAISVEPNFKPPVYYDTKDIILKVGVPVAAATLLLFIIVGVFWKK--RRDKN  650
                   .  *     .   .. . . ..        .. ..      *: .::

Col LRR1          QSMPALRVLDLS--FTSTRKIPVSISQLVELRHLN-----------LAGTKITTLPRELA  382
Rco LRR gi: 255546155  LLMPSLRVLDLS--LTSLRELPASINRLVELQHLD-----------LSGTKITALPKELG  590
Col LRR-TM-PK     SAENELKDLDLQTGIFSLRQIKAATNNFDAENKIGEGGGFGSVYKGLLSDGTVIAVKQLSS  690
Ath LRR gi:42561789  DIDKELRGLDLQTGFTFLRQIKAATDNFDVTRKIGEGGFGSVYKGELSEGKLIAVKQLSA  710
                     *: ***.    ::*:::. .: ..   .:::.        *:   .: ::  :.

Col LRR1          SLAKLMYLNLSRTYSLRTVPPREALSGLS------ELVVLNLYYSYEVREVRNFEGEGVE  436
Rco LRR gi: 255546155  HLSKLKHLDLQRATSLRTIPQQALSGLL------QLRVLNFYYSYAGWGGNNSETAKEVG  644
Col LRR-TM-PK     KSKQGNREFVNEIGMISALQHPNLVKLYGCCVEGNQLLLVYEYMEHNCVSPALFGKGSTP  750
Ath LRR gi:42561789  KSRQGNREFVNEIGMISALQHPNLVKLYGCCVEGNQLILVYEYLENNCLSRALFGKDESS  770
                   : :             : . :     *    .   :  ::  :       :

Col LRR1          FEVLETLTQLRILGLTISSIASLNRLFGLRNLVRCIHYLLKECEGLTELVFSS--ASGL  494
Rco LRR gi: 255546155  FADLECLKHLTTLGITIKESKMLKKLGIFSSLLNTIQYLYIKECKRLFCLQISSNTSYGK  704
Col LRR-TM-PK     KLKLDWSTRKNICLGIARGLAYLHEESRIKIVHRDIKTSNVLLDKNLNAKISDFGLAKLN  810
Ath LRR gi:42561789  RLKLDWSTRKKIFLGIAKGLTFLHEESRIKIVHRDIKASNVLLDKDLNAKISDFGLAKLN  830
                      *:   .:.       *:.    :  : :  *:     *         :       *

Col LRR1          TLRRLSITDCYDFNYLVVNAEDGQK-WLPNLEVLSLHGLPKVTSVWKSPVRKASLQNLRL  553
Rco LRR gi: 255546155  NLRRLSINNCYDLKYLEVDEEAGDK-WLLSLEVLALHGLPSLVVVWKNPVTRECLQNLRS  763
Col LRR-TM-PK     DDDKTHISTRIAGTIGYMAPEYAMRGYLTSKADVYSFGVVALEIVSGKSNTNYRPTEDFV  870
Ath LRR gi:42561789  DDGNTHISTRIAGTIGYMAPEYAMRGYLTEKADVYSFGVVALEIVSGKSNTNFRPTEDFV  890
                       .  *.   .   :   *  : .:*   .  :.:  . :* : :      :
```

Figure 7a

```
Col LRR1              LNIWYCHSLKNVSWVLLLPKLEAIYLFYCKKMEQVVSGEEGLLEPDPKAFSRLKTIE---  610
Rco LRR gi: 255546155 VNIWMCHKLKEVSWVFQLQNLEFLYLMYCNEMEEVVSRENMPMEA-PKAFPSLKTLS---  819
Col LRR-TM-PK         YLLDWAYVLRERGSLLELVDPELGSEYSSEEAMVMLNVALLCTNAAPTLRPTMSQVVSML  930
Ath LRR gi:42561789   YLLDWAYVLQERGSLLELVDPTLASDYSEEEAMLMLNVALMCTNASPTLRPTMSQVVSLI  950
                       : .: *:: . :: * .         ::   ::.      :. *.  . :.:

Col LRR1              --IRDLPELKSISPWTLAFPCLKSIA--VIDCPKLKKLPIGTHNSSTLPTVYCSEE----  662
Rco LRR gi: 255546155 --IRNLPKLRSIAQRALAFPTLETIA--VIDCPKLKMLPIKTHSTLTLPTVYGSKEWWDG  875
Col LRR-TM-PK         EGQTSVQDILSDPGFSSMNSKFKALVNHFWQNP-SQTMSLSSNGPNTDSSSSNIEDIEEN  989
Ath LRR gi:42561789   EGKTAMQELLSDPSFSTVNPKLKALRNHFWQNELSRSLSFSTSGPRTASANS-LVDAEEK  1009
                       : .: * . :    . :::: .  . :   :..: : .. * .:     :

Col LRR1              --------------(SEQ ID NO:20)
Rco LRR gi: 255546155 LE----------- 877(SEQ ID NO:48)
Col LRR-TM-PK         SHLLRVSSIQSEA 1002(SEQ ID NO:49)
Ath LRR gi:42561789   TGLLD-------- 1014(SEQ ID NO:50)
```

Figure 7b

```
Col CCH type                    ------------------------------------------------------------
Ptc CCH type GI: 109676362      MASGQVFAKERLHRIKNHKHYRFRQEENYCTLPLLGIGRARPLTMVLLQLMAVAQPNGRV   60

Col CCH type                    ------------------------------------------------------------
Ptc CCH type GI: 109676362      PTGASLTATDDSPSWPSASGEFAFGFRQLENKDYPLLSTWYEKTPEKTVVWYAIGEDPTD  120

Col CCH type                    ------------------------------------------------------------
Ptc CCH type GI: 109676362      DPAVPRGSKLELTDDRGLLLADPQGNQIWSSGIPPGAAVSSGVHNDTGNFVLQNRNSFRL  180

Col CCH type                    ------------------------------------------------------------
Ptc CCH type GI: 109676362      WESFRNPTDTPLLPTQIMEVGGVVSSRRTETNFSLGRPQLRLLDNGNLVLNYMNLPTKFVY  240

Col CCH type                    ------------------------------------------------------------
Ptc CCH type GI: 109676362      DDYYSSETSDASRSSNSGYRLIFNESGYMYILRRNGLYEDLIKTALPTIDFYHRACLNSD  300

Col CCH type                    ------------------------------------------------------------
Ptc CCH type GI: 109676362      GVFTQYFYPKASSGNRSWSSVWSKPDDICVNMGADLGSGACGYNSICNLKADKRPECKCP  360

Col CCH type                    -RPIPISGNE----------------------------NTDWPTADYEWIKPCSLEE   28
Ptc CCH type GI: 109676362      QGFSLLDQNDRYGSCIPDPELSCRDDGLNSTEDQYDFVELINVDWPTSDYERYKPINEDE  420
                                 *  :. *:                              *.****.***  **. .:*

Col CCH type                    CKTQCLQDCLCTVAVFNENGCWKKALPLPFGRQDPDVKSNSYLRVRKPSFSQKNPLPFLD   88
Ptc CCH type GI: 109676362      CRKSCLNDCLCSVATFR-DGCWKKKLPLSNGRFDIGMNGKAFLKFPKGYVPLDRPPQLP  479
                                *:,.:*:****:.**:*, :***** ***. *** ..::::::**. *  .. ..* *

Col CCH type                    -IKKNQNSLVILVSVLLGSSVFVNFILVGVLCSGSFFLYQRKIARNGRKYKNGIQNNLRC  147
Ptc CCH type GI: 109676362      GEKKKPDIKFITGSVVLGTSVFVNFVLVGAPCLTSSFIYRKKTEK-VKEGGSGLETNLRY  538
                                 **::.* **:**:******:****.*:*.* *::**::*:*.:* :  .**.*

Col CCH type                    FSYKELESATNGFKEELGRGAFGIVYKGLIKTDAQQPTEAAVKKLDRVVQDKDNEFRTEV  207
Ptc CCH type GI: 109676362      FTYKELAEATNDFKDEVGRGGFGVVYKGTIQAGSTR--VVAVKKLDKVVQDGEKEFKTEV  596
                                *:****.****:**:*.****.**:**** *:.  .  ..******:***. ::**:**

Col CCH type                    SVIAQTHHRNLVKLLGYCDEGQCRMLVYEYLSNKTLASFLFSDQKPSWNQRKQIALGTAR  267
Ptc CCH type GI: 109676362      QVIGQTHHKNLVRLLGFCCEGQNRLLVYEFLSNGTLANFLFSCSKPMWKQRTQIAFGIAR  656
                                 **.****:****:***:* ***.*::***:*** ***.****  :** *:**.***.:**

Col CCH type                    GLLYLHEECSPQIIHCDIKPQNILLDDYYEARISDFGLSKLLGTDQSYTNTAIRGTKGYV  327
Ptc CCH type GI: 109676362      GLLYLHEECGTQIIHCDIKPQNILLDNYYNARISDFGLAKLLVMDQSKTQTAIRGTKGYV  718
                                *********.:*********.**:****:*********:***  ***  *:*********

Col CCH type                    APEWFKTVPVSVKVDVYSFGVLLLEIICCRRNVDMOIGKAKMEILTDWACDCFLEGTLDA  387
Ptc CCH type GI: 109676362      APEWFRNPPITVKVDVYSFGVMLLEIICCRRNVDLEIGEVENPVLTDWAYDCYMDGSLDV  776
                                *****:. *::**********:*********.::*:.: :**** **:**..:: *:*

Col CCH type                    LVDNDADALSDKAKLETFVMVA--------------------------------------  409
Ptc CCH type GI: 109676362      LIGDDTEAKNDISTLERLKPAEQNRTRASSNSPNAAATPVALAPAAPPPLGRHTFSPID  836
                                *:.:*::.*  .* :**  ::   *

Col CCH type                    --IWCIQEDLSL------------------------------------------------  419
Ptc CCH type GI: 109676362      LPPWSNPRSQQIMATKVTGILTAGKKVKRGGSPSRPPWFLRFSCTHAPPVAEAATPNEPI  896
                                  *:.  ...  .:

Col CCH type                    ------------------------------------------------------------
Ptc CCH type GI: 109676362      KANNITKKSPVPYARVTCDKIYGVGHIKTGMGQASREFELMKMRDNESVRDYSGRLMDVV  956

Col CCH type                    ------------------------------------------------------------
Ptc CCH type GI: 109676362      NQMRLLGKAFTDHKVVEKIMVSVPQRFEAKISAIEESCDMNNLTIAELTSKLHVQEQRVQ 1016

Col CCH type                    ------------------------------------------------------------
Ptc CCH type GI: 109676362      MRDEEAIEGAFQANTKERSSGYLQRKKSFKFTKGKTEMSSRKQNYSPCSHCKRTNHAEKD 1076

Col CCH type                    ------------------------------------------------------------
Ptc CCH type GI: 109676362      CWYKDKPSFRCTFCNNLGHSEKYCRAKKKQSQQHIHQNANVSEKEKEDDSHLFMASQVIS 1136

Col CCH type                    ------------------------------------------------------------
Ptc CCH type GI: 109676362      SHEQNIWLIDSGCTSYMTKHLAIFSSIDKSIQPFKVKLGNGDVVQAKGRGTIAVSTKRGYR 1196

Col CCH type                    ------------------------------------------------------------
Ptc CCH type GI: 109676362      IYNLSAAKVQISIDVHFNENSCWKWDLKEVDRTTTAALEPAVGGTGDQSDIEGTSDTSIL 1256

Col CCH type                    ------------------------------------------------------------
Ptc CCH type GI: 109676362      KVRPLSDVYSRCNPVYAKPTSYTEAARFPAWIDAIKSSIDSIERNGTWKLTELPQNKKEI 1316

Col CCH type                    ------------------------------------------------------------
Ptc CCH type GI: 109676362      GVKWVFKTKFNPLGSIFRHKARLVVKGFAQVAGVDYDDTFAPVARHDTIRLLLALAGQKK 1376

Col CCH type                    ------------------------------------------------------------
Ptc CCH type GI: 109676362      WKVYHLDVKFAPLNGILLEEIYVQQPEGFVVTSHEHKNVYKLHKALYGLKQAPRAWYNRID 1436

Col CCH type                    ------------------------------------------------------------
Ptc CCH type GI: 109676362      TYLIQLGFKRSENEVPLYLRQDQDGLQLVISLYVDDMLVFGSNVKLLASFRREMQDVFEM 1496

Col CCH type                    ------------------------------------------------------------
Ptc CCH type GI: 109676362      SDLGTINYFLGMEIHQUSSGIFLSQRKYAVDILKREFKLESCKEVTTLMAQMEKISKNDGE 1556
```

Figure 8a

```
Col CCH type                        ------------------------------------------------------------
Ptc CCH type GI: 109676362          KLEEPSAYRSLVGSLLYLTATKPDLMFLAGLLSRFMSSPSNFHMGVAKRVLKYIRGTTNL 1616

Col CCH type                        ------------------------------------------------------------
Ptc CCH type GI: 109676362          GILYSKSGGVNLSGYADSDWAGSVDDMKSTFGYVFTIGSGTICWNANKQEVVAQSTAEAE 1676

Col CCH type                        ------------------------------------------------------------
Ptc CCH type GI: 109676362          YIFLAAAANQAIWLNKLLAKNKVHQLSFIVITFAMLLSAVAFESEIRSFLGAGYYRRFV 1736

Col CCH type                        ------------------------------------------------------------
Ptc CCH type GI: 109676362          ENFSRISAPLTKLTQKNVKFQWSEACEKSFLELKERLTTAPVLAVPSGSGGYTVYCDASR 1796

Col CCH type                        ------------------------------------------------------------
Ptc CCH type GI: 109676362          VGLGCVLMQHGKVIAYASRQLKKHEQNYPTHDLEMTAVIFALKIWRHYLYGETCEIFTDH 1856

Col CCH type                        ------------------------------------------------------------
Ptc CCH type GI: 109676362          KSLKYIFQQRDLNLRQRRWMELLKDYDCTIHYHPGKANVVADALSRKSSGSIAHIQEVPR 1916

Col CCH type                        ------------------------------------------------------------
Ptc CCH type GI: 109676362          PLIRELHELVDEGVRFDLSEAGAMIAHFQVKSDLFDKIKAAQKKDDSLLRIRNEVEQGKA 1976

Col CCH type                        ------------------------------------------------------------
Ptc CCH type GI: 109676362          AGFVIGDDDVLRYKDPLCVPDVDDLRRELMVEAHQTVYTVHPGSTKMYKDLKVFDLSEGK 2036

Col CCH type                        -(SEQ ID NO:22)
Ptc CCH type GI: 109676362          G 2037(SEQ ID NO:51)
```

Figure 8b

```
Col TIR-NBS                        ------------------------------------------------------------
Rco nr-triphosphatase gi:255537517 ----------MDLREDSSRFGSVTISTLRNMSSSSSAFFSANQSPFFSPRSPTCQISESTR   51
Ptc TIR-NBS gi:224071947           MLSHYLLCRMDLREDSSRFGLLPVTTSR--ISSSSSAFFSANQSPFFSPRSPTCQVSESTR   59

Col TIR-NBS                        ------------------------------------------------------------
Rco nr-triphosphatase gi:255537517 SDAQCDSIHLSGEHLTSSSGNPLLTSPANVRDAVSDMSRDPVAEIGTDFQKLDRIFSSTG  111
Ptc TIR-NBS gi:224071947           SDAQYDSTHLSGDPLSSSSGIPEPQSLANTRDALADMTRDPVSGIANDFQKFNRISSSTG  119

Col TIR-NBS                        -----------------------------------------------------IGLHGCK    7
Rco nr-triphosphatase gi:255537517 ISNSSPYSYNNLHDIGYSGFREKQRKHERSQVTLYTPVSISLPSYRLRSCDVFIGLHGRK  171
Ptc TIR-NBS gi:224071947           ISSSTLCYTNYARDRGYSGFREKPRKHGRSHGMSYTPVSVS--SCKLRSCDVFIGLHGRK  177
                                                                                        ***** *

Col TIR-NBS                        PSLLRFANWLRAELEVQGMSCFVSDRARFRNSRKEGTIERAMDVSSFGVVTLTEKSFRNP   67
Rco nr-triphosphatase gi:255537517 PSLLRFANWIRAELEVQGISCFISDRARCRNSRKEGLVERAMDVSSFGIVILTKKSFRNP  231
Ptc TIR-NBS gi:224071947           PSLMRFANWLRAELEVQGMSCFVSDRARCRNSRKNGIVDRAMDVSSFGIVILTKKSFRNP  237
                                   ***:*****:******** .***:****** **.:.::*********:*:** ******

Col TIR-NBS                        YTIEELRFFSSKKNLVPIYFDLRPGDCLVRDIVEKRGDLWEKHGGELWVFYGGLEKEWKE  127
Rco nr-triphosphatase gi:255537517 YTIEELRFFTSKKMLVPLFFDLSPDDCLVRDIVENRGELWEKHGGELWLLYGGLENEWKE  291
Ptc TIR-NBS gi:224071947           YAIEELQYFESKKNLVPVFFDLSPDDCLVRDIIEKRGELWEKHGGELWHLYGGLENEWKE  297
                                   *:****::* ***:***::***.**:*******:*:*************::****:****

Col TIR-NBS                        AVSGLFRVDEWKLEAQDGNWRDCILRVVTILAMKLGRRSVVERLTKWKEKVDKEEFPFPR  187
Rco nr-triphosphatase gi:255537517 AVNSLSRVDEWKLEAQEGNWRDCILRAVTLLAMRLGRRSVVERMTKWKEKVDKDEFPFPR  351
Ptc TIR-NBS gi:224071947           AVNGISRVDEWKLEAQEGNWRDCILRAVTLLALRLGRRSVVERLTKWREVVEKEEFPFPR  357
                                   **..: *********:*********.**:**::*********:***:: *::*******

Col TIR-NBS                        NENFIGRKKELSELEFILFGDISGESERDYFELKARSRRRNLTIGWSKSTSVEEPRREQ   247
Rco nr-triphosphatase gi:255537517 NENFIGRKKELSELEFILFGDVSGDSERDYFELKTKPRRKNLTIGWSKSSSMEEKRRDWK  411
Ptc TIR-NBS gi:224071947           NENFVGRKKELSELEFTLFGDVSGNSERDYFELKARPRRKNLTVGWNKNSSVEEKRREQQ  417
                                   ****:*********** ****:**:*********::.:*::***:**.*:.:** **:

Col TIR-NBS                        REDGSRKGKEPVVWKESEKEIEMQSTER-----QHYQRPRGGR-NSQRKRSAKVVYGKGIAC  303
Rco nr-triphosphatase gi:255537517 WENRAKEGKEPVVWKESEKEIEMQSGDFSQRQHLVKPKSSGRYGKRKRSTKIVYGKGVAC  471
Ptc TIR-NBS gi:224071947           GDNSSEEGKEPVVWKESEREIEMQSGDFSQRQHLVKPKSSGRYGKRKRSTKILYGKGIAC  477
                                     :: :.*********::******        **  :.: .  :****:*:: *:****

Col TIR-NBS                        VTGESGLGKTELLLEFAYKYEQRYKMVLWIGGESRYIRQNYLNLWSFLEVDVGVENCTDK  363
Rco nr-triphosphatase gi:255537517 VSGESGIGKTELLLEFAYRYEQRYKMVLWIGGESRYIRHNYLNLWSFLEVDVGVQNCPGK  531
Ptc TIR-NBS gi:224071947           VSGESGIGKTELLLEFAYRYEQRYKMVLWIGGESRYIRQNYLNLRSFLQVDIGVENYSGK  537
                                   *:****:***********::*****************::**** ***:**:**:*  *

Col TIR-NBS                        SRMKSFEEQEEAAISRVRKELMRNIPFLVVIDNLESEKDWWDRKLVMDLLPRFGGETHIL  423
Rco nr-triphosphatase gi:255537517 SRIRNFEEQEEEAISRVRKELMRNIPFLVVIDNLESEKDWWDHKLVMDLLPRFGGETHII  591
Ptc TIR-NBS gi:224071947           SRIRSFEEQEEEAISKVRKELLRNIPFLVVIDNLESEKDWWDHKIVMDLLPRFGGETHII  597
                                   **::.****** ***:*****:************************************:

Col TIR-NBS                        IATRLPRVMNLEPLKLSYLSGVEAMSLMQGSGKDYPIAEIDALRVIEEKVGRLTLGLAIV  483
Rco nr-triphosphatase gi:255537517 ISTRLPRVMNLEPLKLSYLSGVEATCIMQGSGKDYSIAEIEALRVIEEKLGRLTLGLAIV  651
Ptc TIR-NBS gi:224071947           ISTRLPRVMNLEPLKLSYLSAVEAMCLMQGSDKDYSIAEIDALRVIEEKVGRLTLGLAIV  657
                                   *:******************.*** .:****.***.****:*******:**********

Col TIR-NBS                        GAILSELPINPSRLLDTINRMPLRDFSWSGKEAYSLRKNSFLLQLFEVCFSIFDHAEGPR  543
Rco nr-triphosphatase gi:255537517 GAILSELPINPSRLLDTINRMPLREISWSGREANSLTKNSFLLQLFEVCFSIFDHADGPR  711
Ptc TIR-NBS gi:224071947           GAILSELPINPSRLLDTINRMPLREMSWSGREAHSMRKNTFLLQLFEVCFSIFDHADGPR  717
                                   ***********************::.****:** *: **.**************.****

Col TIR-NBS                        SLATRMVQVSGWFAPAAIPVSLLAMAAHKIPEKHKRTRFWRELLPSLTCGLSSSSYSKRSE  603
Rco nr-triphosphatase gi:255537517 SLATRMVQASGWFAPAAIPVSLLALAANKIPQKHRGTQLWRELLRSLSCGLSSSYTKRSE  771
Ptc TIR-NBS gi:224071947           SLATRMVQASAWFAPAAIPVSLLALAAKKIPEKHKGTHLWRKLLSSLSCGLSSSYTKRSE  777
                                   ********.*.*************:**:***:**: *::**:** **:****** ****

Col TIR-NBS                        TEASSMLLRFNIARSSTPKQGYVHFNELIKVYSRKRGVAGVAHAMVQAVVSRGSILDHSEH  663
Rco nr-triphosphatase gi:255537517 AEASSMLLRFNIARSSTKQGYVHVNELVKIYMRKRGTAIVAQAMVQAVISRGGISHHSEH  831
Ptc TIR-NBS gi:224071947           AEASSMLLRFNIARSSTKQGYVHVNELIKLYAPKRGVTGVAQAMVHAVISRGGVSHHSEH  837
                                   :*******:********:*****.***::* .***.: **:***:**:***..*:****

Col TIR-NBS                        MWAACFLLFGFGNDPTAVELKVSDLLYLVKEVVPLAIRTFITFSRCSAALELLRLCTNA  723
Rco nr-triphosphatase gi:255537517 IWAALFLLFGFSNDPKAVELKVSELLYLVREMVPLAIRTFISFSRCNAALELLRLCTNA  891
Ptc TIR-NBS gi:224071947           IWAACFLLFAFGTDPKAVELKVSELLYLVKQVVLPLAIRTFITFSRCSAALELLRLCTNA  897
                                   :*** ****.*. ** *******:*****::. *:********:*****************

Col TIR-NBS                        LEAADQAFVTPVEKWLDKSLCWRPIQTNAQLNPYLWQELALSRATVLETRAKLMLRGGQF  783
Rco nr-triphosphatase gi:255537517 LEAADQAFVTPVEKWLDKSLCWRPIQTNAQLNPYLWQELALSRATVLETRAKLMLRGGQF  951
Ptc TIR-NBS gi:224071947           LEAADQAFVTPVEKWLDKSLCWRPIQTNAQLNPYLWQELALSRATVLETRAKLMLRGGQF  957
                                   ************************************************************

Col TIR-NBS                        DIGD----------------------------------------   787(SEQ ID NO:24)
Rco nr-triphosphatase gi:255537517 DIGDDLIRKVIFIRTSICGDDHPETVSARETLSKLTRLLANVQIYTSP  999(SEQ ID NO:52)
Ptc TIR-NBS gi:224071947           DIGDDLIRKAIFIRTSICGDDHPDTVSARETLSKLTRLHANVQIQNSS 1005(SEQ ID NO:53)
                                   ****
```

Figure 9

```
Col RGA2                      KVDMAGELFGGAPLSATLQVLFDRLASREVVDFIRGKKL-EVLVKKLKPVLLSVKAVLDD  59
Rco RGA2 GI: 255568719        ---MAGALIGGSFLSAFLQVLFDRMASREVLDPFKGQKLNDALLNKLKTTMISVNAVLDD  57
Col RGA1                      ---MADAIVN-VFLEKLLSTLAE--EGRYVTEFR-------DQFEKLQTELQLLQCFLKD  47
Rco RGA2 GI: 255561034        ---MVDAVVT-VFLERLLNTLVE--EGRVVNEFR-------DRFENLQKELELMQSVLKD  47
                                 *.. :.   **..*   :.   .* *.  :*         .:*  .::..*:.*

Col RGA2                      AEDKQITNQNVKEWLSELKDGVYDAEDLLDEIAYEALKRRLETTTS-------------- 105
Rco RGA2 GI: 255568719        AEEEQITKPAVKEWLDELKDAAYEADDLLDEIAYECLRSEVEATSQTDVDQVRNFFSNFS 117
Col RGA1                      ADRLFRKNHTIRKILADLRELIYEAEDILADCQLQSRDENQFSQSWLACFSPPK------ 101
Rco RGA2 GI: 255561034        ADKRKRKDGTLHTIMGNLPELIYEAEDILADCQLQSPEDDRLSNGWLTCIHPPN------ 101
                              *:  : .. :: : ::*::  *:*:*:*    :.       .   :

Col RGA2                      -------AKGILESKLEETLERLELLVDQTERLG----LKECRGGETLSQRLPPTSVVDE 154
Rco RGA2 GI: 255568719        PFKKVKEVKLEEVSKLEETLERLELLVKQKEALG----LREG-IEERHSHKIPTTSLVDE 172
Col RGA1                      -----LHFKYQSGKRLKEITEKITSIKQNISSFLGGPLLFQPEVISAQDQMPRWSSQVYD 156
Rco RGA2 GI: 255561034        -----LHFQYKTGKRLREINEKITKIKQDISYLDLSNSNQMGRRDAHNDQMSRWSSPVYD 156
                                     . .:*.**  *:: .:. .:.     .:            :*   *  :

Col RGA2                      SC-VYGRVDEKEAIMKLLHPENPT-QNQIDVIPIVGMGGVGKTTLAQLIYNDNRLEEWFD 212
Rco RGA2 GI: 255568719        SVGIYGRDFDKKAIVKQLFEAN---GNDLSVIPIVGMGGVGKTTLAQYVYNEPRVQESFD 229
Col RGA1                      HTQVVGLESDTQKMKDWIFDAVHEGAQEILAIGVVGMGGLGKTTIAQKVFNERDIEHHFD 216
Rco RGA2 GI: 255561034        HTQVVGLEGDTQKIKNWLFEADDG----ILAIGVVGMGGLGKTTIAQKVFNDREIDDHFE 212
                               :  *   ..:: ..*  ..        :.* :*****:****:**  ::*:   ::  *:

Col RGA2                      LKAWVCVSDEFDAFRVTKTILQQIASDWDDRLDLNQLQVKLQEKLLGKRFLFVLDDVWND 272
Rco RGA2 GI: 255568719        LKAWVCVSAVFDVFRVTKDILEDVTRKKCDITTLNLLQLELKEKLKGKRFLLVLDDVWDD 289
Col RGA1                      RRMWVSVSQTFTEEQIMRSMLRNLG-DASVGDDRNELLKKINQYLLGKRFLIVMDDVWSE 275
Rco RGA2 GI: 255561034        RRMWISVSQTLDEVQIMRSMLRNLG-DASIGDNQGELLKKINQYLLGKRFLIVMDDVWGL 271
                                *:.**    :   ::  ::.::     .    * ::: * ***:*:*:****.

Col RGA2                      KYIEWKQLTSPFSAGAKDSKIVVTTRSDNVANIMR-TVPAYQLFILSDSD-CCLLFAKHA 330
Rco RGA2 GI: 255568719        NYANWDVLRKPLKSGALGSKIIVTTRHETVASIMGNVLHHHHLTELSDHD-CWLLFSKHA 348
Col RGA1                      DVLWWQRICEGLPKGN-GSCIIITTRIEKVARKMGVKEARIHRPKFLNKDYSWLLFRKIA 334
Rco RGA2 GI: 255561034        DVNWWRRIYEGLPKGN-GSSIIITTRIEEVAPKMGVTEVRIHRPKFLSKDDSWLLFRKIA 330
                               .  : .:   . *: *   * *::**** : **  *     .: * *::   * ***.

Col RGA2                      FVN-TSPSEQPDLKLIGEAIVKRCKGLPLAVKAVGGFLRWKL-DVDEWR----------- 377
Rco RGA2 GI: 255568719        FGE-GNSAAHPELAILGQEIVRKCRGLPLAAKALGGVLRSKR-DTKEWERIFKSLLWELS 406
Col RGA1                      FAASGGGECTSTDLEDVGKEIVEKCKGLPLAIKAVGGMMLCKAPYYREWR---------- 383
Rco RGA2 GI: 255561034        FAATGGECRHPELENVGTEIVQKCKGLPLAIKAIGGLLLYKS-HYHEWR----------- 378
                              *    .  .  . :*  :* :: *:*:*****: **:**  :.**    *   **

Col RGA2                      ------------------------------------------------------NMNME 382
Rco RGA2 GI: 255568719        NDEILPALRLSYHYLPPHLKRCFAYCAVFPKDYNFSKEELILLWRAEGFIVQPKGSREKE 466
Col RGA1                      ------------------------------------------------------------
Rco RGA2 GI: 255561034        ------------------------------------------------------------

Col RGA2                      EQRYEYIKDLESRSFFQKLSGDESCFVMHDLISDLAKSVSGEFFCRLEGGDGGSCV1TKK 442
Rco RGA2 GI: 255568719        DVGAEYFEDLVSRSFFQKSHLYKSAFVMHDLINDLAKYVSGEFCFQWENGD--SCEVAKR 524
Col RGA1                      ----------------------------------------RIADHFRDELEEND------ 397
Rco RGA2 GI: 255561034        ----------------------------------------QIAGNFRDELAEND------ 392
                                                                      ::..*    . .*

Col RGA2                      TRHLSNIQEPYDVRKKFETLCEAKGLRTFLTLNLKSSFLSSSFVTNRLMDDLIVKSSRLR 502
Rco RGA2 GI: 255568719        TRHLSYLRTNHDTSVKFESIYRAKHLR---TLRVKWSWWT-----DRKVKYDLLPSLRRLR 635
Col RGA1                      -------------------NSVMASLQLS-------------------YDELPSYLKSC 418
Rco RGA2 GI: 255561034        -------------------DSVMASLQLS-------------------YDELPPYLKSC 413
                                                  :::  *                    *

Col RGA2                      VLSLTDYMNINIREIQEGIGNLKHLRYLDLSNTLIQRLPNRVCTLYNLQTILKLFGCGKLV 562
Rco RGA2 GI: 255568719        VLSLFQCDDDVVL--LPNTIGNLKHLRYLDLSGTSIKRLPDSINSLYNLETLLMYGCQDLI 635
Col RGA1                      LLSFSLYPEDCV------ITKEQLVHWWIGEGFAPQRSSRSSTDAGEDCFSGLTNRCLLE 472
Rco RGA2 GI: 255561034        FLSFSLYPEDCV------IKKEQLVHWWIGEGFVPLRIGRSSTEAGEGCFSGLTNRCLVE 467
                              .**:    :   :            *  : :::   .. *      :   :        :

Col RGA2                      ELPKDMGRLINMHHLDIRDTGLNWMPSGIGKLKDLKVLTNFFVGKHHGSSIGELGKLKHL 622
Rco RGA2 GI: 255568719        KLPITMSSLISLCHLDIRETKLQEMPLKMSKLTKLEMLTDFVLGKESGSSIKELGELQNL 695
Col RGA1                      VVDKTYNGTICTCKMHDMVRDLVLKIAKDDAFYNATGTNYRHLGVDNSMDKNQLIANQKL 532
Rco RGA2 GI: 255561034        VVDKTYNGTIATCKIHDMVRDLVIKMAGDDAFFKLNGIGCPHLAICSNMDQKRLTANQKL 527
                                :      .  . *    ::.       *          . ..      :*   :  ::*

Col RGA2                      QGSVAIWNLQNVVCAKDAMDANLKDKVNLKELRLIWSKDADVDDDSERDREVLEQLEPHT 682
Rco RGA2 GI: 255568719        RGSLCIWNLQNVADAQDAMAANLNKNKKHLRMLDLRWDGET---DDSLHERAIVEQLQPHM 752
Col RGA1                      RGLVSTTKTCEVNKIESGYAKRFSECKYLRVLDVS---------KSIFELPLSSLLYRVG 583
Rco RGA2 GI: 255561034        RALLSTTKTGEVNRIVSSIANKFSECKYLRVLDLC---------KSIFEVPLTNLLYQIG 578
                              :. :.   :  *:     ..: ..:   .:    *:     *         .   *   *

Col RGA2                      DLQHLDIMFYRGTRFPEWIGHSSFSKVVSMELIDCKSCELLPPLRQLSSLKSLSISGCVK 742
Rco RGA2 GI: 255568719        NVESLCIVGYGGTRFPDWIANPTFSHMVTLELSRGVSLPLPLPGQLVSLKSLYIIALDS 812
Col RGA1                      TLQHLTYLGLSNT-HPLVELPDSLENLTNLQILDVSYCQNLK------FLPQYLIKFKK 635
Rco RGA2 GI: 255561034        DLQHLTYLSLSNT-HPLIELPPSLEKLKNLQILDMSYCQNLK------MLPPYLITFKK 630
                              :: *     :.*   ::.::  :::  ..: .*.*    *.   *  :

Col RGA2                      IVRLGDEFYGSGDALSNPFGCLEVLKFEDMSEWEEWTCLKEE----AFSNLRELVIRDCP 798
Rco RGA2 GI: 255568719        IVSVGLEFYGSCTHPKKPFGSLEILHFERMPQWREWICHVDEGENGAFPLLQQLYINECP 872
Col RGA1                      LKVLDVSFCGSLENLPKGLG------------------------------RLSNLE 661
Rco RGA2 GI: 255561034        LRVLDVSHCGSLEYLPKGLG------------------------------RLSNLE 656
                                :.. ..  **           : :*                         : :
```

Figure 10a

```
Col RGA2                      KLSKSLPKYLPCLKKLKIRRCGKLEGILPEAPSIEEVQLEGCDALQMEALPSGLRELQID  858
Rco RGA2 GI: 255568719        NLIQTLPGNLPSLTTIKIVGCPQLAASFPSAPAIQKLKLK-DDHRNVLLQNFDFSSLKVV  931
Col RGA1                      VLLGFRPARS--NNGCRIGELRNLTRLRTLGLHLTHADEVEDSEFNAMMNLQDLEKLSIS  719
Rco RGA2 GI: 255561034        VLMGFRPSRLGQLGGCRIAELRNLTRLRTLSLHLTQGDEIEDNEVNALVNLQELEHLTIS  716
                                *     *            :*       :*   . .:. .   .:         * :
Col RGA2                      GLRINAS----------ILKQMLQP--CTILEQLQISKCNRLRSLPEGSNLPMR-LKKLR  905
Rco RGA2 GI: 255568719        KFHSVDP----------LLQGMEKIGVLFISEEIEVGNCDSLKCFPLELFPELYSLEIYR  981
Col RGA1                      FFDSHGSASDLTSKIDKLCP----------------------------------------  739
Rco RGA2 GI: 255561034        CFDSQG--NDLIGKLDRLYP----------------------------------------  734
                                :                     :
Col RGA2                      IEESNVLNDSKILMY--TSLESLKIRNSRWNGVESFPLG--SFPLLNRLDITGCEELKWI  961
Rco RGA2 GI: 255568719        CQNLECISEAEVTSKGLNVLESIKIR--ECPKLISFPKGGLNAPNLTSLHLCDCSNLKSL  1039
Col RGA1                      ------------------------------------------------------------
Rco RGA2 GI: 255561034        ------------------------------------------------------------

Col RGA2                      IGASEGEDAPLSCRLNSLEIYNCPNFVCFEKLEGFCAPNLTSLELVGCSNLKALPEQMHS  1021
Rco RGA2 GI: 255568719        P----ECMHSLLPS-LYALAINNCPKLESFP--EGGLPPKLYSLVIESCDKLVTGRMKWNL  1093
Col RGA1                      ----------------------------------------PQQLHELSVMFYPGKISPLWLNPL  763
Rco RGA2 GI: 255561034        ----------------------------------------PPEIYELSLAFYPGKMSPVWLNPI  758
                                                                           . ::  .*  :          :
Col RGA2                      LFPSLEELWISFCPKIEGFPKEG-LPSTLKALFIQ-------------------------G  1056
Rco RGA2 GI: 255568719        QTISLKYFSISKNEDVESFPEKMLLPSTLTCLQISNFQNLKSLDYDGIQHLTSLTELTIS  1153
Col RGA1                      ALPMLKYLSISSGN----------------------------------------------  777
Rco RGA2 GI: 255561034        SLPMLRYLSISSGN----------------------------------------------  772
                                * . : **
Col RGA2                      GCKKLIKG-----MMRRDRDTEWGLQSLPSLEE----FIISGGGEEIEGIESFP---DEHL  1105
Rco RGA2 GI: 255568719        NCPKLQSVTEQELPLTVTYLDIWDLQNLKSLDFRGLCYLTSLKELEIWNCPNLQSMPEDG  1213
Col RGA1                      --------------LAKMHQNFWGG---------------------------DNN  791
Rco RGA2 GI: 255561034        --------------LAQMHQSFWG----------------------------EDN  785
                                               : *.              :  *.   ** * ::* : :
Col RGA2                      LPSSLTSLSISYFPNLKSLESKGFQHLTSLRQLGIYFCPRLQSIPEKRVISSLSYLEIAK  1165
Rco RGA2 GI: 255568719        LPSSLVCLTISNLQNLQSLNFKGLQDLTFLIELDILDCPKLESIPEEGLPTSLSSLIIYN  1273
Col RGA1                      IVWKVEGLMLESLSDLELQWPKLQQLMQILRVVNVSWCPELVSFPIEDVG----------  841
Rco RGA2 GI: 255561034        SVWKIEALLLESLSELGMDWSMIQNVMFSLRIVNSSWCPDLSAFPIEEIG----------  835
                                .: *  :: *    : :   *  :   .    *  *.   ** * ::* : :
Col RGA2                      CPKLRENREKEKGKHWPNISHIYPVINFDGFDPVII  1200 (SEQ ID NO:28)
Rco RGA2 GI: 255568719        CPSLKQRCKQEKGEDWPKISHRHIEIDGDTMNKC  1308 (SEQ ID NO:54)
Col RGA1                      ---------FRGGVWIKEQIRN-------------  854 (SEQ ID NO:26)
Rco RGA2 GI: 255561034        ---------FRGGVWTKEEQRN-------------  848 (SEQ ID NO:55)
                                       :*  *  :  .
```

NUCLEIC ACID MOLECULES ENCODING ENZYMES THAT CONFER DISEASE RESISTANCE IN JUTE

RELATED APPLICATIONS

This application is a National Stage application of PCT/US12/041467 filed Jun. 8, 2012, which claims the benefit of priority to U.S. Provisional Patent Application Ser. No. 61/500,407, filed Jun. 23, 2011.

FIELD OF THE INVENTION

One aspect of the invention relates to polynucleotides that encode polypeptides that confer disease resistance in jute. The invention further relates to vectors and bacteria containing such a nucleic acid molecule, as well as plant cells and plants transformed with at least one of the nucleic acid molecules.

BACKGROUND OF THE INVENTION

Unlike humans, plants do not have an immune system, but at different stages of evolution they have developed a wide array of defense mechanisms in order to withstand pathogenic challenges. A well-characterized mechanism of plant defense is mediated by interaction between a plant's disease-resistance proteins, encoded by disease-resistance (R) genes, and the corresponding avirulence (Avr) genes expressed by the pathogen. (Bent, A F and Mackey, D, 2007, Elicitors, Evectors, and R-genes: the new paradigm and a lifetime supply of questions, *Annu Rev Phytopathol,* 45:399-436.). This interaction leads to activation of the plant's response, which in turn results in increased resistance to disease. The putative ligand-receptor complex initiates a series of signal transduction cascades contributing to disease resistance. (Baker, B et al., 1997, Signaling in plant-microbe interactions, *Science,* 273:726-733). Some cellular events that characterize resistance include oxidative burst, induction of defense gene expression, and rapid cell death at the site of infection. (Dhalowal, H S and Uchimiya, H, 1999, Genetic engineering for disease and pest resistance in plants, *Plant Biotechnol,* 16:255-261).

There are various types of disease-resistance genes. During different evolutionary events, plants have gained and omitted different disease-resistance genes. Therefore, a plant that displays resistance against a certain pathogen may have the gene(s) necessary for resistance against that pathogen. Consequently, identification of disease-resistant genes is a promising field of plant molecular biotechnology.

Disease resistance (R) genes, which interact with the Avr genes of different pathogens, have been isolated from numerous plant species. These genes confer resistance to a wide range of plant pathogens, including bacteria, fungi, oomycetes, viruses, and nematodes. (Baker et al., 1997; Bent, 1996; Hammond-Kosack, K E and Jones, J D G, 1997, Plant disease resistance genes, *Annual Review of Plant Physiology and Plant Molecular Biology,* 48:573-605; Ellis, C N et al., 1988, Topical Tretinoin for Photoaged Skin-Reply, *JAMA,* 259(22):3274-78). Although the products of avirulence genes typically have little homology with each other, the reported R genes have conserved functional domains, such as the protein kinase (PK) domain, Leucine-rich regions (LRR), and nucleotide-binding sites (NBS). (Bent, 1996; Ellis et al., 1988).

Based on the structure of R gene products, the R genes can be classified into four main classes: Nucleotide-Binding Site-Leucine-Rich Repeat (NBS-LRR); Leucine-Rich Repeat-Trans-Membrane domain-Protein Kinase (LRR-TM-PK); Leucine-Rich Repeat-Trans-Membrane domain (LRR-TM); and Protein Kinase (PK). (Bent, 1996; Ellis et al., 1988; Hammond-Kosack and Jones, 1997). The largest number of characterized R proteins is of the NBS-LRR type. These NBS-LRR proteins can be further subdivided into two sub-families based on the presence or absence of a region homologous to the toll and interleukin-1 receptor (TIR) domain at their N-terminus. (Baker et al., 1997; Parker, M F et al., 1997, Molecular characterization of adenocarcinoma of the cervix, *Gynecol Oncol.,* 64(2):242-51). The two sub-families are designated TIR and non-TIR, respectively. Most members of the non-TIR subfamily encode a putative coiled-coil (CC) domain at their N-terminus. (Pan, P et al., 2000, Determination of the in situ bactericidal activity of an essential oil mouth rinse using a vital stain method, *J Clin Periodontol.,* 27:256-261). TIR and non-TIR NBS-LRR R genes can be distinguished by amino acid motifs found within the NBS domain itself. (Meyers, B C et al., 2003, Genome-wide analysis of NBS-LRR-encoding genes in *Arabidopsis, Plant Cell,* 15:809-834; Pan et al., 2000). They also differ at the functional level, based on their apparent involvement in different signal transduction pathways. (Aarts, N et al., 1998, Different requirements for EDS1 and NDR1 by disease resistance genes define at least two R gene-mediated signaling pathways in *Arabidopsis, Proc. Natl. Acad. Sci. USA,* 95:10306-10311).

NBS sequences are abundant in plant genomes. (Meyers et al., 1999). In fact, the *Arabidopsis* genome contains 150 NBS-encoding genes, including 85 TIR NBS-LRR genes, 43 non-TIR NBS-LRR genes, and numerous truncated TIR or CC-NBS genes that lack an LRR domain (The *Arabidopsis* Genome Initiative, 2000). No precise functions have yet been established for each of these resistance gene analogs (RGAs). (Kanazin, V. et al., 1996, Resistance gene analogs are conserved and clustered in soybean, *PNAS, USA,* 93(21): 11746-11750; Leister, D et al., 1996, PCR based approach for isolating pathogen resistance genes from potato with potential for wide application in plants, *Nature Genetics,* 14(4):421-429; Yu, Y G et al., 1996, Isolation of a super family of candidate disease-resistance genes in soybean based on a conserved nucleotide-binding site, *PNAS, USA* 93(21):11751-11756). Thus, RGAs are valuable as potential sources of active R genes.

SUMMARY OF THE INVENTION

Among other things, the present invention provides nucleic acid molecules encoding enzymes from jute which are involved in the plant's disease-resistance pathways, and from which genetically-modified plants may be produced with enhanced disease-resistance against various pathogens.

One aspect of the invention is an isolated nucleic acid molecule having at least 90% sequence identity to a nucleic acid sequence selected from the group consisting of: SEQ ID NO: 1, 3, 5, 7, 9, 11, 13, 15, 17, 19, 21, 23, 25, and 27.

In one embodiment, the nucleic acid sequence is selected from the group consisting of: SEQ ID NO: 1, 3, and 5.

In one embodiment, the nucleic acid sequence is selected from the group consisting of SEQ ID NO: 7.

In one embodiment, the nucleic acid sequence is selected from the group consisting of: SEQ ID NO: 9, 11, and 13.

In one embodiment, the nucleic acid sequence is selected from the group consisting of SEQ ID NO: 15.

In one embodiment, the nucleic acid sequence is selected from the group consisting of: SEQ ID NO: 17 and 19.

In one embodiment, the nucleic acid sequence is selected from the group consisting of: SEQ ID NO: 25 and 27.

In one embodiment, the nucleic acid sequence is selected from the group consisting of SEQ ID NO: 23.

One aspect of the invention is an isolated polypeptide molecule having at least 90% sequence identity to an amino acid sequence selected from the group consisting of SEQ ID NO: 2, 4, 6, 8, 10, 12, 14, 16, 18, 20, 22, 24, 26, and 28.

Another aspect of the present invention relates to a pair of primers (forward and reverse) useful for the amplification of cDNA selected from the group consisting of SEQ ID NO 29 and SEQ ID NO 30; SEQ ID NO 31 and SEQ ID NO 32; SEQ ID NO 33 and SEQ ID NO 34; SEQ ID NO 35 and SEQ ID NO 36; and SEQ ID NO 37 and SEQ ID NO 38.

In certain embodiments, the present invention relates to any one of the aforementioned isolated polynucleotide molecules or isolated polypeptide molecules, wherein said molecule has at least 91%, 92%, 93%, 94%, 95%, 96%, 97%, 98%, 99%, or 100% sequence identity to any one of the sequences identified by a SEQ ID NO.

One aspect of the invention is an expression vector comprising an nucleic acid molecule of the present invention.

One aspect of the invention is an isolated antibody or antigen binding fragment thereof that specifically binds to a polypeptide molecule of the present invention.

One aspect of the invention is a plane or plant cell transfected by a vector of the present invention.

One aspect of the invention is a material derived from a transgenic plant of the present invention.

One aspect of the invention is a seed from a plant transfected by a vector of the present invention.

One aspect of the invention is a method for making a transgenic plant, comprising the steps of transfecting at least one plant cell with a vector of the present invention, and growing said at least one plant cell into a plant.

One aspect of the invention is a method of improving growth, fiber yield, fiber strength, disease resistance, or water utilization in a jute plant, comprising incorporating in to a jute plant a non-native nucleic acid sequence of the present invention.

BRIEF DESCRIPTION OF THE DRAWINGS

FIGS. 1a and 1b: Protein sequence alignment of *Corchorus olitorius* Toll and Interleukin-1 Receptor domain at their N-terminus Nucleotide-Binding Site-Leucine-Rich Repeat (ColTIR-NBS-LRR)1 and ColTIR-NBS-LRR2 with plant TIR-NBS-LRR protein sequences.

FIGS. 2a and 2b: Protein sequence alignment of ColTIR-NBS-LRR3 with plant TIR-NBS-LRR and other resistance-like protein sequences. FIG. 2 discloses SEQ ID NOS 6 and 41-42, respectively, in order of appearance.

FIG. 3: Protein sequence alignment of ColNBS-LRR with a plant NBS-LRR protein sequence. FIG. 3 discloses SEQ ID NOS 8 and 43, respectively, in order of appearance.

FIGS. 4a and 4b: Protein sequence alignment of ColCC-NBS-LRR1 with plant CC-NBS-LRR protein sequences. FIG. 4 discloses SEQ ID NOS 10 and 44, respectively, in order of appearance.

FIGS. 5a and 5b: Protein sequence alignment of ColCC-NBS-LRR2 and ColCC-NBS-LRR3 with plant CC-NBS-LRR protein sequences. FIG. 5 discloses SEQ ID NOS 14, 45-46, and 12, respectively, in order of appearance.

FIG. 6: Protein sequence alignment of ColNBS resistance protein with plant NBS resistance protein sequences. FIG. 6 discloses SEQ ID NOS 16 and 47, respectively, in order of appearance.

FIGS. 7a and 7b: Protein sequence alignment of Col-LRR1 and ColLRR-TM-PK protein with plant Leucine-Rich Repeat containing protein sequences. FIG. 7 discloses SEQ ID NOS 20 and 48-50, respectively, in order of appearance.

FIGS. 8a and 8b: Protein sequence alignment of ColCCH type with plant CCH type protein sequences. FIG. 8 discloses SEQ ID NOS 22 and 51, respectively, in order of appearance.

FIG. 9: Protein sequence alignment of ColTIR-NBS resistance protein with plant TIR-NBS resistance proteins sequences. FIG. 9 discloses SEQ ID NOS 24 and 52-53, respectively, in order of appearance.

FIGS. 10a and 10b: Protein sequence alignment of Col-RGA1 and ColRGA2 with plant RGA protein sequences. FIG. 10 discloses SEQ ID NOS 28, 54, 26, and 55, respectively, in order of appearance.

DETAILED DESCRIPTION OF THE INVENTION

Identification of the NBS-LRR Genes

Figure 11:
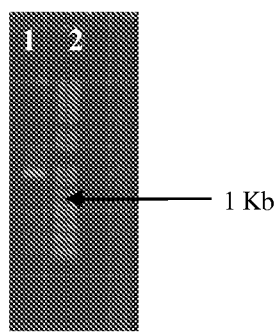
FIG. 11: DNA gel of TIR-NBS-LRR resistance protein.

The identification the NBS encoding genes in *Corchorus olitorius* was done using BLAST (Altschul, S F et al., 1990, Basic local alignment search tool. *J Mol Biol*, 215:403-410) with the in-house NBS disease resistance gene database with a high stringency e-value cutoff of 1e-25. Gene prediction was done with Augustus, and further validation of the sequences was completed using the InterProScan domain prediction program. Selection of the models was based on completeness and homology to a select set of NBS-encoding genes of other plants.

Classification of the Identified Genes

The identified genes were then classified based on their N-terminal regions (Ming et al., 2008). The TIR domain was detected by Pfam HMM searches using a model for TIR (PF01582). (Finn, R D et al., 2008, The Pfam protein families database, *Nucleic Acids Res,* 36:281-288) The Coiled Coil (CC) domains were identified by the COILS program using a threshold of 0.9. (Lupas, A et al., 1991, Predicting coiled coils from protein sequences, *Science,* 252:1162-1164). For the identification of the LRR motifs, Pfam HMM searches using models for LRR-I (PF00560), LRR_2 (PF07723) and LRR_3 (PF07725) were used. (Finn et al., 2008). Conserved motifs within the domains were identified using Multiple Expectation Maximization for Motif Elicitation. (Bailey, T L and Elkan, C, 1995, The value of prior knowledge in discovering motifs with MEME, *Proc. Int. Conf. Intell. Syst. Mol. Biol.,* 3:2119).

Mapping with c-DNA Data:

The c-DNA sequencing of the *C. olitorius* genome was done by the 454 pyrosequencing platform and the identified NBS sequences were mapped to o-DNA sequences using GMAP. (Wu, T D and Watanabe, C K, 2005, GMAP: a genomic mapping and alignment program for mRNA and EST sequences, *Bioinformatics,* 2:1859-1875). The criteria fixed for mapping with an EST was greater than 95% sequence identity. Only the best alignment score were considered for ESTs that can be mapped to multiple locations in the genome.

Figure 1A:
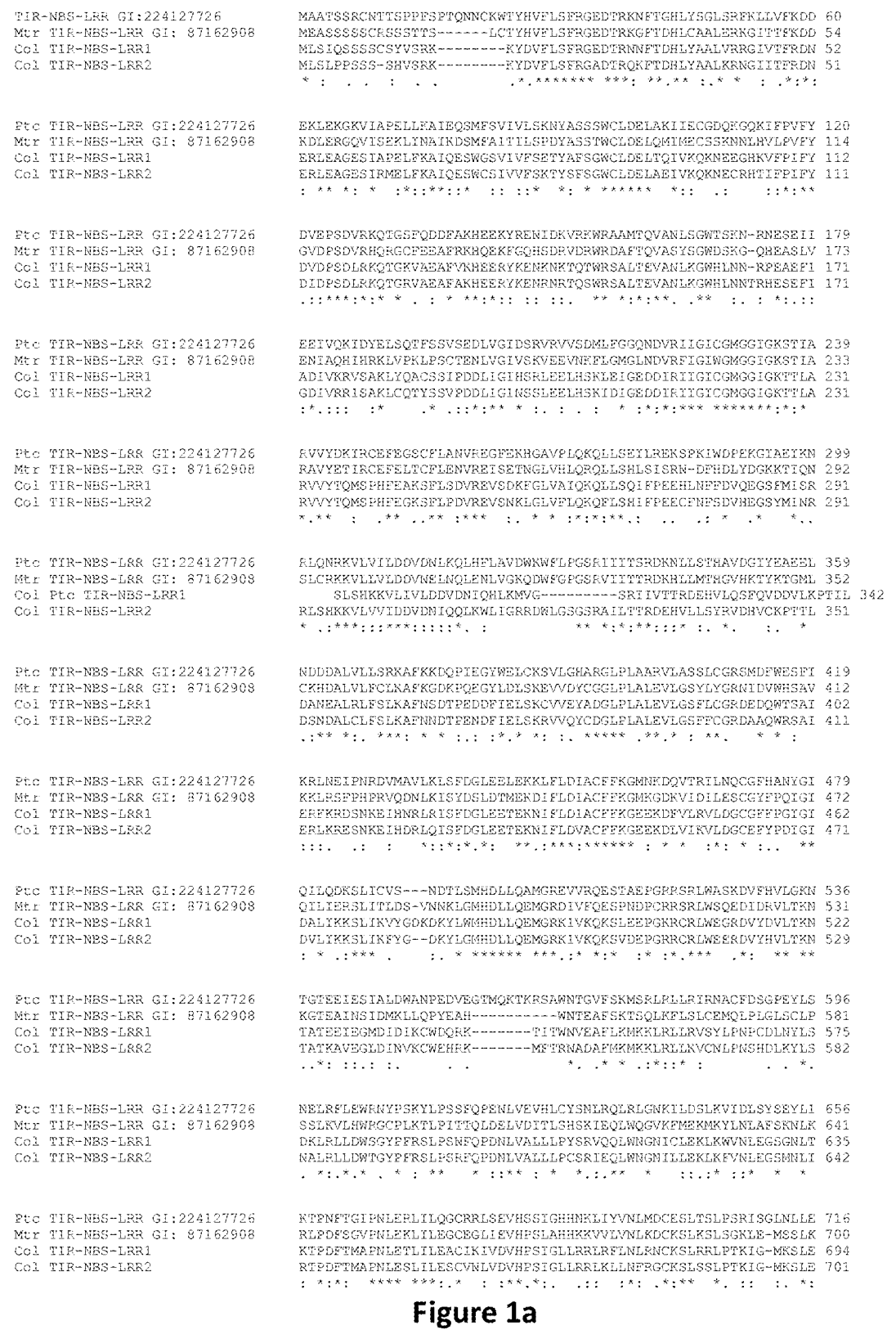

An amino acid sequence alignment of putative proteins encoded by the ColTIR-NBS-LRR1 and ColTIR-NBS-LRR2 genes with other plant TIR-NBS-LRR protein sequences available in the NCBI database, using the CLUSTAL W program, is shown in FIGS. 1a and 1b. The following proteins were aligned with the putative ColTIR-NBS-LRR proteins, with the GeneBank Accession Numbers in parentheses: PtcTIR-NBS-LRR (*Populus tricocarpa*, gi224127726) and MtrTIR-NBS-LRR (*Medicago tranculata*, gi87162908).

An amino acid sequence alignment of putative proteins encoded by the ColTIR-NBS-LRR3 gene with plant TIR-NBS-LRR and other resistance-like protein sequences available in the NCBI database, using the CLUSTAL W program, is shown in FIGS. 2a and 2b. The following proteins were aligned with the putative ColTIR-NBS-LRR3 protein, with the GeneBank Accession Numbers in parentheses: PtcTIR-NBS-LRR (*Populus tricocarpa*, gi224126507) and Stu nematode resistance-like protein (*Solunum tuberosum*, gi37781360).

An amino acid sequence alignment of putative proteins encoded by the ColNBS-LRR gene with other plant NBS-LRR protein sequences available in the NCBI database, using the CLUSTAL W program, is shown in FIG. 3. The following protein was aligned with the putative ColNBS-LRR proteins, with the GeneBank Accession Numbers in parentheses: PtcNBS-LRR (*Populus tricocarpa*, gi224075299).

An amino acid sequence alignment of putative proteins encoded by the ColCC-NBS-LRR1 gene with other plant CC-NBS-LRR protein sequences available in the NCBI database, using the CLUSTAL W program, is shown in FIGS. 4a and 4b. The following protein was aligned with the putative ColCC-NBS-LRR protein, with the GeneBank Accession Numbers in parentheses: PtcCC-NBS-LRR (*Populus tricocarpa*, gi224111284).

An amino acid sequence alignment of putative proteins encoded by the ColCC-NBS-LRR2 and ColCC-NBS-LRR3 genes with other plant CC-NBS-LRR protein sequences available in the NCBI database, using the CLUSTAL W program, is shown in FIGS. 5a and 5b. The following proteins were aligned with the putative ColCC-NBS-LRR proteins, with the GeneBank Accession Numbers in parentheses: PtcCC-NBS-LRR (*Populus tricocarpa*, gi224059584) and PtcCC-NBS-LRR (*Populus tricocarpa*, gi8224132258).

An amino acid sequence alignment of putative proteins encoded by the ColNBS gene with other plant NBS protein sequences available in the NCBI database, using the CLUSTAL W program, is shown in FIG. 6. The following protein was aligned with the putative ColNBS protein, with the GeneBank Accession Numbers in parentheses: PtcNBS (*Populus tricocarpa*, gi224058687).

An amino acid sequence alignment of putative proteins encoded by the ColLLR1 and ColLLR-TM-PK genes with other plant LRR protein sequences available in the NCBI database, using the CLUSTAL W program, is shown in FIGS. 7a and 7b. The following proteins were aligned with the putative ColLRR proteins, with the GeneBank Accession Numbers in parentheses: AthLRR (*Arabidopsis thaliana*, gi42561789) and RcoLRR (*Ricinus communis*, gi255546155).

An amino acid sequence alignment of putative proteins encoded by the ColCCH gene with other plant CCH protein sequences available in the NCBI database, using the CLUSTAL W program, is shown in FIGS. 8a and 8b. The following protein was aligned with the putative ColCCH proteins, with the GeneBank Accession Numbers in parentheses: PtcCCH type (*Ricinus communis*, gi109676362).

An amino acid sequence alignment of putative proteins encoded by the ColTIR-NBS gene with other plant TIR-NBS protein sequences available in the NCBI database, using the CLUSTAL W program, is shown in FIG. 9. The following proteins were aligned with the putative ColTIR-NBS proteins, with the GeneBank Accession Numbers in parentheses: Ptc (*Populus tricocarpa*, gi224071947) and Rco nucleoside-triphosphatase (*Ricinus communis*, gi255537517).

An amino acid sequence alignment of putative proteins encoded by the ColRGA1 and ColRGA2 genes with other plant RGA protein sequences available in the NCBI database, using the CLUSTAL W program, is shown in FIGS. 10a and 10b. The following proteins were aligned with the putative ColRGA proteins, with the GeneBank Accession Numbers in parentheses: RcoRGA2 (*Ricinus communis*, gi255561034) and RcoRGA2 (*Ricinus communis*, gi255568719).

Figure 12:
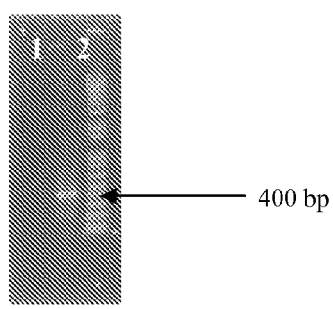
FIG. 12: DNA gel of TIR-NBS-LRR resistance protein.
Figure 13:
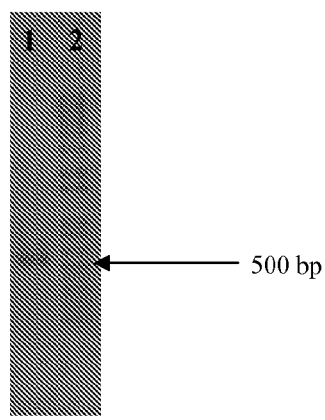
FIG. 13: DNA gel of CC-NBS-LRR1 resistance protein.
Figure 14:
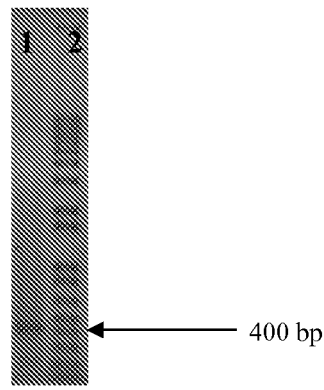
FIG. 14: DNA gel of CC-NBS-LRR3 resistance protein.
Figure 15:
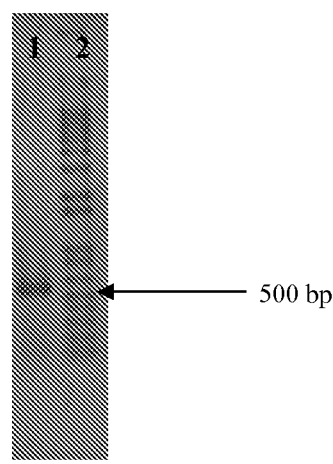
FIG. 15: DNA gel of resistance gene analog (RGA1).

DNA gels of PCR reactions using forward and reverse primers for several jute disease-resistance enzymes are shown in FIGS. 11-15. In FIG. 11, the DNA gel is of TIR-NBS-LRR resistance protein from *Corchorus olitorius*. Lane 1 is the PCR product of TIR-NBS-LRR resistance protein using cDNA as a template. The forward primer and reverse primer are SEQ ID NO. 29 and 30, respectively. Lane 2 is the 1 Kb+ladder. In FIG. 12, the DNA gel is of TIR-NBS-LRR resistance protein from *Corchorus olitorius*. Lane 1 is the PCR product of TIR-NBS-LRR resistance protein using cDNA as a template. The forward primer and reverse primer are SEQ ID NO. 31 and 32, respectively. Lane 2 is the 1 Kb+ladder. In FIG. 13, the DNA gel is of CC-NBS-LRR1 resistance protein from *Corchorus olitorius*. Lane 1 is the PCR product of CC-NBS-LRR1 resistance protein using cDNA as a template. The forward primer and reverse primer are SEQ ID NO. 33 and 34, respectively. Lane 2 is the 1 Kb+ladder. In FIG. 14, the DNA gel is of CC-NBS-LRR3 resistance protein from *Corchorus olitorius*. Lane 1 is the PCR product of CC-NBS-LRR3 resistance protein using cDNA as a template. The forward primer and reverse primer are SEQ ID NO. 35 and 36, respectively. Lane 2 is the 1 Kb+ladder. In FIG. 15, the DNA gel is of RGA1 resistance protein from *Corchorus olitorius*. Lane 1 is the PCR product of RGA1 resistance protein using cDNA as a template. The forward primer and reverse primer are SEQ ID NO. 37 and 38, respectively. Lane 2 is the 1 Kb+ladder.

Definitions

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. The practice of the present invention contemplates a wide variety of stably transformed plant cells.

An "expression cassette" refers to a nucleic acid construct, which when introduced into a host cell, results in transcription and/or translation of a RNA and/or polypeptide, respectively. The expression cassette may include a nucleic acid comprising a promoter sequence, with or without a sequence containing mRNA polyadenylation signals, and one or more restriction enzyme sites located downstream from the promoter allowing insertion of heterologous gene sequences. The expression cassette is capable of directing the expression of a heterologous protein when the gene encoding the heterologous protein is operably linked to the promoter by insertion into one of the restriction sites. The recombinant expression cassette allows expression of the heterologous protein in a host cell when the expression cassette containing the heterologous protein is introduced into the host cell. Expression cassettes can be derived from a variety of sources depending on the host cell to be used for expression. For example, an expression cassette can contain components derived from a viral, bacterial, insect, plant, or mammalian source. In the case of both expression of transgenes and inhibition of endogenous genes (e.g., by antisense, or sense suppression) the inserted polynucleotide sequence need not be identical and can be "substantially identical" to a sequence of the gene from which it was derived. Preferably the recombinant expression cassette allows expression at an early stage of infection and/or it allows expression in substantially all cells of an organism, such as a plant. Examples of expression cassettes suitable for transformation of plants can be found in U.S. Pat. Nos. 5,880,333 and 6,002,072; International Patent Publications Nos. WO/1990/002189 and WO/2000/026388; Ainley and Key, 1990, *Plant Mol. Biol.*, 14:949-967; and Birch, 1997, *Annu. Rev. Plant Physiol. Plant Mol. Biol.*, 48:297-326, all of which are herein incorporated by reference.

The term "host cell" refers to a cell from any organism. Preferred host cells are derived from plants, bacteria, yeast, fungi, insects, or other animals. The term "recombinant host cell" (or simply "host cell") refers to a cell into which a recombinant expression vector has been introduced. It should be understood that the term "host cell" is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Methods for introducing polynucleotide sequences into various types of host cells are well known in the art. Provided are host cells or progeny of host cells transformed with the recombinant expression cassettes of the present invention. The host cells may be plant cells. Preferably, the plant cells are jute cells.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g., enhancers) in an expression cassette. Transcriptional and translational control sequences are DNA regulatory sequences, such as promoters, enhancers, polyadenylation signals, terminators, and the like, that provide for the expression of a coding sequence in a host cell.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The term "nucleic acid construct" or "DNA construct" is sometimes used to refer to a coding sequence or sequences operably linked to appropriate regulatory sequences and inserted into an expression cassette for transforming a cell. This term may be used interchangeably with the term "transforming DNA" or "transgene". Such a nucleic acid construct may contain a coding sequence for a gene product of interest, along with a selectable marker gene and/or a reporter gene. The term "selectable marker gene" refers to a gene encoding a product that, when expressed, confers a selectable phenotype such as antibiotic resistance on a transformed cell. The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. When the heterologous region encodes a plant gene, the gene will usually be flanked by DNA that does not flank the plant genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct" is also used to refer to a heterologous region, particularly one constructed for use in transformation of a cell.

The term "vector" is intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

"Percentage of sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 25% sequence identity compared to a reference sequence as determined using the programs described herein; preferably BLAST using standard parameters, as described. Alternatively, percent identity can be any integer from 25% to 100%. More preferred embodiments include polynucleotide sequences that have at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% sequence identity compared to a reference sequence. These values can be appropriately adjusted to determine corresponding identity of proteins encoded by two nucleotide sequences by taking into account codon degeneracy, amino acid similarity, reading frame positioning, and the like.

The term "substantial identity" of amino acid sequences (and of polypeptides having these amino acid sequences) normally means sequence identity of at least 40% compared to a reference sequence as determined using the programs described herein; preferably BLAST using standard parameters, as described. Preferred percent identity of amino acids can be any integer from 40% to 100%. More preferred embodiments include amino acid sequences that have at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence. Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

INCORPORATION BY REFERENCE

All of the U.S. patents, U.S. published patent applications, and published PCT applications that designate the U.S. cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed.

```
Organism Name: Corchorus olitorius
Type: DNA
Length: 3639
Sequence Name: TIR-NBS-LRR1 resistance protein; complete cDNA
```

SEQ ID NO: 1

```
ATGCTGTCCATACAATCATCTTCTTCTTGTTCCTATGTTTCTCGAAAGAAGTATGATGTTTTCCTGAGTTT

CAGAGGAGAAGATACCCGCAATAACTTCACCGATCATCTTTATGCCGCTCTAGTCAGGAGAGGAATCG

TCACTTTCAGGGACAATGAAAGGCTCGAGGCCGGAGAATCGATCGCACCGGAACTCTTTAAAGCAAT

TCAGGAATCATGGGGTTCAGTAATTGTATTCTCGGAAACTTATGCCTTTTCAGGTTGGTGCTTGGACGA

GCTAACCCAGATTGTCAAACAGAAAAATGAAGAAGGGCATAAAGTTTTCCCCATTTTCTATGATGTTGA

TCCATCTGATTTAAGAAAACAGACAGGGAAAGTTGCAGAAGCCTTTGTCAAACATGAAGAAAGATATA

AGGAGAATAAAAACAAGACACAAACTTGGCGATCTGCTTTGACTGAAGTGGCTAATTTAAAGGGATG

GCATCTAAATAATAGACCCGAAGCAGAATTCATTGCAGACATCGTTAAAAGGGTGTCAGCAAAGTTAT

ACCAAGCCTGTTCTAGCATTCCTGATGACTTAATTGGAATTCATTCACGCTTGGAAGAGTTGCATTCCA

AACTAGAAATTGGGGAAGATGATATCCGCATTATAGGAATTTGTGGTATGGGTGGCATTGGCAAAACA

ACTCTCGCAAGAGTTGTTTACACTCAAATGTCACCTCATTTTGAAGCCAAAAGTTTTCTTTCTGATGTC

CGAGAAGTTTCAGATAAATTTGGACTTGTAGCTATACAGAAACAGCTTCTTTCTCAAATCTTCCCAGAG

GAACACCTCAATTTTTTTGATGTCCAAGAAGGAAGTTTCATGATAAGTCGTAGCCTATCTCACAAAAAA
```

-continued

```
GTTCTTATAGTTCTTGATGATGTTGATAACATACAACACTTGAAAATGGTTGGGAGCAGGATCATCGTA

ACTACAAGAGATGAACATGTGCTACAATCTTTTCAAGTGGATGATGTGTTAAAGCCTACAATATTAGAT

GCCAATGAAGCACTTCGTCTTTTTAGCTTAAAAGCTTTCAATAGTGATACACCAGAAGATGATTTCATT

GAGCTTTCTAAATGTGTTGTAGAATATGCTGATGGCCTTCCCTTAGCTCTTGAAGTATTGGGTTCATTTT

TATGTGGTAGGGATGAAGATCAATGGACAAGTGCCATTGAAAGGTTTAAAAGAGACTCTAACAAAGA

AATTCACAACCGGCTTCGAATAAGCTTTGATGGATTAGAAGAAACTGAGAAAAATATTTTTTTGGATAT

TGCATGTTTCTTTAAAGGGGAGGAGAAAGATTTTGTACTGAGAGTACTGGATGGTTGTGGGTTTTTCC

CAGGTATTGGAATAGATGCTCTCATTAAGAAATCTCTCATAAAGTTTATGGGGACAAGGACAAATATT

TGTGGATGCATGACTTGCTACAAGAGATGGGAAGGAAAATTGTGAAGCAAAATCGCTAGAAGAACC

TGGAAAACGTTGTAGATTGTGGGAGGGAAGGGATGTCTATGACGTGCTAACAAAGAACACTGCTACA

GAAGAAATTGAGGGCATGGACATCGACATCAAGTGTTGGGATCAGAGAAAGACAATCACTTGGAATG

TTGAAGCCTTCTTGAAGATGAAAAAATTAAGATTGCTCAGAGTCTCTTATCTCCCAAATCCCTGTGATCT

CAATTATCTTTCTGATAAGCTACGACTTTTAGATTGGAGTGGATATCCTTTTAGATCCTTACCTTCAAACT

TCCAACCAGACAACCTTGTTGCACTTCTCCTACCTTATAGCCGCGTTCAACAGCTATGGAATGGAAACA

TATGTTTAGAAAAGTTGAAATGGGTTAACCTCGAAGGCTCTGGAAACCTGACCAAGACCCCAGACTTT

ACAATGGCTCCAAATCTCGAAACTTTGATTTTGGAAGCTTGTATCAAGATAGTAGATGTTCATCCCTCCA

TTGGACTTCTGAGGAGACTCAGATTTCTGAATTTAAGAAACTGCAAAGTCTTAGGAGACTTCCAACC

AAAATTGGCATGAAATCTCTTGAAACATGGATTCTTTCAGGTTGCTCAAATCTTGAAAGGTTACCAGAT

CAGATTGATGGGAAATGGAATGTTTAGTTGAGCTTTATTTAGATGGGACGGGCATTCGACATCTTCC

CTCTCTAATTGGACATCTGAGTGGTCTTGTTTTATTAAATCTGAAAGGTTGCAGGAACTTGGCGAGCCT

CCCAAGCAACATTAATGGGTTGAAACGCTTAAAAATTTTTGATCTCTCTGGCTGCTCTAAACTTGAAAT

TTTGCCAGAAAGTTTGCAGCAAGTAGAATCTTTGGAGGAGCTTGATTTAAGTGAAACTGCCATAAGAC

AACCGCCATCCTTCATATTTCAATTTAAAAATCTTAAACATCTGTCTTTCCGTGGATGCAAGGGGCCACT

GTCTAAATTAAGACCAAATCTGCCTTCTCTTTTCAAGGTTATGCAAAGCAGAAGTTTGAATTCCATGGC

TCTAATGTTACCTCCTTTGTCAGGTTTGAGTTCTTTAACAAATCTGGATATAAGTTACTGCAATCTTGGT

GAAGAGGCTATTCCTAGCGATGTTTACCGGTTATCCTCTTTGAAAAAATTAAATCTTTGTGGTAACAATT

TCATCAGCCTGCCTGCAAATCTTGAACGACTTTCCAATCTTAAGTGTCTCGTATTGACACATTGTATGGA

GCTTAAATCATTGCCTGAGTTTCTAACAAGCACGGCCAGTTCATGCAATATTATAGGTCGTCATAGTGTA

GACCTATCTGCAAATGCAACAGTACGCAACTCAGTAAGCTGTGCTTCTATTTGGTTAACTAATTGCTTCA

GATTGAGTGAGAATACAGACATAGTAACATTGCTGAAAAAACATCTTAAGGCATCTGCAAATTCAAGA

CAATTGAACATTGTTCTACCCGGAAGTGAAATCCCAGAGTGGTTCAGCAATCAGAGGGATGGATGTTC

GATAAAGATACCTCTGCCTTACCAGATTTTGAATGATAGTCAGTGTATTGGAGTTGCTTTCTGCTGTGTC

TTTGTCAATGCTATAGAAATGCGCCGCAAAGCTTTTATCCATGGTAGAAAGTCTCAAAATGTGGATAAT

CATGTGTTGTGCATTACAAATGGCTGCTCCTCGGTCACTAAAGACCACCTCTTGCTAGGTTATTGGTCT

CGTGACTACTTTTATTCAATTTATTCCTTGGAGGAGAAATGTGGTGAAACTGAGCAATTATCAAGCCTA

GAATCCGATGAACTTGAGGTTGTGGTTGAGGTTGATGAGGATGAGATGTTGTCATCTAAGCCGACCAT

CAAGAAGTGTGGAATTCATATAGTTTATAAGAAAGATGTGGAAGAGATGGAACAAATAAAAGAACACC

ACATTCTGCAAATTGGCAATACAACTATTGAGGATATCCCTCAGCCTCAGAACGGTGATGAATCGGAG

ATAGGGAAGGGAGCTCTTGTAAAGCGAAAACGCAACTTCATGAGAAAAGTGAGAGTGACAAAATTG

AAGAGAGACCACAACCTAAACGGCTTCAACAATTTCTAAAATGTATAATGCGGAAGGAGCTTTAA
```

-continued

Organism Name: *Corchorus olitorius*
Type: PRT
Length: 1212
Sequence name: TIR-NBS-LRR1 resistance protein peptide

SEQ ID NO: 2

MLSIQSSSSCSYVSRKKYDVFLSFRGEDTRNNFTDHLYAALVRRGIVTFR
DNERLEAGESIAPELFKAIQESWGSVIVFSETYAFSGWCLDELTQIVKQK
NEEGHKVFPIFYDVDPSDLRKQTGKVAEAFVKHEERYKENKNTQTWR
SALTEVANLKGWHLNNRPEAEFIADIVKRVSAKLYQACSSIPDDLIGIHS
RLEELHSKLEIGEDDIRIIGICGMGGIGKTTLARVVYTQMSPHFEAKSFLS
DVREVSDKFGLVAIQKQLLSQIFPEEHLNFFDVQEGSFMISRSLSHKKVL
IVLDDVDNIQHLKMVGSRIIVTTRDEHVLQSFQVDDVLKPTILDANEALR
LFSLKAFNSDTPEDDFIELSKCVVEYADGLPLALEVGSFLCGRDEDQWT
SAIERFKRDSNKEIHNRLRISFDGLEETEKNIFLDIACFFKGEEKDFVLRVL
DGCGFFPGIGIDALIKKSLIKVYGDKDYLWMHDLLQEMGRKIVKQKSL
EEPGKRCRLWEGRDVYDVLTKNTATEEIEGMDIDIKCWDQRKTITWNV
EAFLKMKKLRLLRVSYLPNPCDLNYLSDKLRLLDWSGYPFRSLPSNFQPD
NLVALLLPYSRVQQLWNGNICLEKLKWVNLEGSGNLTKTPDFTMAPNL
ETLILEACIKIVDVHPSIGLLRRLRFLNLRNCKSLRRLPTKIGMKSLETWIL
SGCSNLERLPDQIDGEMECLVELYLDGTGIRHLPSLIGHLSGLVLLNLKG
CRNLASLPSNINGLKRLKIFDLSGCSKLEILPESLQQVESLEELDLSETAIR
QPPSFIFQFKNLKHLSFRGCKGPLSKLRPNLPSLFKVMQSRSLNSMALM
LPPLSGLSSLTNLDISYCNLGEEAIPSDVYRLSSLKKLNLCGNNFISLPANL
ERSNLKCLVLTHCMELKSLPEFLTSTASSCNIIGRHSVDLSANATVRNS
VSCASIWLTNCFRLSENTDIVTLLKKHLKASANSRQLNIVLPGSEIPEWF
SNQRDGCSIKIPLPYQILNDSQCIGVAFCCVFVNAIEMRRKAFIHGRKSQ
NVDNHVLCITNGCSSVTKDHLLLGYWSRDYFYSIYSLEEKCGETEQLSSL
ESDELEVVVEVDEDEMLSSKPTIKKCGIHIVYKKDVEEMEQIKEHHILQI
GNTTIEDIPQPQNGDESEIGKGALVKRKRNFYEKSESDKIEERPQPKRLQ
QFLKCIMRKEL

Organism Name: *Corchorus olitorius*
Type: DNA
Length: 3621
Sequence Name: TIR-NBS-LRR2 resistance protein; complete cDNA

SEQ ID NO: 3

ATGTTGTCCTTACCACCATCATCCTCTTCCCATGTTTCTCGAAAAAGTATGATGTTTTCTTGAGTTTCAG
AGGAGCAGATACTCGCCAAAAGTTCACCGATCATCTCTATGCTGCCTTGAAAAGAAATGGAATCATCA
CTTTCAGGGACAATGAAAGGCTTGAGGCTGGTGAATCGATCAGGATGGAACTCTTTAAAGCAATTCA
GGAATCATGGTGTTCTATAGTTGTATTCTCAAAAACTTATTCCTTTTCAGGTTGGTGCTTGGACGAGCTT
GCTGAGATTGTCAAACAGAAAAATGAATGCAGGCATACAATTTTCCCCATTTTCTATGATATCGATCCAT
CTGATCTAAGAAAGCAGACGGGAAGAGTTGCAGAAGCCTTTGCCAAACATGAAGAGAGATACAAGG
AGAATAGAAACAGGACACAAAGCTGGCGATCTGCTTTAACTGAAGTGGCTAATTTAAAGGGATGGCA
TCTAAATAATACAAGACATGAATCAGAATTCATTGGAGACATTGTTAGAAGGATATCAGCAAAGTTATG
CCAAACCTATTCCTCTGTTCCAGATGACTTGATTGGAATTAATTCAAGTTTGGAAGAGTTGCATTCTAA
AATAGACATTGGGGAAGATGACATTCGTATTATAGGAATTTGTGGTATGGGTGGCATTGGCAAACAA
CTCTTGCAAGAGTTGTTTACACTCAAATGTCACCTCATTTTGAAGGTAAAAGCTTTCTTCCCGATGTTC

-continued

```
GAGAAGTTTCAAATAAACTTGGACTTGTATTTTTACAGAAGCAGTTTCTTTCTCACATTTTCCCAGAAG

AATGCTTCAATTTTTCTGATGTTCATGAAGGAAGTTACATGATTAATCGTAGGCTATCTCACAAAAAGGT

TCTTGTAGTTATCGATGATGTCGATAACATACAACAGTTGAAATGGTTGATTGGAAGGCGTGATTGGCT

TGGTTCAGGTAGCAGAGCCATTTTAACTACTAGAGATGAACATGTTCTGCTATCATACAGAGTGGATCA

TGTTTGTAAGCCAACAACATTAGATTCCAATGATGCACTTTGCCTTTTTAGTTTGAAAGCTTTCAATAAT

GATACACCAGAAAATGATTTCATTGAGCTTTCTAAACGTGTTGTACAATATTGTGATGGCCTTCCCTTAG

CTCTTGAAGTTTTGGGTTCATTTTTTTGTGGAAGAGATGCAGCTCAATGGAGAAGTGCAATTGAAAG

GCTTAAAAGAGAGTCTAACAAGGAAATTCATGACCGGCTTCAAATAAGCTTTGATGGATTAGAAGAAA

CAGAGAAAAACATATTTTTGGATGTTGCTTGTTTCTTTAAAGGGGAGGAGAAAGATTTAGTAATCAAA

GTTCTAGATGGTTGCGAGTTTTACCCAGATATTGGAATAGATGTTCTCATCAAGAAATCTCTCATCAAAT

TTTATGGTGACAAGTATTTGGGGATGCATGATTTGCTGCAAGAGATGGGTAGAAAAATTGTCAAGCAA

AAATCTGTTGATGAACCTGGACGACGTTGTAGATTGTGGGAGGAAAGGGATGTCTATCATGTGCTAAC

AAAGAACACGGCTACGAAAGCAGTTGAAGGCTTGGACATCAACGTTAAATGCTGGGAGCACAGAAA

GATGTTCACTAGGAATGCTGATGCCTTCATGAAGATGAAAAAATTAAGATTGCTCAAAGTCTGTAATCT

CCCAAATTCTCATGATCTCAAATATCTTTCTAATGCGCTACGGCTTTTAGATTGGACTGGATATCCTTTCA

GATCCTTGCCTTCACGCTTCCAACCAGACAACCTTGTTGCACTTCTCCTACCTTGTAGCCGCATTGAAC

AACTATGGAACGGAAACATACTTTTAGAAAAACTGAAATTCGTCAACCTCGAAGGATCCATGAACCTG

ATCAGGACACCAGACTTTACAATGGCCCCAAATCTGGAAAGTTTGATTTTGGAAAGTTGTGTCAACTT

AGTAGATGTTCATCCATCCATCGGCCTTCTAAGGAGACTAAAACTTCTGAATTTTAGAGGCTGCAAAAG

TCTTAGCAGTCTTCCAACCAAAATTGGAATGAAATCTCTTGAAACATTGATTCTTTCAGGTTGCTCAAAT

CTTGAAAGGTTACCAGATCAGATTGATGGGAAGATGGAATGTTTGGTCGAGCTTCATTTAGATGGGAC

CGGTGTGGGACATCTTTCCTCTGCAATTGGACATCTGAGTGGTCTTGTTTTATTGAATCTGAAAGATTG

CAGAAATTTAGCAAGTCTCCCAAGCAGCATTAATGGGCTGAAATGTCTGAAAACTCTTAATCTCTCAGG

CTGCTCTAATCTTGAACATTTTCCAGAGAATTTGCAGCAATTAGAATCTTTAGAGGAGCTTGATTTAAG

TGGAACTGCTATAACAAAGCCACCATCCTTCATTTTCCAATTCAAGAATCTTAAACATCTGTCTTTCCAT

GGATGCAAGGCACCACCAACTAAATTACAACCAAATCAGCCTTCTCTAGGATGTATGAACTGCATGGC

GCTAACCTTACCGCCTTTGTCAGGTCTGAGTTCTTTAACACAGCTGAATATAAGTTACTGCAATCTTTAT

GAAGGAGCTATTCCGAGTGATATTTGCTCCTTATCCTCTTTGAAAAGACTAGATCTTCGCGGTAACAAT

TTCTTCAGCCTACCTGCGAATCTTGATAGACTTTCCAATCTCGACTATCTCGGATTGACAGATTGTATGG

AGCTTAAATCATTGCCTGAGCTTCTAACAAGCACACTAGTTCCTATTTCAAATGATTGCAGTTTTCCAGT

GGGACTATTTGCAAATGCAAGAGCATGCAATTCAATGGATTGGGCACCTGCTTCTATTTGGTTAACTAA

TTGCTACAGACTGGCTGAGAACACAAATGTATTAACATTGCTGAAAAAACATCTTAAGGTGTTTGCAA

AGGCAAGAGAAACTTTGGACATTATTTTACCCGGAAGTCAAATCCCAGATTGGTTCAGCCATCAGAGC

AATGAATCGTCAATCAAGATACCTCTGCCTCACCATCTTCAGAGTAATAGTAAGTGGATTGGAGTTGCT

TTCTGCTGTGTCTTCGTCGATGTTGTTGGTATCGACTGCAAAGCTTTTGTCCATGGTAGAATGTCCCAC

GACATTAATGGTTACGGGTTGTATTTTGGACATGGCTCCTCGGTCACAAAGGATCATCTTTGGCTACGT

TATTGGTCTCGTAACAAGTTATATTCGTTTGCCTTGGATGACAAATGTGGTGAAACAGGGCATCCACAG

AGCCTAAAATGTCCGGTAGATCAAGAATCCGATGAATTCGAGGTTGCTGTTGAGGTTGAGGTTGAGTT

GTCACGGTCACGTTTTAAGAAAGTGAAGAAGTGTGGGGTTAGACTAGTTTATGAGAAAGATTTGCAA

GAGTTGGAGCAACTTCTGCAAATCTGCAATTCAACTTGTGCAGATGAATCAAAAACAGGGGAGGTTC
```

-continued

CGGTAAAGCGAAAACGCAACATCTATGAAGAGGAGGCAGAACTAAGTGAGAGTGACAGCTTCCGAG

GGCCGGAACGATTTCTAAGATATATAATGCAGAAGAAGGAACATAATTGA

Organism Name: *Corchorus olitorius*
Type: PRT
Length: 1206
Sequence name: TIR-NBS-LRR2 resistance protein peptide

SEQ ID NO: 4

M L S L P P S S S S H V S R K K Y D V F L S F R G A D T R Q K F T D H L Y A A L K R N G I I T F R D

N E R L E A G E S I R M E L F K A I Q E S W C S I V V F S K T Y S F S G W C L D E L A E I V Q K N

E C R H T I F P I F Y D I D P S D L R K Q T G R V A E A F A K H E E R Y K E N R N R T Q S W R S A L

T E V A N L K G W H L N N T R H E S E F I G D I V R R I S A K L C Q T Y S S V P D D L I G I N S S L

E E L H S K I D I G E D D I R I I G I C G M G G I G K T T L A R V V Y T Q M S P H F E G K S F L P D

V R E V S N K L G L V F L Q K Q F L S H I F P E E C F N F S D V H E G S Y M I N R R L S H K K V L V

V I D D V D N I Q Q L K W L I G R R D W L G S G S R A I L T T R D E H V L L S Y R V D H V C K P T

T L D S N D A L C L F S L K A F N N D T P E N D F I E L S K R V V Q Y C D G L P L A L E V L G S F F

C G R D A A Q W R S A I E R L K R E S N K E I H D R L Q I S F D G L E E T E K N I F L D V A C F F K

G E E K D L V I K V L D G C E F Y P D I G I D V L I K K S L I K F Y G D K Y L G M H D L L Q E M G R

K I V K Q K S V D E P G R R C R L W E E R D V Y H V L T K N T A T K A V E G L D I N V K C W E H

R K M F T R N A D A F M K M K K L R L L K V C N L P N S H D L K Y L S N A L R L L D W T G Y P F

R S L P S R F Q P D N L V A L L L P C S R I E Q L W N G N I L L E K L K F V N L E G S M N L I R T P

D F T M A P N L E S L I L E S C V N L V D V H P S I G L L R R L K L L N F R G C K S L S S L P T K I G

M K S L E T L I L S G C S N L E R L P D Q I D G K M E C L V E L H L D G T G V G H L S S A I G H L S

G L V L L N L K D C R N L A S L P S S I N G L K C L K T L N L S G C S N L E H F P E N L Q Q L E S L E

E L D L S G T A I T K P P S F I F Q F K N L K H L S F H G C K A P P T K L Q P N Q P S L G C M N C

M A L T L P P L S G L S S L T Q L N I S Y C N L Y E G A I P S D I C S L S S L K R L D L R G N N F F S

L P A N L D R L S N L D Y L G L T D C M E L K S L P E L L T S T L V P I S N D C S F P V G L F A N A

R A C N S M D W A P A S I W L T N C Y R L A E N T N V L T L L K K H L K V F A K A R E T L D I I L

P G S Q I P D W F S H Q S N E S S I K I P L P H H L Q S N S K W I G V A F C C V F V D V V G I D C

K A F V H G R M S H D I N G Y G L Y F G H G S S V T K D H L W L R Y W S R N K L Y S F A L D D K

C G E T G H P Q S L K C P V D Q E S D E F E V A V E V E V E L S R S R F K K V K K C G V R L V Y E

K D L Q E L E Q L L Q I C N S T C A D E S K T G E V P V K R K R N I Y E E E A E L S E S D S F R G P

E R F L R Y I M Q K K E H N

Organism Name: *Corchorus olitorius*
Type: DNA
Length: 719
Sequence Name: TIR-NBS-LRR3 resistance protein; partial cDNA

SEQ ID NO: 5

TTGCGAGTCTCCCAAGCAGCATTCATGAGTTGAAATGTCTAAAAACTCTTGATCTCTCAGGCTGCTCTA

AACTTGAAAATTTGCCAGAGAGTTTGCAGCAAGTAGAATCTCTCGAGGAGCTTGATTTAAGTGGGAC

TGCCATAACAAAACCACCATCCTTCATTTTTCAATTGAAAAATCTTAAACATCTGTCTTTCCGCGGATGC

AAGGGAACAGTTTCTAAATCACGACCCAATCTGCTTTCTCTTTTCAAGGTAATGCAAAGAGGAGGAG

GAAGTGTGAATTCAGTGGCTCTAACCTTACCTCCCTTGTCAGGTTTGACTTGTTTGACAAAGCTGGATA

TAAGTTACTGCAATCTTGGTGAAGGGGCTATTCCTAGCGATATTTGCCACTTATCCTCTTTGAGAGACTT

GAATCTTAGTGGTAACACTTTCTCCAGCCTTCCTGCAAACCTTGATCGACTTTCCAATCTTGAGCGTATC

AGACTGAGACATTGTACGGAGCTTAAATCATTGCCTGAGCTTCTTAGGAGCACATACCATTCGGTTGG

AGTATTTGCGAATGCTGCAATACGCAACTCGCGAGATTGGGCATGTATTTTTTTACCTAATTGCTACAG

AATAGCTGAGAATACAAATATAGTAACCTTGCTGAAGAAGAATCTTAAGGTTGGTCTCTATATCTCTCCC

CCTAATCAGCTCACACAAAGAAATTTATGA

Organism Name: *Corchorus olitorius*
Type: PRT
Length: 238
Sequence name: TIR-NBS-LRR3 resistance protein peptide

SEQ ID NO: 6

A S L P S S I H E L K C L K T L D L S G C S K L E N L P E S L Q Q V E S L E E L D L S G T A I T K P P S

F I F Q L K N L K H L S F R G C K G T V S K S R P N L L S L F K V M Q R G G G S V N S V A L T L P P

L S G L T C L T K L D I S Y C N L G E G A I P S D I C H L S S L R D L N L S G N T F S S L P A N L D R

L S N L E R I R L R H C T E L K S L P E L L R S T Y H S V G V F A N A A I R N S R D W A C I F L P N

C Y R I A E N T N I V T L L K K N L K V G L Y I S P P N Q L T Q R N L

Organism Name: *Corchorus olitorius*
Type: DNA
Length: 2583
Sequence Name: NBS-LRR resistance protein; complete cDNA

SEQ ID NO: 7

ATGGCTGAAGCTGCTGTTTCCTTTGTGCTAGAGAGGCTAGCTGACATACTGGAAGAAATTGATTTTCA

AACAAATGTTCGGAATGAAGTTGTGCGTTTACAAGATGAACTGAAGAGGATGCGTTGTTTCTTGCGTG

ATGCAGATGCAAAGCAAGATGATGATGATAGAGTGCGCAACTGGGTGTCTGATATTAGAAATGTAGCT

TATGATGCTGAGGATCTCATTGACACATTCATTCTCAGAATTGATGCCGTTCAAAAAAAGAACTCCATC

AAAAAGTATGCTTCCGTTTTCAAAGATTGGAAACGTCGCTCCAAGATTGCAAATGAGCTCATTGCTATC

CAGAGAAGAATCCTTGATGTTTCTCAGAGTCGTGAAAAGTATGGTATCAAGAACATTGGAGAGGGGA

TTAGCACAGCAAAGAGAGGCTCCGCAAGCAGAGAAGATCATCTCCTCGCGGTGAAGAGAAAGATA

TTGTTGGACTGGACGATGATATAGCTAAGCTGGTGACACAACTTGTTGATGCTGAGGACCAATGGCAT

GCCATTTCAGTAGTGGGAATGGGAGGGATCGGCAAGACAACTCTTGCCAAGAAGGTTTACAATCATG

CTGATATCCAGGCCCGTTTTCCTACCCGAGCATGGGTTTATGTATCCCAGGAATACAGCATTCGAGACA

TATTTCAGGCAATTATAAAGCAAGTGGCATCAACAGGAAGGAATTTGGAAAAACTGCGGGAAGAAGA

GTTGGAAGAAATTCTCTATGAACACCTCCGGAAAAAACGGTATTTGGTGGTCTTGGATGATGTATGGA

GCATAGAAGCATGGAATTCTCTTTCTGAGGCCTTTCCGGATAGCAGCAGCAATGGAAGCAGAGTGAT

GCTAACGACTCGCAACAAGAGTATTGCTCTCAAAGCAGATGCTAGAAGTGTTCCTTATGATTTGCACTT

TATGAATGAAGAAATGGATGGATGTTGTTCTGCAAGAAAGCTTTCATTCAAAGTGCTGATTCACATCG

TTCCCCACGTTTGGAGGAAATCGGGAAGGAGATTGTTGAAAAATGTGCTGGTTTACCACTGGCCATCA

TTGTGATGGAGGATTGCTTTCAACAAAAAGAAGTTTAGCAGAATGGAAAAGGGTTCTCTCCAACAT

GAGCTCATTCTTTGCTCAAGACCCGAATGGGTATCAGCAATACTGGCTTTGAGTTACAACGACTTGC

CATATTATCTCAAATCTTGTTTCCTCCATCTAGGACAGTTCCCAGAAGACCAGCCAATTCCAACACATAA

ATTGTTTAGGCTATGGATTGCTGAGGGCTTGATACCACAGCAAGGTGAAAGGGTGGAGGATGTAGCA

GAGGACTACTTGAATGAGCTAATAGAGAGAAACATGGTTCAAGTAGCCAAATGGAGTGTCAACGAGA

GAGTTAAACAATGTCGTCTTCATGATCTATTACGAGATCTCTCCATTTCAAAGGCCAAAGCAGAGAGCT

TTCATGAGATTCAAGGGAGCCAAAGCCTCGAACCTTCTGCTAGATCACGTCGTCATGCCATCTATTCCA

CCTTTCATTGGCCCCAATGTAAGTATTCCAATCCTCAACTTCGGACACTTCTCCTATTTAGAGTTGATCAT

AACCAAAGCCAGGTAATTATTATATAAATGATCCCTATAAAATGGAAGGCAGCGATCTAGATTATATTA

GCAAAAACTTCAAATTACTGAGGGTCTTGGAGTTGGAGGGTATACCATGTGCTACCATTCCAAGCATA

ATTGGGTTACTAATTCATTTGAAGTACTTGGGGCTAAAGGAGACTAACCTGCAAGAGCTTTCATCCGC

CATTGGTTCTTTGAGGAGCCTGCAGACTCTTGATATAGCTGCAAATCTTCATCTTCTAACAATTCCCAAT

-continued

```
GTCATATGGAAGTTAAAAAGATTAAGGCATCTTTACATGTGCGGGCATAAATATGGGGGCCTCTGCG

AATCGACACATTACAGCATCTTCAAGCTCTGTCTGAAATAAATGTCCAGAGATGGATGCAAAATGATCC

TGCCAATTTAACCAGCCTGCGAACTGAAGAGGCTGATTTTCCATCTCTCACACAACTTTCTGCTCTTCA

AAATCTTGTCAAGTTGCATATGAGAGGAACAATAAGGCAGTTGCCAAACTCAGAGGAATTCCCACCAA

ATCTCTGTCAGCTGACCTTGGAACATACCCATCTCCAGCAAGATTCAGTGGGAATTCTTGAGAAATTGC

CAAGATTGTTGATTTTGAGACTAAAAGCACGGTCCTACGATGGAGAAAAATGAAATATCAGTCAGC

GGCTTTCCCCAACTTGAAGTCCTGGAGCTTGTTTCATTGGAATCATTGGAAGAGTTGAATCTTGAAGA

AGGTGCAATGCTAAGGCTTAGGAGTTTTCGGATTATAAAGTGTGAGAAATTGAAGATGCTTCCTGAGG

GAATGAAAACCCTAACCGGTCTCCGTGAGTTGGACATTGAATTGATGCCAAAATCATTCGTGGATAGG

ATTCGTGGGAAGATTTCTACAAAGTGCAGCATGTTCCCTCTATCTTGTTTGTTTGA
```

Organism Name: *Corchorus olitorius*
Type: PRT
Length: 860
Sequence name: NBS-LRR resistance protein peptide

SEQ ID NO: 8

```
M A E A A V S F V L E R L A D I L E E I D F Q T N V R N E V V R L Q D E L K R M R C F L R D A D A

K Q D D D D R V R N W V S D I R N V A Y D A E D L I D T F I L R I D A V Q K K N S I K K Y A S V F

K D W K R R S K I A N E L I A I Q R R I L D V S Q S R E K Y G I K N I G E G I S T A K E R L R K Q R R

S S P R G E E K D I V G L D D D I A K L V T Q L V D A E D Q W H A I S V V G M G G I G K T T L A K

K V Y N H A D I Q A R F P T R A W V Y V S Q E Y S I R D I F Q A I I K Q V A S T G R N L E K L R E E

E L E E I L Y E H L R K K R Y L V V L D D V W S I E A W N S L S E A F P D S S S N G S R V M L T T R

N K S I A L K A D A R S V P Y D L H F M N E E N G W M L F C K K A F I Q S A D S H R S P R L E E I

G K E I V E K C A G L P L A I I V M G G L L S T K R S L A E W K R V L S N M S S F F A Q D P N G V

S A I L A L S Y N D L P Y Y L K S C F L H L G Q F P E D Q P I P T H K L F R L W I A E G L I P Q Q G E

R V E D V A E D Y L N E L I E R N M V Q V A K W S V N E R V K Q C R L H D L L R D L S I S K A K A

E S F H E I Q G S Q S L E P S A R S R R H A I Y S T F H W P Q C K Y S N P Q L R T L L L F R V D H N

Q S Q V N Y Y I N D P Y K M E G S D L D Y I S K N F K L L R V L E L E G I P C A T I P S I I G L L I H L

K Y L G L K E T N L Q E L S S A I G S L R S L Q T L D I A A N L H L L T I P N V I W K L K R L R H L Y

M C G H K Y G G P L R I D T L Q H L Q A L S E I N V Q R W M Q N D P A N L T S L R T E E A D F P

S L T Q L S A L Q N L V K L H M R G T I R Q L P N S E E F P P N L C Q L T L E H T H L Q Q D S V G

I L E K L P R L L I L R L K A R S Y D G E K M K I S V S G F P Q L E V L E L V S L E S L E E L N L E E G

A M L R L R S F R I I K C E K L K M L P E G M K T L T G L R E L D I E L M P K S F V D R I R G E D F

Y K V Q H V P S I L F V
```

Organism Name: *Corchorus olitorius*
Type: DNA
Length: 6459
Sequence Name: CC-NBS-LRR1 resistance protein; complete cDNA

SEQ ID NO: 9

```
ATGGAGTTTGTTGTAGGCATTGTTAGCTCT

```
CATCATGGGAGTGCATGGCATGGGTGGCGTTGGCAAGACCATGCTTGTTAAAGAAGTTGCTAGACAA
GTTAAGGAGGGGAGGCTATTTGATTATGTGGTTATGGCAAAAGTGACTCAGACTGTTGATGTCAAGAC
AATTCAGAATGATATTGCTGAGTTACTGGGTTTAAGATTTGACGAACAGAGTATTGTTAGGAGGGCTG
ATCGACTGCGAGAAAGATTGAAGAGAGAGACAAAAGTTCTTGTTGTTCTGGATGACGTATGGGAAAG
ATTAGATCTGGAGGAAGTTGGGATTCCAGTTGCAGATGAACACAAGGGGTGCAAGATACTGCTGACG
TCCAGAGATCTCAATGTTTTATCCAATGGGATGAACAGTGAGAAAATTTTGTGGTTGGCCTTCTCACT
GAAGAAGAAACCTGGAACCTTTTTAAGAAGAAGGCCGGTTATGTTGTTGAAAGTTCTGATATAAAGCC
TACGGCTATCGAGGTGGCAAAGAAATGTGCAAAATTGCCAATCGCCATCGCCACAGTTGCAGGGGCT
TTGAGGAACAAAGAGGCGTTCCATTGGAAGGATGCTCTGTGCCAATTACAGAAGCCTTCAACAGTAA
ACCTCAAAGGGGTAGCAACGACTGTACATTCAGCTATAAAGCTTAGCTACGATTTTTTAGAAAGCGAG
GAAGTTAAATTCACTTTCTTGCTTTGCTGTTTATTGGGCCGCAATGGTTTGATTGAGGACTTGTTGAAG
TATGTTATTGGTATGAGATTATTTCAAGGCATCACAATAGAGGAAACAAGAAACAGAGTATTGACTGTG
GTGAGTAATCTGAAAGCCTCTTGCCTGTTACTTGATAGCTATAATAATGAAAAGTTTGATATCCATGATG
TTGTTTGGGATGTTGCTCTATTGATTGCATCAAGAGACCGCCATATGTTTGTCTTAAGAGATGGTGAAG
AGCTAAAAGACTGGCCTACCCAGGAGATGAAGGAGAATTGCAGTGCGATTAACTTTCGTTGTCCTCGT
ATTATGACCGAGCTACCTGATGAGATGGAAGGTTTACGTCTTTCCTTATTGCGCTTGGACAATGTAGGC
GCATTGGAAATTCCAGCCAACTTCTTTAGACGGATGGAAAGACTCGATGTCTTACATTTCACTAGAATG
CATTTTTCCTCCCTACCTGTTTCAATTAGTCTCCTTACAAACCTTCACACACTGTGTCTCAGTGATTGTGC
ACTGCAAGATATAACCATTGTTGGAAAGCTGAAGAATTTAGAAATCCTTAGCCTTGCACGTTCAGTTAT
TGAAGCCCTGCCCGAGGAGACAGCGCAATTGACTCGGTTAAGGCTGTTAGATTTGAGTCATTGTTCTA
AACTTCAGCTCATTCCACCAAATGTTCTATCAAGTTTGTCCAAGTTGGAAGAATTATATTTGTACAATAG
CTTTGTTCAATGGGAAGGTGAAGTACATAGCAGCGGAAGGAGAAATGCTAGCCTTGATGAACTAAAG
CATTTGTCTCATCTTACCACTTTGTATGTTCATATCCCCAATGCCGAAATAGTTCCAAAAGATCTTTTCAT
TGAGAGATTGGAAAGATTCAGTATTTTGATTGAAGATGAGCGGCGTTGGTACAGTGAGTTTGAATACT
CAAGAACTTTGAAATTGAAGATATATACAAGCATTTATTTGGATCATGCGGTGAGAATGTTATTGAAGA
AAACTGAAGATCTACATCTATACCAACTTAAAGGTATCAAGAATGTGCTTGATGAGTTAATTGATGGTGT
AGAATTGCCGCATCTAAAGAACCTTCATATTCGCAATGGTTCGGAGGTCCAATATATCATGAGGAAGAA
AATTGAGTGCGCTCAATTAAAGTCCATGACACTTGAAGGTCTGCCGAAACTGATTAGCTTTTGGTTTG
AAGACAAAAGGTGTTCCACATCTCATGAGGAGCGAGCTACGAGTTCCAATCCCCTGCCACTTTTCAAT
AAACAGCTTGTGTTCCCTTGCTTGGAAAGCCTGCGATTGTCCTCAATTAATGCTGAAAGAATATGGCAC
AGCCCTCTTTCGGAGAATTGTACTTTTGCTGCAAATTTGAAAAGCTTGACGGTTGAAGGCTGTGGCGA
ATTGGAGCATCTATTATCACCCTCTGTTGCCAGAAGTCTTGTCCAGCTTACACACTTCGAGGTAGCAAG
ATGCCAGCGCCTAAGAGAGATAATATCTACAGAGGAAATAGAAGATGAGAGTGTTGCGATTTGTTTCC
CCCAATTAAACTCCTTAGAGATAAGAAGTCTCCAGAATCTAGCAAACTTTTGTGCAGGAAACTATAATA
TTGAATTCCAGCACTTAAAGTATTGGAGGTTAATGGCTGCCCTGTATTAAAGGAATTCATTAGGGTGA
ATAAAAGTGAGTTTCATGTGCCGGCTCTCTTCAATGAAAAGGTTGCTCTTCCTAGCTTGGAAAGGATG
GAATTCTCCTACCTGAAAAATGTGAAGATGATATTTGACAAGCAACTTCTGGCAGGTTCCTTTTGCAAA
TTAAAAGCAATGTCAGTTTATCATTGTGATGCATTATTGACTATTTTTTCATCTAATATATTTGGAGCATTT
CAGAGTCTAGAAAATCTTGATGTGTACAGATGTAATTCACTTGAAATGATATTTGAGGTTGGAGGGTTA
AATATCAGAGAACCACACGTTGTACACTCTCAACTAAGATCTCTGTATATTTCCTCGCTGCCTGCATTGA
```

-continued

```
AGCATGTTTGGAATAAAGATCCCCAAGGAATTCTTTCCTTCCAAAATCTTCATACAGTAGATTTGTCTTT
TTGTCGGAATTTGAAAAGTCTATTTCCAGTGTCAGTAGCCAAACACCTTCAACAGCTCGAAAATCTGA
GACTGTGTAATTCTGCGGTGGAGGAGATTGTGTTTTCAGAAGAAGGATTAGAAGAGCCCATTGGGTT
CGAGTTTGCTCAACTGTCTTCCCTTGTGCTTTATAATCTAAGAGAGCTCAAATGCTTCTATCGAGGGCA
GCATACAATAGTGTGGGCGATGTTGAAAAAGTTGGAGACGGATCATTCTACTTTACTGAAGATAGTAG
GTAGTAATTCACAACATCTTGGCATCCAAGAAATGAATAGCAATGACCCACCAGAATGCACAACTGGA
CAACCACTTTTTTCGACTGAAAAGGTCATTCCCATTTTAGAGGAACTGCATTTGCGGTTAACAAACCCT
GATGACATTTCAAAGATATGTGATGGCCATTTTCTCCAAAGATTCTGCAATTTGGAAAGTTTAGAACTT
TCATCTTCTGAAGGAGATGATGCTCAGATACTACCAGATGCGGTGACACTTCCACGAATTAAAACATTA
ATATTGTCTTCTTGCAACTTTCTTAAGCATATATGGGAGAAGAAGGATTCAGAGCTAGGGCACATTCTT
CAAAAGCTCGAAATTCTTGAAGTTAACGAGTGTGGCGATTTGACAAGTTTTGGACCGTCCTCGGCATC
TTTTCAAAATCTCACAACTTTGGAAGTGACATACTGCAACATGATGATAAACTTGGCTACACCCTCAGT
AGTCCAGAATCTGGTACAATTAACAACCATGAGGATAGCATACTGCAGGGGAATGGCAGAAATAGTTG
CAAATGAGGGAGGTGAAGCAACACCAACATATGAGATCAATTTCAGCAAGTTGCAAAGTTTAGAACT
CAATCGGTTACATCGCCTCACAAGCTTTTCTCCAGGGAATTACACCATCAACTTTCCTTCCTTGCAAGA
ATTAATGAGAGTAAAAGAATCACATAATGATCGAAAAGGGCGTTGGGCCGGTGACCTTAATACCACCA
TACAACTTTTGTACAGCGTAAATGTTGTTGAGGGATACCATGGCATATGTAATTTGAAATTATCAGACAC
CTCTCCTGAGTTGATGGAAATATGGAATGGAAGGAACCCTCATGAAATTGTGGACTTGAAATTCCTTG
GACGTGTGGAATTTTGTAACTGTAGCAGCTTGAAATACATTTTTACTCTGTCCAGGTTGTTGAGCCTCA
AGCACCTATCTTATTTAGTAGTAAAAGAATGCAGTACTCTGAAAGAAGTTGTGATGGAACAGGAAATT
GAGGAGGAAGCAACAACCGATAACTTCATATTCCCTAATCTCCGGTACATTAAAATTGAGTCATGTTCC
AGCTTGAGATGCTTTTATTTGGGAAGTGGAGCTCTTGAAATTCCACGGTTGGAAATTATTGAGATAACT
GACTGTCCAAAAATGACTACGTTTGCTTCTTCATTCCCAAGAGATGAGGAGAAAGAGATTAGTGCTGA
TGGAAGTGAAAAAGGGTTGGCCATGGCGACCTCAATATTGAACCGTTTTTCAGCGATAAGGTGGCC
TTGCCTAGTTTAGAAAGGTTGAGAATCAAAGGCATGGGGAAATGTAGAAAGATATGGCAAGACCAAC
TCACTGTGAATTCATTTTGCGAGCTAAAGTATATACTGGTAGAAAGCTGTGAAAAACTCTCAAATATTTT
TCCATTCAACATGATGGAAAGGCTTGAGAAACTAGAAGAGTTGCAGATTGTGAATTGTGATTCATTAG
AAGAAATCTTTGAGCCAGAAGCCCTCACTAATAATCAATCACATGGAGTTGCCACTACTGAATCTATTG
TAGAAGAGACAATGGCTAAGTTTGTATTTCCCAGTGCTACATACCTTCGACTTGAAAACTTGCCCAACT
TGAAATGTTTTTACTCGAGGACACATGCTACCGAATGGCCATCTCTGAAAAAAATGAAGGTTCTCGATT
GCCAAAATGTGCAGATTTTTGCTTCAGAATGTCCTGCCTTTGGAGAAACACAAGGAGCGAGCACAGA
AATTAATATCTCAAATCAACCTCCTCTGTTTCGGGTCAACGAGGTTACATTCCCAATCTTAGAAGAATTA
AAATTGAAGCCAGATGATACATGGCATGGACAAGTACTCTCAACAGAGTGTTTCAGCAAATTGAAAGT
TCTAGAGCTCATCTGCATTCCTGAGAAGGCAACAGATCTTGCATGTTGCTTCATTCAATCATTGCCGAA
TCTTGAAAAGTTACTTGTGAAGGATTCTTCTTTCTGTCAAATATTCCAGTTTGAAGGACTCAGTGATGA
TGACCAAAGACATGCAGCACTCACTCGGTTAAGTGAATTGAGATTGTCTAAACTTCCAGAGTTGACAC
ATCTCTGGACGGAAGAATTCCAACCCGGAGCAGCATTTTCTAACCTGAAACTTCTTGAAGTGCTTCATT
GTGTCAAATTAAAGACTTTAGTCCCATCTTTGGTGTCTTTCAACAATTTAACAACTCTGAAAGTTTCAG
GATGTCATGGATTAACCAATTTAGTAACATGCTCAATAGCTACAAGCTTGATGCAACTCAAAAGAATGA
GTATAACTGATTGCAACATGATAGAAGAGATCATAGCATGTGATGCTGATGAAATTCAAGGTGCCATTG
TTTTCTCCCAGTTGAGATATTTGAAACTCAGCTGTCTACCAAGTTTGGCAAGCTTTTGCTTAGGCAATC
```

-continued

```
AGAGCTTTGATTTCCCAACCTTGCAAAAGTTGATTGTTCATGAATGCCCAAAACTGGAGATTTTCTGTC

AAGGAGACTTAACCACCCCAAAGCTGCAGCAAGTGCTATTGCCAGAGTATGAATATGAATACTATGAT

GCAGAAGAGTATGAAGATGAATATGATGCAGAAGAGTATGAAGAAAACAGCATGTGGGAGGGCGAC

CTTAAAAGTACTATAAGAAAGCTGTTCGAAGAAATGGCAGAGGATGAAGATGAAGATGAAGATGAAG

ATGATGATGAAGAGCATGAAGATGAAGATGAAGATGAAGATGATGATGAAGAGCATGAAGATGAAGA

TGAAGATGAAGATGATGATGGTTGA
```

Organism Name: *Corchorus olitorius*
Type: PRT
Length: 2152
Sequence name: CC-NBS-LRR1 resistance protein peptide

SEQ ID NO: 10

```
M E F V V G I V S S I F T P A V Q L I I S P I K N K I K Y I S N H E N N V Q T L K N Q V E S L K D E R
K R V Q H S V D A A R Q N G E E I E D D V K K W Q K T V D Q K I A D E V E K V I A D E E K A K K
K C F V G L C P N L W A R Y K H S V K A E E K G K V V A K L L E Q G K F D K V S Y R P A P Q G A
S V T A A F V K G F E E F K S R E V L L K G I M E A L N D D K I N I M G V H G M G G V G K T M L
V K E V A R Q V K E G R L F D Y V V M A K V T Q T V D V K T I Q N D I A E L L G L R F D E Q S I V
R R A D R L R E R L K R E T K V L V V L D D V W E R L D L E E V G I P V A D E H K G C K I L L T S R
D L N V L S N G M N S E K N F V V G L L T E E E T W N L F K K K A G Y V V E S S D I K P T A I E V
A K K C A K L P I A I A T V A G A L R N K E A F H W K D A L C Q L Q K P S T V N L K G V A T T V H
S A I K L S Y D F L E S E E V K F T F L L C C L L G R N G L I E D L L K Y V I G M R L F Q G I T I E E T
R N R V L T V V S N L K A S C L L L D S Y N N E K F D I H D V V W D V A L L I A S R D R H M F V L
R D G E E L K D W P T Q E M K E N C S A I N F R C P R I M T E L P D E M E G L R L S L L R L D N V
G A L E I P A N F F R R M E R L D V L H F T R M H F S S L P V S I S L L T N L H T L C L S D C A L Q
D I T I V G K L K N L E I L S L A R S V I E A L P E E T A Q L T R L R L L D L S H C S K L Q L I P P N V
L S S L S K L E E L Y L Y N S F V Q W E G E V H S S G R R N A S L D E L K H L S H L T T L Y V H I P
N A E I V P K D L F I E R L E R F S I L I E D E R R W Y S E F E Y S R T L K L K I Y T S I Y L D H A V R
M L L K K T E D L H L Y Q L K G I K N V L D E L I D G V E L P H L K N L H I R N G S E V Q Y I M R K
K I E C A Q L K S M T L E G L P K L I S F W F E D K R C S T S H E E R A T S S N P L P L F N K Q L V
F P C L E S L R L S S I N A E R I W H S P L S E N C T F A A N L K S L T V E G C G E L E H L L S P S V
A R S L V Q L T H F E V A R C Q R L R E I I S T E E I E D E S V A I C F P Q L N S L E I R S L Q N L A
N F C A G N Y N I E F P A L K V L E V N G C P V L K E F I R V N K S E F H V P A L F N E K V A L P S
L E R M E F S Y L K N V K M I F D K Q L L A G S F C K L K A M S V Y H C D A L L T I F S S N I F G A
F Q S L E N L D V Y R C N S L E M I F E V G G L N I R E P H V V H S Q L R S L Y I S S L P A L K H V
W N K D P Q G I L S F Q N L H T V D L S F C R N L K S L F P V S V A K H L Q Q L E N L R L C N S A
V E E I V F S E E G L E E P I G F E F A Q L S S L V L Y N L R E L K C F Y R G Q H T I V W A M L K K
L E T D H S T L L K I V G S N S Q H L G I Q E M N S N D P P E C T T G Q P L F S T E K V I P I L E E L
H L R L T N P D D I S K I C D G H F L Q R F C N L E S L E L S S S E G D D A Q I L P D A V T L P R I K
T L I L S S C N F L K H I W E K K D S E L G H I L Q K L E I L E V N E C G D L T S F G P S S A S F Q N
L T T L E V T Y C N M M I N L A T P S V V Q N L V Q L T T M R I A Y C R G M A E I V A N E G G E
A T P T Y E I N F S K L Q S L E L N R L H R L T S F S P G N Y T I N F P S L Q E L M R V K E S H N D
R K G R W A G D L N T T I Q L L Y S V N V V E G Y H G I C N L K L S D T S P E L M E I W N G R N
P H E I V D L K F L G R V E F C N C S S L K Y I F T L S R L L S L K H L S Y L V V K E C S T L K E V V
M E Q E I E E E A T T D N F I F P N L R Y I K I E S C S S L R C F Y L G S G A L E I P R L E I I E I T D C
```

```
PKMTTFASSFPRDEEKEISADGSEKRVGHGDLNIEPFFSDKVALPSLERL
RIKGMGKCRKIWDQLTVNSFCELKYILVESCEKLSNIFPFNMMERLEK
LEELQIVNCDSLEEIFEPEALTNNQSHGVATTESIVEETMAKFVFPSATYL
RLENLPNLKCFYSRTHATEWPSLKKMVLDCQNVQIFASECPAFGETQG
ASTEINISNQPPLFRVNEVTFPILEELKLKPDDTWHGQVLSTECFSKLKVL
ELICIPEKATDLACCFIQSLPNLEKLLVKDSSFCQIFQFEGLSDDDQRHAA
LTRLSELRLSKLPELTHLWTEEFQPGAAFSNLKLLEVLHCVKLKTLVPSLV
SFNNLTTLKVSGCHGLTNLVTCSIATSLMQLKRMSITDCNMIEEIIACDA
DEIQGAIVFSQLRYLKLSCLPSLASFCLGNQSFDFPTLQKLIVHECPKLEIF
CQGDLTTPKLQQVLLPEYEYEYYDAEEYEDEYDAEEYEENSMWEGDLKS
TIRKLFEEMAEDEDEDEDEDDDEEHEDEDEDEDDDEEHEDEDEDEDDDG
```

Organism Name: *Corchorus olitorius*
Type: DNA
Length: 928
Sequence Name: CC-NBS-LRR2 resistance protein; partial cDNA

SEQ ID NO: 11

```
ATGAAATGTCCTCAACTTTTGTGCCTGATGGATGAAGAGAATGAGCTGCCCTCCAATCTGGAGTATGTG
GAAATTGAAGATTGTAGTAACCTGGCAAAGCTTCCAAATGGGCTACAAAAGCTTCGATCATTGAAAGA
TTTGAGTGTTAAATGGTGCCCCAAACTGATGTCTTTTCCAAATGCAGAGTTGCCATCTACGCTGAAAAC
TTTGTCAATCTTGGGATGTGAATCTTTAGAGTCTTTACCCAAGGGACTGGTGCACAATGGTAGCAGCA
GCATTGGTAGATGTAATCTTGATAACCTGGAGATTCTAGGATGTCCATCTCTTAGATTGTTTTCAACTGG
TGAGCTACCAACTTGCCTTAAGCAACTCGATATTTGGGATTGCATGCAGTTGAAGTGTATTCCAGAGA
GATTGCTGGAGAATAGTCAGTCACTTGAATTTATTCGTATTGGGAACTGCAAAAATTTGAAAACCTTAC
CGCAGTGCCTATACAGGTTTGATTATCTAACTGAGTTGCATGTAAATCAATGCCCTTCCTTGGAGTCTTT
CCCAGAAAAGGGCTTGCCTATTCGCAACCTCAATCTGGTTTTAATATCCAACTGTGTGAATCTTAAGTC
CCTACCAAATCGGATGCATTACCTCACATCCCTGCAGTATTTGACTTTATTTGGTTGTCCAAGTGTAGAA
TCCTTTCCGGAAGAAGAGTTTACTATTCCAACAACTCTTGTCCACCTGCGAGTCCAGAGTCTACCTAAT
CTGGAATATTTATCTAAGGGGCTCCAGGACCTTGTTTTTCTTGAATCATTGGATGTCTGGAATTGCCCTA
AGCTTCAGTACTTGCCAAAGGATGGCCTGCCAAGCATGCTTGGTTTACTTCAGATCAGAAACTGTCCT
CTTCTAGAAAAAAAATGCTTATATGAGAAAG
```

Organism Name: *Corchorus olitorius*
Type: PRT
Length: 309
Sequence name: CC-NBS-LRR2 resistance protein peptide

SEQ ID NO: 12

```
MKCPQLLCLMDEENELPSNLEYVEIEDCSNLAKLPNGLQKLRSLKDLSVK
WCPKLMSFPNAELPSTLKTLSILGCESLESLPKGLVHGSSSIGRCNLDN
LEILGCPSLRLFSTGELPTCLKQLDIWDCMQKCIPERLLENSQSLEFIRI
GNCKNLKTLPQCLYRFDYLTELHVNQCPSLESFPEKGLPIRNLNLVLISN
CVNLKSLPNRMHYLTSLQYLTLFGCPSVESFPEEEFTIPTTLVHLRVQSLP
NLEYLSKGLQDLVFLESLDVWNCPKLQYLPKDGLPSMGLLQIRNCPLLE
KKCLYEK
```

Organism Name: Corchorus olitorius
Type: DNA
Length: 565
Sequence Name: CC-NBS-LRR3 resistance protein; partial cDNA

SEQ ID NO: 13

ATGCCGAGCAATTTTGGTGCATTAACTAATCTTCAACTGCTATCAGATTTTGTTGTGGGCAAAGACAAG

GGATATCAAATAAGGGAGCTACAGGATTTATCAAATCTCAAGGGTTCACTTTATATTTCAGGGTTAGAG

AATGTTGTTGAAACTGAAGATGCATCAAAGGCTAAGATACATGATAAGTCAGGACTAGATAAGTTGGT

GTTAGACTGGAAGAGTGGAATGAAGAAGAATAGAGACTTTGAGAATATAAGAGAAGATGTTGAGCAA

AAGGTGTTGGATTTGCTTGAACCATCTAAACAACTTAAAAAGCTTGTTATTATGCACTACAGAGGTTTG

ATGTTGGCAAAATGGGTGGGAAATTCTTCATTGACTAATTTAGAATCTTTACAGCTTATAAATTGTACCA

ATTGCTTGTCATTGCCATCGCTTGGGGAACTACCATTGTTGAAAAATGGTGATCAGGAGATTGGATA

GTATAAGCAGTGTGGGAGTAGAGTTCCTTGGAGAAAAAACGATGGAACCTTTTCGAGCATTGGAGCT

TTTACAATTTGAAGACA

Organism Name: Corchorus olitorius
Type: PRT
Length: 188
Sequence name: CC-NBS-LRR3 resistance protein peptide

SEQ ID NO: 14

M P S N F G A L T N L Q L L S D F V V G K D K G Y Q I R E L Q D L S N L K G S L Y I S G L E N V V

E T E D A S K A K I H D K S G L D K L V L D W K S G M K K N R D F E N I R E D V E Q K V L D L L E

P S K Q L K K L V I M H Y R G L M L A K W V G N S S L T N L E S L Q L I N C T N C L S L P S L G E L

P L L K N V V I R R L D S I S S V G V E F L G E K T M E P F R A L E L L Q F E D

Organism Name: Corchorus olitorius
Type: DNA
Length: 3141
Sequence Name: NBS resistance protein; complete cDNA

SEQ ID NO: 15

ATGGATCCATTACAAGCTGTTGCAGCTGCAACACAAATAATATCCAGTATGGTTGGGGCTGTTGGAGC

ATTAGAACAAGCCTCCAGAAATCTTGATGAAGCTCCAAAGAGAATCCGAAGCCTAGAAGAATTTGTGT

GTGATCTTGAGAATTTGGCACAACGAATTAGGCAAAAACATGCCAACAAGCTTCACAATGCTCAGTTA

GATTACCAACTTCAAAGTTTGCATGCCCTTATAGAAAGGCTGCGCCCAAACATCAGGAAGGCAAGAA

CAGTTGTATCAAAAAGTAAAATCAAGAACTTGGCTAAGGTATTCTGGAATTCCATGGCCGGAGATCCG

CTTGGAAAACTGACAGTTTTAATTAAAGATGACTTAAATTGGTGGCTTGATACTCAAATGTTGGCACAA

AATGTTGAGAAAGTACTAGAATCAACCGCACAAGATACGCCAGTTCGATTGAAAATAAAGACTGATCA

AGGCTACCCAACTTCTAGTAAATGTATCTTTGTGAAGGAGTTGCTTGAACAGGAGGATACTCATCGAG

TCATTCTAATTGTTGGGTTATCTGGTATTGGAAAGTCTTGTTTAGCTCGTCAAGTAGCTTCTGATCCACC

CAAAAAATTTGCAGGTGGAGCACTTGAACTTGGATTTGGGCAATGGTGTAGTCGTGCTGCTTGCAAT

GGCAGTAAGGTTGAATATCAGAAGCGTTTGGCAAGGAAAATTAGTAAATTCCTGGTGCAGATTGGGT

TCTGGAAAAAGATTAAGGAGGAGAATAGTGGAGATCTTGATTATGTTTGTTACTTGCTTCAAGAAGCC

TTGTATGGGAAAAGCATTTTAGTCCTTCTTGATGATGTATGGGAGCAGGACATAGTTCAGCGGTTTGCT

AAACTGTATGATAACAATTGTAAGTACTTAGTAACAACAAGAAATGAAGCCGTCCATGAAATTACAGAA

GCTGAAAAGGTAGAGCTAAGCAAGGATGATATAAGGGAGATAAGCAAGGGAATCCTTCTGTACCATA

GCCTCCTTAGTGAAGAAGAGCTTCCGGGTATAGCAGAGAGCTTACTTGAACGGTGTGGCCACCACCC

TCTAACAGTTGCTGTTATGGGAAAGGCTCTTAGAAAAGAAGTAAGAGCTGAGAAATGGGAGAAGGCT

ATAACCAACCTATCAACTTTTGCTACATGCGCACCAGGTCCAGTCTCATATGTGAATGAGAAAGATGCT

GAGGACACATTAACCATTTTTGGTTCATTTGAGTTCAGTCTAGAAGCAATGCCTGTTGACTCAAAGAG

ACTCTTCATCGCTCTTGCTTCTCTTTCATGGGCAGAACCGGTACCAGAAGCATGCATAGAGGCTATATG

```
GTCATGTATCGGGCAGGAGAGCTTGTTTTCACTCATTGTCTGCAAGCTTGTCGAAGGGTCTTTATTGAT

GAAGGTAGACATGGATCCACTATACCAAGTACATGACATGGTTTCATTGTACCTTGATAGCAAGACTAC

TGATTCAATTGAGATGCTACTGCATAGATCTAAACCAGAAGAAACTGCATTTATTTGCCCTTGGCTTCTT

ATTTTTGGGAAAGAGAATGTGAAAAAGATTGTTGAAGAGAGGATGAAGCTTTTCTTTGATATTTTAGA

TGAAAAACAAGTGGTTATCACCTTAGAATCCAGTATTGAGGCTCTAATGGCAAGCAAATCCATATCTGA

ACTCGAAGCAAGCAGAGCAAGCTTTAGTAGGATATTGGGACCCAAGATTACGGATATTGTCTCAACTA

ATTCACAGAGTATGATTGCAGTGTCTGCAGAAGCATCATAATCATTTTTATAAGACTGATTATTGCAA

CTATTTTCCATCCCTTGAAACTGACAGTACAGTTGATAAGTTGGCAAGTATGTTAGAAGATTGCGAAGA

TCCTGTAATCCAAACAAACATTTTAACCATCCTTGCCAAGATTGCTGAGTTTGGAAGCCCGGAGATTGT

TGATAAGGTGCTTCAAAGTATCCCCTTTAACCAGGTTGCTGACTTGCTCTCTCCCAATGCCAAGGATTG

GCATGAGAGCATGTTTACAATATTGATGTCTTTGACCAAAGCTGGAAAGTCAAAAGCTGTTGAAAGAA

TGTTTGCTTTTCAGATTGATAAAAATCTGATTAACCTTATAGAGAGTGAATCTGAACTAGTGCAACACCA

TGCCATTGTCACTTTGAAGGCATTTTATGAGCTGGCTGGCCCTTCTTTGAATAGTTCTCTTCGACCTGCT

AATCTAGACCTCTTGCCATGGCAAGTGAGACTTCGTTTAGAGAGATTTGTTATGCCAGACCGGAACAT

TCCCCTTTCCCCGAAACCACAAACTTTTGAAGATCTTATCCACAAGATGCTAGATAATGACAACAAACA

GGTGTTGGAGGCTATGCAGGATCTTGTGCCGATAATTGAAAAGGCTGGAGACCCAGGTTTCAGACAG

ATGATTGTTCAAAGTCCCCTAATTAGAAGGTTATCAGAACTTCTGCAACATGGACATACCGAACAAAAT

TCTATAAGATCAGAATCTGCATTTTTACTAATGAAGCTAGCTTACTCTGGTGGGAACCCTGCATCAATA

AGTTTCTAGAGTTTGATGTTATTCCTGAGCTGGTAAAGATGATGCAGTGCAACACTGCAGAGTTGCAG

GATTCAGCCTATACAGCTCTGCACCAAATGCTTTTTGGCAATGGTGGGGTTCTTGTTTTGAGTAAGATC

TTCAAAATGGGTCTAATAGACAAGATTCCTTATGCACTTGAGAGCAAATCTGCGAAGACTCGGGAAGT

CCTGCTGCATTTTGTATTTGATATTGTTGAGCTGGGAAGCAAAGCCTGCTTAGAGAAAATGCTATCTTT

GCAAGTTGTGGAGAAACTCACCAAGTTAGAAAAAAGTGGTGGGGCTCTGGTGAAATTGTGATTGG

ATTTCTGAAGGCGATGGATAAGTGTAAGCATCTCACAGTAGCGGAGCGAAAGGTGATGAAACAACAG

GTGGTTAGAAAGGTAAGAGCCTCCTTGAAAGGCCACAAATTCGAAACTCGGATTTTAGCGGCTGTAG

AAGCTTTCCTCTCTGGAGGGTCAAGGGGTGCAAGTGGTAGTGGCAGTGGTCGGAATAGGAAGTAA
```

Organism Name: *Corchorus olitorius*
Type: PRT
Length: 1046
Sequence name: NBS resistance protein peptide

SEQ ID NO: 16

```
M D P L Q A V A A A T Q I I S S M V G A V G A L E Q A S R N L D E A P K R I R S L E E F V C D L E

N L A Q R I R Q K H A N K L H N A Q L D Y Q L Q S L H A L I E R L P N I R K A R T V V S K S K I K

N L A K V F W N S M A G D P L G K L T V L I K D D L N W W L D T Q M L A Q N V E K V L E S T A

Q D T P V R L K I K T D Q G Y P T S S K C I F V K E L L E Q E D T H R V I L I V G L S G I G K S C L A

R Q V A S D P P K K F A G G A L E L G F G Q W C S R A A C N G S K V E Y Q K R L A R K I S K F L V

Q I G F W K K I K E E N S G D L D Y V C Y L L Q E A L Y G K S I L V L L D D V W E Q D I V Q R F A

K L Y D N N C K Y L V T T R N E A V H E I T E A E K V E L S K D D I R E I S K G I L L Y H S L L S E E E

L P G I A E S L L E R C G H H P L T V A V M G K A L R K E V R A E K W E K A I T N L S T F A T C A

P G P V S Y V N E K D A E D T L T I F G S F E F S L E A M P V D S K R L F I A L A S L S W A E P V P

E A C I E A I W S C I G Q E S L F S L I V C K L V E G S L L M K V D M D P L Y Q V H D M V S L Y L

D S K T T D S I E M L L H R S K P E E T A F I C P W L L I F G K E N V K K I V E E R M K L F F D I L D

E K Q V V I T L E S S I E A L M A S K S I S E L E A S R A S F S R I L G P K I T D I V S T N S Q S M I A
```

```
V S A E A I I I I F S K T D Y C N Y F P S L E T D S T V D K L A S M L E D C E D P V I Q T N I L T I L A

K I A E F G S P E I V D K V L Q S I P F N Q V A D L L S P N A K D W H E S M F T I L M S L T K A G

K S K A V E R M F A F Q I D K N L I N L I E S E S E L V Q H H A I V T L K A F Y E L A G P S L N S S L

R P A N L D L L P W Q V R L R L E R F V M P D R N I P L S P K P Q T F E D L I H K M L D N D N K

Q V L E A M Q D L V P I I E K A G D P G F R Q M I V Q S P L I R R L S E L L Q H G H T E Q N S I R

S E S A F L L M K L A Y S G G E P C I N K F L E F D V I P E L V K M M Q C N T A E L Q D S A Y T A

L H Q M L F G N G G V L V L S K I F K M G L I D K I P Y A L E S K S A K T R E V L L H F V F D I V E

L G S K A C L E K M L S L Q V V E K L T K L E K S G G G S G E I V I G F L K A M D K C K H L T V A E

R K V M K Q Q V V R K V R A S L K G H K F E T R I L A A V E A F L S G G S R G A S G S G S G R N

R K
```

Organism Name: *Corchorus olitorius*
Type: DNA
Length: 3009
Sequence Name: Leucine-rich repeat trans-membrane protein kinase (LRR-TM-PK); complete cDNA

SEQ ID NO: 17

ATGGGAAGAGCTGATTTTACAACTACTACTCCAAAGCTGCTACTTCTACTTGTTTTCATTGCAATGCTCT

GGCTTTCAACCTTTGGATTTGCTGCTGCTACTCCTCTTCTTCATTCTGAAGAAGTGAAGGCACTGAAA

GCAATAGGGAAGAAGATGGGGAAGAAGGATTGGGATTTTGGGGTGGATCCTTGCAGTGGAAAGGG

GAAGTGGATTGAGGGAGATGAAGAAACTGGATTTGCAAGCAAGGTCACCTGCAATTGCTCTTTCAAC

AACAACACCACCTGCCATGTAGTAACCATGGACCTAAGTCGCAACTACTTCACAGGTTCTATTCCTAAA

GAATGGGCTACCATGAAGTTGGACATGCTCTCTTTCATGGGGAACCGGTTGTCTGGTCCATTCCCAAA

AGTTCTTACCAACATCACAAGCCTCACAAACTTGTCTATTGAAGGGAACAACTTTTCAGGACCCATTCC

TCCAGAGATTGGAAAGTTGATCAATTTACAGAAACTTGTTCTCTCATCTAATGCCTTAAGTGGAGAATT

GCCTGCAGAACTAGCCAAGTTGGTCAACTTGACTGATATACGGTTTAGCGACAATAACTTCTCTGGAA

AGATACCTGATTTTATCAGTAACTGGAAGCAGATTCAAAAACTGCAGTTTCAAGGTTGCTCTCTTGAG

GGGCCTATACCTTCCAGCATTTCTACTTTGACTAGCTTATCTGATTTGAGGATTAGTGACTTGAAAGGC

AAAGGGTCCCCATTTCCGCTATTGCGTAACCATGACTCACTGAAGACATTGATACTAAGGAACTGCAA

GATACATGGAGAAATCCCAGAGTATATTGGGGATATGAAGAAATTGAAAACCCTGGATCTCAGCTATAA

TAACTTGACTGGAGAAATTCCCAGTTCATTCTACAAACTGACAAAAGCTGATTTCTTGTATTTGACTCG

GAATCAGCTCACCGGGTCTGTCCCTGAGTGGATCCTAGAAAGAAATAAAAATGCGGATATATCTTTCAA

CAATTTCACCTGGGACACATCAAGTCCAATAGAATGTCCTCGAGGGAGCGTGAACTTGGTTGAGAGCT

ACTCCACACCAACAAATAAACTAAGTAAAGTTCATTCATGTCTAAAACAGAATTTCCCATGTTCAGCTTC

AACTAGTCAACATAAATACTCCTTGCACATAAATTGTGGGGGCAGGAATTAAATGTCAATGGTGATGC

CAAATATGAAGCTGATATGGAACCAAGAGGTGCTTCCATGTTTTACCTGGGGCACAACTGGGCATTAA

GCAGCACTGGAAACTTCATGGATAACGATATTGATGCAGATGACTATATTGTTACCAATACTTCTGCATT

GTCCAATGTATCTGCAACTCATTCCGAACTCTACACAACTGCGCGTGTTTCTCCCCTCTCTCTCACATACT

ATGGACTCTGCCTAGGGAATGGGAACTACACTGTTAATCTTCATTTTGCAGAGATTATTTATATAAATGA

TCGATCATTTTACAGCCTTGGGAAACGCATATTCGATGTCTATATTCAGGGAGAATTGGTGCTGAAAGA

CTTTAATATTCAAGATGAAGCTGGAGGTACTGGTAAGCCCATTGTAAAGAACTTTACAGCCGTCGTGA

CAAGAAATACATTAAAAATCCACTTATACTGGGCTGGAAGGGGAACAACAGGCATACCAGCAAGGGG

GATGTATGGTCCACTCTATATCAGCTATATCAGTGGTTTCAAACTTTGAGCCCCCAACTGTTGTTGGCAA

GAAGAATTATCTCATAATTGCGGCAGGGGCAGCTTCTGCAGCAATACTTATAGTCCTTATGGTCTTAGG

TATCATTTGGAGAAAAGGCTGGCTGGGAGGCAAAATCTCTGCTGAAAACGAGCTGAAAGACCTGGAT

-continued

```
CTGCAAACAGGAATTTTCAGTCTAAGGCAGATTAAAGCTGCCACCAACAACTTCGATGCTGAGAACA

AAATTGGTGAGGGTGGATTTGGTTCTGTTTACAAGGGTTTATTATCAGATGGGACAGTTATCGCAGTG

AAGCAGCTTTCATCAAAATCTAAGCAGGGAAATCGTGAATTTGTGAATGAAATAGGCATGATATCTGCA

CTGCAGCATCCGAATCTTGTGAAGCTCTATGGATGTTGTGTAGAAGGAAACCAGTTATTGCTAGTTTAT

GAGTACATGGAACATAACTGTGTATCTCGTGCTCTTTTTGGGAAGGGCTCAACACCCAAATTGAAACT

GGACTGGTCTACCCGGAAAAACATTTGCCTTGGTATTGCCAGGGGTTTGGCCTACCTCCATGAAGAGT

CGAGAATTAAAATTGTGCACAGGGATATTAAAACAAGTAATGTGTTGCTTGACAAGAATCTAAATGCAA

AAATTTCTGATTTTGGTTTGGCAAAGCTAAATGATGATGACAAAACCCACATCAGCACTCGTATAGCCG

GGACAATTGGTTATATGGCTCCTGAGTATGCAATGCGTGGATACCTAACCAGCAAAGCTGATGTCTATA

GCTTTGGTGTTGTTGCATTGGAAATTGTTAGTGGAAAGAGCAACACAAACTACAGACCAACTGAGGA

CTTTGTTTACCTTCTTGACTGGGCCTATGTTTTGAGAGAGAGGGGAAGTTTGTTGGAGTTGGTTGATC

CAGAGTTGGGATCAGAGTACTCATCAGAGGAGGCAATGGTGATGCTGAATGTGGCTCTACTATGCACC

AATGCAGCCCCCACCCTGAGGCCTACCATGTCACAGGTTGTGAGCATGCTCGAAGGCCAAACCTCAG

TTCAAGACATCCTCTCCGACCCTGGATTTTCATCCATGAATTCGAAATTCAAGGCCTTAGTTAATCACTT

CTGGCAAAATCCAAGCCAAACAATGAGTTGTCAAGCAATGGCCCAAATACAGATTCCTCAAGTTCAA

ACATAGAAGACATAGAAGAGAATAGTCATCTTTTGAGAGTTAGTTCTATTCAATCCGAGGCGTGA
```

Organism Name: *Corchorus olitorius*
Type: PRT
Length: 1002
Sequence name: Leucine-rich repeat trans-membrane protein kinase (LRR-TM-PK) peptide

SEQ ID NO: 18

```
M G R A D F T T T T P K L L L L L V F I A M L W L S T F G F A A A T P L L H S E E V K A L K A I G K

K M G K K D W D F G V D P C S G K G K W I E G D E E T G F A S K V T C N C S F N N N T T C H V

V T M D L S R N Y F T G S I P K E W A T M K L D M L S F M G N R L S G P F P K V L T N I T S L T

N L S I E G N N F S G P I P P E I G K L I N L Q K L V L S S N A L S G E L P A E L A K L V N L T D I R F

S D N N F S G K I P D F I S N W K Q I Q K L Q F Q G C S L E G P I P S S I S T L T S L S D L R I S D L

K G K G S P F P L L R N H D S L K T L I L R N C K I H G E I P E Y I G D M K K L K T L D L S Y N N L T

G E I P S S F Y K L T K A D F L Y L T R N Q L T G S V P E W I L E R N K N A D I S F N N F T W D T S

S P I E C P R G S V N L V E S Y S T P T N K L S K V H S C L K Q N F P C S A S T S Q H K Y S L H I N

C G G Q E L N V N G D A K Y E A D M E P R G A S M F Y L G H N W A L S S T G N F M D N D I D

A D D Y I V T N T S A L S N V S A T H S E L Y T T A R V S P L S L T Y Y G L C L G N G N Y T V N L H

F A E I I Y I N D R S F Y S L G K R I F D V Y I Q G E L V L K D F N I Q D E A G G T G K P I V K N F T

A V V T R N T L K I H L Y W A G R G T T G I P A R G M Y G P L I S A I S V V S N F E P P T V V G K

K N Y L I I A A G A A S A A I L I V L M V G I I W R K G W L G G K I S A E N E L K D L D Q T G I

F S L R Q I K A A T N N F D A E N K I G E G G F G S V Y K G L L S D G T V I A V K Q L S S K S K Q G

N R E F V N E I G M I S A L Q H P N L V K L Y G C C V E G N Q L L L V Y E Y M E H N C V S R A L F

G K G S T P K L K L D W S T R K N I C L G I A R G L A Y L H E E S R I K I V H R D I K T S N V L L D K

N L N A K I S D F G L A K L N D D D K T H I S T R I A G T I G Y M A P E Y A M R G Y L T S K A D V

Y S F G V V A L E I V S G K S N T N Y R P T E D F V Y L L D W A Y V L R E R G S L L E L V D P E L G

S E Y S S E E A M V M L N V A L L C T N A A P T L R P T M S Q V V S M L E G Q T S V Q D I L S D

P G F S S M N S K F K A L V N H F W Q N P S Q T M S L S S N G P N T D S S S S N I E D I E E N S

H L L R V S S I Q S E A
```

Organism Name: *Corchorus olitorius*
Type: DNA
Length: 1989
Sequence Name: Leucine-Rich Repeat containing protein 1 (LRR1); partial cDNA

SEQ ID NO: 19

AGAATTTGTTGTCAGTAAGATCCAACAGTCCATTGTGGCCAGGTTGGGATTGCCATGGGAAGAAAAT

GATTCCTATGAGCTACAAACTTCAAAGATTCACAATGTTTTAAAAAATAAGAGGTTCCTCCTATTGCTG

GATGATGTTTGGGAAGGAATTGATCTTAGTGAAATTGGGATTCCTCTTCCTGATGAGGAAAATAAATGC

AAGCTGATATTTACAACGCGGTCCATGGATGTTTGCACTGACATGGATGCTCATAGGAAGCTCAAAGT

AGAATTTCTGGACGAGGAGAAATCATGGCGATTATTCTGTGAGAAGGTTGGAAGAATGGAGATTTTA

GAGTCACCACCTGTTAGAACTTATGCTGAGACCATTGTCAGGAAATGTGGAGGTCTACCGCTTGCCTT

AATCACTGTGGGGAGAGCCATGGCCAATAAGGAGACTGAAGAAGAATGGAAATATGCAATTGAATTA

CTCAACAAATCTCCTTCTGAACTTAGAGGTATGGAAGATGTCTTTACCCTTTTAAAGTTTAGCTATGACA

ATTTGGATAGTGAAACAACAAAAATGTGCTTTTTGTATTGTTCTCTTTTCCCGGCAAGCTGTTCCATTG

AGAAACAACAGCTTGTAGAGTATTGGATTGGTGAAGGATTCCTAGACAGTTCTAATGCTCATAATAAA

GGGTTTGCTGCAATTGGGTCCCTAAAAGTAGCTTGTTTATTGGAAACAGGCGATGAGGAAACCCAAG

TAAAGATGAATGATGTTATCCGAAGTTTTGCCTTATGGATAGCATCTGAATCTGGGGTAAATAAGGGAA

ACCTTTTGGTAGAAGCAAGCTTGGGCCTTATTGAAGCTCCTGGAGTTGAAAACTGGGAAGAAGCAAA

AAGGATTTCCTTGTTAGACAATGGAATCACAGTACTAGAACAAGTACCAATATGCCCAAATCTGTTGAC

TCTGTTGCTTCAGTGGAATAATGGTCTGAATCGAATAGCAGCTAACTTTTTTCAATCTATGCCTGCTCTT

AGAGTCTTGGATTTGTCATTTACAAGCATTAGAAAGATCCCAGTAAGCATCAGTCAATTAGTAGAGCTT

CGGCATCTTAATTTAGCAGGTACAAAAATAACAACATTGCCTAGGGAGCTAGCAAGTTTAGCAAAGCT

GAATTACTTGAATCTCTCACGCACATATTCTCTTCGAACGGTTCCACGTGAGGCTTTATCTGGACTTTCA

GAGTTAGTGGTCTTGAATTTGTATTACAGTTATGAGGTTCGCGAAGTTCGGAATTTTGAAGGTGAAGG

TGAAGTTGAATTTGAGGTATTGGAGACCTTGACACAACTCCGTATCCTTGGTTTAACAATCTCCTCAAT

AGCCTCCCTGAATAGACTCTTTGGTTTGAGAAATCTGGTTAGATGCATACACTATTTACTCCTAAAGGA

GTGTGAAGGTTTAACAGAATTAGTATTTTCATCAGCTTCTGGCTTAACATTGAGAAGACTTAGCATCAC

AGACTGCTATGATTTCAATTACTTAGTAGTGAATGCTGAGGTGGACAAAAGTGGTTGCCTAATTTGGA

GGTTTTATCTTTGCATGGTCTACCAAAAGTGACTTCAGTGTGGAAATCCCCAGTAAGAAAAGCAAGCC

TGCAAAATTTGCGCTTGTTGAATATCTGGTATTGTCATAGCTTGAAGAATGTTTCTTGGGTATTACTACT

TCCAAAGTTAGAAGCAATTTACTTGTTCTATTGCAAGAAAATGGAACAAGTTGTAAGTGGAGAAGAG

GGACTACTAGAGCCTGATCCAAGGCATTTTCAAGGCTTAAAACTATAGAGATCCGCGACCTTCCTGA

ATTAAAGAGTATCAGTCCATGGAATTGGCTTTCCCCTGCTTGAAGAGCATTGCTGTGATTGATTGTCC

AAAGCTGAAGAAACTACCAATTGGAACCCATAATTCCTCAACTCTTCCAACTGTGTACTGTAGTGAAGA

ATG

Organism Name: *Corchorus olitorius*
Type: PRT
Length: 662
Sequence name: Leucine-Rich Repeat containing protein 1 (LRR1) peptide

SEQ ID NO: 20

E F V V S K I Q Q S I V A R L G L P W E E N D S Y E L Q T S K I H N V L K N K R F L L L L D D V W E

G I D L S E I G I P L P D E E N K C K L I F T T R S M D V C T D M D A H R K L K V E F L D E E K S W

R L F C E K V G R M E I L E S P P V R T Y A E T I V R K C G G L P L A L I T V G R A M A N K E T E E

E W K Y A I E L L N K S P S E L R G M E D V F T L L K F S Y D N L D S E T T K M C F L Y C S L F P A

S C S I E K Q Q L V E Y W I G E G F L D S S N A H N K G F A A I G S L K V A C L L E T G D E E T Q

V K M N D V I R S F A L W I A S E S G V N K G N L L V E A S L G L I E A P G V E N W E E A K R I S

-continued

LLDNGITVLEQVPICPNLLTLLLQWNNGLNRIAANFFQSMPALRVLDLSF

TSIRKIPVSISQLVELRHLNLAGTKITTLPRELASLAKLNYLNLSRTYSLRT

VPREALSGLSELVVLNLYYSYEVREVRNFEGEGEVEFEVLETLTQLRILGL

TISSIASLNRLFGLRNLVRCIHYLLLKECEGLTELVFSSASGLTLRRLSITD

CYDFNYLVVNAEDGQKWLPNLEVLSHGLPKVTSVWKSPVRKASLQNL

RLLNIWYCHSLKNVSWVLLLPKLEAIYLFYCKKMEQVVSGEEGLLEPDPK

AFSRLKTIEIRDLPELKSISPWTLAFPCLKSIAVIDCPKLKKLPIGTHNSST

LPTVYCSEE

Organism Name: *Corchorus olitorius*
Type: DNA
Length: 1258
Sequence Name: CCH-type integrase; partial cDNA

SEQ ID NO: 21

AGATTTATACCAATTAGTGGAAATGAAAATACAGATTGGCCAACGGCGGATTATGAGTGGATTAAGCCT

TGCAGTTTAGAAGAATGCAAAACTCAATGCTTGCAAGATTGTCTTTGTACTGTGGCAGTGTTCAATGA

GAATGGCTGTTGGAAGAAGGCGCTACCGCTGCCATTTGGTAGGCAAGACCCAGATGTGAAATCCAAC

TCCTACCTGAAAGTAAGAAAACCAGAATTTTCCCAGAAAAACCCTCTTCCATTTCTAGACACTAAAAAG

AACCAAAATTCATTGGTAATTCTGGTTTCAGTTCTCTTGGGTAGCTCTGTGTTTGTCAACTTTATATTGG

TTGGGGTTTTATGTTCGGGATCGTTTTTCCTGTATCAGAAAAAGATTGCAAGAAATGGGAGAAAGTAC

AAGAATGGGATACAGAACAATTTGAGGTGTTTTAGTTACAAGGAGCTTGAAGAAGCTACAAATGGTT

TCAAGGAAGAGCTAGGAAGGGGAGCATTCGGCATAGTTTATAAAGGGCTAATAAAACAGATGCTCA

AGATCCAACTGAAGCTGCAGTTAAGAAGTTAGACAGAGTGGTTCAAGACAAAGACAACGAATTCAG

AACTGAAGTGAGTGTGATTGCTCAAACACATCATAGGAATCTGGTCAAGTTGCTTGGATATTGTGACG

AAGGTCAGTGTCGGATGCTGGTGTATGAATACTTAAGCAATAAAACATTAGCAAGCTTTCTTTTTGGG

GATCAAAAACCCAGTTGGAACCAAAGGAAACAGATTGCTTTGGGAATTGCAAGAGGATTGCTTTACT

TGCATGAGGAATGCAGCCCTCAAATAATCCATTGTGATATAAAGCCTCAAAACATACTTCTTGATGATTA

CTATGAAGCTCGGATATCTGACTTTGGGTTGTCAAAGCTTCTAGGGACTGACCAATCATATACTAATACC

GCCATAAGGGGAACGAAAGGGTATGTCGCGCCAGAATGGTTCAAGACAGTGCCTGTATCCGTGAAGG

TTGATGTGTATAGCTTTGGTGTCCTGCTGCTAGAAATCATTTGTTGTAGAAGAAATGTAGACATGGATAT

TGGCAAAGCGAAAATGGAAATTTTGACAGATTGGGCTTGTGATTGCTTCCTGGAAGGCACTTTAGAT

GCTCTTGTTGACAATGATGCAGACGCCTTAAGCGACAAGGCGAAGCTTGAGACCTTTGTTATGGTTGC

CATTTGGTGCATTCAAGAAGACTTGTCTCTCA

Organism Name: *Corchorus olitorius*
Type: PRT
Length: 419
Sequence name: CCH-type integrase peptide

SEQ ID NO: 22

RFIPISGNENTDWPTADYEWIKPCSLEECKTQCLQDCLCTVAVFNENGC

WKKALPLPFGRQDPDVKSNSYLKVRKPEFSQKNPLPFLDTKKNQNSLVI

LVSVLLGSSVFVNFILVGVLCSGSFFLYQKKIARNGRKYKNGIQNNLRCF

SYKELEEATNGFKEELGRGAFGIVYKGLIKTAQDPTEAAVKKLDRVVQ

DKDNEFRTEVSVIAQTHHRNLVKLLGYCDEGQCRMLVYEYLSNKTLASF

LFGDQKPSWNQRKQIALGIARGLLYLHEECSPQIIHCDIKPQNILLDDYY

EARISDFGLSKLLGTDQSYTNTAIRGTKGYVAPEWFKTVPSVKVDVYSF

G V L L L E I I C C R R N V D M D I G K A K M E I L T D W A C D C F L E G T L D A L V D N D A D A

L S D K A K L E T F V M V A I W C I Q E D L S L

Organism Name: *Corchorus olitorius*
Type: DNA
Length: 2362
Sequence Name: TIR-NBS resistance protein; partial cDNA

SEQ ID NO: 23

```
ATAGGATTGCATGGTTGCAAACCTTCGTTACTGAGGTTTGCAAATTGGCTCCGTGCTGAGTTGGAAGT

TCAAGGGATGAGTTGCTTTGTATCTGATAGAGCTCGGTTCAGGAACTCTCGTAAGCATGGAATTATTGA

AAGGGCAATGGATGTTTCTTCATTCGGTGTTGTAATCCTAACGAGGAAGTCTTTCAGGAATCCATATAC

TATTGAGGAGCTCAGATTTTTCTCGAGCAAGAAAAATTTGGTCCCGATCTATTTTGATCTGCGTCCTGG

TGATTGCCTTGTCCGGGATATTGTTGAGAAGAGAGGAGACTTGTGGGAAAAACATGGGGGTGAATTA

TGGGTTTTCTATGGAGGATTGGAGAAGGAGTGGAAGGAAGCTGTTAGTGGCCTTTTCCGAGTGGATG

AATGGAAACTGGAAGCTCAGGATGGTAATTGGAGAGACTGCATATTAAGGGTTGTTACCATTTTGGCA

ATGAAGTTAGGAAGAAGAAGTGTTGTAGAGCGATTGACAAAGTGGAAAGAAAAGGTAGACAAAGA

GGAATTCCCATTTCCTCGAAATGAAAATTTTATTGGCCGAAAGAAAGAATTGTCAGAGCTAGAATTTAT

ACTTTTTGGTGATATTAGTGGAGAATCAGAAAGAGATTATTTTGAGCTCAAGGCTAGGTCAAAGAGAA

GAAATTTGACAATTGGGTGGAGTAAGAGCACTTCAGTGGAGGAAAGACGTAGGGAAAGACAGCGG

GAGGATGGCAGCCGGAAGGGCAAAGAACCTGTGGTTTGGAAGGAGTCAGAAAAGGAGATTGAGAT

GCAAAGCACAGAAAGACAGCACTATCAAAGACCAAGAGGTGGACGGAATTCACAGAGAAAGAGATC

AGCGAAAGTTGTCTATGGGAAGGGCATTGCCTGTGTAACAGGGGAATCAGGACTGGGGAAAACTGA

GCTTCTTCTGGAGTTTGCCTATAAATATCACCAGAGGTATAAGATGGTCCTGTGGATAGGAGGGGAAA

GCAGGTATATTAGACAGAATTATCTAAACCTCTGGTCATTTTTAGAAGTTGACGTAGGGGTTGAAAATT

GCACAGATAAAAGCAGGATGAAAAGCTTTGAAGAGCAGGAAGAGGCTGCCATTTCTAGAGTCCGGA

AAGAGCTAATGAGAAACATTCCTTTTCTGGTGGTGATTGATAATTTAGAGAGTGAAAAGGATTGGTGG

GATCGCAAGCTTGTAATGGATCTTCTTCCCCGTTTTGGCGGAGAGACCCACATTCTGATAGCTACGCGC

CTTCCCCGTGTGATGAATTTAGAACCTTTGAAACTGTCATACTTGTCTGGAGTAGAGGCAATGTCATTA

ATGCAGGGTAGCGGCAAAGACTACCCTATTGCTGAGATTGATGCGCTTAGGGTCATTGAGGAGAAAG

TTGGAAGGCTGACTTTGGGCCTTGCTATAGTAGGCGCAATTCTATCTGAACTACCCATAAATCCAAGCA

GGCTATTGGATACCATCAACAGAATGCCCTTGAGAGACTTTTCATGGAGTGGTAAGGAAGCTTATTCG

CTGAGGAAAACAGTTTCCTCCTGCAACTCTTTGAGGTATGTTTTTCAATATTTGATCATGCAGAGGGA

CCAAGGAGCTTAGCAACGAGAATGGTCCAGGTGAGTGGTTGGTTTGCACCTGCTGCCATTCCTGTTT

CCCTGTTAGCCATGGCTGCTCACAAGATACCTGAGAAACATAAAAGGACCCGCTTTTGGAGAAGATTA

TTGCGCTCCTTAACTTGTGGGCTTTCTTCATCATACTCCAAGAGGTCTGAAACAGAAGCATCTTCAATG

TTGTTGAGATTTAATATTGCACGAAGCAGTACCAAGCAAGGTTATGTTCATTTTAATGAGCTCATCAAG

GTTTACTCTCGGAAGAGAGGAGTTGCTGGAGTTGCACATGCCATGGTCCAAGCTGTTGTTAGTCGTG

GATCAATTTTAGATCACTCAGAACATATGTGGGCAGCATGCTTTTTGCTATTTGGATTTGGTAATGATCC

TACAGCTGTTGAGCTCAAGGTGTCGGACCTATTATACCTTGTCAAAGAGGTGGTTTTGCCTCTTGCAAT

TCGGACATTCATTACATTCTCTAGGTGCAGTGCTGCTCTTGAACTCCTCCGGCTCTGTACCAATGCTTTG

GAGGCAGCAGATCAAGCATTTGTTACACCAGTTGAAAAATGGTTGGACAAATCACTTTGTTGGAGGC

CCATTCAAACTAATGCTCAGTTAAATCCATATCTTTGGCAGGAGTTGGCATTATCAAGAGCTACTGTGCT

AGAAACCAGGGCCAAGTTGATGCTAAGAGGGGGGCAATTTGACATAGGAGATG
```

-continued

Organism Name: *Corchorus olitorius*
Type: PRT
Length: 787
Sequence name: TIR-NBS resistance protein peptide

SEQ ID NO: 24

I G L H G C K P S L L R F A N W L R A E L E V Q G M S C F V S D R A R F R N S R K H G I I E R A M

D V S S F G V V I L T R K S F R N P Y T I E E L R F F S S K K N L V P I Y F D L R P G D C L V R D I V

E K R G D L W E K H G G E L W V F Y G G L E K E W K E A V S G L F R V D E W K L E A Q D G N

W R D C I L R V V T I L A M K L G R R S V V E R L T K W K E K V D K E E F P F P R N E N F I G R K

K E L S E L E F I L F G D I S G E S E R D Y F E L K A R S K R R N L T I G W S K S T S V E E R R R E R

Q R E D G S R K G K E P V V W K E S E K E I E M Q S T E R Q H Y Q R P R G G R N S Q R K R S A K

V V Y G K G I A C V T G E S G L G K T E L L L E F A Y K Y H Q R Y K M V L W I G G E S R Y I R Q N

Y L N L W S F L E V D V G V E N C T D K S R M K S F E E Q E E A A I S R V R K E L M R N I P F L V

V I D N L E S E K D W W D R K L V M D L L P R F G G E T H I L I A T R L P R V M N L E P L K L S Y

L S G V E A M S L M Q G S G K D Y P I A E I D A L R V I E E K V G R L T L G L A I V G A I L S E L P I

N P S R L L D T I N R M P L R D F S W S G K E A Y S L R K N S F L L Q L F E V C F S I F D H A E G P

R S L A T R M V Q V S G W F A P A A I P V S L L A M A A H K I P E K H K R T R F W R R L L R S L T

C G L S S S Y S K R S E T E A S S M L L R F N I A R S S T K Q G Y V H F N E L I K V Y S R K R G V A

G V A H A M V Q A V V S R G S I L D H S E H M W A A C F L L F G F G N D P T A V E L K V S D L L

Y L V K E V V L P L A I R T F I T F S R C S A A L E L L R L C T N A L E A A D Q A F V T P V E K W L D

K S L C W R P I Q T N A Q L N P Y L W Q E L A L S R A T V L E T R A K L M L R G G Q F D I G D

Organism Name: *Corchorus olitorius*
Type: DNA
Length: 2565
Sequence Name: Resistance gene analog 1 (RGA1); complete cDNA

SEQ ID NO: 25

ATGGCGGATGCAATAGTCAATGTATTCTTGGAAAAGCTGTTAAGCACTCTTGCAGAGGAAGGCCGCTA

TGTTACTGAATTCAGGGATCAGTTTGAGAAACTACAAACTGAGCTTCAATTGCTGCAATGCTTCCTCAA

GGATGCAGATAGGCTGAAGAGGAAAAATCACACTATACGAAAAATCTTGGCTGATCTTCGCGAGTTAA

TATATGAAGCTGAAGATATCCTAGCAGATTGCCAGCTTCAGTCAAGGGATGAAAACCAATTTTCCCAAA

GCTGGTTAGCTTGTTTCTCTCCACCAAAGCTTCATTTCAAGTACCAAAGTGGGAAGCGTCTTAAGGAA

ATTACTGAGAAAATCACAAGCATTAAACAAAACATCTCATCATTCCTTGGAGGGCCTCTTTTATTCCAAC

CAGAGGTCATAAGCGCGCAGGACCAAATGCCTAGATGGAGTTCGCAGGTGTATGATCACACTCAAGT

GGTTGGACTAGAATCAGACACTCAAAAGATGAAAGACTGGATATTTGATGCAGTTCATGAAGGAGCT

CAGGAAATACTAGCAATTGGAGTTGTTGGTATGGGTGGGCTTGGAAAGACTACCATTGCTCAAAAGG

TTTTTAATGAAAGAGATATAGAACATCACTTTGACAGAAGAATGTGGGTTTCTGTTTCTCAAACATTCA

CTGAAGAACAAATTATGAGAAGTATGTTGAGGAACTTGGGAGATGCAAGTGTGGGAGATGATAGAAA

TGAACTGCTGAAGAAAATTAACCAATATCTCTTAGGAAAGAGGTATTTGATTGTGATGGATGATGTGTG

GAGTGAAGATGTTCTGTGGTGGCAACGAATCTGTGAAGGGCTGCCTAAAGGAAATGGTAGTTGTATC

ATCATAACAACTAGAATTGAAAAGGTTGCAAGAAAGATGGGTGTGAAAGAAGCAAGGATTCACAGGC

CTAAATTCCTTAACAAAGATTATAGCTGGCTTCTGTTTCGAAAAATAGCTTTTGCTGCAAGTGGTGGAG

AGTGCACTTCCACTGATCTTGAGGATGTTGGAAAAGAGATTGTAGAGAAGTGTAAAGGTCTTCCCTTG

GCCATCAAAGCTGTTGGAGGAATGATGCTTTGTAAAGCACCATATTACCGTGAATGGAGGCGAATTGC

AGATCATTTCAGAGATGAGTTGGAAGAAAATGATAACTCTGTCATGGCTTCACTACAATTGAGTTATGA

TGAGCTCCCTTCCTACTTGAAGTCCTGCTTGCTTAGCTTCTCTCTTTATCCTGAGGATTGTGTCATAACA

AAAGAGCAATTAGTTCATTGGTGGATTGGTGAGGGATTTGCCCCACAAAGGAGTAGTAGATCTTCAAC

-continued

```
TGATGCTGGAGAAGATTGTTTCTCAGGATTAACAAATCGATGTTTGTTAGAGGTAGTCGACAAGACTT
ATAATGGTACAATTTGCACTTGCAAAATGCATGATATGGTTCGTGATTTGGTTCTTAAGATAGCAAAAG
ATGATGCATTTTACAATGCAACGGGTACTAATTATCGCCATTTGGGAGTTGATAACAGCATGGATAAGA
AGCAACTTATTGCTAATCAGAAGTTGAGAGGATTGGTGTCCACAACAAAAACTTGTGAGGTAACAA
GATTGAATCAGGTATTGCAAAAGATTTAGTGAGTGCAAATACTTGAGAGTTTTGGATGTTTCCAAATC
AATATTTGAATTGCCTCTCAGTAGCTTGCTATATCGTGTTGGCACACTTCAACATCTGACTTATCTTGGTT
TAAGCAACACTCATCCTTTGGTTGAACTTCCAGATTCACTAGAAAATCTCACTAACCTTCAAATTTTGGA
TGTTAGTTACTGTCAGAATCTGAAATTCTTGCCTCAGTATCTCATTAAATTCAAGAAGCTCAAAGTCTTA
GATGTGAGCTTTTGTGGTTCCCTAGAAAACTTACCAAAAGGCTTGGGAAGGCTTTCAAACCTTGAAG
TTTTGCTGGGTTTTAGACCTGCAAGGTCAAATAATGGTTGCAGGATTGGAGAATTAAGAAACTTGACG
CGATTGAGGACGCTTGGATTACATCTAACACACGCTGATGAAGTTGAAGATAGCGAGTTCAACGCGAT
GATGAACCTTCAAGACTTGGAAAAGCTATCAATAAGTTTCTTTGATAGCCATGGCAGTGCAAGTGATCT
GACCTCTAAAATTGACAAACTCTGCCCTCCACAACAACTCCATGAACTATCCGTCATGTTCTATCCAGGA
AAGATAAGTCCACTTTGGCTCAACCCTTTAGCACTTCCCATGCTTAAATATCTGTCAATCTCTTCAGGAA
ATCTTGCAAAAATGCATCAGAACTTTTGGGGTGGTGACAACAACATTGTTTGGAAAGTTGAAGGCTTA
ATGTTGGAATCATTGTCTGATTTGGAACTGCAGTGGCCAAAGTTGCAACAGCTTATGCAAATCCTGCG
AGTTGTGAATGTTAGTTGGTGTCCGGAATTAGTTTCTTTCCCAATTGAAGATGTTGGATTCAGGGGTG
GAGTATGGATTAAGGAACAAATTAGGAACTGA
```

Organism Name: *Corchorus olitorius*
Type: PRT
Length: 854
Sequence name: Resistance gene analog 1 (RGA1) peptide

SEQ ID NO: 26

```
M A D A I V N V F L E K L L S T L A E E G R Y V T E F R D Q F E K L Q T E L Q L L Q C F L K D A D R
L K R K N H T I R K I L A D L R E L I Y E A E D I L A D C Q L Q S R D E N Q F S Q S W L A C F S P P
K L H F K Y Q S G K R L K E I T E K I T S I K Q N I S S F L G G P L L F Q P E V I S A Q D Q M P R W
S S Q V Y D H T Q V V G L E S D Q K M K D W I F D A V H E G A Q E I L A I G V V G M G G L G
K T T I A Q K V F N E R D I E H H F D R R M W V S V S Q T F T E E Q I M R S M L R N L G D A S V
G D D R N E L L K K I N Q Y L L G K R Y L I V M D D V W S E D V L W W Q R I C E G L P K G N G S
C I I I T T R I E K V A R K M G V K E A R I H R P K F L N K D Y S W L L F R K I A F A A S G G E C T S
T D L E D V G K E I V E K C K G L P L A I K A V G G M M L C K A P Y Y R E W R R I A D H F R D E L
E E N D N S V M A S L Q L S Y D E L P S Y L K S C L L S F S L Y P E D C V I T K E Q L V H W W I G E
G F A P Q R S S R S S T D A G E D C F S G L T N R C L L E V V D K T Y N G T I C T C K M H D M V
R D L V L K I A K D D A F Y N A T G T N Y R H L G V D N S M D K K Q L I A N Q K L R G L V S T T K
T C E V N K I E S G I A K R F S E C K Y L R V L D V S K S I F E L P L S S L L Y R V G T L Q H L T Y L G
L S N T H P L V E L P D S L E N L T N L Q I L D V S Y C Q N L K F L P Q Y L I K F K K L K V L D V S F
C G S L E N L P K G L G R L S N L E V L L G F R P A R S N N G C R I G E L R N L T R L R T L G L H L
T H A D E V E D S E F N A M M N L Q D L E K L S I S F F D S H G S A S D L T S K I D K L C P P Q Q
L H E L S V M F Y P G K I S P L W L N P L A L P M L K Y L S I S S G N L A K M H Q N F W G G D N
N I V W K V E G L M L E S L S D L E L Q W P K L Q Q L M Q I L R V V N V S W C P E L V S F P I E
D V G F R G G V W I K E Q I R N
```

Organism Name: Corchorus olitorius
Type: DNA
Length: 3604
Sequence Name: Resistance gene analog 2 (RGA2); partial cDNA

SEQ ID NO: 27

```
AAAAGTAGACATGGCGGGTGATTATTCGGTGGAGCTTTTCTCTCTGCCACTCTCCAAGTTTTGTTCG
ACCGGTTGGCTTCTCGTGAGGTGGTGGACTTCATCAGGGGAAAGAAACTTGAGGTTTTGGTCAAGA
AACTGAAGCCAGTGTTGCTGTCCGTCAAAGCAGTGCTGGATGATGCTGAAGACAAGCAGATCACCAA
CCAGAATGTGAAAGAGTGGCTCTCCGAGCTCAAAGATGGTGTTTATGATGCAGAGGACCTCCTCGATG
AGATCGCTTATGAAGCTCTTAAAAGGAGGCTGGAAACCACTACTTCAGCCAAGGGGATATTGGAGTC
AAAGTTAGAGGAGATCCTTGAGAGGCTAGAACTTCTAGTCGACCAAACAGAACGCCTGGGGTTGAA
GGAGTGTAGAGGTGGTGAAACCTTGTCTCAAAGGTTGCCTCCAACTTCTGTGGTGGATGAGTCTTGT
GTTTATGGTAGAGTTGATGAAAAAGAAGCAATCATGAAGTTGCTACACCCTGAAAACCCGACTCAGAA
TCAGATTGATGTGATTCCCATAGTGGGTATGGGAGGGGTTGGTAAAACCACCCTTGCTCAATTGATCTA
CAATGACAACAGATTGGAGGAATGGTTTGACCTCAAAGCTTGGGTGTGTGTTTCAGATGAATTTGATG
CTTTCAGGGTTACCAAAACCATTCTTCAACAGATTGCTTCTGATTGGGATGATCGTCTCGACCTAAATC
AGCTTCAAGTTAAACTACAGGAGAAGCTGTTGGGGAAGAGGTTTCTATTTGTTTTAGATGATGTTTGG
AATGACAAATATATTGAGTGGAAACAGTTGACAAGTCCTTTCAGTGCTGGGGCAAAAGACAGCAAGA
TTGTTGTGACTACACGTAGTGATAATGTTGCAAACATCATGAGGACAGTTCCAGCTTATCAGCTTCCAA
TCTTATCTGATTCTGATTGTTGCTTGTTATTTGCAAAGCATGCGTTCGTCAATACAAGCCCAAGTGAGCA
GCCAGATTTGAAGCTAATTGGGGAAGCAATTGTCAAAAGGTGCAAAGGGCTACCTCTAGCAGTGAAA
GCAGTTGGAGGTTTTCTTCGTTGGAAACTAATGTTGATGAATGGAGAAATATGAATATGGAAGAGCA
AAGGTATGAGTACATCAAAGATTTAGAGTCAAGGTCATTTTTCCAAAAATTAAGCGGGGATGAATCCT
GCTTTGTCATGCATGACCTCATCAGTGACTTGGCTAAATCTGTGTCTGGAGAATTTTTTTGCAGATTGG
AAGGTGGCGATGGAGGTTCATGTGTTATAACTAAAAAGACCCGCCATTTGTCTAATATCCAAGAACCTT
ATGATGTGCGTAAGAAATTTGAGACCTTATGTGAAGCAAAAGGTTTGCGGACATTCCTAACTCTGAATC
TGAAGTCATCATTTCTATCTTCTTCTTTTGTTACTAACAGGCTAATGGATGATTTGATTGTAAAATCAAGT
CGCTTACGAGTTCTTTCTTTGACTGATTATAATAATATTAATATCAGGGAAATACAAGAAGGAATTGGAA
ATTTGAAGCATTTGCGATATTTGGACCTCTCTAATACTTTAATTCAAAGGTTGCCGAACCGTGTGTGTAC
TTTGTATAATTTACAAACATTAAAATTGTTTGGATGTGGCAAGCTTGTTGAGTTGCCAAAAGATATGGG
AAGATTGATCAATATGCATCATCTTGATATCAGGGATACAGGGTTAAATTGGATGCCATCAGGAATAGG
AAAATTGAAAGATCTTAAAGTTTTAACAATTTTTTTGTTGGTAAGCATAAGGGTTCAAGCATTGGTGA
GTTGGGAAAGCTGAAGCATCTACAAGGAAGTGTTGCCATTTGGAATTTACAAAATGTTGTTTGTGCAA
AGGATGCTATGGATGCCAATTTGAAGGACAAGGTGAACCTTAAGGAGTTGAGATTGATATGGAGTAA
GGATGCTGATGTTGATGATGATTCAGAGCGAGATAGAGAAGTACTTGAACAACTGGAGCCTCACACA
GACTTGCAGCATCTTGACATCATGTTTTATAGAGGTACCAGATTTCCAGAGTGGATTGGGCATTCTTCT
TTCTCAAAAGTAGTATCTATGGAGTTAATTGATTGTAAAAGTTGTGAATTGTTGCCCCCACTACGCCAAC
TATCATCCCTGAAATCTCTCTCTATTAGTGGGTGTGTTAAGATAGTTAGACTGGGTGATGAGTTCTACGG
TAGTGGTGATGCATTGAGTAACCCATTTGGATGTCTTGAAGTTCTAAAATTTGAGGATATGTCAGAATG
GGAAGAATGGATTTGTTTGAAGGAAGAAGCTTTCTCTAATCTACGAGAATTAGTCATAAGAGATTGTC
CCAAGTTAAGCAAGTCTTTGCCCAAGTACCTCCCTTGTTTAAAGAAACTTAAGATTAGAAGATGTGGA
AAGCTCGAAGGCATACTTCCAGAGGCACCAAGCATTGAAGAAGTGCAGCTAGAGGGGTGTGATGCC
TTGCAAATGGAGGCATTGCCAAGTGGGCTTAGAGAATTGCAGATTGATGGTTTGCGAATCAATGCTTC
```

-continued

```
CATATTGAAGCAGATGTTGCAACCTTGCACTATTCTTGAACAATTGCAAATTTCTAAGTGTAATAGGCTG

AGATCCCTTCCTGAAGGTAGTAATTTGCCTATGAGACTGAAGAAATTGAGAATCGAAGAGAGTAATGT

GTTGAATGATTCTAAAATCCTCATGTATACATCCCTTGAATCCTTAAAAATAAGAAATAGCAGGTGGAAT

GGGGTGGAATCTTTCCCATTAGGATCATTCCCTTTGCTAAATCGTCTTGACATAACGGGATGTGAAGAG

TTGAAGTGGATTATTGGTGCATCAGAGGGAGAAGATGCTCCTCTCTCATGTCGTCTCAATTCTTTGGAG

ATCTATAATTGCCCTAATTTTGTATGTTTTGAGAAATTAGAGGGATTCTGTGCCCCAATTTGACATCAC

TTGAGCTGGTGGGATGTTCAAATTTAAAGGCATTGCCTGAGCAAATGCACTCCCTCTTCCCATCCCTTG

AAGAATTGTGGATATCATTTTGTCCAAAAATAGAGGGATTTCCAAAAGAGGGTTTACCCTCCACATTAA

AAGCTCTTTTTATCCAAGGAGGATGTAAGAAACTAATAAAGGGGATGATGAGGAGAGATAGAGATAC

GGAATGGGGCTTGCAATCACTCCCTTCACTTGAAGAGTTCATAATCTCAGGTGGTGGAGAAGAGATA

GAAGGGATAGAGAGTTTTCCAGATGAACATCTGCTGCCCTCTTCTCTTACCTCTCTTTCTATCTCTTATT

TTCCAAATCTAAAGAGTTTGGAGTCTAAGGGCTTTCAACACCTCACCTCTCTCCGTCAATTGGGTATCT

ACTTTTGTCCGAGGCTCCAATCCATACCGGAAAAGAGGGTCATTTCCTCTCTTTCTTATTTGGAGATTG

CAAAATGTCCAAAGCTGAGAGAAAATCGTGAAAAGGAGAAAGGCAAACATTGGCCCAACATTTCCCA

CATCCCTGTCATCAACTTTGATGGGTTTGATCCAGTCATTATATAG
```

Organism Name: Corchorus olitorius
Type: PRT
Length: 1200
Sequence name: Resistance gene analog 2 (RGA2) peptide

SEQ ID NO: 28

```
K V D M A G E L F G G A F L S A T L Q V L F D R L A S R E V V D F I R G K K L E V L V K K L K P V L

L S V K A V L D D A E D K Q I T N Q N V K E W L S E L K D G V Y D A E D L L D E I A Y E A L K R R

L E T T T S A K G I L E S K L E E I L E R L E L L V D Q T E R L G L K E C R G G E T L S Q R L P P T S V

V D E S C V Y G R V D E K E A I M K L L H P E N P T Q N Q I D V I P I V G M G G V G K T T L A Q L

I Y N D N R L E E W F D L K A W V C V S D E F D A F R V T K T I L Q Q I A S D W D D R L D L N Q

L Q V K L Q E K L L G K R F L F V L D D V W N D K Y I E W K Q L T S P F S A G A K D S K I V V T T

R S D N V A N I M R T V P A Y Q L P I L S D S D C C L L F A K H A F V N T S P S E Q P D L K L I G E

A I V K R C K G L P L A V K A V G G F L R W K L D V D E W R N M N E E Q R Y E Y I K D L E S R

S F F Q K L S G D E S C F V M H D L I S D L A K S V S G E F F C R L E G G D G G S C V I T K K T R H

L S N I Q E P Y D V R K K F E T L C E A K G L R T F L T L N L K S S F L S S S F V T N R L M D D L I V

K S S R L R V L S L T D Y N N I N I R E I Q E G I G N L K H L R Y L D L S N T L I Q R L P N R V C T L

Y N L Q T L K L F G C G K L V E L P K D M G R L I N M H H L D I R D T G L N W M P S G I G K L K

D L K V L T N F F V G K H K G S S I G E L G K L K H L Q G S V A I W N L Q N V V C A K D A M D A

N L K D K V N L K E L R L I W S K D A D V D D D S E R D R E V L E Q L E P H T D L Q H L D I M F Y

R G T R F P E W I G H S S F S K V V S M E L I D C K S C E L L P P L R Q L S S L K S L S I S G C V K I

V R L G D E F Y G S G D A L S N P F G C L E V L K F E D M S E W E E W I C L K E E A F S N L R E L

V I R D C P K L S K S L P K Y L P C L K K L K I R R C G K L E G I L P E A P S I E E V Q L E G C D A L Q

M E A L P S G L R E L Q I D G L R I N A S I L K Q M L Q P C T I L E Q L Q I S K C N R L R S L P E G S

N L P M R L K K L R I E E S N V L N D S K I L M Y T S L E S L K I R N S R W N G V E S F P L G S F P

L L N R L D I T G C E E L K W I I G A S E G E D A P L S C R L N S L E I Y N C P N F V C F E K L E G F

C A P N L T S L E L V G C S N L K A L P E Q M H S L F P S L E E L W I S F C P K I E G F P K E G L P S
```

```
T L K A L F I Q G G C K K L I K G M M R R D R D T E W G L Q S L P S L E E F I I S G G G E E I E G I

E S F P D E H L L P S S L T S L S I S Y F P N L K S L E S K G F Q H L T S L R Q L G I Y F C P R L Q S I

P E K R V I S S L S Y L E I A K C P K L R E N R E K E K G K H W P N I S H I P V I N F D G F D P V I I
```

Organism Name: *Corchorus olitorius*
Type: DNA
Length: 20
Sequence Name: Forward primer 1

SEQ ID NO: 29

TGGACGAGCTAACCCAGATT

Organism Name: *Corchorus olitorius*
Type: DNA
Length: 20
Sequence Name: Reverse primer 1

SEQ ID NO: 30

GGACAAGTGCCATTGAAAGG

Organism Name: *Corchorus olitorius*
Type: DNA
Length: 20
Sequence Name: Forward primer 5

SEQ ID NO: 31

CTGCCATAACAAAACCACCA

Organism Name: *Corchorus olitorius*
Type: DNA
Length: 20
Sequence Name: Reverse primer 5

SEQ ID NO: 32

ATTCGGTTGGAGTATTTGCG

Organism Name: *Corchorus olitorius*
Type: DNA
Length: 20
Sequence Name: Forward primer 9

SEQ ID NO: 33

TCAACATCATGGGAGTGCAT

Organism Name: *Corchorus olitorius*

Type: DNA
Length: 20
Sequence Name: Reverse primer 9

SEQ ID NO: 34

TTTGAGGAACAAAGAGGCGT

Organism Name: *Corchorus olitorius*
Type: DNA
Length: 20
Sequence Name: Forward primer 13

SEQ ID NO: 35

GTGGGCAAAGACAAGGGATA

Organism Name: *Corchorus olitorius*
Type: DNA
Length: 20
Sequence Name: Reverse primer 13

SEQ ID NO: 36

GCTTGGGGAACTACCATTGT

Organism Name: *Corchorus olitorius*
Type: DNA
Length: 20
Sequence Name: Forward primer 25

SEQ ID NO: 37

TGGGAAGCGTCTTAAGGAAA

Organism Name: *Corchorus olitorius*
Type: DNA
Length: 20
Sequence Name: Reverse primer 25

SEQ ID NO: 38

CTGTTAAGGGCTGCCTAAAG

SEQUENCE LISTING

<160> NUMBER OF SEQ ID NOS: 55

<210> SEQ ID NO 1
<211> LENGTH: 3639
<212> TYPE: DNA
<213> ORGANISM: Corchorus olitorius

<400> SEQUENCE: 1

| | | | | | |
|---|---|---|---|---|---|
| atgctgtcca | tacaatcatc | ttcttcttgt | tcctatgttt | ctcgaaagaa | gtatgatgtt | 60 |
| ttcctgagtt | tcagaggaga | agatacccgc | aataacttca | ccgatcatct | ttatgccgct | 120 |
| ctagtcagga | gaggaatcgt | cactttcagg | gacaatgaaa | ggctcgaggc | cggagaatcg | 180 |
| atcgcaccgg | aactctttaa | agcaattcag | gaatcatggg | gttcagtaat | tgtattctcg | 240 |
| gaaacttatg | cctttcagg | ttggtgcttg | gacgagctaa | cccagattgt | caaacagaaa | 300 |
| aatgaagaag | gcataaagt | tttccccatt | ttctatgatg | ttgatccatc | tgatttaaga | 360 |
| aaacagacag | ggaaagttgc | agaagccttt | gtcaaacatg | aagaaagata | taggagaat | 420 |
| aaaaacaaga | cacaaacttg | gcgatctgct | ttgactgaag | tggctaattt | aaagggatgg | 480 |
| catctaaata | atagacccga | agcagaattc | attgcagaca | tcgttaaaag | ggtgtcagca | 540 |
| aagttatacc | aagcctgttc | tagcattcct | gatgacttaa | ttggaattca | ttcacgcttg | 600 |
| gaagagttgc | attccaaact | agaaatttggg | gaagatgata | tccgcattat | aggaatttgt | 660 |
| ggtatgggtg | gcattggcaa | acaactctc | gcaagagttg | tttacactca | aatgtcacct | 720 |
| cattttgaag | ccaaaagttt | tcttctgat | gtccgagaag | tttcagataa | atttggactt | 780 |
| gtagctatac | agaaacagct | tctttctcaa | atcttcccag | aggaacacct | caattttttt | 840 |
| gatgtccaag | aaggaagttt | catgataagt | cgtagcctat | ctcacaaaaa | agttcttata | 900 |
| gttcttgatg | atgttgataa | catacaacac | ttgaaaatgg | ttgggagcag | gatcatcgta | 960 |
| actacaagag | atgaacatgt | gctacaatct | tttcaagtgg | atgatgtgtt | aaagcctaca | 1020 |
| atattagatg | ccaatgaagc | acttcgtctt | tttagcttaa | aagcttttcaa | tagtgataca | 1080 |
| ccagaagatg | atttcattga | gctttctaaa | tgtgttgtag | aatatgctga | tggccttccc | 1140 |
| ttagctcttg | aagtattggg | ttcattttta | tgtggtaggg | atgaagatca | atggacaagt | 1200 |
| gccattgaaa | ggtttaaaag | agactctaac | aaagaaattc | acaaccggct | tcgaataagc | 1260 |
| tttgatggat | tagaagaaac | tgagaaaaat | atttttttgg | atattgcatg | tttctttaaa | 1320 |
| ggggaggaga | aagattttgt | actgagagta | ctggatggtt | gtgggttttt | cccaggtatt | 1380 |
| ggaatagatg | ctctcattaa | gaaatctctc | ataaaagttt | atggggacaa | ggacaaatat | 1440 |
| ttgtggatgc | atgacttgct | acaagagatg | ggaaggaaaa | ttgtgaagca | aaaatcgcta | 1500 |
| gaagaacctg | gaaaacgttg | tagattgtgg | gagggaaggg | atgtctatga | cgtgctaaca | 1560 |
| aagaacactg | ctacagaaga | aattgagggc | atggacatcg | acatcaagtg | ttgggatcag | 1620 |
| agaaagacaa | tcacttggaa | tgttgaagcc | ttcttgaaga | tgaaaaaatt | aagattgctc | 1680 |
| agagtctctt | atctcccaaa | tccctgtgat | ctcaattatc | tttctgataa | gctacgactt | 1740 |
| ttagattgga | gtggatatcc | ttttagatcc | ttaccttcaa | acttccaacc | agacaacctt | 1800 |
| gttgcacttc | tcctacctta | tagccgcgtt | caacagctat | ggaatggaaa | catatgttta | 1860 |
| gaaaagttga | atgggttaa | cctcgaaggc | tctggaaacc | tgaccaagac | cccagacttt | 1920 |
| acaatggctc | caaatctcga | aactttgatt | ttggaagctt | gtatcaagat | agtagatgtt | 1980 |
| catcccctcca | ttggacttct | gaggagactc | agatttctga | atttaagaaa | ctgcaaaagt | 2040 |
| cttaggagac | ttccaaccaa | aattggcatg | aaatctcttg | aaacatggat | tctttcaggt | 2100 |

```
tgctcaaatc ttgaaaggtt accagatcag attgatgggg aaatggaatg tttagttgag    2160
ctttatttag atgggacggg cattcgacat cttccctctc taattggaca tctgagtggt    2220
cttgttttat taaatctgaa aggttgcagg aacttggcga gcctcccaag caacattaat    2280
gggttgaaac gcttaaaaat tttgatctc tctggctgct ctaaacttga aattttgcca    2340
gaaagtttgc agcaagtaga atctttggag gagcttgatt taagtgaaac tgccataaga    2400
caaccgccat ccttcatatt tcaatttaaa aatcttaaac atctgtcttt ccgtggatgc    2460
aaggggccac tgtctaaatt aagaccaaat ctgccttctc ttttcaaggt tatgcaaagc    2520
agaagtttga attccatggc tctaatgtta cctcctttgt caggtttgag ttctttaaca    2580
aatctggata taagttactg caatcttggt gaagaggcta ttcctagcga tgtttaccgg    2640
ttatcctctt tgaaaaaatt aaatctttgt ggtaacaatt tcatcagcct gcctgcaaat    2700
cttgaacgac tttccaatct taagtgtctc gtattgacac attgtatgga gcttaaatca    2760
ttgcctgagt ttctaacaag cacggccagt tcatgcaata ttataggtcg tcatagtgta    2820
gacctatctg caaatgcaac agtacgcaac tcagtaagct gtgcttctat ttggttaact    2880
aattgcttca gattgagtga gaatacagac atagtaacat tgctgaaaaa acatcttaag    2940
gcatctgcaa attcaagaca attgaacatt gttctacccg gaagtgaaat cccagagtgg    3000
ttcagcaatc agagggatgg atgttcgata aagatacctc tgccttacca gattttgaat    3060
gatagtcagt gtattggagt tgctttctgc tgtgtctttg tcaatgctat agaaatgcgc    3120
cgcaaagctt ttatccatgg tagaaagtct caaaatgtgg ataatcatgt gttgtgcatt    3180
acaaatggct gctcctcggt cactaaagac cacctcttgc taggttattg gtctcgtgac    3240 tactttttatt caatttattc cttggaggag aaatgtggtg aaactgagca attatcaagc    3300
ctagaatccg atgaacttga ggttgtggtt gaggttgatg aggatgagat gttgtcatct    3360
aagccgacca tcaagaagtg tggaattcat atagtttata agaaagatgt ggaagagatg    3420
gaacaaataa aagaacacca cattctgcaa attggcaata caactattga ggatatccct    3480
cagcctcaga acggtgatga atcggagata gggaagggag ctcttgtaaa gcgaaaacgc    3540
aacttctatg agaaaagtga gagtgacaaa attgaagaga gaccacaacc taaacggctt    3600
caacaatttc taaaatgtat aatgcggaag gagcttttaa                          3639
```

<210> SEQ ID NO 2
<211> LENGTH: 1212
<212> TYPE: PRT
<213> ORGANISM: Corchorus olitorius

<400> SEQUENCE: 2

Met Leu Ser Ile Gln Ser Ser Ser Cys Ser Tyr Val Ser Arg Lys
1               5                   10                  15

Lys Tyr Asp Val Phe Leu Ser Phe Arg Gly Glu Asp Thr Arg Asn Asn
                20                  25                  30

Phe Thr Asp His Leu Tyr Ala Ala Leu Val Arg Arg Gly Ile Val Thr
            35                  40                  45

Phe Arg Asp Asn Glu Arg Leu Glu Ala Gly Glu Ser Ile Ala Pro Glu
        50                  55                  60

Leu Phe Lys Ala Ile Gln Glu Ser Trp Gly Ser Val Ile Val Phe Ser
65                  70                  75                  80

Glu Thr Tyr Ala Phe Ser Gly Trp Cys Leu Asp Glu Leu Thr Gln Ile
                85                  90                  95

```
Val Lys Gln Lys Asn Glu Glu Gly His Lys Val Phe Pro Ile Phe Tyr
            100                 105                 110

Asp Val Asp Pro Ser Asp Leu Arg Lys Gln Thr Gly Lys Val Ala Glu
        115                 120                 125

Ala Phe Val Lys His Glu Glu Arg Tyr Lys Glu Asn Lys Asn Lys Thr
    130                 135                 140

Gln Thr Trp Arg Ser Ala Leu Thr Glu Val Ala Asn Leu Lys Gly Trp
145                 150                 155                 160

His Leu Asn Asn Arg Pro Glu Ala Glu Phe Ile Ala Asp Ile Val Lys
                165                 170                 175

Arg Val Ser Ala Lys Leu Tyr Gln Ala Cys Ser Ser Ile Pro Asp Asp
            180                 185                 190

Leu Ile Gly Ile His Ser Arg Leu Glu Glu Leu His Ser Lys Leu Glu
        195                 200                 205

Ile Gly Glu Asp Asp Ile Arg Ile Ile Gly Ile Cys Gly Met Gly Gly
    210                 215                 220

Ile Gly Lys Thr Thr Leu Ala Arg Val Val Tyr Thr Gln Met Ser Pro
225                 230                 235                 240

His Phe Glu Ala Lys Ser Phe Leu Ser Asp Val Arg Glu Val Ser Asp
                245                 250                 255

Lys Phe Gly Leu Val Ala Ile Gln Lys Gln Leu Leu Ser Gln Ile Phe
            260                 265                 270

Pro Glu Glu His Leu Asn Phe Asp Val Gln Glu Gly Ser Phe Met
        275                 280                 285

Ile Ser Arg Ser Leu Ser His Lys Lys Val Leu Ile Val Leu Asp Asp
    290                 295                 300

Val Asp Asn Ile Gln His Leu Lys Met Val Gly Ser Arg Ile Ile Val
305                 310                 315                 320

Thr Thr Arg Asp Glu His Val Leu Gln Ser Phe Gln Val Asp Asp Val
                325                 330                 335

Leu Lys Pro Thr Ile Leu Asp Ala Asn Glu Ala Leu Arg Leu Phe Ser
            340                 345                 350

Leu Lys Ala Phe Asn Ser Asp Thr Pro Glu Asp Asp Phe Ile Glu Leu
        355                 360                 365

Ser Lys Cys Val Val Glu Tyr Ala Asp Gly Leu Pro Leu Ala Leu Glu
    370                 375                 380

Val Leu Gly Ser Phe Leu Cys Gly Arg Asp Glu Asp Gln Trp Thr Ser
385                 390                 395                 400

Ala Ile Glu Arg Phe Lys Arg Asp Ser Asn Lys Glu Ile His Asn Arg
                405                 410                 415

Leu Arg Ile Ser Phe Asp Gly Leu Glu Glu Thr Glu Lys Asn Ile Phe
            420                 425                 430

Leu Asp Ile Ala Cys Phe Phe Lys Gly Glu Glu Lys Asp Phe Val Leu
        435                 440                 445

Arg Val Leu Asp Gly Cys Gly Phe Phe Pro Gly Ile Gly Ile Asp Ala
    450                 455                 460

Leu Ile Lys Lys Ser Leu Ile Lys Val Tyr Gly Asp Lys Asp Lys Tyr
465                 470                 475                 480

Leu Trp Met His Asp Leu Leu Gln Glu Met Gly Arg Lys Ile Val Lys
                485                 490                 495

Gln Lys Ser Leu Glu Glu Pro Gly Lys Arg Cys Arg Leu Trp Glu Gly
            500                 505                 510

Arg Asp Val Tyr Asp Val Leu Thr Lys Asn Thr Ala Thr Glu Glu Ile
```

-continued

```
            515                 520                 525
Glu Gly Met Asp Ile Asp Ile Lys Cys Trp Asp Gln Arg Lys Thr Ile
530                 535                 540

Thr Trp Asn Val Glu Ala Phe Leu Lys Met Lys Lys Leu Arg Leu Leu
545                 550                 555                 560

Arg Val Ser Tyr Leu Pro Asn Pro Cys Asp Leu Asn Tyr Leu Ser Asp
                565                 570                 575

Lys Leu Arg Leu Leu Asp Trp Ser Gly Tyr Pro Phe Arg Ser Leu Pro
                580                 585                 590

Ser Asn Phe Gln Pro Asp Asn Leu Val Ala Leu Leu Pro Tyr Ser
                595                 600                 605

Arg Val Gln Gln Leu Trp Asn Gly Asn Ile Cys Leu Glu Lys Leu Lys
610                 615                 620

Trp Val Asn Leu Glu Gly Ser Gly Asn Leu Thr Lys Thr Pro Asp Phe
625                 630                 635                 640

Thr Met Ala Pro Asn Leu Glu Thr Leu Ile Leu Glu Ala Cys Ile Lys
                645                 650                 655

Ile Val Asp Val His Pro Ser Ile Gly Leu Leu Arg Arg Leu Arg Phe
                660                 665                 670

Leu Asn Leu Arg Asn Cys Lys Ser Leu Arg Arg Leu Pro Thr Lys Ile
                675                 680                 685

Gly Met Lys Ser Leu Glu Thr Trp Ile Leu Ser Gly Cys Ser Asn Leu
690                 695                 700

Glu Arg Leu Pro Asp Gln Ile Asp Gly Glu Met Glu Cys Leu Val Glu
705                 710                 715                 720

Leu Tyr Leu Asp Gly Thr Gly Ile Arg His Leu Pro Ser Leu Ile Gly
                725                 730                 735

His Leu Ser Gly Leu Val Leu Leu Asn Leu Lys Gly Cys Arg Asn Leu
                740                 745                 750

Ala Ser Leu Pro Ser Asn Ile Asn Gly Leu Lys Arg Leu Lys Ile Phe
                755                 760                 765

Asp Leu Ser Gly Cys Ser Lys Leu Glu Ile Leu Pro Glu Ser Leu Gln
770                 775                 780

Gln Val Glu Ser Leu Glu Glu Leu Asp Leu Ser Glu Thr Ala Ile Arg
785                 790                 795                 800

Gln Pro Pro Ser Phe Ile Phe Gln Phe Lys Asn Leu Lys His Leu Ser
                805                 810                 815

Phe Arg Gly Cys Lys Gly Pro Leu Ser Lys Leu Arg Pro Asn Leu Pro
                820                 825                 830

Ser Leu Phe Lys Val Met Gln Ser Arg Ser Leu Asn Ser Met Ala Leu
                835                 840                 845

Met Leu Pro Pro Leu Ser Gly Leu Ser Ser Leu Thr Asn Leu Asp Ile
850                 855                 860

Ser Tyr Cys Asn Leu Gly Glu Glu Ala Ile Pro Ser Asp Val Tyr Arg
865                 870                 875                 880

Leu Ser Ser Leu Lys Lys Leu Asn Leu Cys Gly Asn Asn Phe Ile Ser
                885                 890                 895

Leu Pro Ala Asn Leu Glu Arg Leu Ser Asn Leu Lys Cys Leu Val Leu
                900                 905                 910

Thr His Cys Met Glu Leu Lys Ser Leu Pro Glu Phe Leu Thr Ser Thr
                915                 920                 925

Ala Ser Ser Cys Asn Ile Ile Gly Arg His Ser Val Asp Leu Ser Ala
930                 935                 940
```

Asn Ala Thr Val Arg Asn Ser Val Ser Cys Ala Ser Ile Trp Leu Thr
945                 950                 955                 960

Asn Cys Phe Arg Leu Ser Glu Asn Thr Asp Ile Val Thr Leu Leu Lys
            965                 970                 975

Lys His Leu Lys Ala Ser Ala Asn Ser Arg Gln Leu Asn Ile Val Leu
        980                 985                 990

Pro Gly Ser Glu Ile Pro Glu Trp Phe Ser Asn Gln Arg Asp Gly Cys
    995                 1000                1005

Ser Ile Lys Ile Pro Leu Pro Tyr Gln Ile Leu Asn Asp Ser Gln
    1010                1015                1020

Cys Ile Gly Val Ala Phe Cys Cys Val Phe Val Asn Ala Ile Glu
    1025                1030                1035

Met Arg Arg Lys Ala Phe Ile His Gly Arg Lys Ser Gln Asn Val
    1040                1045                1050

Asp Asn His Val Leu Cys Ile Thr Asn Gly Cys Ser Ser Val Thr
    1055                1060                1065

Lys Asp His Leu Leu Leu Gly Tyr Trp Ser Arg Asp Tyr Phe Tyr
    1070                1075                1080

Ser Ile Tyr Ser Leu Glu Glu Lys Cys Gly Glu Thr Glu Gln Leu
    1085                1090                1095

Ser Ser Leu Glu Ser Asp Glu Leu Glu Val Val Glu Val Asp
    1100                1105                1110

Glu Asp Glu Met Leu Ser Ser Lys Pro Thr Ile Lys Lys Cys Gly
    1115                1120                1125

Ile His Ile Val Tyr Lys Lys Asp Val Glu Glu Met Glu Gln Ile
    1130                1135                1140

Lys Glu His His Ile Leu Gln Ile Gly Asn Thr Thr Ile Glu Asp
    1145                1150                1155

Ile Pro Gln Pro Gln Asn Gly Asp Glu Ser Glu Ile Gly Lys Gly
    1160                1165                1170

Ala Leu Val Lys Arg Lys Arg Asn Phe Tyr Glu Lys Ser Glu Ser
    1175                1180                1185

Asp Lys Ile Glu Glu Arg Pro Gln Pro Lys Arg Leu Gln Gln Phe
    1190                1195                1200

Leu Lys Cys Ile Met Arg Lys Glu Leu
    1205                1210

<210> SEQ ID NO 3
<211> LENGTH: 3621
<212> TYPE: DNA
<213> ORGANISM: Corchorus olitorius

<400> SEQUENCE: 3
atgttgtcct taccaccatc atcctcttcc catgtttctc gaaaaaagta tgatgttttc      60
ttgagtttca gaggagcaga tactcgccaa aagttcaccg atcatctcta tgctgccttg     120
aaaagaaatg gaatcatcac tttcagggac aatgaaaggc ttgaggctgg tgaatcgatc     180
aggatggaac tctttaaagc aattcaggaa tcatggtgtt ctatagttgt attctcaaaa     240
acttattcct tttcaggttg gtgcttggac gagcttgctg agattgtcaa acagaaaaat     300
gaatgcaggc atacaatttt ccccattttc tatgatatcg atccatctga tctaagaaag     360
cagacgggaa gagttgcaga agcctttgcc aacatgaaga gagatacaa ggagaataga     420 aacaggacac aaagctggcg atctgcttta actgaagtgg ctaatttaaa gggatggcat     480

``` 
ctaaataata caagacatga atcagaattc attggagaca ttgttagaag gatatcagca    540
aagttatgcc aaacctattc ctctgttcca gatgacttga ttggaattaa ttcaagtttg    600
gaagagttgc attctaaaat agacattggg gaagatgaca ttcgtattat aggaatttgt    660
ggtatgggtg gcattggcaa aacaactctt gcaagagttg tttacactca aatgtcacct    720
cattttgaag gtaaaagctt tcttcccgat gttcgagaag tttcaaataa acttggactt    780
gtatttttac agaagcagtt tctttctcac attttcccag aagaatgctt caatttttct    840
gatgttcatg aaggaagtta catgattaat cgtaggctat ctcacaaaaa ggttcttgta    900
gttatcgatg atgtcgataa catacaacag ttgaaatggt tgattggaag gcgtgattgg    960
cttggttcag gtagcagagc cattttaact actagagatg aacatgttct gctatcatac   1020
agagtggatc atgtttgtaa gccaacaaca ttagattcca atgatgcact ttgccttttt   1080
agtttgaaag ctttcaataa tgatacacca gaaaatgatt tcattgagct ttctaaacgt   1140
gttgtacaat attgtgatgg ccttccctta gctcttgaag ttttgggttc atttttttgt   1200
ggaagagatg cagctcaatg gagaagtgca attgaaaggc ttaaaagaga gtctaacaag   1260
gaaattcatg accggcttca aataagcttt gatggattag aagaaacaga gaaaaacata   1320
tttttggatg ttgcttgttt ctttaaaggg gaggagaaag atttagtaat caaagttcta   1380
gatggttgcg agttttaccc agatattgga atagatgttc tcatcaagaa atctctcatc   1440
aaatttatg gtgacaagta tttggggatg catgatttgc tgcaagagat gggtagaaaa   1500
attgtcaagc aaaaatctgt tgatgaacct ggacgacgtt gtagattgtg ggaggaaagg   1560
gatgtctatc atgtgctaac aaagaacacg gctacgaaag cagttgaagg cttggacatc   1620
aacgttaaat gctgggagca cagaaagatg ttcactagga atgctgatgc cttcatgaag   1680
atgaaaaaat taagattgct caaagtctgt aatctcccaa attctcatga tctcaaatat   1740
ctttctaatg cgctacggct tttagattgg actggatatc ctttcagatc cttgccttca   1800
cgcttccaac cagacaacct tgttgcactt ctcctacctt gtagccgcat tgaacaacta   1860
tggaacggaa acatactttt agaaaaactg aaattcgtca acctcgaagg atccatgaac   1920
ctgatcagga caccagactt tacaatggcc ccaaatctgg aaagtttgat tttggaaagt   1980
tgtgtcaact tagtagatgt tcatccatcc atcggccttc taaggagact aaaacttctg   2040
aattttagag gctgcaaaag tcttagcagt cttccaacca aaattggaat gaaatctctt   2100
gaaacattga ttctttcagg ttgctcaaat cttgaaaggt taccagatca gattgatggg   2160
aagatggaat gtttggtcga gcttcattta gatgggaccg gtgtgggaca tctttcctct   2220
gcaattggac atctgagtgg tcttgtttta ttgaatctga aagattgcag aaatttagca   2280
agtctcccaa gcagcattaa tggctgaaa tgtctgaaaa ctcttaatct ctcaggctgc   2340
tctaatcttg aacattttcc agagaatttg cagcaattag aatctttaga ggagcttgat   2400
ttaagtggaa ctgctataac aaagccacca tccttcattt tccaattcaa gaatcttaaa   2460
catctgtctt tccatggatg caaggcacca ccaactaaat tacaaccaaa tcagccttct   2520
ctaggatgta tgaactgcat ggcgctaacc ttaccgcctt tgtcaggtct gagttcttta   2580
acacagctga atataagtta ctgcaatctt tatgaaggag ctattccgag tgatatttgc   2640
tccttatcct ctttgaaaag actagatctt cgcggtaaca atttcttcag cctacctgcg   2700
aatcttgata gactttccaa tctcgactat ctcggattga cagattgtat ggagcttaaa   2760
tcattgcctg agcttctaac aagcacacta gttcctattt caaatgattg cagttttcca   2820
gtgggactat ttgcaaatgc aagagcatgc aattcaatgg attgggcacc tgcttctatt   2880
```

```
tggttaacta attgctacag actggctgag aacacaaatg tattaacatt gctgaaaaaa    2940
catcttaagg tgtttgcaaa ggcaagagaa actttggaca ttattttacc cggaagtcaa    3000
atcccagatt ggttcagcca tcagagcaat gaatcgtcaa tcaagatacc tctgcctcac    3060
catcttcaga gtaatagtaa gtggattgga gttgctttct gctgtgtctt cgtcgatgtt    3120
gttggtatcg actgcaaagc ttttgtccat ggtagaatgt cccacgacat taatggttac    3180
gggttgtatt ttggacatgg ctcctcggtc acaaaggatc atctttggct acgttattgg    3240
tctcgtaaca agttatattc gtttgccttg gatgacaaat gtggtgaaac agggcatcca    3300
cagagcctaa aatgtccggt agatcaagaa tccgatgaat tcgaggttgc tgttgaggtt    3360
gaggttgagt tgtcacggtc acgttttaag aaagtgaaga agtgtggggt tagactagtt    3420
tatgagaaag atttgcaaga gttggagcaa cttctgcaaa tctgcaattc aacttgtgca    3480
gatgaatcaa aaacagggga ggttccggta aagcgaaaac gcaacatcta tgaagaggag    3540
gcagaactaa gtgagagtga cagcttccga gggccggaac gatttctaag atatataatg    3600
cagaagaagg aacataattg a                                              3621

<210> SEQ ID NO 4
<211> LENGTH: 1206
<212> TYPE: PRT
<213> ORGANISM: Corchorus olitorius

<400> SEQUENCE: 4

Met Leu Ser Leu Pro Pro Ser Ser Ser His Val Ser Arg Lys Lys
1               5                   10                  15

Tyr Asp Val Phe Leu Ser Phe Arg Gly Ala Asp Thr Arg Gln Lys Phe
                20                  25                  30

Thr Asp His Leu Tyr Ala Ala Leu Lys Arg Asn Gly Ile Ile Thr Phe
            35                  40                  45

Arg Asp Asn Glu Arg Leu Glu Ala Gly Glu Ser Ile Arg Met Glu Leu
        50                  55                  60

Phe Lys Ala Ile Gln Glu Ser Trp Cys Ser Ile Val Val Phe Ser Lys
65                  70                  75                  80

Thr Tyr Ser Phe Ser Gly Trp Cys Leu Asp Glu Leu Ala Glu Ile Val
                85                  90                  95

Lys Gln Lys Asn Glu Cys Arg His Thr Ile Phe Pro Ile Phe Tyr Asp
            100                 105                 110

Ile Asp Pro Ser Asp Leu Arg Lys Gln Thr Gly Arg Val Ala Glu Ala
        115                 120                 125

Phe Ala Lys His Glu Glu Arg Tyr Lys Glu Asn Arg Asn Arg Thr Gln
    130                 135                 140

Ser Trp Arg Ser Ala Leu Thr Glu Val Ala Asn Leu Lys Gly Trp His
145                 150                 155                 160

Leu Asn Asn Thr Arg His Glu Ser Glu Phe Ile Gly Asp Ile Val Arg
                165                 170                 175

Arg Ile Ser Ala Lys Leu Cys Gln Thr Tyr Ser Ser Val Pro Asp Asp
            180                 185                 190

Leu Ile Gly Ile Asn Ser Ser Leu Glu Glu Leu His Ser Lys Ile Asp
        195                 200                 205

Ile Gly Glu Asp Asp Ile Arg Ile Gly Ile Cys Gly Met Gly Gly
    210                 215                 220

Ile Gly Lys Thr Thr Leu Ala Arg Val Val Tyr Thr Gln Met Ser Pro
225                 230                 235                 240
```

```
His Phe Glu Gly Lys Ser Phe Leu Pro Asp Val Arg Glu Val Ser Asn
                245                 250                 255

Lys Leu Gly Leu Val Phe Leu Gln Lys Gln Phe Leu Ser His Ile Phe
            260                 265                 270

Pro Glu Glu Cys Phe Asn Phe Ser Asp Val His Glu Gly Ser Tyr Met
        275                 280                 285

Ile Asn Arg Arg Leu Ser His Lys Lys Val Leu Val Ile Asp Asp
    290                 295                 300

Val Asp Asn Ile Gln Gln Leu Lys Trp Leu Ile Gly Arg Arg Asp Trp
305                 310                 315                 320

Leu Gly Ser Gly Ser Arg Ala Ile Leu Thr Thr Arg Asp Glu His Val
                325                 330                 335

Leu Leu Ser Tyr Arg Val Asp His Val Cys Lys Pro Thr Thr Leu Asp
            340                 345                 350

Ser Asn Asp Ala Leu Cys Leu Phe Ser Leu Lys Ala Phe Asn Asn Asp
        355                 360                 365

Thr Pro Glu Asn Asp Phe Ile Glu Leu Ser Lys Arg Val Val Gln Tyr
    370                 375                 380

Cys Asp Gly Leu Pro Leu Ala Leu Glu Val Leu Gly Ser Phe Phe Cys
385                 390                 395                 400

Gly Arg Asp Ala Ala Gln Trp Arg Ser Ala Ile Glu Arg Leu Lys Arg
                405                 410                 415

Glu Ser Asn Lys Glu Ile His Asp Arg Leu Gln Ile Ser Phe Asp Gly
            420                 425                 430

Leu Glu Glu Thr Glu Lys Asn Ile Phe Leu Asp Val Ala Cys Phe Phe
        435                 440                 445

Lys Gly Glu Glu Lys Asp Leu Val Ile Lys Val Leu Asp Gly Cys Glu
    450                 455                 460

Phe Tyr Pro Asp Ile Gly Ile Asp Val Leu Ile Lys Lys Ser Leu Ile
465                 470                 475                 480

Lys Phe Tyr Gly Asp Lys Tyr Leu Gly Met His Asp Leu Leu Gln Glu
                485                 490                 495

Met Gly Arg Lys Ile Val Lys Gln Lys Ser Val Asp Glu Pro Gly Arg
            500                 505                 510

Arg Cys Arg Leu Trp Glu Glu Arg Asp Val Tyr His Val Leu Thr Lys
        515                 520                 525

Asn Thr Ala Thr Lys Ala Val Glu Gly Leu Asp Ile Asn Val Lys Cys
    530                 535                 540

Trp Glu His Arg Lys Met Phe Thr Arg Asn Ala Asp Ala Phe Met Lys
545                 550                 555                 560

Met Lys Lys Leu Arg Leu Leu Lys Val Cys Asn Leu Pro Asn Ser His
                565                 570                 575

Asp Leu Lys Tyr Leu Ser Asn Ala Leu Arg Leu Leu Asp Trp Thr Gly
            580                 585                 590

Tyr Pro Phe Arg Ser Leu Pro Ser Arg Phe Gln Pro Asp Asn Leu Val
        595                 600                 605

Ala Leu Leu Leu Pro Cys Ser Arg Ile Glu Gln Leu Trp Asn Gly Asn
    610                 615                 620

Ile Leu Leu Glu Lys Leu Lys Phe Val Asn Leu Glu Gly Ser Met Asn
625                 630                 635                 640

Leu Ile Arg Thr Pro Asp Phe Thr Met Ala Pro Asn Leu Glu Ser Leu
                645                 650                 655
```

-continued

Ile Leu Glu Ser Cys Val Asn Leu Val Asp Val His Pro Ser Ile Gly
            660                 665                 670

Leu Leu Arg Arg Leu Lys Leu Leu Asn Phe Arg Gly Cys Lys Ser Leu
        675                 680                 685

Ser Ser Leu Pro Thr Lys Ile Gly Met Lys Ser Leu Glu Thr Leu Ile
    690                 695                 700

Leu Ser Gly Cys Ser Asn Leu Glu Arg Leu Pro Asp Gln Ile Asp Gly
705                 710                 715                 720

Lys Met Glu Cys Leu Val Glu Leu His Leu Asp Gly Thr Gly Val Gly
                725                 730                 735

His Leu Ser Ser Ala Ile Gly His Leu Ser Gly Leu Val Leu Leu Asn
            740                 745                 750

Leu Lys Asp Cys Arg Asn Leu Ala Ser Leu Pro Ser Ser Ile Asn Gly
        755                 760                 765

Leu Lys Cys Leu Lys Thr Leu Asn Leu Ser Gly Cys Ser Asn Leu Glu
    770                 775                 780

His Phe Pro Glu Asn Leu Gln Gln Leu Glu Ser Leu Glu Glu Leu Asp
785                 790                 795                 800

Leu Ser Gly Thr Ala Ile Thr Lys Pro Pro Ser Phe Ile Phe Gln Phe
                805                 810                 815

Lys Asn Leu Lys His Leu Ser Phe His Gly Cys Lys Ala Pro Pro Thr
            820                 825                 830

Lys Leu Gln Pro Asn Gln Pro Ser Leu Gly Cys Met Asn Cys Met Ala
        835                 840                 845

Leu Thr Leu Pro Pro Leu Ser Gly Leu Ser Ser Leu Thr Gln Leu Asn
    850                 855                 860

Ile Ser Tyr Cys Asn Leu Tyr Glu Gly Ala Ile Pro Ser Asp Ile Cys
865                 870                 875                 880

Ser Leu Ser Ser Leu Lys Arg Leu Asp Leu Arg Gly Asn Asn Phe Phe
                885                 890                 895

Ser Leu Pro Ala Asn Leu Asp Arg Leu Ser Asn Leu Asp Tyr Leu Gly
            900                 905                 910

Leu Thr Asp Cys Met Glu Leu Lys Ser Leu Pro Glu Leu Leu Thr Ser
        915                 920                 925

Thr Leu Val Pro Ile Ser Asn Asp Cys Ser Phe Pro Val Gly Leu Phe
    930                 935                 940

Ala Asn Ala Arg Ala Cys Asn Ser Met Asp Trp Ala Pro Ala Ser Ile
945                 950                 955                 960

Trp Leu Thr Asn Cys Tyr Arg Leu Ala Glu Asn Thr Asn Val Leu Thr
                965                 970                 975

Leu Leu Lys Lys His Leu Lys Val Phe Ala Lys Ala Arg Glu Thr Leu
            980                 985                 990

Asp Ile Ile Leu Pro Gly Ser Gln Ile Pro Asp Trp Phe Ser His Gln
        995                 1000                1005

Ser Asn Glu Ser Ser Ile Lys Ile Pro Leu Pro His His Leu Gln
    1010                1015                1020

Ser Asn Ser Lys Trp Ile Gly Val Ala Phe Cys Cys Val Phe Val
    1025                1030                1035

Asp Val Val Gly Ile Asp Cys Lys Ala Phe Val His Gly Arg Met
    1040                1045                1050

Ser His Asp Ile Asn Gly Tyr Gly Leu Tyr Phe Gly His Gly Ser
    1055                1060                1065

Ser Val Thr Lys Asp His Leu Trp Leu Arg Tyr Trp Ser Arg Asn

```
              1070                1075                1080
Lys Leu Tyr Ser Phe Ala Leu Asp Asp Lys Cys Gly Glu Thr Gly
    1085                1090                1095

His Pro Gln Ser Leu Lys Cys Pro Val Asp Gln Glu Ser Asp Glu
    1100                1105                1110

Phe Glu Val Ala Val Glu Val Glu Val Glu Leu Ser Arg Ser Arg
    1115                1120                1125

Phe Lys Lys Val Lys Lys Cys Gly Val Arg Leu Val Tyr Glu Lys
    1130                1135                1140

Asp Leu Gln Glu Leu Glu Gln Leu Leu Gln Ile Cys Asn Ser Thr
    1145                1150                1155

Cys Ala Asp Glu Ser Lys Thr Gly Glu Val Pro Val Lys Arg Lys
    1160                1165                1170

Arg Asn Ile Tyr Glu Glu Glu Ala Glu Leu Ser Glu Ser Asp Ser
    1175                1180                1185

Phe Arg Gly Pro Glu Arg Phe Leu Arg Tyr Ile Met Gln Lys Lys
    1190                1195                1200

Glu His Asn
    1205

<210> SEQ ID NO 5
<211> LENGTH: 719
<212> TYPE: DNA
<213> ORGANISM: Corchorus olitorius

<400> SEQUENCE: 5
ttgcgagtct cccaagcagc attcatgagt tgaaatgtct aaaaactctt gatctctcag      60
gctgctctaa acttgaaaat ttgccagaga gtttgcagca agtagaatct ctcgaggagc     120
ttgatttaag tgggactgcc ataacaaaac caccatcctt catttttcaa ttgaaaaatc     180
ttaaacatct gtctttccgc ggatgcaagg gaacagtttc taaatcacga cccaatctgc     240
tttctctttt caaggtaatg caaagaggag gaggaagtgt gaattcagtg gctctaacct     300
tacctcccct gtcaggtttg acttgtttga caaagctgga tataagttac tgcaatcttg     360
gtgaaggggc tattcctagc gatatttgcc acttatcctc tttgagagac ttgaatctta     420
gtggtaacac tttctccagc cttcctgcaa accttgatcg actttccaat cttgagcgta     480
tcagactgag acattgtacg gagcttaaat cattgcctga gcttcttagg agcacatacc     540
attcggttgg agtatttgcg aatgctgcaa tacgcaactc gcgagattgg gcatgtattt     600
ttttacctaa ttgctacaga atagctgaga atacaaatat agtaaccttg ctgaagaaga     660
atcttaaggt tggtctctat atctctcccc ctaatcagct cacacaaaga aatttatga      719

<210> SEQ ID NO 6
<211> LENGTH: 238
<212> TYPE: PRT
<213> ORGANISM: Corchorus olitorius

<400> SEQUENCE: 6

Ala Ser Leu Pro Ser Ser Ile His Glu Leu Lys Cys Leu Lys Thr Leu
  1               5                  10                  15

Asp Leu Ser Gly Cys Ser Lys Leu Glu Asn Leu Pro Glu Ser Leu Gln
                 20                  25                  30

Gln Val Glu Ser Leu Glu Glu Leu Asp Leu Ser Gly Thr Ala Ile Thr
             35                  40                  45

Lys Pro Pro Ser Phe Ile Phe Gln Leu Lys Asn Leu Lys His Leu Ser
```

```
                50                  55                  60
Phe Arg Gly Cys Lys Gly Thr Val Ser Lys Ser Arg Pro Asn Leu Leu
 65                  70                  75                  80

Ser Leu Phe Lys Val Met Gln Arg Gly Gly Ser Val Asn Ser Val
                 85                  90                  95

Ala Leu Thr Leu Pro Pro Leu Ser Gly Leu Thr Cys Leu Thr Lys Leu
                100                 105                 110

Asp Ile Ser Tyr Cys Asn Leu Gly Glu Gly Ala Ile Pro Ser Asp Ile
            115                 120                 125

Cys His Leu Ser Ser Leu Arg Asp Leu Asn Leu Ser Gly Asn Thr Phe
        130                 135                 140

Ser Ser Leu Pro Ala Asn Leu Asp Arg Leu Ser Asn Leu Glu Arg Ile
145                 150                 155                 160

Arg Leu Arg His Cys Thr Glu Leu Lys Ser Leu Pro Glu Leu Leu Arg
                165                 170                 175

Ser Thr Tyr His Ser Val Gly Val Phe Ala Asn Ala Ala Ile Arg Asn
            180                 185                 190

Ser Arg Asp Trp Ala Cys Ile Phe Leu Pro Asn Cys Tyr Arg Ile Ala
        195                 200                 205

Glu Asn Thr Asn Ile Val Thr Leu Leu Lys Lys Asn Leu Lys Val Gly
    210                 215                 220

Leu Tyr Ile Ser Pro Pro Asn Gln Leu Thr Gln Arg Asn Leu
225                 230                 235

<210> SEQ ID NO 7
<211> LENGTH: 2583
<212> TYPE: DNA
<213> ORGANISM: Corchorus olitorius

<400> SEQUENCE: 7
atggctgaag ctgctgtttc ctttgtgcta gagaggctag ctgacatact ggaagaaatt      60
gattttcaaa caaatgttcg gaatgaagtt gtgcgtttac aagatgaact gaagaggatg     120
cgttgtttct tgcgtgatgc agatgcaaag caagatgatg atgatagagt gcgcaactgg     180
gtgtctgata ttagaaatgt agcttatgat gctgaggatc tcattgacac attcattctc     240
agaattgatg ccgttcaaaa aaagaactcc atcaaaaagt atgcttccgt tttcaaagat     300
tggaaacgtc gctccaagat tgcaaatgag ctcattgcta ccagagaag aatccttgat     360 gtttctcaga gtcgtgaaaa gtatggtatc aagaacattg gagagggat agcacagca     420 aaagagaggc tccgcaagca gaagatcatc tctcctcgcg tgaagagaa agatattgtt     480 ggactggacg atgatatagc taagctggtg acacaacttg ttgatgctga ggaccaatgg     540
catgccattt cagtagtggg aatgggaggg atcggcaaga caactcttgc caagaaggtt     600
tacaatcatg ctgatatcca ggcccgtttt cctacccgag catgggttta tgtatcccag     660
gaatacagca ttcgagacat atttcaggca attataaagc aagtggcatc aacaggaagg     720
aatttggaaa aactgcggga agaagagttg gaagaaattc tctatgaaca cctccggaaa     780
aaacggtatt tggtggtctt ggatgatgta tggagcatag aagcatggaa ttctctttct     840
gaggcctttc cggatagcag cagcaatgga agcagagtga tgctaacgac tcgcaacaag     900
agtattgctc tcaaagcaga tgctagaagt gttccttatg atttgcactt tatgaatgaa     960
gaaaatggat ggatgttgtt ctgcaagaaa gctttcattc aaagtgctga ttcacatcgt    1020
tccccacgtt tggaggaaat cgggaaggag attgttgaaa aatgtgctgg tttaccactg    1080
```

```
gccatcattg tgatgggagg attgctttca acaaaaagaa gtttagcaga atggaaaagg    1140
gttctctcca acatgagctc attctttgct caagacccga atggggtatc agcaatactg    1200
gctttgagtt acaacgactt gccatattat ctcaaatctt gtttcctcca tctaggacag    1260
ttcccagaag accagccaat tccaacacat aaattgttta ggctatggat tgctgagggc    1320
ttgataccac agcaaggtga aagggtggag gatgtagcag aggactactt gaatgagcta    1380
atagagagaa acatggttca agtagccaaa tggagtgtca acgagagagt taaacaatgt    1440
cgtcttcatg atctattacg agatctctcc atttcaaagg ccaaagcaga gagctttcat    1500
gagattcaag ggagccaaag cctcgaacct tctgctagat cacgtcgtca tgccatctat    1560
tccacctttc attggcccca atgtaagtat tccaatcctc aacttcggac acttctccta    1620
tttagagttg atcataacca aagccaggtt aattattata taaatgatcc ctataaaatg    1680
gaaggcagcg atctagatta tattagcaaa aacttcaaat tactgagggt cttggagttg    1740
gagggtatac catgtgctac cattccaagc ataattgggt tactaattca tttgaagtac    1800
ttggggctaa aggagactaa cctgcaagag ctttcatccg ccattggttc tttgaggagc    1860
ctgcagactc ttgatatagc tgcaaatctt catcttctaa caattcccaa tgtcatatgg    1920
aagttaaaaa gattaaggca tctttacatg tgcgggcata aatatggggg gcctctgcga    1980
atcgacacat acagcatctt caagctctg tctgaaataa atgtccagag atggatgcaa    2040
aatgatcctg ccaatttaac cagcctgcga actgaagagg ctgattttcc atctctcaca    2100
caactttctg ctcttcaaaa tcttgtcaag ttgcatatga aggaacaat aaggcagttg    2160
ccaaactcag aggaattccc accaaatctc tgtcagctga ccttggaaca tacccatctc    2220
cagcaagatt cagtgggaat tcttgagaaa ttgccaagat tgttgatttt gagactaaaa    2280
gcacggtcct acgatggaga aaaatgaaa atatcagtca gcggctttcc ccaacttgaa    2340
gtcctggagc ttgttcatt ggaatcattg gaagagttga atcttgaaga aggtgcaatg    2400
ctaaggctta ggagttttcg gattataaag tgtgagaaat tgaagatgct tcctgaggga    2460
atgaaaaccc taaccggtct ccgtgagttg acattgaat tgatgccaaa atcattcgtg    2520
gataggattc gtggggaaga tttctacaaa gtgcagcatg ttccctctat cttgtttgtt    2580
tga                                                                  2583

<210> SEQ ID NO 8
<211> LENGTH: 860
<212> TYPE: PRT
<213> ORGANISM: Corchorus olitorius

<400> SEQUENCE: 8

Met Ala Glu Ala Ala Val Ser Phe Val Leu Glu Arg Leu Ala Asp Ile
1               5                   10                  15

Leu Glu Glu Ile Asp Phe Gln Thr Asn Val Arg Asn Glu Val Val Arg
            20                  25                  30

Leu Gln Asp Glu Leu Lys Arg Met Arg Cys Phe Leu Arg Asp Ala Asp
        35                  40                  45

Ala Lys Gln Asp Asp Asp Arg Val Arg Asn Trp Val Ser Asp Ile
    50                  55                  60

Arg Asn Val Ala Tyr Asp Ala Glu Asp Leu Ile Asp Thr Phe Ile Leu
65                  70                  75                  80

Arg Ile Asp Ala Val Gln Lys Lys Asn Ser Ile Lys Lys Tyr Ala Ser
                85                  90                  95

Val Phe Lys Asp Trp Lys Arg Arg Ser Lys Ile Ala Asn Glu Leu Ile
```

```
            100                 105                 110
Ala Ile Gln Arg Arg Ile Leu Asp Val Ser Gln Ser Arg Glu Lys Tyr
            115                 120                 125

Gly Ile Lys Asn Ile Gly Glu Gly Ile Ser Thr Ala Lys Glu Arg Leu
    130                 135                 140

Arg Lys Gln Arg Arg Ser Ser Pro Arg Gly Glu Lys Asp Ile Val
145                 150                 155                 160

Gly Leu Asp Asp Ile Ala Lys Leu Val Thr Gln Leu Val Asp Ala
                165                 170                 175

Glu Asp Gln Trp His Ala Ile Ser Val Val Gly Met Gly Ile Gly
            180                 185                 190

Lys Thr Thr Leu Ala Lys Lys Val Tyr Asn His Ala Asp Ile Gln Ala
            195                 200                 205

Arg Phe Pro Thr Arg Ala Trp Val Tyr Val Ser Gln Glu Tyr Ser Ile
    210                 215                 220

Arg Asp Ile Phe Gln Ala Ile Ile Lys Gln Val Ala Ser Thr Gly Arg
225                 230                 235                 240

Asn Leu Glu Lys Leu Arg Glu Glu Leu Glu Glu Ile Leu Tyr Glu
                245                 250                 255

His Leu Arg Lys Lys Arg Tyr Leu Val Val Leu Asp Asp Val Trp Ser
            260                 265                 270

Ile Glu Ala Trp Asn Ser Leu Ser Glu Ala Phe Pro Asp Ser Ser Ser
    275                 280                 285

Asn Gly Ser Arg Val Met Leu Thr Thr Arg Asn Lys Ser Ile Ala Leu
    290                 295                 300

Lys Ala Asp Ala Arg Ser Val Pro Tyr Asp Leu His Phe Met Asn Glu
305                 310                 315                 320

Glu Asn Gly Trp Met Leu Phe Cys Lys Lys Ala Phe Ile Gln Ser Ala
                325                 330                 335

Asp Ser His Arg Ser Pro Arg Leu Glu Glu Ile Gly Lys Glu Ile Val
            340                 345                 350

Glu Lys Cys Ala Gly Leu Pro Leu Ala Ile Ile Val Met Gly Gly Leu
            355                 360                 365

Leu Ser Thr Lys Arg Ser Leu Ala Glu Trp Lys Arg Val Leu Ser Asn
    370                 375                 380

Met Ser Ser Phe Phe Ala Gln Asp Pro Asn Gly Val Ser Ala Ile Leu
385                 390                 395                 400

Ala Leu Ser Tyr Asn Asp Leu Pro Tyr Tyr Leu Lys Ser Cys Phe Leu
                405                 410                 415

His Leu Gly Gln Phe Pro Glu Asp Gln Pro Ile Pro Thr His Lys Leu
            420                 425                 430

Phe Arg Leu Trp Ile Ala Glu Gly Leu Ile Pro Gln Gln Gly Glu Arg
            435                 440                 445

Val Glu Asp Val Ala Glu Asp Tyr Leu Asn Glu Leu Ile Glu Arg Asn
    450                 455                 460

Met Val Gln Val Ala Lys Trp Ser Val Asn Glu Arg Val Lys Gln Cys
465                 470                 475                 480

Arg Leu His Asp Leu Leu Arg Asp Leu Ser Ile Ser Lys Ala Lys Ala
                485                 490                 495

Glu Ser Phe His Glu Ile Gln Gly Ser Gln Ser Leu Glu Pro Ser Ala
            500                 505                 510

Arg Ser Arg Arg His Ala Ile Tyr Ser Thr Phe His Trp Pro Gln Cys
            515                 520                 525
```

| | | | | | | | | | | | | |
|---|---|---|---|---|---|---|---|---|---|---|---|---|
| Lys | Tyr | Ser | Asn | Pro | Gln | Leu | Arg | Thr | Leu | Leu | Phe | Arg | Val | Asp |
| | 530 | | | | 535 | | | | 540 | | | |

His Asn Gln Ser Gln Val Asn Tyr Tyr Ile Asn Asp Pro Tyr Lys Met
545 550 555 560

Glu Gly Ser Asp Leu Asp Tyr Ile Ser Lys Asn Phe Lys Leu Arg
565 570 575

Val Leu Glu Leu Glu Gly Ile Pro Cys Ala Thr Ile Pro Ser Ile Ile
580 585 590

Gly Leu Leu Ile His Leu Lys Tyr Leu Gly Leu Lys Glu Thr Asn Leu
595 600 605

Gln Glu Leu Ser Ser Ala Ile Gly Ser Leu Arg Ser Leu Gln Thr Leu
610 615 620

Asp Ile Ala Ala Asn Leu His Leu Leu Thr Ile Pro Asn Val Ile Trp
625 630 635 640

Lys Leu Lys Arg Leu Arg His Leu Tyr Met Cys Gly His Lys Tyr Gly
645 650 655

Gly Pro Leu Arg Ile Asp Thr Leu Gln His Leu Gln Ala Leu Ser Glu
660 665 670

Ile Asn Val Gln Arg Trp Met Gln Asn Asp Pro Ala Asn Leu Thr Ser
675 680 685

Leu Arg Thr Glu Glu Ala Asp Phe Pro Ser Leu Thr Gln Leu Ser Ala
690 695 700

Leu Gln Asn Leu Val Lys Leu His Met Arg Gly Thr Ile Arg Gln Leu
705 710 715 720

Pro Asn Ser Glu Glu Phe Pro Asn Leu Cys Gln Leu Thr Leu Glu
725 730 735

His Thr His Leu Gln Gln Asp Ser Val Gly Ile Leu Glu Lys Leu Pro
740 745 750

Arg Leu Leu Ile Leu Arg Leu Lys Ala Arg Ser Tyr Asp Gly Glu Lys
755 760 765

Met Lys Ile Ser Val Ser Gly Phe Pro Gln Leu Glu Val Leu Glu Leu
770 775 780

Val Ser Leu Glu Ser Leu Glu Glu Leu Asn Leu Glu Glu Gly Ala Met
785 790 795 800

Leu Arg Leu Arg Ser Phe Arg Ile Ile Lys Cys Glu Lys Leu Lys Met
805 810 815

Leu Pro Glu Gly Met Lys Thr Leu Thr Gly Leu Arg Glu Leu Asp Ile
820 825 830

Glu Leu Met Pro Lys Ser Phe Val Asp Arg Ile Arg Gly Glu Asp Phe
835 840 845

Tyr Lys Val Gln His Val Pro Ser Ile Leu Phe Val
850 855 860

<210> SEQ ID NO 9
<211> LENGTH: 6459
<212> TYPE: DNA
<213> ORGANISM: Corchorus olitorius
<400> SEQUENCE: 9

```
atggagtttg ttgtaggcat tgttagctct attttcacgc tgctgtaca attgattatc      60 tcccccatca aaacaaaat caaatacatt tccaatcatg agaacaatgt ccaaactctc     120
aagaatcaag ttgagagcct gaaggatgaa agaaagagag ttcaacattc tgttgatgcc     180
gctagacaaa acggggaaga gattgaagat gatgttaaaa agtggcagaa gacggtcgac     240
```

```
cagaagatcg ctgatgaagt agagaaagta attgcagatg aggagaaagc taagaaaaaa      300
tgtttcgttg gcttgtgtcc gaatctctgg gctcgttata agcatagtgt gaaagctgaa      360
gagaagggga aggttgtggc taagttgctt gaacagggca aatttgacaa ggtttcttat      420
cgtccagctc cacaaggtgc cagtgtcact gctgcatttg ttaaaggttt tgaagaattc      480
aagtcaagag aagtgctttt gaaaggaatc atggaggcgc tgaacgatga taaaatcaac      540
atcatgggag tgcatggcat gggtggcgtt ggcaagacca tgcttgttaa agaagttgct      600
agacaagtta aggaggggag gctatttgat tatgtggtta tggcaaaagt gactcagact      660
gttgatgtca agacaattca gaatgatatt gctgagttac tgggtttaag atttgacgaa      720
cagagtattg ttaggagggc tgatcgactg cgagaaagat tgaagagaga gacaaaagtt      780
cttgttgttc tggatgacgt atgggaaaga ttagatctgg aggaagttgg gattccagtt      840
gcagatgaac acaaggggtg caagatactg ctgacgtcca gagatctcaa tgtttttatcc     900 aatgggatga acagtgagaa aaattttgtg gttggccttc tcactgaaga agaaacctgg      960 aacctttttta gaagaaggc cggttatgtt gttgaaagtt ctgatataaa gcctacggct      1020
atcgaggtgg caaagaaatg tgcaaaattg ccaatcgcca tcgccacagt tgcaggggct      1080
ttgaggaaca aagaggcgtt ccattggaag gatgctctgt gccaattaca gaagccttca      1140
acagtaaacc tcaagggggt agcaacgact gtacattcag ctataaagct tagctacgat      1200 ttttttagaaa gcgaggaagt taaattcact ttcttgcttt gctgtttatt gggccgcaat     1260
ggtttgattg aggacttgtt gaagtatgtt attggtatga gattatttca aggcatcaca      1320
atagaggaaa caagaaacag agtattgact gtggtgagta atctgaaagc ctcttgcctg      1380
ttacttgata gctataataa tgaaaagttt gatatccatg atgttgtttg ggatgttgct      1440
ctattgattg catcaagaga ccgccatatg tttgtcttaa gagatggtga agagctaaaa      1500
gactggccta cccaggagat gaaggagaat tgcagtgcga ttaactttcg ttgtcctcgt      1560
attatgaccg agctacctga tgagatggaa ggtttacgtc tttccttatt gcgcttggac      1620
aatgtaggcg cattggaaat tccagccaac ttctttagac ggatggaaag actcgatgtc      1680
ttacatttca ctagaatgca ttttttcctcc ctacctgttt caattagtct ccttacaaac     1740
cttcacacac tgtgtctcag tgattgtgca ctgcaagata taaccattgt tggaaagctg      1800
aagaatttag aaatccttag ccttgcacgt tcagttattg aagccctgcc cgaggagaca      1860
gcgcaattga ctcggttaag gctgttagat ttgagtcatt gttctaaact tcagctcatt      1920
ccaccaaatg ttctatcaag tttgtccaag ttggaagaat tatatttgta caatagcttt      1980
gttcaatggg aaggtgaagt acatagcagc ggaaggagaa atgctagcct tgatgaacta      2040
aagcatttgt ctcatcttac cactttgtat gttcatatcc ccaatgccga aatagttcca      2100
aaagatcttt tcattgagag attggaaaga ttcagtattt tgattgaaga tgagcggcgt      2160
tggtacagtg agtttgaata ctcaagaact ttgaaattga agatatatac aagcatttat      2220
ttggatcatg cggtgagaat gttattgaag aaaactgaag atctacatct ataccaactt      2280
aaaggtatca agaatgtgct tgatgagtta attgatggtg tagaattgcc gcatctaaag      2340
aaccttcata ttcgcaatgg ttcggaggtc caatatatca tgaggaagaa aattgagtgc      2400
gctcaattaa agtccatgac acttgaaggt ctgccgaaac tgattagctt ttggtttgaa      2460
gacaaaaggt gttccacatc tcatgaggag cgagctacga gttccaatcc cctgccactt      2520
ttcaataaac agcttgtgtt cccttgcttg gaaagcctgc gattgtcctc aattaatgct      2580
```

-continued

```
gaaagaatat ggcacagccc tctttcggag aattgtactt ttgctgcaaa tttgaaaagc    2640
ttgacggttg aaggctgtgg cgaattggag catctattat caccctctgt tgccagaagt    2700
cttgtccagc ttacacactt cgaggtagca agatgccagc gcctaagaga gataatatct    2760
acagaggaaa tagaagatga gagtgttgcg atttgtttcc cccaattaaa ctccttagag    2820
ataagaagtc tccagaatct agcaaacttt tgtgcaggaa actataatat tgaattccca    2880
gcacttaaag tattggaggt taatggctgc cctgtattaa aggaattcat tagggtgaat    2940
aaaagtgagt ttcatgtgcc ggctctcttc aatgaaaagg ttgctcttcc tagcttggaa    3000
aggatggaat tctcctacct gaaaaatgtg aagatgatat ttgacaagca acttctggca    3060
ggttcctttt gcaaattaaa agcaatgtca gtttatcatt gtgatgcatt attgactatt    3120
ttttcatcta atatatttgg agcatttcag agtctagaaa atcttgatgt gtacagatgt    3180
aattcacttg aaatgatatt tgaggttgga gggttaaata tcagagaacc acacgttgta    3240
cactctcaac taagatctct gtatatttcc tcgctgcctg cattgaagca tgtttggaat    3300
aaagatcccc aaggaattct ttccttccaa aatcttcata cagtagattt gtcttttgt     3360 cggaatttga aaagtctatt tccagtgtca gtagccaaac accttcaaca gctcgaaaat    3420
ctgagactgt gtaattctgc ggtggaggag attgtgtttt cagaagaagg attagaagag    3480
cccattgggt tcgagtttgc tcaactgtct tcccttgtgc tttataatct aagagagctc    3540
aaatgcttct atcgagggca gcatacaata gtgtgggcga tgttgaaaaa gttggagacg    3600
gatcattcta ctttactgaa gatagtaggt agtaattcac aacatcttgg catccaagaa    3660
atgaatagca atgacccacc agaatgcaca actggacaac cactttttc gactgaaaag      3720 gtcattccca ttttagagga actgcatttg cggttaacaa accctgatga catttcaaag    3780
atatgtgatg gccattttct ccaaagattc tgcaatttgg aaagtttaga actttcatct    3840
tctgaaggag atgatgctca gatactacca gatgcggtga cacttccacg aattaaaaca    3900
ttaatattgt cttcttgcaa cttcttaag catatatggg agaagaagga ttcagagcta    3960
gggcacattc ttcaaaagct cgaaattctt gaagttaacg agtgtggcga tttgacaagt    4020 tttgaccgt cctcggcatc ttttcaaaat ctcacaactt tggaagtgac atactgcaac     4080
atgatgataa acttggctac accctcagta gtccagaatc tggtacaatt aacaaccatg    4140
aggatagcat actgcagggg aatggcagaa atagttgcaa atgagggagg tgaagcaaca    4200
ccaacatatg agatcaattt cagcaagttg caaagtttag aactcaatcg gttacatcgc    4260
ctcacaagct tttctccagg gaattacacc atcaactttc cttccttgca agaattaatg    4320
agagtaaaag aatcacataa tgatcgaaaa gggcgttggg ccggtgacct taataccacc    4380
atacaacttt tgtacagcgt aaatgttgtt gagggatacc atggcatatg taatttgaaa    4440
ttatcagaca cctctcctga gttgatggaa atatggaatg gaaggaaccc tcatgaaatt    4500
gtggacttga aattccttgg acgtgtggaa ttttgtaact gtagcagctt gaaatacatt    4560
tttactctgt ccaggttgtt gagcctcaag cacctatctt atttagtagt aaaagaatgc    4620
agtactctga aagaagttgt gatggaacag gaaattgagg aggaagcaac aaccgataac    4680
ttcatattcc ctaatctccg gtacattaaa attgagtcat gttccagctt gagatgcttt    4740
tatttgggaa gtggagctct tgaaattcca cggttggaaa ttattgagat aactgactgt    4800
ccaaaaatga ctacgtttgc ttcttcattc ccaagagatg aggagaaaga gattagtgct    4860
gatggaagtg aaaaaagggt tggccatggc gacctcaata ttgaaccgtt tttcagcgat    4920
aaggtggcct tgcctagttt agaaaggttg agaatcaaag gcatgggaa  atgtagaaag    4980
```

```
atatggcaag accaactcac tgtgaattca ttttgcgagc taaagtatat actggtagaa    5040
agctgtgaaa aactctcaaa tattttccca ttcaacatga tggaaaggct tgagaaacta    5100
gaagagttgc agattgtgaa ttgtgattca ttagaagaaa tctttgagcc agaagccctc    5160
actaataatc aatcacatgg agttgccact actgaatcta ttgtagaaga acaatggct     5220 aagtttgtat ttcccagtgc tacatacctt cgacttgaaa acttgcccaa cttgaaatgt    5280
ttttactcga ggacacatgc taccgaatgg ccatctctga aaaaaatgaa ggttctcgat    5340
tgccaaaatg tgcagatttt tgcttcagaa tgtcctgcct ttggagaaac acaaggagcg    5400
agcacagaaa ttaatatctc aaatcaacct cctctgtttc gggtcaacga ggttacattc    5460
ccaatcttag aagaattaaa attgaagcca gatgatacat ggcatggaca agtactctca    5520
acagagtgtt tcagcaaatt gaaagttcta gagctcatct gcattcctga aaggcaaca     5580 gatcttgcat gttgcttcat tcaatcattg ccgaatcttg aaaagttact tgtgaaggat    5640
tcttctttct gtcaaatatt ccagtttgaa ggactcagtg atgatgacca agacatgca     5700 gcactcactc ggttaagtga attgagattg tctaaacttc cagagttgac acatctctgg    5760
acggaagaat tccaacccgg agcagcattt tctaacctga aacttcttga agtgcttcat    5820
tgtgtcaaat taaagacttt agtcccatct ttggtgtctt tcaacaattt aacaactctg    5880
aaagtttcag gatgtcatgg attaaccaat ttagtaacat gctcaatagc tacaagcttg    5940
atgcaactca aagaatgag tataactgat tgcaacatga tagaagagat catagcatgt    6000
gatgctgatg aaattcaagg tgccattgtt ttctcccagt tgagatattt gaaactcagc    6060
tgtctaccaa gtttggcaag cttttgctta ggcaatcaga gctttgattt cccaaccttg    6120
caaaagttga ttgttcatga atgcccaaaa ctggagattt tctgtcaagg agacttaacc    6180
accccaaagc tgcagcaagt gctattgcca gagtatgaat atgaatacta tgatgcagaa    6240
gagtatgaag atgaatatga tgcagaagag tatgaagaaa acagcatgtg ggagggcgac    6300
cttaaaagta ctataagaaa gctgttcgaa gaaatggcag aggatgaaga tgaagatgaa    6360
gatgaagatg atgatgaaga gcatgaagat gaagatgaag atgaagatga tgatgaagag    6420
catgaagatg aagatgaaga tgaagatgat gatggttga                          6459
```

<210> SEQ ID NO 10
<211> LENGTH: 2152
<212> TYPE: PRT
<213> ORGANISM: Corchorus olitorius

<400> SEQUENCE: 10

Met Glu Phe Val Val Gly Ile Val Ser Ser Ile Phe Thr Pro Ala Val
1               5                   10                  15

Gln Leu Ile Ile Ser Pro Ile Lys Asn Lys Ile Lys Tyr Ile Ser Asn
            20                  25                  30

His Glu Asn Asn Val Gln Thr Leu Lys Asn Gln Val Glu Ser Leu Lys
        35                  40                  45

Asp Glu Arg Lys Arg Val Gln His Ser Val Asp Ala Ala Arg Gln Asn
    50                  55                  60

Gly Glu Glu Ile Glu Asp Asp Val Lys Lys Trp Gln Lys Thr Val Asp
65                  70                  75                  80

Gln Lys Ile Ala Asp Glu Val Glu Lys Val Ile Ala Asp Glu Glu Lys
                85                  90                  95

Ala Lys Lys Lys Cys Phe Val Gly Leu Cys Pro Asn Leu Trp Ala Arg
            100                 105                 110

```
Tyr Lys His Ser Val Lys Ala Glu Glu Lys Gly Lys Val Val Ala Lys
            115                 120                 125

Leu Leu Glu Gln Gly Lys Phe Asp Lys Val Ser Tyr Arg Pro Ala Pro
    130                 135                 140

Gln Gly Ala Ser Val Thr Ala Ala Phe Val Lys Gly Phe Glu Glu Phe
145                 150                 155                 160

Lys Ser Arg Glu Val Leu Leu Lys Gly Ile Met Glu Ala Leu Asn Asp
                165                 170                 175

Asp Lys Ile Asn Ile Met Gly Val His Gly Met Gly Val Gly Lys
            180                 185                 190

Thr Met Leu Val Lys Glu Val Ala Arg Gln Val Lys Glu Gly Arg Leu
    195                 200                 205

Phe Asp Tyr Val Val Met Ala Lys Val Thr Gln Thr Val Asp Val Lys
210                 215                 220

Thr Ile Gln Asn Asp Ile Ala Glu Leu Leu Gly Leu Arg Phe Asp Glu
225                 230                 235                 240

Gln Ser Ile Val Arg Arg Ala Asp Arg Leu Arg Glu Arg Leu Lys Arg
                245                 250                 255

Glu Thr Lys Val Leu Val Val Leu Asp Asp Val Trp Glu Arg Leu Asp
            260                 265                 270

Leu Glu Glu Val Gly Ile Pro Val Ala Asp Glu His Lys Gly Cys Lys
    275                 280                 285

Ile Leu Leu Thr Ser Arg Asp Leu Asn Val Leu Ser Asn Gly Met Asn
290                 295                 300

Ser Glu Lys Asn Phe Val Gly Leu Leu Thr Glu Glu Thr Trp
305                 310                 315                 320

Asn Leu Phe Lys Lys Lys Ala Gly Tyr Val Val Glu Ser Ser Asp Ile
                325                 330                 335

Lys Pro Thr Ala Ile Glu Val Ala Lys Lys Cys Ala Lys Leu Pro Ile
            340                 345                 350

Ala Ile Ala Thr Val Ala Gly Ala Leu Arg Asn Lys Glu Ala Phe His
    355                 360                 365

Trp Lys Asp Ala Leu Cys Gln Leu Gln Lys Pro Ser Thr Val Asn Leu
370                 375                 380

Lys Gly Val Ala Thr Thr Val His Ser Ala Ile Lys Leu Ser Tyr Asp
385                 390                 395                 400

Phe Leu Glu Ser Glu Glu Val Lys Phe Thr Phe Leu Leu Cys Cys Leu
                405                 410                 415

Leu Gly Arg Asn Gly Leu Ile Glu Asp Leu Leu Lys Tyr Val Ile Gly
            420                 425                 430

Met Arg Leu Phe Gln Gly Ile Thr Ile Glu Glu Thr Arg Asn Arg Val
    435                 440                 445

Leu Thr Val Val Ser Asn Leu Lys Ala Ser Cys Leu Leu Leu Asp Ser
450                 455                 460

Tyr Asn Asn Glu Lys Phe Asp Ile His Asp Val Val Trp Asp Val Ala
465                 470                 475                 480

Leu Leu Ile Ala Ser Arg Asp Arg His Met Phe Val Leu Arg Asp Gly
                485                 490                 495

Glu Glu Leu Lys Asp Trp Pro Thr Gln Glu Met Lys Glu Asn Cys Ser
            500                 505                 510

Ala Ile Asn Phe Arg Cys Pro Arg Ile Met Thr Glu Leu Pro Asp Glu
    515                 520                 525
```

```
Met Glu Gly Leu Arg Leu Ser Leu Leu Arg Leu Asp Asn Val Gly Ala
            530                 535                 540
Leu Glu Ile Pro Ala Asn Phe Phe Arg Met Glu Arg Leu Asp Val
545                 550                 555                 560
Leu His Phe Thr Arg Met His Phe Ser Ser Leu Pro Val Ser Ile Ser
                565                 570                 575
Leu Leu Thr Asn Leu His Thr Leu Cys Leu Ser Asp Cys Ala Leu Gln
            580                 585                 590
Asp Ile Thr Ile Val Gly Lys Leu Lys Asn Leu Glu Ile Leu Ser Leu
            595                 600                 605
Ala Arg Ser Val Ile Glu Ala Leu Pro Glu Glu Thr Ala Gln Leu Thr
610                 615                 620
Arg Leu Arg Leu Leu Asp Leu Ser His Cys Ser Lys Leu Gln Leu Ile
625                 630                 635                 640
Pro Pro Asn Val Leu Ser Ser Leu Ser Lys Leu Glu Glu Leu Tyr Leu
                645                 650                 655
Tyr Asn Ser Phe Val Gln Trp Glu Gly Glu Val His Ser Ser Gly Arg
            660                 665                 670
Arg Asn Ala Ser Leu Asp Glu Leu Lys His Leu Ser His Leu Thr Thr
            675                 680                 685
Leu Tyr Val His Ile Pro Asn Ala Glu Ile Val Pro Lys Asp Leu Phe
            690                 695                 700
Ile Glu Arg Leu Glu Arg Phe Ser Ile Leu Ile Glu Asp Glu Arg Arg
705                 710                 715                 720
Trp Tyr Ser Glu Phe Glu Tyr Ser Arg Thr Leu Lys Leu Lys Ile Tyr
                725                 730                 735
Thr Ser Ile Tyr Leu Asp His Ala Val Arg Met Leu Leu Lys Lys Thr
            740                 745                 750
Glu Asp Leu His Leu Tyr Gln Leu Lys Gly Ile Lys Asn Val Leu Asp
            755                 760                 765
Glu Leu Ile Asp Gly Val Glu Leu Pro His Leu Lys Asn Leu His Ile
770                 775                 780
Arg Asn Gly Ser Glu Val Gln Tyr Ile Met Arg Lys Lys Ile Glu Cys
785                 790                 795                 800
Ala Gln Leu Lys Ser Met Thr Leu Glu Gly Leu Pro Lys Leu Ile Ser
                805                 810                 815
Phe Trp Phe Glu Asp Lys Arg Cys Ser Thr His Glu Glu Arg Ala
            820                 825                 830
Thr Ser Ser Asn Pro Leu Pro Leu Phe Asn Lys Gln Leu Val Phe Pro
            835                 840                 845
Cys Leu Glu Ser Leu Arg Leu Ser Ser Ile Asn Ala Glu Arg Ile Trp
850                 855                 860
His Ser Pro Leu Ser Glu Asn Cys Thr Phe Ala Ala Asn Leu Lys Ser
865                 870                 875                 880
Leu Thr Val Glu Gly Cys Gly Glu Leu Glu His Leu Leu Ser Pro Ser
                885                 890                 895
Val Ala Arg Ser Leu Val Gln Leu Thr His Phe Glu Val Ala Arg Cys
            900                 905                 910
Gln Arg Leu Arg Glu Ile Ile Ser Thr Glu Glu Ile Glu Asp Glu Ser
            915                 920                 925
Val Ala Ile Cys Phe Pro Gln Leu Asn Ser Leu Glu Ile Arg Ser Leu
            930                 935                 940
Gln Asn Leu Ala Asn Phe Cys Ala Gly Asn Tyr Asn Ile Glu Phe Pro
```

-continued

```
945                 950                 955                 960
Ala Leu Lys Val Leu Glu Val Asn Gly Cys Pro Val Leu Lys Glu Phe
            965                 970                 975
Ile Arg Val Asn Lys Ser Glu Phe His Val Pro Ala Leu Phe Asn Glu
            980                 985                 990
Lys Val Ala Leu Pro Ser Leu Glu Arg Met Glu Phe Ser Tyr Leu Lys
            995                 1000                1005
Asn Val Lys Met Ile Phe Asp Lys Gln Leu Leu Ala Gly Ser Phe
    1010                1015                1020
Cys Lys Leu Lys Ala Met Ser Val Tyr His Cys Asp Ala Leu Leu
    1025                1030                1035
Thr Ile Phe Ser Ser Asn Ile Phe Gly Ala Phe Gln Ser Leu Glu
    1040                1045                1050
Asn Leu Asp Val Tyr Arg Cys Asn Ser Leu Glu Met Ile Phe Glu
    1055                1060                1065
Val Gly Gly Leu Asn Ile Arg Glu Pro His Val Val His Ser Gln
    1070                1075                1080
Leu Arg Ser Leu Tyr Ile Ser Ser Leu Pro Ala Leu Lys His Val
    1085                1090                1095
Trp Asn Lys Asp Pro Gln Gly Ile Leu Ser Phe Gln Asn Leu His
    1100                1105                1110
Thr Val Asp Leu Ser Phe Cys Arg Asn Leu Lys Ser Leu Phe Pro
    1115                1120                1125
Val Ser Val Ala Lys His Leu Gln Gln Leu Glu Asn Leu Arg Leu
    1130                1135                1140
Cys Asn Ser Ala Val Glu Glu Ile Val Phe Ser Glu Glu Gly Leu
    1145                1150                1155
Glu Glu Pro Ile Gly Phe Glu Phe Ala Gln Leu Ser Ser Leu Val
    1160                1165                1170
Leu Tyr Asn Leu Arg Glu Leu Lys Cys Phe Tyr Arg Gly Gln His
    1175                1180                1185
Thr Ile Val Trp Ala Met Leu Lys Lys Leu Glu Thr Asp His Ser
    1190                1195                1200
Thr Leu Leu Lys Ile Val Gly Ser Asn Ser Gln His Leu Gly Ile
    1205                1210                1215
Gln Glu Met Asn Ser Asn Asp Pro Pro Glu Cys Thr Thr Gly Gln
    1220                1225                1230
Pro Leu Phe Ser Thr Glu Lys Val Ile Pro Ile Leu Glu Glu Leu
    1235                1240                1245
His Leu Arg Leu Thr Asn Pro Asp Asp Ile Ser Lys Ile Cys Asp
    1250                1255                1260
Gly His Phe Leu Gln Arg Phe Cys Asn Leu Glu Ser Leu Glu Leu
    1265                1270                1275
Ser Ser Ser Glu Gly Asp Asp Ala Gln Ile Leu Pro Asp Ala Val
    1280                1285                1290
Thr Leu Pro Arg Ile Lys Thr Leu Ile Leu Ser Ser Cys Asn Phe
    1295                1300                1305
Leu Lys His Ile Trp Glu Lys Lys Asp Ser Glu Leu Gly His Ile
    1310                1315                1320
Leu Gln Lys Leu Glu Ile Leu Glu Val Asn Glu Cys Gly Asp Leu
    1325                1330                1335
Thr Ser Phe Gly Pro Ser Ser Ala Ser Phe Gln Asn Leu Thr Thr
    1340                1345                1350
```

```
Leu Glu Val Thr Tyr Cys Asn Met Met Ile Asn Leu Ala Thr Pro
    1355                1360                1365

Ser Val Val Gln Asn Leu Val Gln Leu Thr Thr Met Arg Ile Ala
    1370                1375                1380

Tyr Cys Arg Gly Met Ala Glu Ile Val Ala Asn Glu Gly Gly Glu
    1385                1390                1395

Ala Thr Pro Thr Tyr Glu Ile Asn Phe Ser Lys Leu Gln Ser Leu
    1400                1405                1410

Glu Leu Asn Arg Leu His Arg Leu Thr Ser Phe Ser Pro Gly Asn
    1415                1420                1425

Tyr Thr Ile Asn Phe Pro Ser Leu Gln Glu Leu Met Arg Val Lys
    1430                1435                1440

Glu Ser His Asn Asp Arg Lys Gly Arg Trp Ala Gly Asp Leu Asn
    1445                1450                1455

Thr Thr Ile Gln Leu Leu Tyr Ser Val Asn Val Val Glu Gly Tyr
    1460                1465                1470

His Gly Ile Cys Asn Leu Lys Leu Ser Asp Thr Ser Pro Glu Leu
    1475                1480                1485

Met Glu Ile Trp Asn Gly Arg Asn Pro His Glu Ile Val Asp Leu
    1490                1495                1500

Lys Phe Leu Gly Arg Val Glu Phe Cys Asn Cys Ser Ser Leu Lys
    1505                1510                1515

Tyr Ile Phe Thr Leu Ser Arg Leu Leu Ser Leu Lys His Leu Ser
    1520                1525                1530

Tyr Leu Val Val Lys Glu Cys Ser Thr Leu Lys Glu Val Val Met
    1535                1540                1545

Glu Gln Glu Ile Glu Glu Glu Ala Thr Thr Asp Asn Phe Ile Phe
    1550                1555                1560

Pro Asn Leu Arg Tyr Ile Lys Ile Glu Ser Cys Ser Ser Leu Arg
    1565                1570                1575

Cys Phe Tyr Leu Gly Ser Gly Ala Leu Glu Ile Pro Arg Leu Glu
    1580                1585                1590

Ile Ile Glu Ile Thr Asp Cys Pro Lys Met Thr Thr Phe Ala Ser
    1595                1600                1605

Ser Phe Pro Arg Asp Glu Glu Lys Glu Ile Ser Ala Asp Gly Ser
    1610                1615                1620

Glu Lys Arg Val Gly His Gly Asp Leu Asn Ile Glu Pro Phe Phe
    1625                1630                1635

Ser Asp Lys Val Ala Leu Pro Ser Leu Glu Arg Leu Arg Ile Lys
    1640                1645                1650

Gly Met Gly Lys Cys Arg Lys Ile Trp Gln Asp Gln Leu Thr Val
    1655                1660                1665

Asn Ser Phe Cys Glu Leu Lys Tyr Ile Leu Val Glu Ser Cys Glu
    1670                1675                1680

Lys Leu Ser Asn Ile Phe Pro Phe Asn Met Met Glu Arg Leu Glu
    1685                1690                1695

Lys Leu Glu Glu Leu Gln Ile Val Asn Cys Asp Ser Leu Glu Glu
    1700                1705                1710

Ile Phe Glu Pro Glu Ala Leu Thr Asn Asn Gln Ser His Gly Val
    1715                1720                1725

Ala Thr Thr Glu Ser Ile Val Glu Glu Thr Met Ala Lys Phe Val
    1730                1735                1740
```

```
Phe Pro Ser Ala Thr Tyr Leu Arg Leu Glu Asn Leu Pro Asn Leu
    1745                1750                1755

Lys Cys Phe Tyr Ser Arg Thr His Ala Thr Glu Trp Pro Ser Leu
    1760                1765                1770

Lys Lys Met Lys Val Leu Asp Cys Gln Asn Val Gln Ile Phe Ala
    1775                1780                1785

Ser Glu Cys Pro Ala Phe Gly Glu Thr Gln Gly Ala Ser Thr Glu
    1790                1795                1800

Ile Asn Ile Ser Asn Gln Pro Pro Leu Phe Arg Val Asn Glu Val
    1805                1810                1815

Thr Phe Pro Ile Leu Glu Glu Leu Lys Leu Lys Pro Asp Asp Thr
    1820                1825                1830

Trp His Gly Gln Val Leu Ser Thr Glu Cys Phe Ser Lys Leu Lys
    1835                1840                1845

Val Leu Glu Leu Ile Cys Ile Pro Glu Lys Ala Thr Asp Leu Ala
    1850                1855                1860

Cys Cys Phe Ile Gln Ser Leu Pro Asn Leu Glu Lys Leu Leu Val
    1865                1870                1875

Lys Asp Ser Ser Phe Cys Gln Ile Phe Gln Phe Glu Gly Leu Ser
    1880                1885                1890

Asp Asp Asp Gln Arg His Ala Ala Leu Thr Arg Leu Ser Glu Leu
    1895                1900                1905

Arg Leu Ser Lys Leu Pro Glu Leu Thr His Leu Trp Thr Glu Glu
    1910                1915                1920

Phe Gln Pro Gly Ala Ala Phe Ser Asn Leu Lys Leu Leu Glu Val
    1925                1930                1935

Leu His Cys Val Lys Leu Lys Thr Leu Val Pro Ser Leu Val Ser
    1940                1945                1950

Phe Asn Asn Leu Thr Thr Leu Lys Val Ser Gly Cys His Gly Leu
    1955                1960                1965

Thr Asn Leu Val Thr Cys Ser Ile Ala Thr Ser Leu Met Gln Leu
    1970                1975                1980

Lys Arg Met Ser Ile Thr Asp Cys Asn Met Ile Glu Glu Ile Ile
    1985                1990                1995

Ala Cys Asp Ala Asp Glu Ile Gln Gly Ala Ile Val Phe Ser Gln
    2000                2005                2010

Leu Arg Tyr Leu Lys Leu Ser Cys Leu Pro Ser Leu Ala Ser Phe
    2015                2020                2025

Cys Leu Gly Asn Gln Ser Phe Asp Phe Pro Thr Leu Gln Lys Leu
    2030                2035                2040

Ile Val His Glu Cys Pro Lys Leu Glu Ile Phe Cys Gln Gly Asp
    2045                2050                2055

Leu Thr Thr Pro Lys Leu Gln Gln Val Leu Leu Pro Glu Tyr Glu
    2060                2065                2070

Tyr Glu Tyr Tyr Asp Ala Glu Glu Tyr Glu Asp Glu Tyr Asp Ala
    2075                2080                2085

Glu Glu Tyr Glu Glu Asn Ser Met Trp Glu Gly Asp Leu Lys Ser
    2090                2095                2100

Thr Ile Arg Lys Leu Phe Glu Glu Met Ala Glu Asp Glu Asp Glu
    2105                2110                2115

Asp Glu Asp Glu Asp Asp Asp Glu Glu His Glu Asp Glu Asp Glu
    2120                2125                2130

Asp Glu Asp Asp Asp Glu Glu His Glu Asp Glu Asp Glu Asp Glu
```

```
                    2135                2140                2145

Asp Asp  Asp Gly
    2150

<210> SEQ ID NO 11
<211> LENGTH: 928
<212> TYPE: DNA
<213> ORGANISM: Corchorus olitorius

<400> SEQUENCE: 11
atgaaatgtc ctcaactttt gtgcctgatg gatgaagaga atgagctgcc ctccaatctg     60
gagtatgtgg aaattgaaga ttgtagtaac ctggcaaagc ttccaaatgg gctacaaaag    120
cttcgatcat tgaaagattt gagtgttaaa tggtgcccca aactgatgtc tttccaaat    180 gcagagttgc catctacgct gaaaactttg tcaatcttgg gatgtgaatc tttagagtct    240
ttacccaagg gactggtgca caatggtagc agcagcattg gtagatgtaa tcttgataac    300
ctggagattc taggatgtcc atctcttaga ttgttttcaa ctggtgagct accaacttgc    360
cttaagcaac tcgatatttg ggattgcatg cagttgaagt gtattccaga gagattgctg    420
gagaatagtc agtcacttga atttattcgt attgggaact gcaaaaattt gaaaaccta    480 ccgcagtgcc tatacaggtt tgattatcta actgagttgc atgtaaatca atgcccttcc    540
ttggagtctt tcccagaaaa gggcttgcct attcgcaacc tcaatctggt tttaatatcc    600
aactgtgtga atcttaagtc cctaccaaat cggatgcatt acctcacatc cctgcagtat    660
ttgactttat ttggttgtcc aagtgtagaa tcctttccgg aagaagagtt tactattcca    720
acaactcttg tccacctgcg agtccagagt ctacctaatc tggaatattt atctaagggg    780
ctccaggacc ttgtttttct tgaatcattg gatgtctgga attgccctaa gcttcagtac    840
ttgccaaagg atggcctgcc aagcatgctt ggtttacttc agatcagaaa ctgtcctctt    900
ctagaaaaaa aatgcttata tgagaaag                                      928

<210> SEQ ID NO 12
<211> LENGTH: 309
<212> TYPE: PRT
<213> ORGANISM: Corchorus olitorius

<400> SEQUENCE: 12

Met Lys Cys Pro Gln Leu Leu Cys Leu Met Asp Glu Glu Asn Glu Leu
1               5                   10                  15

Pro Ser Asn Leu Glu Tyr Val Glu Ile Glu Asp Cys Ser Asn Leu Ala
            20                  25                  30

Lys Leu Pro Asn Gly Leu Gln Lys Leu Arg Ser Leu Lys Asp Leu Ser
        35                  40                  45

Val Lys Trp Cys Pro Lys Leu Met Ser Phe Pro Asn Ala Glu Leu Pro
    50                  55                  60

Ser Thr Leu Lys Thr Leu Ser Ile Leu Gly Cys Glu Ser Leu Glu Ser
65                  70                  75                  80

Leu Pro Lys Gly Leu Val His Asn Gly Ser Ser Ser Ile Gly Arg Cys
                85                  90                  95

Asn Leu Asp Asn Leu Glu Ile Leu Gly Cys Pro Ser Leu Arg Leu Phe
            100                 105                 110

Ser Thr Gly Glu Leu Pro Thr Cys Leu Lys Gln Leu Asp Ile Trp Asp
        115                 120                 125

Cys Met Gln Leu Lys Cys Ile Pro Glu Arg Leu Leu Glu Asn Ser Gln
    130                 135                 140
```

```
Ser Leu Glu Phe Ile Arg Ile Gly Asn Cys Lys Asn Leu Lys Thr Leu
145                 150                 155                 160

Pro Gln Cys Leu Tyr Arg Phe Asp Tyr Leu Thr Glu Leu His Val Asn
                165                 170                 175

Gln Cys Pro Ser Leu Glu Ser Phe Pro Glu Lys Gly Leu Pro Ile Arg
            180                 185                 190

Asn Leu Asn Leu Val Leu Ile Ser Asn Cys Val Asn Leu Lys Ser Leu
        195                 200                 205

Pro Asn Arg Met His Tyr Leu Thr Ser Leu Gln Tyr Leu Thr Leu Phe
    210                 215                 220

Gly Cys Pro Ser Val Glu Ser Phe Pro Glu Glu Phe Thr Ile Pro
225                 230                 235                 240

Thr Thr Leu Val His Leu Arg Val Gln Ser Leu Pro Asn Leu Glu Tyr
                245                 250                 255

Leu Ser Lys Gly Leu Gln Asp Leu Val Phe Leu Glu Ser Leu Asp Val
            260                 265                 270

Trp Asn Cys Pro Lys Leu Gln Tyr Leu Pro Lys Asp Gly Leu Pro Ser
        275                 280                 285

Met Leu Gly Leu Leu Gln Ile Arg Asn Cys Pro Leu Leu Glu Lys Lys
    290                 295                 300

Cys Leu Tyr Glu Lys
305

<210> SEQ ID NO 13
<211> LENGTH: 565
<212> TYPE: DNA
<213> ORGANISM: Corchorus olitorius

<400> SEQUENCE: 13
atgccgagca attttggtgc attaactaat cttcaactgc tatcagattt tgttgtgggc    60
aaagacaagg gatatcaaat aagggagcta caggatttat caaatctcaa gggttcactt   120
tatatttcag ggttagagaa tgttgttgaa actgaagatg catcaaaggc taagatacat   180
gataagtcag gactagataa gttggtgtta gactggaaga gtggaatgaa gaagaataga   240
gactttgaga atataagaga agatgttgag caaaaggtgt tggatttgct tgaaccatct   300
aaacaactta aaaagcttgt tattatgcac tacagaggtt tgatgttggc aaaatgggtg   360
ggaaattctt cattgactaa tttagaatct ttacagctta taaattgtac caattgcttg   420
tcattgccat cgcttgggga actaccattg ttgaaaaatg tggtgatcag agattggat   480 agtataagca gtgtgggagt agagttcctt ggagaaaaaa cgatggaacc ttttcgagca   540
ttggagcttt tacaatttga agaca                                         565

<210> SEQ ID NO 14
<211> LENGTH: 188
<212> TYPE: PRT
<213> ORGANISM: Corchorus olitorius

<400> SEQUENCE: 14

Met Pro Ser Asn Phe Gly Ala Leu Thr Asn Leu Gln Leu Leu Ser Asp
1               5                   10                  15

Phe Val Val Gly Lys Asp Lys Gly Tyr Gln Ile Arg Glu Leu Gln Asp
                20                  25                  30

Leu Ser Asn Leu Lys Gly Ser Leu Tyr Ile Ser Gly Leu Glu Asn Val
            35                  40                  45
```

-continued

```
Val Glu Thr Glu Asp Ala Ser Lys Ala Lys Ile His Asp Lys Ser Gly
    50                  55                  60

Leu Asp Lys Leu Val Leu Asp Trp Lys Ser Gly Met Lys Lys Asn Arg
65                  70                  75                  80

Asp Phe Glu Asn Ile Arg Glu Asp Val Glu Gln Lys Val Leu Asp Leu
                85                  90                  95

Leu Glu Pro Ser Lys Gln Leu Lys Lys Leu Val Ile Met His Tyr Arg
            100                 105                 110
Gly Leu Met Leu Ala Lys Trp Val Gly Asn Ser Ser Leu Thr Asn Leu
        115                 120                 125
Glu Ser Leu Gln Leu Ile Asn Cys Thr Asn Cys Leu Ser Leu Pro Ser
    130                 135                 140

Leu Gly Glu Leu Pro Leu Leu Lys Asn Val Val Ile Arg Arg Leu Asp
145                 150                 155                 160
Ser Ile Ser Ser Val Gly Val Glu Phe Leu Gly Glu Lys Thr Met Glu
                165                 170                 175
Pro Phe Arg Ala Leu Glu Leu Leu Gln Phe Glu Asp
            180                 185

<210> SEQ ID NO 15
<211> LENGTH: 3141
<212> TYPE: DNA
<213> ORGANISM: Corchorus olitorius

<400> SEQUENCE: 15
atggatccat tacaagctgt tgcagctgca acacaaataa tatccagtat ggttggggct     60
gttggagcat tagaacaagc ctccagaaat cttgatgaag ctccaaagag aatccgaagc    120
ctagaagaat ttgtgtgtga tcttgagaat ttggcacaac gaattaggca aaaacatgcc    180
aacaagcttc acaatgctca gttagattac caacttcaaa gtttgcatgc ccttatagaa    240
aggctgcgcc caaacatcag gaaggcaaga acagttgtat caaaaagtaa aatcaagaac    300
ttggctaagg tattctggaa ttccatggcc ggagatccgc ttggaaaact gacagtttta    360
attaaagatg acttaaattg gtggcttgat actcaaatgt tggcacaaaa tgttgagaaa    420
gtactagaat caaccgcaca agatacgcca gttcgattga aaataaagac tgatcaaggc    480
tacccaactt ctagtaaatg tatctttgtg aaggagttgc ttgaacagga ggatactcat    540
cgagtcattc taattgttgg gttatctggt attggaaagt cttgtttagc tcgtcaagta    600
gcttctgatc cacccaaaaa atttgcaggt ggagcacttg aacttggatt tgggcaatgg    660
tgtagtcgtg ctgcttgcaa tggcagtaag gttgaatatc agaagcgttt ggcaaggaaa    720
attagtaaat tcctggtgca gattgggttc tggaaaaaga ttaaggagga gaatagtgga    780
gatcttgatt atgtttgtta cttgcttcaa gaagccttgt atgggaaaag cattttagtc    840
cttcttgatg atgtatggga gcaggacata gttcagcggt ttgctaaact gtatgataac    900
aattgtaagt acttagtaac aacaagaaat gaagccgtcc atgaaattac agaagctgaa    960
aaggtagagc taagcaagga tgatataagg gagataagca agggaatcct tctgtaccat   1020
agcctcctta gtgaagaaga gcttccgggt atagcagaga gcttacttga acggtgtggc   1080
caccaccctc taacagttgc tgttatggga aaggctctta gaaaagaagt aagagctgag   1140
aaatgggaga aggctataac caacctatca actttttgcta catgcgcacc aggtccagtc   1200
tcatatgtga atgagaaaga tgctgaggac acattaacca tttttggttc atttgagttc   1260
agtctagaag caatgcctgt tgactcaaag agactcttca tcgctcttgc ttctctttca   1320
```

-continued

```
tgggcagaac cggtaccaga agcatgcata gaggctatat ggtcatgtat cgggcaggag   1380
agcttgtttt cactcattgt ctgcaagctt gtcgaagggt ctttattgat gaaggtagac   1440
atggatccac tataccaagt acatgacatg gtttcattgt accttgatag caagactact   1500
gattcaattg agatgctact gcatagatct aaaccagaag aaactgcatt tatttgccct   1560
tggcttctta tttttgggaa agagaatgtg aaaaagattg ttgaagagag gatgaagctt   1620
ttctttgata ttttagatga aaaacaagtg gttatcacct tagaatccag tattgaggct   1680
ctaatggcaa gcaaatccat atctgaactc gaagcaagca gagcaagctt tagtaggata   1740
ttgggaccca agattacgga tattgtctca actaattcac agagtatgat tgcagtgtct   1800
gcagaagcca tcataatcat ttttagtaag actgattatt gcaactattt tccatccctt   1860
gaaactgaca gtacagttga taagttggca agtatgttag aagattgcga agatcctgta   1920
atccaaacaa acattttaac catccttgcc aagattgctg agtttggaag cccggagatt   1980
gttgataagg tgcttcaaag tatccccttt aaccaggttg ctgacttgct ctctcccaat   2040
gccaaggatt ggcatgagag catgtttaca atattgatgt ctttgaccaa agctggaaag   2100
tcaaaagctg ttgaaagaat gtttgctttt cagattgata aaaatctgat taaccttata   2160
gagagtgaat ctgaactagt gcaacaccat gccattgtca ctttgaaggc attttatgag   2220
ctggctggcc cttctttgaa tagttctctt cgacctgcta atctagacct cttgccatgg   2280
caagtgagac ttcgtttaga gagatttgtt atgccagacc ggaacattcc cctttccccg   2340
aaaccacaaa cttttgaaga tcttatccac aagatgctag ataatgacaa caaacaggtg   2400
ttggaggcta tgcaggatct tgtgccgata attgaaaagg ctggagaccc aggtttcaga   2460
cagatgattg ttcaaagtcc cctaattaga aggttatcag aacttctgca acatggacat   2520
accgaacaaa attctataag atcagaatct gcatttttac taatgaagct agcttactct   2580
ggtggggaac cctgcatcaa taagtttcta gagtttgatg ttattcctga gctggtaaag   2640
atgatgcagt gcaacactgc agagttgcag gattcagcct atacagctct gcaccaaatg   2700
ctttttggca atggtggggt tcttgttttg agtaagatct tcaaaatggg tctaatagac   2760
aagattcctt atgcacttga gagcaaatct gcgaagactc gggaagtcct gctgcatttt   2820
gtatttgata ttgttgagct gggaagcaaa gcctgcttag agaaaatgct atctttgcaa   2880
gttgtggaga aactcaccaa gttagaaaaa agtggtgggg gctctggtga aattgtgatt   2940
ggatttctga aggcgatgga taagtgtaag catctcacag tagcggagcg aaaggtgatg   3000
aaacaacagg tggttagaaa ggtaagagcc tccttgaaag gccacaaatt cgaaactcgg   3060
attttagcgg ctgtagaagc tttcctctct ggagggtcaa ggggtgcaag tggtagtggc   3120
agtggtcgga ataggaagta a                                             3141
```

<210> SEQ ID NO 16
<211> LENGTH: 1046
<212> TYPE: PRT
<213> ORGANISM: Corchorus olitorius

<400> SEQUENCE: 16

```
Met Asp Pro Leu Gln Ala Val Ala Ala Ala Thr Gln Ile Ile Ser Ser
1               5                   10                  15

Met Val Gly Ala Val Gly Ala Leu Glu Gln Ala Ser Arg Asn Leu Asp
            20                  25                  30

Glu Ala Pro Lys Arg Ile Arg Ser Leu Glu Glu Phe Val Cys Asp Leu
        35                  40                  45
```

```
Glu Asn Leu Ala Gln Arg Ile Arg Gln Lys His Ala Asn Lys Leu His
    50                  55                  60

Asn Ala Gln Leu Asp Tyr Gln Leu Gln Ser Leu His Ala Leu Ile Glu
65                  70                  75                  80

Arg Leu Arg Pro Asn Ile Arg Lys Ala Arg Thr Val Val Ser Lys Ser
                85                  90                  95

Lys Ile Lys Asn Leu Ala Lys Val Phe Trp Asn Ser Met Ala Gly Asp
                100                 105                 110

Pro Leu Gly Lys Leu Thr Val Leu Ile Lys Asp Asp Leu Asn Trp Trp
            115                 120                 125

Leu Asp Thr Gln Met Leu Ala Gln Asn Val Glu Lys Val Leu Glu Ser
    130                 135                 140

Thr Ala Gln Asp Thr Pro Val Arg Leu Lys Ile Lys Thr Asp Gln Gly
145                 150                 155                 160

Tyr Pro Thr Ser Ser Lys Cys Ile Phe Val Lys Glu Leu Leu Glu Gln
                165                 170                 175

Glu Asp Thr His Arg Val Ile Leu Ile Val Gly Leu Ser Gly Ile Gly
            180                 185                 190

Lys Ser Cys Leu Ala Arg Gln Val Ala Ser Asp Pro Pro Lys Lys Phe
    195                 200                 205

Ala Gly Gly Ala Leu Glu Leu Gly Phe Gly Gln Trp Cys Ser Arg Ala
    210                 215                 220

Ala Cys Asn Gly Ser Lys Val Glu Tyr Gln Lys Arg Leu Ala Arg Lys
225                 230                 235                 240

Ile Ser Lys Phe Leu Val Gln Ile Gly Phe Trp Lys Lys Ile Lys Glu
                245                 250                 255

Glu Asn Ser Gly Asp Leu Asp Tyr Val Cys Tyr Leu Leu Gln Glu Ala
            260                 265                 270

Leu Tyr Gly Lys Ser Ile Leu Val Leu Asp Asp Val Trp Glu Gln
    275                 280                 285

Asp Ile Val Gln Arg Phe Ala Lys Leu Tyr Asp Asn Asn Cys Lys Tyr
    290                 295                 300

Leu Val Thr Thr Arg Asn Glu Ala Val His Glu Ile Thr Glu Ala Glu
305                 310                 315                 320

Lys Val Glu Leu Ser Lys Asp Asp Ile Arg Glu Ile Ser Lys Gly Ile
                325                 330                 335

Leu Leu Tyr His Ser Leu Leu Ser Glu Glu Leu Pro Gly Ile Ala
                340                 345                 350

Glu Ser Leu Leu Glu Arg Cys Gly His His Pro Leu Thr Val Ala Val
    355                 360                 365

Met Gly Lys Ala Leu Arg Lys Glu Val Arg Ala Glu Lys Trp Glu Lys
    370                 375                 380

Ala Ile Thr Asn Leu Ser Thr Phe Ala Thr Cys Ala Pro Gly Pro Val
385                 390                 395                 400

Ser Tyr Val Asn Glu Lys Asp Ala Glu Asp Thr Leu Thr Ile Phe Gly
                405                 410                 415

Ser Phe Glu Phe Ser Leu Glu Ala Met Pro Val Asp Ser Lys Arg Leu
            420                 425                 430

Phe Ile Ala Leu Ala Ser Leu Ser Trp Ala Glu Pro Val Pro Glu Ala
            435                 440                 445

Cys Ile Glu Ala Ile Trp Ser Cys Ile Gly Gln Glu Ser Leu Phe Ser
    450                 455                 460

Leu Ile Val Cys Lys Leu Val Glu Gly Ser Leu Leu Met Lys Val Asp
```

```
            465                 470                 475                 480
        Met Asp Pro Leu Tyr Gln Val His Asp Met Val Ser Leu Tyr Leu Asp
                            485                 490                 495

Ser Lys Thr Thr Asp Ser Ile Glu Met Leu Leu His Arg Ser Lys Pro
                        500                 505                 510

Glu Glu Thr Ala Phe Ile Cys Pro Trp Leu Leu Ile Phe Gly Lys Glu
                    515                 520                 525

Asn Val Lys Lys Ile Val Glu Glu Arg Met Lys Leu Phe Phe Asp Ile
        530                 535                 540

Leu Asp Glu Lys Gln Val Val Ile Thr Leu Glu Ser Ile Glu Ala
        545                 550                 555                 560

Leu Met Ala Ser Lys Ser Ile Ser Glu Leu Glu Ala Ser Arg Ala Ser
                        565                 570                 575

Phe Ser Arg Ile Leu Gly Pro Lys Ile Thr Asp Ile Val Ser Thr Asn
                    580                 585                 590

Ser Gln Ser Met Ile Ala Val Ser Ala Glu Ala Ile Ile Ile Phe
                595                 600                 605

Ser Lys Thr Asp Tyr Cys Asn Tyr Phe Pro Ser Leu Glu Thr Asp Ser
            610                 615                 620

Thr Val Asp Lys Leu Ala Ser Met Leu Glu Asp Cys Glu Asp Pro Val
        625                 630                 635                 640

Ile Gln Thr Asn Ile Leu Thr Ile Leu Ala Lys Ile Ala Glu Phe Gly
                        645                 650                 655

Ser Pro Glu Ile Val Asp Lys Val Leu Gln Ser Ile Pro Phe Asn Gln
                    660                 665                 670

Val Ala Asp Leu Leu Ser Pro Asn Ala Lys Asp Trp His Glu Ser Met
                675                 680                 685

Phe Thr Ile Leu Met Ser Leu Thr Lys Ala Gly Lys Ser Lys Ala Val
            690                 695                 700

Glu Arg Met Phe Ala Phe Gln Ile Asp Lys Asn Leu Ile Asn Leu Ile
        705                 710                 715                 720

Glu Ser Glu Ser Glu Leu Val Gln His His Ala Ile Val Thr Leu Lys
                        725                 730                 735

Ala Phe Tyr Glu Leu Ala Gly Pro Ser Leu Asn Ser Ser Leu Arg Pro
                    740                 745                 750

Ala Asn Leu Asp Leu Leu Pro Trp Gln Val Arg Leu Arg Leu Glu Arg
                755                 760                 765

Phe Val Met Pro Asp Arg Asn Ile Pro Leu Ser Pro Lys Pro Gln Thr
            770                 775                 780

Phe Glu Asp Leu Ile His Lys Met Leu Asp Asn Asp Asn Lys Gln Val
        785                 790                 795                 800

Leu Glu Ala Met Gln Asp Leu Val Pro Ile Ile Glu Lys Ala Gly Asp
                        805                 810                 815

Pro Gly Phe Arg Gln Met Ile Val Gln Ser Pro Leu Ile Arg Arg Leu
                    820                 825                 830

Ser Glu Leu Leu Gln His Gly His Thr Glu Gln Asn Ser Ile Arg Ser
                835                 840                 845

Glu Ser Ala Phe Leu Leu Met Lys Leu Ala Tyr Ser Gly Gly Glu Pro
            850                 855                 860

Cys Ile Asn Lys Phe Leu Glu Phe Asp Val Ile Pro Glu Leu Val Lys
        865                 870                 875                 880

Met Met Gln Cys Asn Thr Ala Glu Leu Gln Asp Ser Ala Tyr Thr Ala
                        885                 890                 895
```

```
Leu His Gln Met Leu Phe Gly Asn Gly Gly Val Leu Val Leu Ser Lys
            900                 905                 910
Ile Phe Lys Met Gly Leu Ile Asp Lys Ile Pro Tyr Ala Leu Glu Ser
            915                 920                 925
Lys Ser Ala Lys Thr Arg Glu Val Leu Leu His Phe Val Phe Asp Ile
            930                 935                 940
Val Glu Leu Gly Ser Lys Ala Cys Leu Glu Lys Met Leu Ser Leu Gln
945                 950                 955                 960
Val Val Glu Lys Leu Thr Lys Leu Glu Lys Ser Gly Gly Ser Gly
                965                 970                 975
Glu Ile Val Ile Gly Phe Leu Lys Ala Met Asp Lys Cys Lys His Leu
            980                 985                 990
Thr Val Ala Glu Arg Lys Val Met  Lys Gln Gln Val Val  Arg Lys Val
            995                1000                1005
Arg Ala  Ser Leu Lys Gly His  Lys Phe Glu Thr Arg  Ile Leu Ala
     1010                1015                1020
Ala Val  Glu Ala Phe Leu Ser  Gly Gly Ser Arg Gly  Ala Ser Gly
     1025                1030                1035
Ser Gly  Ser Gly Arg Asn Arg  Lys
     1040                1045

<210> SEQ ID NO 17
<211> LENGTH: 3009
<212> TYPE: DNA
<213> ORGANISM: Corchorus olitorius

<400> SEQUENCE: 17
atgggaagag ctgattttac aactactact ccaaagctgc tacttctact tgttttcatt    60
gcaatgctct ggctttcaac ctttggattt gctgctgcta ctcctcttct tcattctgaa   120
gaagtgaagg cactgaaagc aatagggaag aagatgggga agaaggattg ggattttggg   180
gtggatcctt gcagtggaaa ggggaagtgg attgaggag atgaagaaac tggatttgca   240
agcaaggtca cctgcaattg ctcttcaac aacaacacca cctgccatgt agtaaccatg   300
gacctaagtc gcaactactt cacaggttct attcctaaag aatgggctac catgaagttg   360
gacatgctct ctttcatggg gaaccggttg tctggtccat cccaaaagt tcttaccaac   420
atcacaagcc tcacaaactt gtctattgaa gggacaact tttcaggacc cattcctcca   480
gagattggaa agttgatcaa tttacagaaa cttgttctct catctaatgc cttaagtgga   540
gaattgcctg cagaactagc caagttggtc aacttgactg atatacggtt tagcgacaat   600
aacttctctg gaaagatacc tgattttatc agtaactgga agcagattca aaaactgcag   660
tttcaaggtt gctctcttga ggggcctata ccttccagca tttctacttt gactagctta   720
tctgatttga ggattagtga cttgaaaggc aaagggtccc catttccgct attgcgtaac   780
catgactcac tgaagacatt gatactaagg aactgcaaga tacatggaga atcccagag   840
tatattgggg atatgaagaa attgaaaacc ctggatctca gctataataa cttgactgga   900
gaaattccca gttcattcta caaactgaca aaagctgatt tcttgtattt gactcggaat   960
cagctcaccg gtctgtccc tgagtggatc ctagaaagaa ataaaaatgc ggatatatct  1020
ttcaacaatt tcacctggga cacatcaagt ccaatagaat gtcctcgagg gagcgtgaac  1080
ttggttgaga gctactccac accaacaaat aaactaagta aagttcattc atgtctaaaa  1140
cagaatttcc catgttcagc ttcaactagt caacataaat actccttgca cataaattgt  1200
```

-continued

```
ggggggcagg aattaaatgt caatggtgat gccaaatatg aagctgatat ggaaccaaga    1260
ggtgcttcca tgttttacct ggggcacaac tgggcattaa gcagcactgg aaacttcatg    1320
gataacgata ttgatgcaga tgactatatt gttaccaata cttctgcatt gtccaatgta    1380
tctgcaactc attccgaact ctacacaact gcgcgtgttt ctcccctctc tctcacatac    1440
tatggactct gcctagggaa tgggaactac actgttaatc ttcattttgc agagattatt    1500
tatataaatg atcgatcatt ttacagcctt gggaaacgca tattcgatgt ctatattcag    1560
ggagaattgg tgctgaaaga ctttaatatt caagatgaag ctggaggtac tggtaagccc    1620
attgtaaaga actttacagc cgtcgtgaca agaaatacat aaaaatcca cttatactgg     1680 gctggaaggg gaacaacagg cataccagca agggggatgt atggtccact catatcagct    1740
atatcagtgg tttcaaactt tgagccccca actgttgttg caagaagaa ttatctcata     1800 attgcggcag gggcagcttc tgcagcaata cttatagtcc ttatggtctt aggtatcatt    1860
tggagaaaag gctggctggg aggcaaaatc tctgctgaaa acgagctgaa agacctggat    1920
ctgcaaacag gaattttcag tctaaggcag attaaagctg ccaccaacaa cttcgatgct    1980
gagaacaaaa ttggtgaggg tggatttggt tctgtttaca agggtttatt atcagatggg    2040
acagttatcg cagtgaagca gctttcatca aaatctaagc agggaaatcg tgaatttgtg    2100
aatgaaatag gcatgatatc tgcactgcag catccgaatc ttgtgaagct ctatggatgt    2160
tgtgtagaag gaaaccagtt attgctagtt tatgagtaca tggaacataa ctgtgtatct    2220
cgtgctcttt ttgggaaggg ctcaacaccc aaattgaaac tggactggtc tacccggaaa    2280
aacatttgcc ttggtattgc caggggtttg gcctacctcc atgaagagtc gagaattaaa    2340
attgtgcaca gggatattaa aacaagtaat gtgttgcttg acaagaatct aaatgcaaaa    2400
atttctgatt ttggtttggc aaagctaaat gatgatgaca aaacccacat cagcactcgt    2460
atagccggga caattggtta tatggctcct gagtatgcaa tgcgtggata cctaaccagc    2520
aaagctgatg tctatagctt tggtgttgtt gcattggaaa ttgttagtgg aaagagcaac    2580
acaaactaca gaccaactga ggactttgtt taccttcttg actgggccta tgttttgaga    2640
gagaggggaa gtttgttgga gttggttgat ccagagttgg gatcagagta ctcatcagag    2700
gaggcaatgg tgatgctgaa tgtggctcta ctatgcacca atgcagcccc cacccctgagg   2760 cctaccatgt cacaggttgt gagcatgctc gaaggccaaa cctcagttca agacatcctc    2820
tccgaccctg gattttcatc catgaattcg aaattcaagg ccttagttaa tcacttctgg    2880
caaaatccaa gccaaacaat gagcttgtca agcaatggcc caaatacaga ttcctcaagt    2940
tcaaacatag aagacataga agagaatagt catcttttga gagttagttc tattcaatcc    3000
gaggcgtga                                                            3009
```

<210> SEQ ID NO 18
<211> LENGTH: 1002
<212> TYPE: PRT
<213> ORGANISM: Corchorus olitorius

<400> SEQUENCE: 18

```
Met Gly Arg Ala Asp Phe Thr Thr Thr Thr Pro Lys Leu Leu Leu Leu
1               5                   10                  15

Leu Val Phe Ile Ala Met Leu Trp Leu Ser Thr Phe Gly Phe Ala Ala
                20                  25                  30

Ala Thr Pro Leu Leu His Ser Glu Glu Val Lys Ala Leu Lys Ala Ile
            35                  40                  45
```

```
Gly Lys Lys Met Gly Lys Lys Asp Trp Asp Phe Gly Val Asp Pro Cys
 50               55                      60
Ser Gly Lys Gly Lys Trp Ile Glu Gly Asp Glu Glu Thr Gly Phe Ala
 65               70                  75                      80
Ser Lys Val Thr Cys Asn Cys Ser Phe Asn Asn Asn Thr Thr Cys His
                 85                  90                  95
Val Val Thr Met Asp Leu Ser Arg Asn Tyr Phe Thr Gly Ser Ile Pro
            100                 105                 110
Lys Glu Trp Ala Thr Met Lys Leu Asp Met Leu Ser Phe Met Gly Asn
            115                 120                 125
Arg Leu Ser Gly Pro Phe Pro Lys Val Leu Thr Asn Ile Thr Ser Leu
130                 135                 140
Thr Asn Leu Ser Ile Glu Gly Asn Asn Phe Ser Gly Pro Ile Pro Pro
145                 150                 155                 160
Glu Ile Gly Lys Leu Ile Asn Leu Gln Lys Leu Val Leu Ser Ser Asn
                165                 170                 175
Ala Leu Ser Gly Glu Leu Pro Ala Glu Leu Ala Lys Leu Val Asn Leu
            180                 185                 190
Thr Asp Ile Arg Phe Ser Asp Asn Asn Phe Ser Gly Lys Ile Pro Asp
            195                 200                 205
Phe Ile Ser Asn Trp Lys Gln Ile Gln Lys Leu Gln Phe Gln Gly Cys
            210                 215                 220
Ser Leu Glu Gly Pro Ile Pro Ser Ser Ile Ser Thr Leu Thr Ser Leu
225                 230                 235                 240
Ser Asp Leu Arg Ile Ser Asp Leu Lys Gly Lys Gly Ser Pro Phe Pro
                245                 250                 255
Leu Leu Arg Asn His Asp Ser Leu Lys Thr Leu Ile Leu Arg Asn Cys
            260                 265                 270
Lys Ile His Gly Glu Ile Pro Glu Tyr Ile Gly Asp Met Lys Lys Leu
            275                 280                 285
Lys Thr Leu Asp Leu Ser Tyr Asn Asn Leu Thr Gly Glu Ile Pro Ser
            290                 295                 300
Ser Phe Tyr Lys Leu Thr Lys Ala Asp Phe Leu Tyr Leu Thr Arg Asn
305                 310                 315                 320
Gln Leu Thr Gly Ser Val Pro Glu Trp Ile Leu Glu Arg Asn Lys Asn
                325                 330                 335
Ala Asp Ile Ser Phe Asn Asn Phe Thr Trp Asp Thr Ser Ser Pro Ile
            340                 345                 350
Glu Cys Pro Arg Gly Ser Val Asn Leu Val Glu Ser Tyr Ser Thr Pro
            355                 360                 365
Thr Asn Lys Leu Ser Lys Val His Ser Cys Leu Lys Gln Asn Phe Pro
370                 375                 380
Cys Ser Ala Ser Thr Ser Gln His Lys Tyr Ser Leu His Ile Asn Cys
385                 390                 395                 400
Gly Gly Gln Glu Leu Asn Val Asn Gly Asp Ala Lys Tyr Glu Ala Asp
                405                 410                 415
Met Glu Pro Arg Gly Ala Ser Met Phe Tyr Leu Gly His Asn Trp Ala
            420                 425                 430
Leu Ser Thr Gly Asn Phe Met Asp Asn Asp Ile Asp Ala Asp Asp
            435                 440                 445
Tyr Ile Val Thr Asn Thr Ser Ala Leu Ser Asn Val Ser Ala Thr His
            450                 455                 460
Ser Glu Leu Tyr Thr Thr Ala Arg Val Ser Pro Leu Ser Leu Thr Tyr
```

```
            465                 470                 475                 480
        Tyr Gly Leu Cys Leu Gly Asn Gly Asn Tyr Thr Val Asn Leu His Phe
                        485                 490                 495
        Ala Glu Ile Ile Tyr Ile Asn Asp Arg Ser Phe Tyr Ser Leu Gly Lys
                        500                 505                 510
        Arg Ile Phe Asp Val Tyr Ile Gln Gly Glu Leu Val Leu Lys Asp Phe
                        515                 520                 525
        Asn Ile Gln Asp Glu Ala Gly Gly Thr Gly Lys Pro Ile Val Lys Asn
                        530                 535                 540
        Phe Thr Ala Val Val Thr Arg Asn Thr Leu Lys Ile His Leu Tyr Trp
        545                 550                 555                 560
        Ala Gly Arg Gly Thr Thr Gly Ile Pro Ala Arg Gly Met Tyr Gly Pro
                        565                 570                 575
        Leu Ile Ser Ala Ile Ser Val Val Ser Asn Phe Glu Pro Pro Thr Val
                        580                 585                 590
        Val Gly Lys Lys Asn Tyr Leu Ile Ile Ala Ala Gly Ala Ala Ser Ala
                        595                 600                 605
        Ala Ile Leu Ile Val Leu Met Val Leu Gly Ile Ile Trp Arg Lys Gly
                        610                 615                 620
        Trp Leu Gly Gly Lys Ile Ser Ala Glu Asn Glu Leu Lys Asp Leu Asp
        625                 630                 635                 640
        Leu Gln Thr Gly Ile Phe Ser Leu Arg Gln Ile Lys Ala Ala Thr Asn
                        645                 650                 655
        Asn Phe Asp Ala Glu Asn Lys Ile Gly Glu Gly Gly Phe Gly Ser Val
                        660                 665                 670
        Tyr Lys Gly Leu Leu Ser Asp Gly Thr Val Ile Ala Val Lys Gln Leu
                        675                 680                 685
        Ser Ser Lys Ser Lys Gln Gly Asn Arg Glu Phe Val Asn Glu Ile Gly
                        690                 695                 700
        Met Ile Ser Ala Leu Gln His Pro Asn Leu Val Lys Leu Tyr Gly Cys
        705                 710                 715                 720
        Cys Val Glu Gly Asn Gln Leu Leu Leu Val Tyr Glu Tyr Met Glu His
                        725                 730                 735
        Asn Cys Val Ser Arg Ala Leu Phe Gly Lys Gly Ser Thr Pro Lys Leu
                        740                 745                 750
        Lys Leu Asp Trp Ser Thr Arg Lys Asn Ile Cys Leu Gly Ile Ala Arg
                        755                 760                 765
        Gly Leu Ala Tyr Leu His Glu Glu Ser Arg Ile Lys Ile Val His Arg
                        770                 775                 780
        Asp Ile Lys Thr Ser Asn Val Leu Leu Asp Lys Asn Leu Asn Ala Lys
        785                 790                 795                 800
        Ile Ser Asp Phe Gly Leu Ala Lys Leu Asn Asp Asp Lys Thr His
                        805                 810                 815
        Ile Ser Thr Arg Ile Ala Gly Thr Ile Gly Tyr Met Ala Pro Glu Tyr
                        820                 825                 830
        Ala Met Arg Gly Tyr Leu Thr Ser Lys Ala Asp Val Tyr Ser Phe Gly
                        835                 840                 845
        Val Val Ala Leu Glu Ile Val Ser Gly Lys Ser Asn Thr Asn Tyr Arg
                        850                 855                 860
        Pro Thr Glu Asp Phe Val Tyr Leu Leu Asp Trp Ala Tyr Val Leu Arg
        865                 870                 875                 880
        Glu Arg Gly Ser Leu Leu Glu Leu Val Asp Pro Glu Leu Gly Ser Glu
                        885                 890                 895
```

```
Tyr Ser Ser Glu Glu Ala Met Val Met Leu Asn Val Ala Leu Leu Cys
            900                 905                 910

Thr Asn Ala Ala Pro Thr Leu Arg Pro Thr Met Ser Gln Val Val Ser
            915                 920                 925

Met Leu Glu Gly Gln Thr Ser Val Gln Asp Ile Leu Ser Asp Pro Gly
            930                 935                 940

Phe Ser Ser Met Asn Ser Lys Phe Lys Ala Leu Val Asn His Phe Trp
945                 950                 955                 960

Gln Asn Pro Ser Gln Thr Met Ser Leu Ser Ser Asn Gly Pro Asn Thr
                965                 970                 975

Asp Ser Ser Ser Ser Asn Ile Glu Asp Ile Glu Asn Ser His Leu
            980                 985                 990

Leu Arg Val Ser Ser Ile Gln Ser  Glu Ala
            995                 1000
```

<210> SEQ ID NO 19
<211> LENGTH: 1989
<212> TYPE: DNA
<213> ORGANISM: Corchorus olitorius

<400> SEQUENCE: 19

```
agaatttgtt gtcagtaaga tccaacagtc cattgtggcc aggttgggat tgccatggga      60
agaaaatgat tcctatgagc tacaaacttc aaagattcac aatgttttaa aaataagag      120
gttcctccta ttgctggatg atgtttggga aggaattgat cttagtgaaa ttgggattcc      180
tcttcctgat gaggaaaata aatgcaagct gatatttaca acgcggtcca tggatgtttg      240
cactgacatg gatgctcata ggaagctcaa agtagaattt ctggacgagg agaaatcatg      300
gcgattattc tgtgagaagg ttggaagaat ggagatttta gagtcaccac ctgttagaac      360
ttatgctgag accattgtca ggaaatgtgg aggtctaccg cttgccttaa tcactgtggg      420
gagagccatg gccaataagg agactgaaga agaatggaaa tatgcaattg aattactcaa      480
caaatctcct tctgaactta gaggtatgga agatgtcttt acccttttaa agtttagcta      540
tgacaatttg gatagtgaaa caacaaaaat gtgcttttg tattgttctc ttttccggc       600
aagctgttcc attgagaaac aacagcttgt agagtattgg attggtgaag gattcctaga      660
cagttctaat gctcataata aagggttgc tgcaattggg tccctaaaag tagcttgttt      720
attggaaaca ggcgatgagg aaacccaagt aaagatgaat gatgttatcc gaagttttgc      780
cttatggata gcatctgaat ctgggataaa taagggaaac cttttggtag aagcaagctt      840
gggccttatt gaagctcctg gagttgaaaa ctgggaagaa gcaaaaagga tttccttgtt      900
agacaatgga atcacagtac tagaacaagt accaatatgc ccaaatctgt tgactctgtt      960
gcttcagtgg aataatggtc tgaatcgaat agcagctaac ttttttcaat ctatgcctgc     1020
tcttagagtc ttggatttgt catttacaag cattagaaag atcccagtaa gcatcagtca     1080
attagtagag cttcggcatc ttaatttagc aggtacaaaa ataacaacat gcctagggga     1140
gctagcaagt ttagcaaagc tgaattactt gaatctctca cgcacatatt ctcttcgaac     1200
ggttccacgt gaggctttat ctggactttc agagttagtg gtcttgaatt tgtattacag     1260
ttatgaggtt cgcgaagttc ggaattttga aggtgaaggt gaagttgaat tgaggtatt      1320
ggagaccttg acacaactcc gtatccttgg tttaacaatc tcctcaatag cctccctgaa     1380
tagactcttt ggtttgagaa atctggttag atgcatacac tatttactcc taaggagtg     1440
tgaaggttta acagaattag tattttcatc agcttctggc ttaacattga aagacttag     1500
```

-continued

```
catcacagac tgctatgatt tcaattactt agtagtgaat gctgaggatg acaaaagtg     1560 gttgcctaat ttggaggttt tatctttgca tggtctacca aaagtgactt cagtgtggaa    1620
atccccagta agaaaagcaa gcctgcaaaa tttgcgcttg ttgaatatct ggtattgtca    1680
tagcttgaag aatgtttctt gggtattact acttccaaag ttagaagcaa tttacttgtt    1740
ctattgcaag aaaatggaac aagttgtaag tggagaagag ggactactag agcctgatcc    1800
aaaggcattt tcaaggctta aaactataga gatccgcgac cttcctgaat taaagagtat    1860
cagtccatgg acattggctt tccccctgctt gaagagcatt gctgtgattg attgtccaaa   1920
gctgaagaaa ctaccaattg gaacccataa ttcctcaact cttccaactg tgtactgtag    1980
tgaagaatg                                                             1989
```

<210> SEQ ID NO 20
<211> LENGTH: 662
<212> TYPE: PRT
<213> ORGANISM: Corchorus olitorius

<400> SEQUENCE: 20

```
Glu Phe Val Val Ser Lys Ile Gln Gln Ser Ile Val Ala Arg Leu Gly
1               5                   10                  15

Leu Pro Trp Glu Glu Asn Asp Ser Tyr Glu Leu Gln Thr Ser Lys Ile
            20                  25                  30

His Asn Val Leu Lys Asn Lys Arg Phe Leu Leu Leu Asp Asp Val
        35                  40                  45

Trp Glu Gly Ile Asp Leu Ser Glu Ile Gly Ile Pro Leu Pro Asp Glu
    50                  55                  60

Glu Asn Lys Cys Lys Leu Ile Phe Thr Thr Arg Ser Met Asp Val Cys
65                  70                  75                  80

Thr Asp Met Asp Ala His Arg Lys Leu Lys Val Glu Phe Leu Asp Glu
                85                  90                  95

Glu Lys Ser Trp Arg Leu Phe Cys Glu Lys Val Gly Arg Met Glu Ile
            100                 105                 110

Leu Glu Ser Pro Pro Val Arg Thr Tyr Ala Glu Thr Ile Val Arg Lys
        115                 120                 125

Cys Gly Gly Leu Pro Leu Ala Leu Ile Thr Val Gly Arg Ala Met Ala
    130                 135                 140

Asn Lys Glu Thr Glu Glu Trp Lys Tyr Ala Ile Glu Leu Leu Asn
145                 150                 155                 160

Lys Ser Pro Ser Glu Leu Arg Gly Met Glu Asp Val Phe Thr Leu Leu
                165                 170                 175

Lys Phe Ser Tyr Asp Asn Leu Asp Ser Glu Thr Thr Lys Met Cys Phe
            180                 185                 190

Leu Tyr Cys Ser Leu Phe Pro Ala Ser Cys Ser Ile Glu Lys Gln Gln
        195                 200                 205

Leu Val Glu Tyr Trp Ile Gly Glu Gly Phe Leu Asp Ser Ser Asn Ala
    210                 215                 220

His Asn Lys Gly Phe Ala Ala Ile Gly Ser Leu Lys Val Ala Cys Leu
225                 230                 235                 240

Leu Glu Thr Gly Asp Glu Thr Gln Val Lys Met Asn Asp Val Ile
                245                 250                 255

Arg Ser Phe Ala Leu Trp Ile Ala Ser Glu Ser Gly Val Asn Lys Gly
            260                 265                 270

Asn Leu Leu Val Glu Ala Ser Leu Gly Leu Ile Glu Ala Pro Gly Val
```

```
                275                 280                 285
Glu Asn Trp Glu Glu Ala Lys Arg Ile Ser Leu Leu Asp Asn Gly Ile
290                 295                 300

Thr Val Leu Glu Gln Val Pro Ile Cys Pro Asn Leu Thr Leu Leu
305                 310                 315                 320

Leu Gln Trp Asn Asn Gly Leu Asn Arg Ile Ala Ala Asn Phe Phe Gln
                325                 330                 335

Ser Met Pro Ala Leu Arg Val Leu Asp Leu Ser Phe Thr Ser Ile Arg
                340                 345                 350

Lys Ile Pro Val Ser Ile Ser Gln Leu Val Glu Leu Arg His Leu Asn
                355                 360                 365

Leu Ala Gly Thr Lys Ile Thr Thr Leu Pro Arg Glu Leu Ala Ser Leu
                370                 375                 380

Ala Lys Leu Asn Tyr Leu Asn Leu Ser Arg Thr Tyr Ser Leu Arg Thr
385                 390                 395                 400

Val Pro Arg Glu Ala Leu Ser Gly Leu Ser Glu Leu Val Val Leu Asn
                405                 410                 415

Leu Tyr Tyr Ser Tyr Glu Val Arg Glu Val Arg Asn Phe Glu Gly Glu
                420                 425                 430

Gly Glu Val Glu Phe Glu Val Leu Glu Thr Leu Thr Gln Leu Arg Ile
                435                 440                 445

Leu Gly Leu Thr Ile Ser Ser Ile Ala Ser Leu Asn Arg Leu Phe Gly
                450                 455                 460

Leu Arg Asn Leu Val Arg Cys Ile His Tyr Leu Leu Leu Lys Glu Cys
465                 470                 475                 480

Glu Gly Leu Thr Glu Leu Val Phe Ser Ser Ala Ser Gly Leu Thr Leu
                485                 490                 495

Arg Arg Leu Ser Ile Thr Asp Cys Tyr Asp Phe Asn Tyr Leu Val Val
                500                 505                 510

Asn Ala Glu Asp Gly Gln Lys Trp Leu Pro Asn Leu Glu Val Leu Ser
                515                 520                 525

Leu His Gly Leu Pro Lys Val Thr Ser Val Trp Lys Ser Pro Val Arg
                530                 535                 540

Lys Ala Ser Leu Gln Asn Leu Arg Leu Leu Asn Ile Trp Tyr Cys His
545                 550                 555                 560

Ser Leu Lys Asn Val Ser Trp Val Leu Leu Pro Lys Leu Glu Ala
                565                 570                 575

Ile Tyr Leu Phe Tyr Cys Lys Lys Met Glu Gln Val Val Ser Gly Glu
                580                 585                 590

Glu Gly Leu Leu Glu Pro Asp Pro Lys Ala Phe Ser Arg Leu Lys Thr
                595                 600                 605

Ile Glu Ile Arg Asp Leu Pro Glu Leu Lys Ser Ile Ser Pro Trp Thr
                610                 615                 620

Leu Ala Phe Pro Cys Leu Lys Ser Ile Ala Val Ile Asp Cys Pro Lys
625                 630                 635                 640

Leu Lys Lys Leu Pro Ile Gly Thr His Asn Ser Ser Thr Leu Pro Thr
                645                 650                 655

Val Tyr Cys Ser Glu Glu
                660

<210> SEQ ID NO 21
<211> LENGTH: 1258
<212> TYPE: DNA
<213> ORGANISM: Corchorus olitorius
```

<400> SEQUENCE: 21

```
agatttatac caattagtgg aaatgaaaat acagattggc caacggcgga ttatgagtgg      60
attaagcctt gcagtttaga agaatgcaaa actcaatgct tgcaagattg tctttgtact     120
gtggcagtgt tcaatgagaa tggctgttgg aagaaggcgc taccgctgcc atttggtagg     180
caagacccag atgtgaaatc caactcctac ctgaaagtaa gaaaaccaga attttcccag     240
aaaaaccctc ttccatttct agacactaaa aagaaccaaa attcattggt aattctggtt     300
tcagttctct tgggtagctc tgtgtttgtc aactttatat tggttggggt tttatgttcg     360
ggatcgtttt tcctgtatca gaaaaagatt gcaagaaatg ggagaaagta caagaatggg     420
atacagaaca atttgaggtg ttttagttac aaggagcttg aagaagctac aaatggtttc     480
aaggaagagc taggaagggg agcattcggc atagtttata aagggctaat aaaaacagat     540
gctcaagatc caactgaagc tgcagttaag aagttagaca gagtggttca agacaaagac     600
aacgaattca gaactgaagt gagtgtgatt gctcaaacac atcataggaa tctggtcaag     660
ttgcttggat attgtgacga aggtcagtgt cggatgctgg tgtatgaata cttaagcaat     720
aaaacattag caagcttcct tttgggggat caaaaaccca gttggaacca aggaaacag      780
attgctttgg gaattgcaag aggattgctt tacttgcatg aggaatgcag ccctcaaata     840
atccattgtg atataaagcc tcaaaacata cttcttgatg attactatga agctcggata     900
tctgactttg ggttgtcaaa gcttctaggg actgaccaat catatactaa taccgccata     960
agggaacga aagggtatgt cgcgccagaa tggttcaaga cagtgcctgt atccgtgaag    1020
gttgatgtgt atagctttgg tgtcctgctg ctagaaatca tttgttgtag aagaaatgta    1080
gacatggata ttggcaaagc gaaaatggaa attttgacag attgggcttg tgattgcttc    1140
ctggaaggca ctttagatgc tcttgttgac aatgatgcag acgccttaag cgacaaggcg    1200
aagcttgaga cctttgttat ggttgccatt tggtgcattc aagaagactt gtctctca      1258
```

<210> SEQ ID NO 22
<211> LENGTH: 419
<212> TYPE: PRT
<213> ORGANISM: Corchorus olitorius

<400> SEQUENCE: 22

```
Arg Phe Ile Pro Ile Ser Gly Asn Glu Asn Thr Asp Trp Pro Thr Ala
1               5                   10                  15

Asp Tyr Glu Trp Ile Lys Pro Cys Ser Leu Glu Glu Cys Lys Thr Gln
            20                  25                  30

Cys Leu Gln Asp Cys Leu Cys Thr Val Ala Val Phe Asn Glu Asn Gly
        35                  40                  45

Cys Trp Lys Lys Ala Leu Pro Leu Pro Phe Gly Arg Gln Asp Pro Asp
    50                  55                  60

Val Lys Ser Asn Ser Tyr Leu Lys Val Arg Lys Pro Glu Phe Ser Gln
65                  70                  75                  80

Lys Asn Pro Leu Pro Phe Leu Asp Thr Lys Lys Asn Gln Asn Ser Leu
                85                  90                  95

Val Ile Leu Val Ser Val Leu Leu Gly Ser Ser Val Phe Val Asn Phe
            100                 105                 110

Ile Leu Val Gly Val Leu Cys Ser Gly Ser Phe Phe Leu Tyr Gln Lys
        115                 120                 125

Lys Ile Ala Arg Asn Gly Arg Lys Tyr Lys Asn Gly Ile Gln Asn Asn
    130                 135                 140
```

Leu Arg Cys Phe Ser Tyr Lys Glu Leu Glu Glu Ala Thr Asn Gly Phe
145                 150                 155                 160

Lys Glu Glu Leu Gly Arg Gly Ala Phe Gly Ile Val Tyr Lys Gly Leu
            165                 170                 175

Ile Lys Thr Asp Ala Gln Asp Pro Thr Glu Ala Ala Val Lys Lys Leu
        180                 185                 190

Asp Arg Val Val Gln Asp Lys Asp Asn Glu Phe Arg Thr Glu Val Ser
        195                 200                 205

Val Ile Ala Gln Thr His His Arg Asn Leu Val Lys Leu Leu Gly Tyr
        210                 215                 220

Cys Asp Glu Gly Gln Cys Arg Met Leu Val Tyr Glu Tyr Leu Ser Asn
225                 230                 235                 240

Lys Thr Leu Ala Ser Phe Leu Phe Gly Asp Gln Lys Pro Ser Trp Asn
            245                 250                 255

Gln Arg Lys Gln Ile Ala Leu Gly Ile Ala Arg Gly Leu Leu Tyr Leu
        260                 265                 270

His Glu Glu Cys Ser Pro Gln Ile Ile His Cys Asp Ile Lys Pro Gln
        275                 280                 285

Asn Ile Leu Leu Asp Asp Tyr Tyr Glu Ala Arg Ile Ser Asp Phe Gly
290                 295                 300

Leu Ser Lys Leu Leu Gly Thr Asp Gln Ser Tyr Thr Asn Thr Ala Ile
305                 310                 315                 320

Arg Gly Thr Lys Gly Tyr Val Ala Pro Glu Trp Phe Lys Thr Val Pro
            325                 330                 335

Val Ser Val Lys Val Asp Val Tyr Ser Phe Gly Val Leu Leu Leu Glu
        340                 345                 350

Ile Ile Cys Cys Arg Arg Asn Val Asp Met Asp Ile Gly Lys Ala Lys
        355                 360                 365

Met Glu Ile Leu Thr Asp Trp Ala Cys Asp Cys Phe Leu Glu Gly Thr
370                 375                 380

Leu Asp Ala Leu Val Asp Asn Asp Ala Asp Ala Leu Ser Asp Lys Ala
385                 390                 395                 400

Lys Leu Glu Thr Phe Val Met Val Ala Ile Trp Cys Ile Gln Glu Asp
            405                 410                 415

Leu Ser Leu

<210> SEQ ID NO 23
<211> LENGTH: 2362
<212> TYPE: DNA
<213> ORGANISM: Corchorus olitorius

<400> SEQUENCE: 23
ataggattgc atggttgcaa accttcgtta ctgaggtttg caaattggct ccgtgctgag      60
ttggaagttc aagggatgag ttgctttgta tctgatagag ctcggttcag gaactctcgt     120
aagcatggaa ttattgaaag ggcaatggat gtttcttcat tcggtgttgt aatcctaacg     180
aggaagtctt tcaggaatcc atatactatt gaggagctca gattttttctc gagcaagaaa    240 aatttggtcc cgatctattt tgatctgcgt cctggtgatt gccttgtccg ggatattgtt     300
gagaagagag gagacttgtg ggaaaaacat ggggtgaat tatgggtttt ctatggagga     360
ttggagaagg agtggaagga agctgttagt ggccttttcc gagtggatga atggaaactg     420
gaagctcagg atggtaattg gagagactgc atattaaggg ttgttaccat tttggcaatg     480
aagttaggaa gaagaagtgt tgtagagcga ttgacaaagt ggaaagaaaa ggtagacaaa     540

-continued

```
gaggaattcc catttcctcg aaatgaaaat tttattggcc gaaagaaaga attgtcagag    600
ctagaattta tacttttggg tgatattagt ggagaatcag aaagagatta ttttgagctc    660
aaggctaggt caaagagaag aaatttgaca attgggtgga gtaagagcac ttcagtggag    720
gaaagacgta gggaaagaca gcggaggat ggcagccgga agggcaaaga acctgtggtt    780
tggaaggagt cagaaaagga gattgagatg caaagcacag aaagacagca ctatcaaaga    840
ccaagaggtg gacggaattc acagagaaag agatcagcga aagttgtcta tgggaagggc    900
attgcctgtg taacagggga atcaggactg gggaaaactg agcttcttct ggagtttgcc    960
tataaatatc accagaggta taagatggtc ctgtggatag gaggggaaag caggtatatt   1020
agacagaatt atctaaacct ctggtcattt ttagaagttg acgtaggggt tgaaaattgc   1080
acagataaaa gcaggatgaa aagctttgaa gagcaggaag aggctgccat ttctagagtc   1140
cggaaagagc taatgagaaa cattcctttt ctggtggtga ttgataattt agagagtgaa   1200
aaggattggt gggatcgcaa gcttgtaatg gatcttcttc cccgttttgg cggagagacc   1260
cacattctga tagctacgcg ccttccccgt gtgatgaatt tagaaccttt gaaactgtca   1320
tacttgtctg gagtagaggc aatgtcatta atgcagggta gcggcaaaga ctaccctatt   1380
gctgagattg atgcgcttag ggtcattgag gagaaagttg aaggctgac tttgggcctt    1440 gctatagtag gcgcaattct atctgaacta cccataaatc caagcaggct attggatacc   1500
atcaacagaa tgcccttgag agacttttca tggagtggta aggaagctta ttcgctgagg   1560
aaaaacagtt tcctcctgca actctttgag gtatgttttt caatatttga tcatgcagag   1620
ggaccaagga gcttagcaac gagaatggtc caggtgagtg gttggtttgc acctgctgcc   1680
attcctgttt ccctgttagc catggctgct cacaagatac ctgagaaaca taaaaggacc   1740
cgcttttgga gaagattatt gcgctcctta acttgtgggc tttcttcatc atactccaag   1800
aggtctgaaa cagaagcatc ttcaatgttg ttgagattta atattgcacg aagcagtacc   1860
aagcaaggtt atgttcattt taatgagctc atcaaggttt actctcggaa gagaggagtt   1920
gctggagttg cacatgccat ggtccaagct gttgttagtc gtggatcaat tttagatcac   1980
tcagaacata tgtgggcagc atgcttttg ctatttggat ttggtaatga tcctacagct   2040
gttgagctca aggtgtcgga cctattatac cttgtcaaag aggtggtttt gcctcttgca   2100
attcggacat tcattacatt ctctaggtgc agtgctgctc ttgaactcct ccggtctctgt   2160 accaatgctt tggaggcagc agatcaagca tttgttacac cagttgaaaa atggttggac   2220
aaatcacttt gttggaggcc cattcaaact aatgctcagt aaatccata tctttggcag   2280 gagttggcat tatcaagagc tactgtgcta gaaaccaggg ccaagttgat gctaagaggg   2340
gggcaatttg acataggaga tg                                           2362
```

<210> SEQ ID NO 24
<211> LENGTH: 787
<212> TYPE: PRT
<213> ORGANISM: Corchorus olitorius

<400> SEQUENCE: 24

Ile Gly Leu His Gly Cys Lys Pro Ser Leu Leu Arg Phe Ala Asn Trp
1               5                   10                  15

Leu Arg Ala Glu Leu Glu Val Gln Gly Met Ser Cys Phe Val Ser Asp
            20                  25                  30

Arg Ala Arg Phe Arg Asn Ser Arg Lys His Gly Ile Ile Glu Arg Ala
        35                  40                  45

-continued

```
Met Asp Val Ser Ser Phe Gly Val Ile Leu Thr Arg Lys Ser Phe
    50                  55                  60
Arg Asn Pro Tyr Thr Ile Glu Glu Leu Arg Phe Ser Ser Lys Lys
65                  70                  75                  80
Asn Leu Val Pro Ile Tyr Phe Asp Leu Arg Pro Gly Asp Cys Leu Val
                    85                  90                  95
Arg Asp Ile Val Glu Lys Arg Gly Asp Leu Trp Glu Lys His Gly Gly
                100                 105                 110
Glu Leu Trp Val Phe Tyr Gly Leu Glu Lys Glu Trp Lys Glu Ala
            115                 120                 125
Val Ser Gly Leu Phe Arg Val Asp Glu Trp Lys Leu Glu Ala Gln Asp
            130                 135                 140
Gly Asn Trp Arg Asp Cys Ile Leu Arg Val Val Thr Ile Leu Ala Met
145                 150                 155                 160
Lys Leu Gly Arg Arg Ser Val Val Glu Arg Leu Thr Lys Trp Lys Glu
                165                 170                 175
Lys Val Asp Lys Glu Glu Phe Pro Phe Pro Arg Asn Glu Asn Phe Ile
                180                 185                 190
Gly Arg Lys Lys Glu Leu Ser Glu Leu Glu Phe Ile Leu Phe Gly Asp
            195                 200                 205
Ile Ser Gly Glu Ser Glu Arg Asp Tyr Phe Glu Leu Lys Ala Arg Ser
    210                 215                 220
Lys Arg Arg Asn Leu Thr Ile Gly Trp Ser Lys Ser Thr Ser Val Glu
225                 230                 235                 240
Glu Arg Arg Arg Glu Arg Gln Arg Glu Asp Gly Ser Arg Lys Gly Lys
                245                 250                 255
Glu Pro Val Val Trp Lys Glu Ser Glu Lys Glu Ile Glu Met Gln Ser
            260                 265                 270
Thr Glu Arg Gln His Tyr Gln Arg Pro Arg Gly Gly Arg Asn Ser Gln
            275                 280                 285
Arg Lys Arg Ser Ala Lys Val Val Tyr Gly Lys Gly Ile Ala Cys Val
    290                 295                 300
Thr Gly Glu Ser Gly Leu Gly Lys Thr Glu Leu Leu Leu Glu Phe Ala
305                 310                 315                 320
Tyr Lys Tyr His Gln Arg Tyr Lys Met Val Leu Trp Ile Gly Gly Glu
                325                 330                 335
Ser Arg Tyr Ile Arg Gln Asn Tyr Leu Asn Leu Trp Ser Phe Leu Glu
            340                 345                 350
Val Asp Val Gly Val Glu Asn Cys Thr Asp Lys Ser Arg Met Lys Ser
            355                 360                 365
Phe Glu Glu Gln Glu Ala Ala Ile Ser Arg Val Arg Lys Glu Leu
    370                 375                 380
Met Arg Asn Ile Pro Phe Leu Val Val Ile Asp Asn Leu Glu Ser Glu
385                 390                 395                 400
Lys Asp Trp Trp Asp Arg Lys Leu Val Met Asp Leu Leu Pro Arg Phe
                405                 410                 415
Gly Gly Glu Thr His Ile Leu Ile Ala Thr Arg Leu Pro Arg Val Met
            420                 425                 430
Asn Leu Glu Pro Leu Lys Leu Ser Tyr Leu Ser Gly Val Glu Ala Met
            435                 440                 445
Ser Leu Met Gln Gly Ser Gly Lys Asp Tyr Pro Ile Ala Glu Ile Asp
    450                 455                 460
```

```
Ala Leu Arg Val Ile Glu Glu Lys Val Gly Arg Leu Thr Leu Gly Leu
465                 470                 475                 480

Ala Ile Val Gly Ala Ile Leu Ser Glu Leu Pro Ile Asn Pro Ser Arg
            485                 490                 495

Leu Leu Asp Thr Ile Asn Arg Met Pro Leu Arg Asp Phe Ser Trp Ser
        500                 505                 510

Gly Lys Glu Ala Tyr Ser Leu Arg Lys Asn Ser Phe Leu Leu Gln Leu
    515                 520                 525

Phe Glu Val Cys Phe Ser Ile Phe Asp His Ala Glu Gly Pro Arg Ser
530                 535                 540

Leu Ala Thr Arg Met Val Gln Val Ser Gly Trp Phe Ala Pro Ala Ala
545                 550                 555                 560

Ile Pro Val Ser Leu Leu Ala Met Ala Ala His Lys Ile Pro Glu Lys
                565                 570                 575

His Lys Arg Thr Arg Phe Trp Arg Arg Leu Leu Arg Ser Leu Thr Cys
            580                 585                 590

Gly Leu Ser Ser Ser Tyr Ser Lys Arg Ser Glu Thr Glu Ala Ser Ser
        595                 600                 605

Met Leu Leu Arg Phe Asn Ile Ala Arg Ser Ser Thr Lys Gln Gly Tyr
610                 615                 620

Val His Phe Asn Glu Leu Ile Lys Val Tyr Ser Arg Lys Arg Gly Val
625                 630                 635                 640

Ala Gly Val Ala His Ala Met Val Gln Ala Val Ser Arg Gly Ser
                645                 650                 655

Ile Leu Asp His Ser Glu His Met Trp Ala Ala Cys Phe Leu Leu Phe
            660                 665                 670

Gly Phe Gly Asn Asp Pro Thr Ala Val Glu Leu Lys Val Ser Asp Leu
        675                 680                 685

Leu Tyr Leu Val Lys Glu Val Val Leu Pro Leu Ala Ile Arg Thr Phe
690                 695                 700

Ile Thr Phe Ser Arg Cys Ser Ala Ala Leu Glu Leu Leu Arg Leu Cys
705                 710                 715                 720

Thr Asn Ala Leu Glu Ala Ala Asp Gln Ala Phe Val Thr Pro Val Glu
                725                 730                 735

Lys Trp Leu Asp Lys Ser Leu Cys Trp Arg Pro Ile Gln Thr Asn Ala
            740                 745                 750

Gln Leu Asn Pro Tyr Leu Trp Gln Glu Leu Ala Leu Ser Arg Ala Thr
        755                 760                 765

Val Leu Glu Thr Arg Ala Lys Leu Met Leu Arg Gly Gly Gln Phe Asp
770                 775                 780

Ile Gly Asp
785

<210> SEQ ID NO 25
<211> LENGTH: 2565
<212> TYPE: DNA
<213> ORGANISM: Corchorus olitorius

<400> SEQUENCE: 25
atggcggatg caatagtcaa tgtattcttg gaaaagctgt taagcactct tgcagaggaa      60
ggccgctatg ttactgaatt cagggatcag tttgagaaac tacaaactga gcttcaattg     120
ctgcaatgct tcctcaagga tgcagatagg ctgaagagga aaatcacac tatacgaaaa      180 atcttggctg atcttcgcga gttaatatat gaagctgaag atatcctagc agattgccag     240
```

```
cttcagtcaa gggatgaaaa ccaatttttcc caaagctggt tagcttgttt ctctccacca    300
aagcttcatt tcaagtacca aagtgggaag cgtcttaagg aaattactga gaaaatcaca    360
agcattaaac aaaacatctc atcattcctt ggagggcctc ttttattcca accagaggtc    420
ataagcgcgc aggaccaaat gcctagatgg agttcgcagg tgtatgatca cactcaagtg    480
gttggactag aatcagacac tcaaaagatg aaagactgga tatttgatgc agttcatgaa    540
ggagctcagg aaatactagc aattggagtt gttggtatgg gtgggcttgg aaagactacc    600
attgctcaaa aggtttttaa tgaaagagat atagaacatc actttgacag aagaatgtgg    660
gtttctgttt ctcaaacatt cactgaagaa caaattatga gaagtatgtt gaggaacttg    720
ggagatgcaa gtgtgggaga tgatagaaat gaactgctga gaaaattaa ccaatatctc     780
ttaggaaaga ggtatttgat tgtgatggat gatgtgtgga gtgaagatgt tctgtggtgg    840
caacgaatct gtgaagggct gcctaaagga atggtagtt gtatcatcat aacaactaga    900
attgaaaagg ttgcaagaaa gatgggtgtg aagaagcaa ggattcacag gcctaaattc     960
cttaacaaag attatagctg gcttctgttt cgaaaaatag cttttgctgc aagtggtgga   1020
gagtgcactt ccactgatct tgaggatgtt ggaaaagaga ttgtagagaa gtgtaaaggt   1080
cttcccttgg ccatcaaagc tgttggagga atgatgcttt gtaaagcacc atattaccgt   1140
gaatggaggc gaattgcaga tcatttcaga gatgagttgg aagaaaatga taactctgtc   1200
atggcttcac tacaattgag ttatgatgag ctcccttcct acttgaagtc ctgcttgctt   1260
agcttctctc tttatcctga ggattgtgtc ataacaaaag agcaattagt tcattggtgg   1320
attggtgagg gatttgcccc acaaaggagt agtagatctt caactgatgc tggagaagat   1380
tgtttctcag gattaacaaa tcgatgtttg ttagaggtag tcgacaagac ttataatggt   1440
acaatttgca cttgcaaaat gcatgatatg gttcgtgatt tggttcttaa gatagcaaaa   1500
gatgatgcat tttacaatgc aacgggtact aattatcgcc atttgggagt tgataacagc   1560
atggataaga agcaacttat tgctaatcag aagttgagag gattggtgtc cacaacaaaa   1620
acttgtgagg tgaacaagat tgaatcaggt attgcaaaaa gatttagtga gtgcaaatac   1680
ttgagagttt tggatgtttc caaatcaata tttgaattgc ctctcagtag cttgctatat   1740
cgtgttggca cacttcaaca tctgacttat cttggtttaa gcaacactca tcctttggtt   1800
gaacttccag attcactaga aaatctcact aaccttcaaa ttttggatgt tagttactgt   1860
cagaatctga aattcttgcc tcagtatctc attaaattca agaagctcaa agtcttagat   1920
gtgagctttt gtggttccct agaaaactta ccaaaaggct tgggaaggct ttcaaacctt   1980
gaagttttgc tgggtttag acctgcaagg tcaaataatg gttgcaggat tggagaatta   2040
agaaacttga cgcgattgag gacgcttgga ttacatctaa cacacgctga tgaagttgaa   2100
gatagcgagt tcaacgcgat gatgaacctt caagacttgg aaaagctatc aataagtttc   2160
tttgatagcc atggcagtgc aagtgatctg acctctaaaa ttgacaaact ctgccctcca   2220
caacaactcc atgaactatc cgtcatgttc tatccaggaa agataagtcc actttggctc   2280
aacccttag cacttcccat gcttaaatat ctgtcaatct cttcaggaaa tcttgcaaaa    2340
atgcatcaga acttttgggg tggtgacaac aacattgttt ggaaagttga aggcttaatg   2400
ttggaatcat tgtctgattt ggaactgcag tggccaaagt tgcaacagct tatgcaaatc   2460
ctgcgagttg tgaatgttag ttggtgtccg gaattagttt cttttcccaat tgaagatgtt   2520
ggattcaggg gtggagtatg gattaaggaa caaattagga actga                  2565
```

<210> SEQ ID NO 26
<211> LENGTH: 854
<212> TYPE: PRT
<213> ORGANISM: Corchorus olitorius

<400> SEQUENCE: 26

Met Ala Asp Ala Ile Val Asn Val Phe Leu Glu Lys Leu Leu Ser Thr
1               5                   10                  15

Leu Ala Glu Glu Gly Arg Tyr Val Thr Glu Phe Arg Asp Gln Phe Glu
            20                  25                  30

Lys Leu Gln Thr Glu Leu Gln Leu Leu Gln Cys Phe Leu Lys Asp Ala
        35                  40                  45

Asp Arg Leu Lys Arg Lys Asn His Thr Ile Arg Lys Ile Leu Ala Asp
    50                  55                  60

Leu Arg Glu Leu Ile Tyr Glu Ala Glu Asp Ile Leu Ala Asp Cys Gln
65                  70                  75                  80

Leu Gln Ser Arg Asp Glu Asn Gln Phe Ser Gln Ser Trp Leu Ala Cys
                85                  90                  95

Phe Ser Pro Pro Lys Leu His Phe Lys Tyr Gln Ser Gly Lys Arg Leu
            100                 105                 110

Lys Glu Ile Thr Glu Lys Ile Thr Ser Ile Lys Gln Asn Ile Ser Ser
        115                 120                 125

Phe Leu Gly Gly Pro Leu Leu Phe Gln Pro Glu Val Ile Ser Ala Gln
    130                 135                 140

Asp Gln Met Pro Arg Trp Ser Ser Gln Val Tyr Asp His Thr Gln Val
145                 150                 155                 160

Val Gly Leu Glu Ser Asp Thr Gln Lys Met Lys Asp Trp Ile Phe Asp
                165                 170                 175

Ala Val His Glu Gly Ala Gln Glu Ile Leu Ala Ile Gly Val Val Gly
            180                 185                 190

Met Gly Gly Leu Gly Lys Thr Thr Ile Ala Gln Lys Val Phe Asn Glu
        195                 200                 205

Arg Asp Ile Glu His His Phe Asp Arg Arg Met Trp Val Ser Val Ser
    210                 215                 220

Gln Thr Phe Thr Glu Glu Gln Ile Met Arg Ser Met Leu Arg Asn Leu
225                 230                 235                 240

Gly Asp Ala Ser Val Gly Asp Asp Arg Asn Glu Leu Leu Lys Lys Ile
                245                 250                 255

Asn Gln Tyr Leu Leu Gly Lys Arg Tyr Leu Ile Val Met Asp Asp Val
            260                 265                 270

Trp Ser Glu Asp Val Leu Trp Trp Gln Arg Ile Cys Glu Gly Leu Pro
        275                 280                 285

Lys Gly Asn Gly Ser Cys Ile Ile Ile Thr Thr Arg Ile Glu Lys Val
    290                 295                 300

Ala Arg Lys Met Gly Val Lys Glu Ala Arg Ile His Arg Pro Lys Phe
305                 310                 315                 320

Leu Asn Lys Asp Tyr Ser Trp Leu Leu Phe Arg Lys Ile Ala Phe Ala
                325                 330                 335

Ala Ser Gly Gly Glu Cys Thr Ser Thr Asp Leu Glu Asp Val Gly Lys
            340                 345                 350

Glu Ile Val Glu Lys Cys Lys Gly Leu Pro Leu Ala Ile Lys Ala Val
        355                 360                 365

Gly Gly Met Met Leu Cys Lys Ala Pro Tyr Tyr Arg Glu Trp Arg Arg
    370                 375                 380

```
Ile Ala Asp His Phe Arg Asp Glu Leu Glu Asn Asp Asn Ser Val
385                 390                 395                 400

Met Ala Ser Leu Gln Leu Ser Tyr Asp Glu Leu Pro Ser Tyr Leu Lys
            405                 410                 415

Ser Cys Leu Leu Ser Phe Ser Leu Tyr Pro Glu Asp Cys Val Ile Thr
        420                 425                 430

Lys Glu Gln Leu Val His Trp Trp Ile Gly Glu Gly Phe Ala Pro Gln
    435                 440                 445

Arg Ser Ser Arg Ser Ser Thr Asp Ala Gly Glu Asp Cys Phe Ser Gly
450                 455                 460

Leu Thr Asn Arg Cys Leu Leu Glu Val Val Asp Lys Thr Tyr Asn Gly
465                 470                 475                 480

Thr Ile Cys Thr Cys Lys Met His Asp Met Val Arg Asp Leu Val Leu
            485                 490                 495

Lys Ile Ala Lys Asp Asp Ala Phe Tyr Asn Ala Thr Gly Thr Asn Tyr
        500                 505                 510

Arg His Leu Gly Val Asp Asn Ser Met Asp Lys Lys Gln Leu Ile Ala
    515                 520                 525

Asn Gln Lys Leu Arg Gly Leu Val Ser Thr Thr Lys Thr Cys Glu Val
530                 535                 540

Asn Lys Ile Glu Ser Gly Ile Ala Lys Arg Phe Ser Glu Cys Lys Tyr
545                 550                 555                 560

Leu Arg Val Leu Asp Val Ser Lys Ser Ile Phe Glu Leu Pro Leu Ser
            565                 570                 575

Ser Leu Leu Tyr Arg Val Gly Thr Leu Gln His Leu Thr Tyr Leu Gly
        580                 585                 590

Leu Ser Asn Thr His Pro Leu Val Glu Leu Pro Asp Ser Leu Glu Asn
    595                 600                 605

Leu Thr Asn Leu Gln Ile Leu Asp Val Ser Tyr Cys Gln Asn Leu Lys
610                 615                 620

Phe Leu Pro Gln Tyr Leu Ile Lys Phe Lys Lys Leu Lys Val Leu Asp
625                 630                 635                 640

Val Ser Phe Cys Gly Ser Leu Glu Asn Leu Pro Lys Gly Leu Gly Arg
            645                 650                 655

Leu Ser Asn Leu Glu Val Leu Gly Phe Arg Pro Ala Arg Ser Asn
        660                 665                 670

Asn Gly Cys Arg Ile Gly Glu Leu Arg Asn Leu Thr Arg Leu Arg Thr
    675                 680                 685

Leu Gly Leu His Leu Thr His Ala Asp Glu Val Glu Asp Ser Glu Phe
690                 695                 700

Asn Ala Met Met Asn Leu Gln Asp Leu Glu Lys Leu Ser Ile Ser Phe
705                 710                 715                 720

Phe Asp Ser His Gly Ser Ala Ser Asp Leu Thr Ser Lys Ile Asp Lys
            725                 730                 735

Leu Cys Pro Pro Gln Gln Leu His Glu Leu Ser Val Met Phe Tyr Pro
        740                 745                 750

Gly Lys Ile Ser Pro Leu Trp Leu Asn Pro Leu Ala Leu Pro Met Leu
    755                 760                 765

Lys Tyr Leu Ser Ile Ser Ser Gly Asn Leu Ala Lys Met His Gln Asn
770                 775                 780

Phe Trp Gly Gly Asp Asn Asn Ile Val Trp Lys Val Glu Gly Leu Met
785                 790                 795                 800

Leu Glu Ser Leu Ser Asp Leu Glu Leu Gln Trp Pro Lys Leu Gln Gln
```

```
                805                 810                 815
Leu Met Gln Ile Leu Arg Val Val Asn Val Ser Trp Cys Pro Glu Leu
        820                 825                 830

Val Ser Phe Pro Ile Glu Asp Val Gly Phe Arg Gly Gly Val Trp Ile
        835                 840                 845

Lys Glu Gln Ile Arg Asn
    850

<210> SEQ ID NO 27
<211> LENGTH: 3604
<212> TYPE: DNA
<213> ORGANISM: Corchorus olitorius

<400> SEQUENCE: 27
aaaagtagac atggcgggtg aattattcgg tggagctttt ctctctgcca ctctccaagt     60
tttgttcgac cggttggctt ctcgtgaggt ggtggacttc atcaggggaa agaaacttga    120
ggttttggtc aagaaactga agccagtgtt gctgtccgtc aaagcagtgc tggatgatgc    180
tgaagacaag cagatcacca accagaatgt gaaagagtgg ctctccgagc tcaaagatgg    240
tgtttatgat gcagaggacc tcctcgatga gatcgcttat gaagctctta aaaggaggct    300
ggaaaccact acttcagcca aggggatatt ggagtcaaag ttagaggaga tccttgagag    360
gctagaactt ctagtcgacc aaacagaacg cctggggttg aaggagtgta gaggtggtga    420
aaccttgtct caaaggttgc ctccaacttc tgtggtggat gagtcttgtg tttatggtag    480
agttgatgaa aaagaagcaa tcatgaagtt gctacaccct gaaaacccga ctcagaatca    540
gattgatgtg attcccatag tgggtatggg aggggttggt aaaaccaccc ttgctcaatt    600
gatctacaat gacaacagat ggaggaatg gtttgacctc aaagcttggg tgtgtgtttc    660
agatgaattt gatgctttca gggttaccaa aaccattctt caacagattg cttctgattg    720
ggatgatcgt ctcgacctaa atcagcttca agttaaacta caggagaagc tgttggggaa    780
gaggtttcta tttgttttag atgatgtttg gaatgacaaa tatattgagt ggaaacagtt    840
gacaagtcct ttcagtgctg ggcaaaagac agcaagattg ttgtgactac cacgtagtga    900
taatgttgca aacatcatga ggacagttcc agcttatcag cttccaatct tatctgattc    960
tgattgttgc ttgttatttg caaagcatgc gttcgtcaat acaagcccaa gtgagcagcc   1020
agatttgaag ctaattgggg aagcaattgt caaaaggtgc aaagggctac ctctagcagt   1080
gaaagcagtt ggaggttttc ttcgttggaa actagatgtt gatgaatgga gaaatatgaa   1140
tatggaagag caaggtatg agtacatcaa agatttagag tcaaggtcat ttttccaaaa   1200
attaagcggg gatgaatcct gctttgtcat gcatgacctc atcagtgact ggctaaatc    1260 tgtgtctgga gaattttttt gcagattgga aggtggcgat ggaggttcat gtgttataac   1320
taaaaagacc cgccatttgt ctaatatcca agaaccttat gatgtgcgta agaaatttga   1380
gaccttatgt gaagcaaaag gtttgcggac attcctaact ctgaatctga agtcatcatt   1440
tctatcttct tcttttgtta ctaacaggct aatggatgat tgattgtaa aatcaagtcg   1500 cttacgagtt ctttctttga ctgattataa taatattaat atcagggaaa tacaagaagg   1560
aattggaaat ttgaagcatt tgcgatattt ggacctctct aatactttaa ttcaaaggtt   1620
gccgaaccgt gtgtgtactt tgtataattt acaaacatta aaattgtttg gatgtggcaa   1680
gcttgttgag ttgccaaaag atatgggaag attgatcaat atgcatcatc ttgatatcag   1740
ggatacaggg ttaaattgga tgccatcagg aataggaaaa ttgaaagatc ttaaagtttt   1800
```

-continued

```
aacaaattttt tttgttggta agcataaggg ttcaagcatt ggtgagttgg gaaagctgaa    1860
gcatctacaa ggaagtgttg ccatttggaa tttacaaaat gttgtttgtg caaaggatgc    1920
tatggatgcc aatttgaagg acaaggtgaa ccttaaggag ttgagattga tatggagtaa    1980
ggatgctgat gttgatgatg attcagagcg agatagagaa gtacttgaac aactggagcc    2040
tcacacagac ttgcagcatc ttgacatcat gttttataga ggtaccagat ttccagagtg    2100
gattgggcat tcttctttct caaaagtagt atctatggag ttaattgatt gtaaaagttg    2160
tgaattgttg cccccactac gccaactatc atccctgaaa tctctctcta ttagtgggtg    2220
tgttaagata gttagactgg gtgatgagtt ctacggtagt ggtgatgcat tgagtaaccc    2280
atttggatgt cttgaagttc taaaatttga ggatatgtca gaatgggaag aatggatttg    2340
tttgaaggaa gaagctttct ctaatctacg agaattagtc ataagagatt gtcccaagtt    2400
aagcaagtct ttgcccaagt acctcccttg tttaaagaaa cttaagatta gaagatgtgg    2460
aaagctcgaa ggcatacttc agaggcacc aagcattgaa gaagtgcagc tagaggggtg     2520
tgatgccttg caaatggagg cattgccaag tgggcttaga gaattgcaga ttgatggttt    2580
gcgaatcaat gcttccatat tgaagcagat gttgcaacct tgcactattc ttgaacaatt    2640
gcaaatttct aagtgtaata ggctgagatc ccttcctgaa ggtagtaatt tgcctatgag    2700
actgaagaaa ttgagaatcg aagagagtaa tgtgttgaat gattctaaaa tcctcatgta    2760
tacatccctt gaatccttaa aaataagaaa tagcaggtgg aatggggtgg aatctttccc    2820
attaggatca ttccctttgc taaatcgtct tgacataacg ggatgtgaag agttgaagtg    2880
gattattggt gcatcagagg gagaagatgc tcctctctca tgtcgtctca attctttgga    2940
gatctataat tgccctaatt ttgtatgttt tgagaaatta gagggattct gtgccccaa     3000 tttgacatca cttgagctgg tgggatgttc aaatttaaag gcattgcctg agcaaatgca    3060
ctccctcttc ccatcccttg aagaattgtg gatatcattt tgtccaaaaa tagagggatt    3120
tccaaaagag ggtttaccct ccacattaaa agctctttt atccaaggag gatgtaagaa     3180
actaataaag gggatgatga ggagagatag agatacggaa tggggcttgc aatcactccc    3240
ttcacttgaa gagttcataa tctcaggtgg tggagaagag atagaaggga tagagagttt    3300
tccagatgaa catctgctgc cctcttctct tacctctctt tctatctctt attttccaaa    3360
tctaaagagt ttggagtcta agggctttca acacctcacc tctctccgtc aattgggtat    3420
ctacttttgt ccgaggctcc aatccatacc ggaaaagagg gtcatttcct ctctttctta    3480
tttggagatt gcaaaatgtc caaagctgag agaaaatcgt gaaaaggaga aaggcaaaca    3540
ttggcccaac atttcccaca tccctgtcat caactttgat gggtttgatc cagtcattat    3600
atag                                                                 3604
```

<210> SEQ ID NO 28
<211> LENGTH: 1200
<212> TYPE: PRT
<213> ORGANISM: Corchorus olitorius

<400> SEQUENCE: 28

```
Lys Val Asp Met Ala Gly Glu Leu Phe Gly Gly Ala Phe Leu Ser Ala
 1               5                  10                  15

Thr Leu Gln Val Leu Phe Asp Arg Leu Ala Ser Arg Glu Val Val Asp
             20                  25                  30

Phe Ile Arg Gly Lys Lys Leu Glu Val Leu Val Lys Lys Leu Lys Pro
         35                  40                  45
```

```
Val Leu Leu Ser Val Lys Ala Val Leu Asp Asp Ala Glu Asp Lys Gln
     50              55                  60

Ile Thr Asn Gln Asn Val Lys Glu Trp Leu Ser Glu Leu Lys Asp Gly
 65              70                  75                  80

Val Tyr Asp Ala Glu Asp Leu Leu Asp Glu Ile Ala Tyr Glu Ala Leu
                 85                  90                  95

Lys Arg Arg Leu Glu Thr Thr Thr Ser Ala Lys Gly Ile Leu Glu Ser
            100                 105                 110

Lys Leu Glu Glu Ile Leu Glu Arg Leu Glu Leu Leu Val Asp Gln Thr
        115                 120                 125

Glu Arg Leu Gly Leu Lys Glu Cys Arg Gly Glu Thr Leu Ser Gln
    130                 135                 140

Arg Leu Pro Pro Thr Ser Val Val Asp Glu Ser Cys Val Tyr Gly Arg
145                 150                 155                 160

Val Asp Glu Lys Glu Ala Ile Met Lys Leu Leu His Pro Glu Asn Pro
                165                 170                 175

Thr Gln Asn Gln Ile Asp Val Ile Pro Ile Val Gly Met Gly Gly Val
            180                 185                 190

Gly Lys Thr Thr Leu Ala Gln Leu Ile Tyr Asn Asp Asn Arg Leu Glu
        195                 200                 205

Glu Trp Phe Asp Leu Lys Ala Trp Val Cys Val Ser Asp Glu Phe Asp
    210                 215                 220

Ala Phe Arg Val Thr Lys Thr Ile Leu Gln Gln Ile Ala Ser Asp Trp
225                 230                 235                 240

Asp Asp Arg Leu Asp Leu Asn Gln Leu Gln Val Lys Leu Gln Glu Lys
                245                 250                 255

Leu Leu Gly Lys Arg Phe Leu Phe Val Leu Asp Asp Val Trp Asn Asp
            260                 265                 270

Lys Tyr Ile Glu Trp Lys Gln Leu Thr Ser Pro Phe Ser Ala Gly Ala
        275                 280                 285

Lys Asp Ser Lys Ile Val Val Thr Thr Arg Ser Asp Asn Val Ala Asn
    290                 295                 300

Ile Met Arg Thr Val Pro Ala Tyr Gln Leu Pro Ile Leu Ser Asp Ser
305                 310                 315                 320

Asp Cys Cys Leu Leu Phe Ala Lys His Ala Phe Val Asn Thr Ser Pro
                325                 330                 335

Ser Glu Gln Pro Asp Leu Lys Leu Ile Gly Glu Ala Ile Val Lys Arg
            340                 345                 350

Cys Lys Gly Leu Pro Leu Ala Val Lys Ala Val Gly Gly Phe Leu Arg
        355                 360                 365

Trp Lys Leu Asp Val Asp Glu Trp Arg Asn Met Asn Met Glu Glu Gln
    370                 375                 380

Arg Tyr Glu Tyr Ile Lys Asp Leu Glu Ser Arg Ser Phe Phe Gln Lys
385                 390                 395                 400

Leu Ser Gly Asp Glu Ser Cys Phe Val Met His Asp Leu Ile Ser Asp
                405                 410                 415

Leu Ala Lys Ser Val Ser Gly Glu Phe Phe Cys Arg Leu Glu Gly Gly
            420                 425                 430

Asp Gly Gly Ser Cys Val Ile Thr Lys Lys Thr Arg His Leu Ser Asn
        435                 440                 445

Ile Gln Glu Pro Tyr Asp Val Arg Lys Lys Phe Glu Thr Leu Cys Glu
    450                 455                 460

Ala Lys Gly Leu Arg Thr Phe Leu Thr Leu Asn Leu Lys Ser Ser Phe
```

```
              465                 470                 475                 480
Leu Ser Ser Ser Phe Val Thr Asn Arg Leu Met Asp Asp Leu Ile Val
                    485                 490                 495
Lys Ser Ser Arg Leu Arg Val Leu Ser Leu Thr Asp Tyr Asn Asn Ile
                500                 505                 510
Asn Ile Arg Glu Ile Gln Glu Gly Ile Gly Asn Leu Lys His Leu Arg
            515                 520                 525
Tyr Leu Asp Leu Ser Asn Thr Leu Ile Gln Arg Leu Pro Asn Arg Val
        530                 535                 540
Cys Thr Leu Tyr Asn Leu Gln Thr Leu Lys Leu Phe Gly Cys Gly Lys
545                 550                 555                 560
Leu Val Glu Leu Pro Lys Asp Met Gly Arg Leu Ile Asn Met His His
                565                 570                 575
Leu Asp Ile Arg Asp Thr Gly Leu Asn Trp Met Pro Ser Gly Ile Gly
                580                 585                 590
Lys Leu Lys Asp Leu Lys Val Leu Thr Asn Phe Phe Val Gly Lys His
                595                 600                 605
Lys Gly Ser Ser Ile Gly Glu Leu Gly Lys Leu Lys His Leu Gln Gly
        610                 615                 620
Ser Val Ala Ile Trp Asn Leu Gln Asn Val Val Cys Ala Lys Asp Ala
625                 630                 635                 640
Met Asp Ala Asn Leu Lys Asp Lys Val Asn Leu Lys Glu Leu Arg Leu
                645                 650                 655
Ile Trp Ser Lys Asp Ala Asp Val Asp Asp Ser Glu Arg Asp Arg
                660                 665                 670
Glu Val Leu Glu Gln Leu Glu Pro His Thr Asp Leu Gln His Leu Asp
        675                 680                 685
Ile Met Phe Tyr Arg Gly Thr Arg Phe Pro Glu Trp Ile Gly His Ser
        690                 695                 700
Ser Phe Ser Lys Val Val Ser Met Glu Leu Ile Asp Cys Lys Ser Cys
705                 710                 715                 720
Glu Leu Leu Pro Pro Leu Arg Gln Leu Ser Ser Leu Lys Ser Leu Ser
                725                 730                 735
Ile Ser Gly Cys Val Lys Ile Val Arg Leu Gly Asp Glu Phe Tyr Gly
                740                 745                 750
Ser Gly Asp Ala Leu Ser Asn Pro Phe Gly Cys Leu Glu Val Leu Lys
                755                 760                 765
Phe Glu Asp Met Ser Glu Trp Glu Glu Trp Ile Cys Leu Lys Glu Glu
                770                 775                 780
Ala Phe Ser Asn Leu Arg Glu Leu Val Ile Arg Asp Cys Pro Lys Leu
785                 790                 795                 800
Ser Lys Ser Leu Pro Lys Tyr Leu Pro Cys Leu Lys Lys Leu Lys Ile
                805                 810                 815
Arg Arg Cys Gly Lys Leu Glu Gly Ile Leu Pro Glu Ala Pro Ser Ile
                820                 825                 830
Glu Glu Val Gln Leu Glu Gly Cys Asp Ala Leu Gln Met Glu Ala Leu
            835                 840                 845
Pro Ser Gly Leu Arg Glu Leu Gln Ile Asp Gly Leu Arg Ile Asn Ala
        850                 855                 860
Ser Ile Leu Lys Gln Met Leu Gln Pro Cys Thr Ile Leu Glu Gln Leu
865                 870                 875                 880
Gln Ile Ser Lys Cys Asn Arg Leu Arg Ser Leu Pro Glu Gly Ser Asn
                885                 890                 895
```

-continued

```
Leu Pro Met Arg Leu Lys Lys Leu Arg Ile Glu Glu Ser Asn Val Leu
            900                 905                 910

Asn Asp Ser Lys Ile Leu Met Tyr Thr Ser Leu Glu Ser Leu Lys Ile
        915                 920                 925

Arg Asn Ser Arg Trp Asn Gly Val Glu Ser Phe Pro Leu Gly Ser Phe
    930                 935                 940

Pro Leu Leu Asn Arg Leu Asp Ile Thr Gly Cys Glu Glu Leu Lys Trp
945                 950                 955                 960

Ile Ile Gly Ala Ser Glu Gly Glu Asp Ala Pro Leu Ser Cys Arg Leu
                965                 970                 975

Asn Ser Leu Glu Ile Tyr Asn Cys Pro Asn Phe Val Cys Phe Glu Lys
            980                 985                 990

Leu Glu Gly Phe Cys Ala Pro Asn  Leu Thr Ser Leu Glu  Leu Val Gly
        995                 1000                 1005

Cys Ser  Asn Leu Lys Ala Leu  Pro Glu Gln Met His  Ser Leu Phe
1010                 1015                 1020

Pro Ser  Leu Glu Glu Leu Trp  Ile Ser Phe Cys Pro  Lys Ile Glu
    1025                 1030                 1035

Gly Phe  Pro Lys Glu Gly Leu  Pro Ser Thr Leu Lys  Ala Leu Phe
    1040                 1045                 1050

Ile Gln  Gly Gly Cys Lys Lys  Leu Ile Lys Gly Met  Met Arg Arg
    1055                 1060                 1065

Asp Arg  Asp Thr Glu Trp Gly  Leu Gln Ser Leu Pro  Ser Leu Glu
    1070                 1075                 1080

Glu Phe  Ile Ile Ser Gly Gly  Gly Glu Glu Ile Glu  Gly Ile Glu
    1085                 1090                 1095

Ser Phe  Pro Asp Glu His Leu  Leu Pro Ser Ser Leu  Thr Ser Leu
    1100                 1105                 1110

Ser Ile  Ser Tyr Phe Pro Asn  Leu Lys Ser Leu Glu  Ser Lys Gly
    1115                 1120                 1125

Phe Gln  His Leu Thr Ser Leu  Arg Gln Leu Gly Ile  Tyr Phe Cys
    1130                 1135                 1140

Pro Arg  Leu Gln Ser Ile Pro  Glu Lys Arg Val Ile  Ser Ser Leu
    1145                 1150                 1155

Ser Tyr  Leu Glu Ile Ala Lys  Cys Pro Lys Leu Arg  Glu Asn Arg
    1160                 1165                 1170

Glu Lys  Glu Lys Gly Lys His  Trp Pro Asn Ile Ser  His Ile Pro
    1175                 1180                 1185

Val Ile  Asn Phe Asp Gly Phe  Asp Pro Val Ile Ile
    1190                 1195                 1200

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      Forward primer 1

<400> SEQUENCE: 29
tggacgagct aacccagatt                                              20

<210> SEQ ID NO 30
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      Reverse primer 1

<400> SEQUENCE: 30
ggacaagtgc cattgaaagg                                            20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      Forward primer 5

<400> SEQUENCE: 31
ctgccataac aaaaccacca                                            20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      Reverse primer 5

<400> SEQUENCE: 32
attcggttgg agtatttgcg                                            20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      Forward primer 9

<400> SEQUENCE: 33
tcaacatcat gggagtgcat                                            20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      Reverse primer 9

<400> SEQUENCE: 34
tttgaggaac aaagaggcgt                                            20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      Forward primer 13

<400> SEQUENCE: 35
gtgggcaaag acaagggata                                            20

<210> SEQ ID NO 36
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
     Reverse primer 13

<400> SEQUENCE: 36
gcttggggaa ctaccattgt                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
     Forward primer 25

<400> SEQUENCE: 37
tgggaagcgt cttaaggaaa                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
     Reverse primer 25

<400> SEQUENCE: 38
ctgttaaggg ctgcctaaag                                              20

<210> SEQ ID NO 39
<211> LENGTH: 1203
<212> TYPE: PRT
<213> ORGANISM: Populus trichocarpa

<400> SEQUENCE: 39

Met Ala Ala Thr Ser Ser Arg Cys Asn Thr Thr Ser Pro Pro Phe Ser
1               5                   10                  15

Pro Thr Gln Asn Asn Cys Lys Trp Thr Tyr His Val Phe Leu Ser Phe
            20                  25                  30

Arg Gly Glu Asp Thr Arg Lys Asn Phe Thr Gly His Leu Tyr Ser Gly
        35                  40                  45

Leu Ser Arg Phe Lys Leu Leu Val Phe Lys Asp Asp Glu Lys Leu Glu
    50                  55                  60

Lys Gly Lys Val Ile Ala Pro Glu Leu Leu Lys Ala Ile Glu Gln Ser
65                  70                  75                  80

Met Phe Ser Val Ile Val Leu Ser Lys Asn Tyr Ala Ser Ser Ser Trp
                85                  90                  95

Cys Leu Asp Glu Leu Ala Lys Ile Ile Glu Cys Gly Asp Gln Lys Gly
            100                 105                 110

Gln Lys Ile Phe Pro Val Phe Tyr Asp Val Glu Pro Ser Asp Val Arg
        115                 120                 125

Lys Gln Thr Gly Ser Phe Gln Asp Asp Phe Ala Lys His Glu Glu Lys
    130                 135                 140

Tyr Arg Glu Asn Ile Asp Lys Val Arg Lys Trp Arg Ala Ala Met Thr
145                 150                 155                 160

Gln Val Ala Asn Leu Ser Gly Trp Thr Ser Lys Asn Arg Asn Glu Ser
                165                 170                 175

Glu Ile Ile Glu Glu Ile Val Gln Lys Ile Asp Tyr Glu Leu Ser Gln
            180                 185                 190

Thr Phe Ser Ser Val Ser Glu Asp Leu Val Gly Ile Asp Ser Arg Val
        195                 200                 205

```
Arg Val Val Ser Asp Met Leu Phe Gly Gly Gln Asn Asp Val Arg Ile
    210                 215                 220
Ile Gly Ile Cys Gly Met Gly Gly Ile Gly Lys Ser Thr Ile Ala Arg
225                 230                 235                 240
Val Val Tyr Asp Lys Ile Arg Cys Glu Phe Glu Gly Ser Cys Phe Leu
                245                 250                 255
Ala Asn Val Arg Glu Gly Phe Glu Lys His Gly Ala Val Pro Leu Gln
                260                 265                 270
Lys Gln Leu Leu Ser Glu Ile Leu Arg Glu Lys Ser Pro Lys Ile Trp
            275                 280                 285
Asp Pro Glu Lys Gly Ile Ala Glu Ile Lys Asn Arg Leu Gln Asn Arg
290                 295                 300
Lys Val Leu Val Ile Leu Asp Asp Val Asp Asn Leu Lys Gln Leu His
305                 310                 315                 320
Phe Leu Ala Val Asp Trp Lys Trp Phe Leu Pro Gly Ser Arg Ile Ile
                325                 330                 335
Ile Thr Ser Arg Asp Lys Asn Leu Leu Ser Thr His Ala Val Asp Gly
                340                 345                 350
Ile Tyr Glu Ala Glu Leu Asn Asp Asp Ala Leu Val Leu Leu
                355                 360                 365
Ser Arg Lys Ala Phe Lys Lys Asp Gln Pro Ile Glu Gly Tyr Trp Glu
    370                 375                 380
Leu Cys Lys Ser Val Leu Gly His Ala Arg Gly Leu Pro Leu Ala Ala
385                 390                 395                 400
Arg Val Leu Ala Ser Ser Leu Cys Gly Arg Ser Met Asp Phe Trp Glu
                405                 410                 415
Ser Phe Ile Lys Arg Leu Asn Glu Ile Pro Asn Arg Asp Val Met Ala
                420                 425                 430
Val Leu Lys Leu Ser Phe Asp Gly Leu Glu Glu Leu Glu Lys Lys Leu
                435                 440                 445
Phe Leu Asp Ile Ala Cys Phe Phe Lys Gly Met Asn Lys Asp Gln Val
    450                 455                 460
Thr Arg Ile Leu Asn Gln Cys Gly Phe His Ala Asn Tyr Gly Ile Gln
465                 470                 475                 480
Ile Leu Gln Asp Lys Ser Leu Ile Cys Val Ser Asn Asp Thr Leu Ser
                485                 490                 495
Met His Asp Leu Leu Gln Ala Met Gly Arg Glu Val Val Arg Gln Glu
                500                 505                 510
Ser Thr Ala Glu Pro Gly Arg Arg Ser Arg Leu Trp Ala Ser Lys Asp
            515                 520                 525
Val Phe His Val Leu Gly Lys Asn Thr Gly Thr Glu Glu Ile Glu Ser
    530                 535                 540
Ile Ala Leu Asp Trp Ala Asn Pro Glu Asp Val Glu Gly Thr Met Gln
545                 550                 555                 560
Lys Thr Lys Arg Ser Ala Trp Asn Thr Gly Val Phe Ser Lys Met Ser
                565                 570                 575
Arg Leu Arg Leu Leu Arg Ile Arg Asn Ala Cys Phe Asp Ser Gly Pro
                580                 585                 590
Glu Tyr Leu Ser Asn Glu Leu Arg Phe Leu Glu Trp Arg Asn Tyr Pro
                595                 600                 605
Ser Lys Tyr Leu Pro Ser Ser Phe Gln Pro Glu Asn Leu Val Glu Val
    610                 615                 620
```

-continued

His Leu Cys Tyr Ser Asn Leu Arg Gln Leu Arg Leu Gly Asn Lys Ile
625                 630                 635                 640

Leu Asp Ser Leu Lys Val Ile Asp Leu Ser Tyr Ser Glu Tyr Leu Ile
            645                 650                 655

Lys Thr Pro Asn Phe Thr Gly Ile Pro Asn Leu Glu Arg Leu Ile Leu
            660                 665                 670

Gln Gly Cys Arg Arg Leu Ser Glu Val His Ser Ser Ile Gly His His
            675                 680                 685

Asn Lys Leu Ile Tyr Val Asn Leu Met Asp Cys Glu Ser Leu Thr Ser
690                 695                 700

Leu Pro Ser Arg Ile Ser Gly Leu Asn Leu Leu Glu Glu Leu His Leu
705                 710                 715                 720

Ser Gly Cys Ser Lys Leu Lys Glu Phe Pro Glu Ile Glu Gly Asn Lys
            725                 730                 735

Lys Cys Leu Arg Lys Leu Cys Leu Asp Gln Thr Ser Ile Glu Glu Leu
            740                 745                 750

Pro Pro Ser Ile Gln Tyr Leu Val Gly Leu Ile Ser Leu Ser Leu Lys
            755                 760                 765

Asp Cys Lys Lys Leu Ser Cys Leu Pro Ser Ser Ile Asn Gly Leu Lys
770                 775                 780

Ser Leu Lys Thr Leu His Leu Ser Gly Cys Ser Glu Leu Glu Asn Leu
785                 790                 795                 800

Pro Glu Asn Phe Gly Gln Leu Glu Cys Leu Asn Glu Leu Asp Val Ser
            805                 810                 815

Gly Thr Ala Ile Arg Glu Pro Pro Val Ser Ile Phe Ser Leu Lys Asn
            820                 825                 830

Leu Lys Ile Leu Ser Phe His Gly Cys Ala Glu Ser Ser Arg Ser Thr
            835                 840                 845

Thr Asn Ile Trp Gln Arg Leu Met Phe Pro Leu Met Pro Gly Lys Arg
850                 855                 860

Ala Asn Ser Thr Ser Leu Val Leu Pro Ser Leu Ser Gly Leu Ser Ser
865                 870                 875                 880

Leu Thr Arg Leu Gly Leu Ser Asn Cys Asn Leu Gly Glu Gly Ala Val
            885                 890                 895

Pro Asn Asp Ile Gly Tyr Leu Ser Ser Leu Arg Gln Leu Asn Leu Ser
            900                 905                 910

Arg Asn Lys Phe Val Ser Leu Pro Thr Ser Ile Asp Gln Leu Ser Gly
            915                 920                 925

Leu Gln Phe Leu Arg Met Glu Asp Cys Lys Met Leu Gln Ser Leu Pro
930                 935                 940

Glu Leu Pro Ser Asn Leu Glu Glu Phe Arg Val Asn Gly Cys Thr Ser
945                 950                 955                 960

Leu Glu Lys Met Gln Phe Ser Arg Lys Leu Cys Gln Leu Asn Tyr Leu
            965                 970                 975

Arg Tyr Leu Phe Ile Asn Cys Trp Arg Leu Ser Glu Ser Asp Cys Trp
            980                 985                 990

Asn Asn Met Phe Pro Thr Leu Leu Arg Lys Cys Phe Gln Gly Pro Pro
            995                 1000                1005

Asn Leu Ile Glu Ser Phe Ser Val Ile Ile Pro Gly Ser Glu Ile
      1010                1015                1020

Pro Thr Trp Phe Ser His Gln Ser Glu Gly Ser Ser Val Ser Val
      1025                1030                1035

Gln Thr Pro Pro His Ser His Glu Asn Asp Glu Trp Leu Gly Tyr

```
            1040            1045              1050
Ala Val Cys Ala Ser Leu Gly Tyr Pro Asp Phe Pro Pro Asn Val
            1055            1060              1065

Phe Arg Ser Pro Met Gln Cys Phe Phe Asn Gly Asp Gly Asn Glu
        1070            1075              1080

Ser Glu Ser Ile Tyr Val Arg Leu Lys Pro Cys Glu Ile Leu Ser
        1085            1090              1095

Asp His Leu Trp Phe Leu Tyr Phe Pro Ser Arg Phe Lys Arg Phe
        1100            1105              1110

Asp Arg His Val Arg Phe Arg Phe Glu Asp Asn Cys Ser Gln Thr
        1115            1120              1125

Lys Val Ile Lys Cys Gly Val Arg Leu Val Tyr Gln Gln Asp Val
        1130            1135              1140

Glu Glu Leu Asn Arg Met Thr Asn Leu Tyr Glu Asn Ser Thr Phe
        1145            1150              1155

Glu Gly Val Asp Glu Cys Phe Gln Glu Ser Gly Gly Ala Leu Val
        1160            1165              1170

Lys Arg Leu Gly His Thr Asn Asp Val Gly Glu Ala Ser Gly Ser
        1175            1180              1185

Val Ser Ser Asp Glu Gln Pro Pro Thr Lys Lys Leu Lys Gln Ile
        1190            1195              1200

<210> SEQ ID NO 40
<211> LENGTH: 1134
<212> TYPE: PRT
<213> ORGANISM: Medicago truncatula

<400> SEQUENCE: 40

Met Glu Ala Ser Ser Ser Ser Cys Arg Ser Ser Ser Thr Thr Ser
1               5                   10                  15

Leu Cys Thr Tyr His Val Phe Leu Ser Phe Arg Gly Glu Asp Thr Arg
            20                  25                  30

Lys Gly Phe Thr Asp His Leu Cys Ala Ala Leu Glu Arg Lys Gly Ile
            35                  40                  45

Thr Thr Phe Lys Asp Asp Lys Asp Leu Glu Arg Gly Gln Val Ile Ser
    50                  55                  60

Glu Lys Leu Ile Asn Ala Ile Lys Asp Ser Met Phe Ala Ile Thr Ile
65                  70                  75                  80

Leu Ser Pro Asp Tyr Ala Ser Ser Thr Trp Cys Leu Asp Glu Leu Gln
                85                  90                  95

Met Ile Met Glu Cys Ser Ser Lys Asn Asn Leu His Val Leu Pro Val
                100                 105                 110

Phe Tyr Gly Val Asp Pro Ser Asp Val Arg His Gln Arg Gly Cys Phe
            115                 120                 125

Glu Glu Ala Phe Arg Lys His Gln Glu Lys Phe Gly Gln His Ser Asp
        130                 135                 140

Arg Val Asp Arg Trp Arg Asp Ala Phe Thr Gln Val Ala Ser Tyr Ser
145                 150                 155                 160

Gly Trp Asp Ser Lys Gly Gln His Glu Ala Ser Leu Val Glu Asn Ile
                165                 170                 175

Ala Gln His Ile His Arg Lys Leu Val Pro Lys Leu Pro Ser Cys Thr
            180                 185                 190

Glu Asn Leu Val Gly Ile Val Ser Lys Val Glu Glu Val Asn Lys Phe
        195                 200                 205
```

-continued

```
Leu Gly Met Gly Leu Asn Asp Val Arg Phe Ile Gly Ile Trp Gly Met
    210                 215                 220

Gly Gly Ile Gly Lys Ser Thr Ile Ala Arg Ala Val Tyr Glu Thr Ile
225                 230                 235                 240

Arg Cys Glu Phe Glu Leu Thr Cys Phe Leu Glu Asn Val Arg Glu Ile
                245                 250                 255

Ser Glu Thr Asn Gly Leu Val His Leu Gln Arg Gln Leu Leu Ser His
            260                 265                 270

Leu Ser Ile Ser Arg Asn Asp Phe His Asp Leu Tyr Asp Gly Lys Lys
        275                 280                 285

Thr Ile Gln Asn Ser Leu Cys Arg Lys Lys Val Leu Leu Val Leu Asp
    290                 295                 300

Asp Val Asn Glu Leu Asn Gln Leu Glu Asn Leu Val Gly Lys Gln Asp
305                 310                 315                 320

Trp Phe Gly Pro Gly Ser Arg Val Ile Ile Thr Thr Arg Asp Lys His
                325                 330                 335

Leu Leu Met Thr His Gly Val His Lys Thr Tyr Lys Thr Gly Met Leu
            340                 345                 350

Cys Lys His Asp Ala Leu Val Leu Phe Cys Leu Lys Ala Phe Lys Gly
        355                 360                 365

Asp Lys Pro Gln Glu Gly Tyr Leu Asp Leu Ser Lys Glu Val Val Asp
    370                 375                 380

Tyr Cys Gly Gly Leu Pro Leu Ala Leu Glu Val Leu Gly Ser Tyr Leu
385                 390                 395                 400

Tyr Gly Arg Asn Ile Asp Val Trp His Ser Ala Val Lys Lys Leu Arg
                405                 410                 415

Ser Phe Pro His Pro Arg Val Gln Asp Asn Leu Lys Ile Ser Tyr Asp
            420                 425                 430

Ser Leu Asp Thr Met Glu Lys Asp Ile Phe Leu Asp Ile Ala Cys Phe
        435                 440                 445

Phe Lys Gly Met Lys Gly Asp Lys Val Ile Asp Ile Leu Glu Ser Cys
    450                 455                 460

Gly Tyr Phe Pro Gln Ile Gly Ile Gln Ile Leu Ile Glu Arg Ser Leu
465                 470                 475                 480

Ile Thr Leu Asp Ser Val Asn Asn Lys Leu Gly Met His Asp Leu Leu
                485                 490                 495

Gln Glu Met Gly Arg Asp Ile Val Phe Gln Glu Ser Pro Asn Asp Pro
            500                 505                 510

Cys Arg Arg Ser Arg Leu Trp Ser Gln Glu Asp Ile Asp Arg Val Leu
        515                 520                 525

Thr Lys Asn Lys Gly Thr Glu Ala Ile Asn Ser Ile Asp Met Lys Leu
    530                 535                 540

Leu Gln Pro Tyr Glu Ala His Trp Asn Thr Glu Ala Phe Ser Lys Thr
545                 550                 555                 560

Ser Gln Leu Lys Phe Leu Ser Leu Cys Glu Met Gln Leu Pro Leu Gly
                565                 570                 575

Leu Ser Cys Leu Pro Ser Ser Leu Lys Val Leu His Trp Arg Gly Cys
            580                 585                 590

Pro Leu Lys Thr Leu Pro Ile Thr Thr Gln Leu Asp Glu Leu Val Asp
        595                 600                 605

Ile Thr Leu Ser His Ser Lys Ile Glu Gln Leu Trp Gln Gly Val Lys
    610                 615                 620

Phe Met Glu Lys Met Lys Tyr Leu Asn Leu Ala Phe Ser Lys Asn Leu
```

```
            625                 630                 635                 640
Lys Arg Leu Pro Asp Phe Ser Gly Val Pro Asn Leu Glu Lys Leu Ile
                645                 650                 655
Leu Glu Gly Cys Glu Gly Leu Ile Glu Val His Pro Ser Leu Ala His
                660                 665                 670
His Lys Lys Val Val Leu Val Asn Leu Lys Asp Cys Lys Ser Leu Lys
                675                 680                 685
Ser Leu Ser Gly Lys Leu Glu Met Ser Ser Leu Lys Lys Leu Ile Leu
                690                 695                 700
Ser Gly Ser Ser Lys Phe Lys Phe Leu Pro Glu Phe Gly Lys Met
705                 710                 715                 720
Glu Asn Leu Ser Met Leu Ala Leu Glu Gly Thr Asp Ile Arg Lys Leu
                725                 730                 735
Pro Leu Ser Leu Gly Arg Leu Val Gly Leu Thr Asn Leu Asn Leu Lys
                740                 745                 750
Asp Cys Lys Ser Leu Val Cys Leu Pro Asp Thr Ile His Gly Leu Asn
                755                 760                 765
Ser Leu Ile Thr Leu Asp Ile Ser Gly Cys Ser Lys Leu Cys Arg Leu
                770                 775                 780
Pro Asp Gly Leu Lys Glu Ile Lys Cys Leu Glu Glu Leu His Ala Asn
785                 790                 795                 800
Asp Thr Ala Ile Asp Glu Leu Pro Ser Ser Ile Phe Tyr Leu Asp Ser
                805                 810                 815
Leu Lys Val Leu Ser Phe Ala Gly Cys Gln Gly Pro Ser Thr Thr Ser
                820                 825                 830
Met Asn Trp Phe Leu Pro Phe Asn Leu Met Phe Gly Ser Gln Pro Ala
                835                 840                 845
Ser Asn Gly Phe Arg Leu Pro Ser Ser Val Met Gly Leu Pro Ser Leu
                850                 855                 860
Glu Tyr Leu Asn Leu Ser Tyr Cys Asn Leu Ser Glu Glu Ser Phe Pro
865                 870                 875                 880
Asn Tyr Phe His His Leu Ser Ser Leu Lys Ser Leu Asp Leu Thr Gly
                885                 890                 895
Asn Asn Phe Val Ile Ile Pro Ser Ser Ile Ser Lys Leu Ser Arg Leu
                900                 905                 910
Arg Phe Leu Cys Leu Asn Trp Cys Gln Lys Leu Gln Leu Leu Pro Glu
                915                 920                 925
Leu Pro Leu Thr Met Thr Gln Leu Asn Ala Ser Asn Cys Asp Ser Leu
930                 935                 940
Asp Thr Met Lys Phe Asn Pro Ala Lys Leu Cys Ser Leu Phe Ala Ser
945                 950                 955                 960
Pro Arg Lys Leu Ser Tyr Val Gln Glu Leu Tyr Lys Arg Phe Glu Asp
                965                 970                 975
Arg Cys Leu Pro Thr Thr Arg Phe Asp Met Leu Ile Pro Gly Asp Glu
                980                 985                 990
Ile Pro Ser Trp Phe Val Pro Gln Arg Ser Val Ser Trp Ala Lys Val
            995                 1000                1005
His Ile Pro Asn Asn Phe Pro Gln Asp Glu Trp Val Gly Phe Ala
        1010                1015                1020
Leu Cys Phe Leu Leu Val Ser Tyr Ala Asp Pro Pro Glu Leu Cys
        1025                1030                1035
Lys His Glu Ile Asp Cys Tyr Leu Phe Ala Ser Asn Gly Lys Lys
        1040                1045                1050
```

```
Leu Ile Thr Thr Arg Ser Leu Pro Pro Met Asp Pro Cys Tyr Pro
    1055                1060                1065

His Leu Tyr Ile Leu Tyr Met Ser Ile Asp Glu Phe Arg Asp Glu
    1070                1075                1080

Ile Leu Lys Asp Asp Tyr Trp Ser Glu Ser Gly Ile Glu Phe Val
    1085                1090                1095

Leu Lys Cys Tyr Cys Cys Gln Ser Leu Gln Val Val Ser Cys Gly
    1100                1105                1110

Ser Arg Leu Val Cys Lys Gln Asp Val Glu Asp Trp Ser Lys Met
    1115                1120                1125

Ser His Phe Asn Glu Ser
    1130

<210> SEQ ID NO 41
<211> LENGTH: 980
<212> TYPE: PRT
<213> ORGANISM: Solunum tuberosum

<400> SEQUENCE: 41

His Glu Ala Gly Val Ile Glu Arg Ile Ala Glu Asp Ile Met Ala Arg
1               5                   10                  15

Leu Gly Ser Gln Arg His Ala Ser Asn Val Gly Asn Leu Val Gly Met
            20                  25                  30

Glu Leu His Met His Gln Val Tyr Lys Met Leu Gly Val Gly Ser Gly
        35                  40                  45

Gly Val Arg Phe Leu Gly Ile Leu Gly Met Ser Gly Val Gly Lys Thr
    50                  55                  60

Thr Leu Ala Arg Val Ile Tyr Asp Asn Ile Arg Ser Gln Phe Gln Gly
65                  70                  75                  80

Thr Cys Phe Leu His Glu Val Arg Asp Arg Ser Ala Lys Gln Gly Leu
                85                  90                  95

Glu Arg Leu Gln Glu Ile Leu Leu Ser Glu Ile Leu Val Val Lys Lys
            100                 105                 110

Leu Arg Ile Asn Asp Leu Phe Glu Gly Ala Asn Met Gln Lys Gln Arg
        115                 120                 125

Leu Arg Tyr Lys Lys Val Leu Leu Val Leu Asp Asp Val Asp His Ile
    130                 135                 140

Asp Gln Leu Asp Thr Leu Ala Gly Glu Arg Glu Trp Phe Gly Asp Gly
145                 150                 155                 160

Ser Arg Ile Ile Ile Thr Thr Lys Asp Lys His Leu Leu Val Lys Tyr
                165                 170                 175

Glu Thr Glu Lys Ile Tyr Arg Met Gly Thr Leu Asp Lys Tyr Glu Ser
            180                 185                 190

Leu Gln Leu Phe Lys Gln His Ala Phe Lys Lys Asn His Pro Thr Lys
        195                 200                 205

Glu Phe Glu Asp Leu Ser Ala Gln Val Ile Glu His Thr Gly Gly Leu
    210                 215                 220

Pro Val Ala Leu Lys Val Leu Gly Ser Phe Leu Tyr Gly Arg Gly Leu
225                 230                 235                 240

Asp Glu Trp Leu Ser Glu Val Glu Arg Leu Lys Gln Ile Pro Gln Asn
                245                 250                 255

Glu Ile Leu Lys Lys Leu Glu Pro Ser Phe Ile Gly Leu Asn Asn Ile
            260                 265                 270

Glu Gln Lys Ile Phe Leu Asp Ile Ala Cys Phe Phe Ser Gly Lys Lys
```

```
            275                 280                 285
Lys Asp Ser Val Thr Arg Ile Leu Glu Ser Phe His Phe Ser Pro Val
290                 295                 300
Ile Gly Ile Lys Val Leu Met Glu Lys Cys Leu Ile Thr Ile Leu Gln
305                 310                 315                 320
Gly Arg Ile Ala Ile His Gln Leu Ile Gln Asp Met Gly Trp His Ile
                325                 330                 335
Val Arg Arg Glu Ala Ser Tyr Asn Pro Arg Ile Cys Ser Arg Leu Trp
                340                 345                 350
Lys Arg Glu Asp Ile Cys Pro Val Leu Glu Arg Asn Leu Ala Thr Asp
                355                 360                 365
Lys Ile Glu Gly Ile Ser Leu His Leu Thr Asn Glu Glu Val Asn
370                 375                 380
Phe Gly Gly Lys Ala Phe Met Gln Met Thr Ser Leu Arg Phe Leu Lys
385                 390                 395                 400
Phe Arg Asn Ala Tyr Val Cys Gln Gly Pro Glu Phe Leu Pro Asp Glu
                405                 410                 415
Leu Arg Trp Leu Asp Trp His Gly Tyr Pro Ser Lys Ser Leu Pro Asn
                420                 425                 430
Ser Phe Lys Gly Asp Gln Leu Val Ser Leu Thr Leu Lys Lys Ser Arg
                435                 440                 445
Ile Ile Gln Leu Trp Lys Thr Ser Lys Asp Leu Gly Lys Leu Lys Tyr
                450                 455                 460
Met Asn Leu Ser His Ser Gln Lys Leu Ile Arg Thr Pro Asp Phe Ser
465                 470                 475                 480
Val Met Pro Asn Leu Glu Arg Leu Val Leu Glu Glu Cys Lys Ser Leu
                485                 490                 495
Val Glu Ile Asn Phe Ser Ile Gly Asp Leu Gly Lys Leu Val Leu Leu
                500                 505                 510
Asn Leu Lys Asn Cys Arg Asn Leu Lys Thr Leu Pro Lys Arg Ile Arg
                515                 520                 525
Leu Glu Lys Leu Glu Ile Leu Val Leu Ser Gly Cys Ser Lys Leu Arg
                530                 535                 540
Thr Phe Pro Glu Ile Glu Glu Lys Met Asn Cys Leu Ala Glu Leu Tyr
545                 550                 555                 560
Leu Gly Ala Thr Ala Leu Ser Glu Leu Ser Ala Ser Val Glu Asn Leu
                565                 570                 575
Ser Gly Val Gly Val Ile Asn Leu Cys Tyr Cys Lys His Leu Glu Ser
                580                 585                 590
Leu Pro Ser Ser Ile Phe Arg Leu Lys Cys Leu Lys Thr Leu Asp Val
                595                 600                 605
Ser Gly Cys Ser Lys Leu Lys Asn Leu Pro Asp Asp Leu Gly Leu Leu
                610                 615                 620
Val Gly Leu Glu Glu Phe His Cys Thr His Thr Ala Ile Gln Thr Ile
625                 630                 635                 640
Pro Ser Ser Ile Ser Leu Leu Lys Asn Leu Lys His Leu Ser Leu Arg
                645                 650                 655
Gly Cys Asn Ala Leu Ser Ser Gln Val Ser Ser Ser His Gly Gln
                660                 665                 670
Lys Ser Val Gly Val Asn Phe Gln Asn Leu Ser Gly Leu Cys Ser Leu
                675                 680                 685
Ile Met Leu Asp Leu Ser Asp Cys Asn Ile Ser Asp Gly Gly Ile Leu
                690                 695                 700
```

Ser Asn Leu Gly Phe Leu Pro Ser Leu Ala Gly Ile Leu Asp Gly
705                 710                 715                 720

Asn Asn Phe Ser Asn Ile Pro Ala Ala Ser Ile Ser Arg Leu Thr Arg
            725                 730                 735

Leu Glu Ile Leu Ala Leu Ala Gly Cys Arg Arg Leu Glu Ser Leu Pro
            740                 745                 750

Glu Leu Pro Pro Ser Ile Lys Glu Ile Tyr Ala Asp Glu Cys Thr Ser
            755                 760                 765

Leu Met Ser Ile Asp Gln Leu Thr Lys Tyr Ser Met Leu His Glu Val
            770                 775                 780

Ser Phe Thr Lys Cys His Gln Leu Val Thr Asn Lys Gln His Ala Ser
785                 790                 795                 800

Met Val Asp Ser Leu Leu Lys Gln Met His Lys Gly Leu Tyr Leu Asn
                805                 810                 815

Gly Ser Phe Ser Met Tyr Ile Pro Gly Val Glu Ile Pro Glu Trp Phe
                820                 825                 830

Thr Tyr Lys Asn Ser Gly Thr Glu Ser Ile Ser Val Ala Leu Pro Lys
                835                 840                 845

Asn Trp Tyr Thr Pro Thr Phe Arg Gly Ile Ala Ile Cys Val Val Phe
                850                 855                 860

Asp Met Met Thr Pro Phe Ile Leu Trp Lys Pro Asn Ser Asp Glu Pro
865                 870                 875                 880

Phe Ser Phe Pro Asn Val Lys Cys Ser Lys Thr Phe Gln Gly Leu Val
                885                 890                 895

Met Trp Phe Ser Phe Thr Gly His Asp Gly Leu Trp His Arg Phe Arg
                900                 905                 910

Thr Cys Leu Gly Ser Ile Gly Ser Glu Lys Pro Val Gly Leu Gly Asn
                915                 920                 925

Thr Phe Leu Ala Gln Val Pro Leu Asp Arg Phe Trp Arg Leu Glu Asp
                930                 935                 940

Asp Asn Tyr Ile Phe Asn Asp Phe Ile Gln Leu Glu Val Gly Val Cys
945                 950                 955                 960

Asp Asn Ile His Glu Asp Val Val Lys Gly Leu Gly Val Arg Leu
                965                 970                 975

Val Tyr Glu Asn
            980

<210> SEQ ID NO 42
<211> LENGTH: 1741
<212> TYPE: PRT
<213> ORGANISM: Populus tricocarpa

<400> SEQUENCE: 42

Met Ala Ser Ser Ser Met Gln Lys Ala Ala Ser Ser Tyr Ser Pro
1               5                   10                  15

Pro Gln Trp Lys Tyr Asp Val Phe Leu Ser Phe Arg Gly Lys Asp Thr
                20                  25                  30

Arg Asn Asn Phe Thr Ser His Leu Tyr Ser Asn Leu Glu Gln Arg Gly
            35                  40                  45

Ile Asp Val Tyr Met Asp Asp Arg Gly Leu Glu Arg Gly Lys Thr Ile
        50                  55                  60

Glu Pro Ala Leu Trp Gln Ala Ile Glu Asp Ser Arg Phe Ser Ile Val
65                  70                  75                  80

Val Phe Ser Arg Asp Tyr Ala Ser Ser Pro Trp Cys Leu Asp Glu Leu

```
            85                  90                  95
Val Lys Ile Val Gln Cys Met Lys Glu Met Gly His Thr Val Leu Pro
            100                 105                 110

Val Phe Tyr Asp Val Asp Pro Ser Glu Val Ala Asp Gln Lys Gly Asn
            115                 120                 125

Tyr Lys Lys Ala Phe Ile Glu His Lys Glu Lys His Ser Gly Asn Leu
            130                 135                 140

Asp Lys Val Lys Cys Trp Ser Asp Cys Leu Ser Thr Val Ala Asn Leu
145                 150                 155                 160

Ser Gly Trp Asp Val Arg Asn Arg Asp Glu Ser Gln Ser Ile Lys Lys
                    165                 170                 175

Ile Val Glu Tyr Ile Gln Cys Lys Leu Ser Phe Thr Leu Pro Thr Ile
                    180                 185                 190

Ser Lys Asn Leu Val Gly Ile Asp Ser Arg Leu Lys Val Leu Asn Glu
                    195                 200                 205

Tyr Ile Asp Glu Gln Ala Asn Asp Thr Leu Phe Ile Gly Ile Cys Gly
            210                 215                 220

Met Gly Gly Met Gly Lys Thr Thr Val Ala Arg Val Leu Tyr Asp Arg
225                 230                 235                 240

Ile Arg Trp Gln Phe Gly Gly Ser Cys Phe Leu Ala Asn Val Arg Glu
                    245                 250                 255

Val Phe Ala Glu Lys Asp Gly Leu Cys Arg Leu Gln Glu Gln Leu Leu
            260                 265                 270

Ser Glu Ile Ser Met Glu Leu Pro Thr Ala Arg Asp Ser Ser Arg Arg
            275                 280                 285

Ile Asp Leu Ile Lys Arg Arg Leu Arg Leu Lys Lys Val Leu Leu Ile
            290                 295                 300

Leu Asp Asp Val Asp Asp Glu Glu Gln Leu Gln Met Leu Ala Ala Glu
305                 310                 315                 320

His Gly Thr Phe Gly Pro Gly Ser Arg Ile Ile Ile Thr Ser Arg Asn
                    325                 330                 335

Lys His Val Leu Asp Ser His Gly Val Thr Arg Ile Tyr Glu Ala Asp
            340                 345                 350

Lys Leu Asn Asp Lys Asp Ala Leu Met Leu Phe Ser Trp Lys Ala Phe
            355                 360                 365

Lys Arg Asp Gln Pro Ala Glu Asp Leu Ser Glu Leu Ser Lys Gln Val
            370                 375                 380

Val Gly Tyr Ala Asn Gly Leu Pro Leu Ala Leu Glu Val Ile Gly Ser
385                 390                 395                 400

Phe Leu His Lys Arg Gly Leu Arg Glu Trp Lys Ser Ala Ile Asp Arg
                    405                 410                 415

Met Asn Asp Ile Pro Asp Arg Lys Ile Ile Asp Val Leu Arg Ile Ser
                    420                 425                 430

Phe Asp Gly Leu His Glu Leu Glu Lys Lys Ile Phe Leu Asp Ile Ala
            435                 440                 445

Cys Phe Leu Lys Gly Met Lys Lys Asp Arg Ile Thr Arg Leu Leu Asp
            450                 455                 460

Ser Cys Gly Phe His Ala Asp Ile Gly Met Gln Ala Leu Ile Glu Lys
465                 470                 475                 480

Ser Leu Ile Arg Val Ser Arg Asp Glu Ile Arg Met His Asn Leu Leu
                    485                 490                 495

Gln Lys Met Gly Glu Glu Ile Val Arg Cys Glu Ser Pro Glu Glu Pro
            500                 505                 510
```

-continued

```
Gly Arg Arg Ser Arg Leu Cys Thr Tyr Lys Asp Val Cys Asp Ala Leu
            515                 520                 525

Lys Asp Ser Thr Gly Lys Ile Glu Ser Ile Phe Val Asp Leu Pro Lys
    530                 535                 540

Ala Lys Glu Ala Pro Trp Asn Met Thr Ala Phe Ser Lys Met Thr Lys
545                 550                 555                 560

Leu Arg Leu Leu Lys Ile His Asn Val Asp Leu Ser Glu Gly Pro Glu
                565                 570                 575

Tyr Leu Ser Asn Glu Leu Arg Phe Leu Glu Trp His Ala Tyr Pro Ser
            580                 585                 590

Lys Ser Leu Pro Ala Cys Phe Arg Leu Asp Asp Leu Val Glu Leu Tyr
        595                 600                 605

Met Ser Cys Ser Ser Ile Glu Gln Leu Trp Cys Gly Cys Lys Leu Leu
    610                 615                 620

Thr Cys Leu Leu His Val Ser Ala Phe Met Arg Arg Leu Cys Thr Ser
625                 630                 635                 640

Ser Asn Val Cys Asn Thr Ser Thr Phe Asp Glu Ser Gln Ser Ile Lys
                645                 650                 655

Lys Ile Ala Glu Tyr Ile Gln Cys Lys Leu Ser Phe Thr Leu Gln Thr
            660                 665                 670

Ile Ser Lys Asn Leu Val Gly Ile Asp Ser Arg Leu Lys Val Leu Asn
        675                 680                 685

Glu Tyr Ile Asp Glu Gln Ala Thr Asp Thr Leu Phe Ile Gly Ile Cys
    690                 695                 700

Gly Met Gly Gly Met Gly Lys Thr Thr Val Ala Arg Val Met Tyr Asp
705                 710                 715                 720

Arg Ile Arg Trp Gln Phe Gln Gly Ser Cys Phe Leu Ala Asn Val Arg
                725                 730                 735

Glu Val Phe Ala Glu Lys Asp Gly Arg Cys Arg Leu Gln Glu Gln Leu
            740                 745                 750

Leu Ser Glu Ile Ser Met Glu Leu Pro Thr Ala Arg Asp Ser Ser Arg
        755                 760                 765

Arg Ile Asp Leu Ile Lys Arg Leu Arg Leu Lys Lys Val Leu Leu
    770                 775                 780

Ile Leu Asp Asp Val Asp Asp Glu Gln Leu Gln Met Leu Ala Ala
785                 790                 795                 800

Glu His Gly Ser Phe Gly Pro Gly Ser Arg Ile Ile Thr Ser Arg
                805                 810                 815

Asn Lys His Val Leu Asp Ser His Gly Val Thr Arg Ile Tyr Glu Ala
            820                 825                 830

Asp Lys Leu Asn Asp Lys Asp Ala Leu Met Leu Phe Ser Trp Lys Ala
        835                 840                 845

Phe Lys Arg Asp Gln Pro Ala Glu Asp Leu Ser Glu Leu Ser Lys Gln
    850                 855                 860

Val Val Gly Tyr Ala Asn Gly Leu Pro Leu Ala Leu Glu Val Ile Gly
865                 870                 875                 880

Ser Phe Leu His Lys Arg Gly Leu Arg Glu Trp Lys Ser Ala Ile Asp
                885                 890                 895

Arg Met Asn Asp Ile Pro Asp Arg Lys Ile Ile Asp Val Leu Arg Ile
            900                 905                 910

Ser Phe Asp Gly Leu His Glu Leu Glu Lys Lys Ile Phe Leu Asp Ile
        915                 920                 925
```

```
Ala Cys Phe Leu Lys Gly Met Lys Lys Asp Arg Ile Ala Arg Leu Leu
    930                 935                 940

Asp Ser Cys Gly Phe His Ala Asp Ile Gly Met Gln Ala Leu Ile Glu
945                 950                 955                 960

Lys Ser Leu Ile Ser Val Ser Arg Asp Glu Ile Arg Met His Asn Leu
                965                 970                 975

Leu Gln Lys Met Gly Glu Glu Ile Val Arg Cys Glu Ser Pro Glu Glu
                    980                 985                 990

Pro Gly Arg Arg Ser Arg Leu Cys Thr Tyr Lys Asp Val Cys Asp Ala
            995                 1000                1005

Leu Glu Asp Ser Thr Glu Lys Ile Gln Ser Ile Phe Leu Asp Leu
1010                1015                1020

Pro Lys Ala Lys Glu Ala Gln Trp Asn Met Thr Ala Phe Ser Lys
1025                1030                1035

Met Thr Lys Leu Arg Leu Leu Lys Ile His Asn Val Asp Leu Ser
1040                1045                1050

Glu Gly Pro Glu Tyr Leu Ser Lys Glu Leu Arg Phe Leu Glu Trp
1055                1060                1065

His Ala Tyr Pro Ser Lys Ser Leu Pro Ala Cys Phe Arg Pro Asp
1070                1075                1080

Glu Leu Val Glu Leu Tyr Met Ser Cys Ser Ser Ile Glu Gln Leu
1085                1090                1095

Trp Cys Gly Cys Lys Ile Leu Val Asn Leu Lys Ile Ile Asn Leu
1100                1105                1110

Ser Asn Ser Leu Tyr Leu Ile Asn Thr Pro Asp Phe Thr Gly Ile
1115                1120                1125

Pro Asn Leu Glu Ser Leu Ile Leu Glu Gly Cys Ala Ser Leu Ser
1130                1135                1140

Glu Val His Pro Ser Phe Gly Arg His Lys Lys Leu Gln Leu Val
1145                1150                1155

Asn Leu Val Asn Cys Tyr Ser Leu Arg Ile Leu Pro Ser Asn Leu
1160                1165                1170

Glu Met Glu Ser Leu Glu Val Cys Thr Leu Ser Ser Cys Ser Lys
1175                1180                1185

Leu Asp Lys Phe Pro Asp Ile Val Gly Asn Ile Asn Cys Leu Arg
1190                1195                1200

Glu Leu Arg Leu Asp Gly Thr Ala Ile Ala Lys Leu Ser Ser Ser
1205                1210                1215

Phe His Cys Leu Ala Gly Leu Val Leu Leu Ser Met Asn Asn Cys
1220                1225                1230

Lys Asn Leu Glu Ser Ile Pro Ser Ser Ile Arg Gly Leu Lys Ser
1235                1240                1245

Leu Lys Arg Leu Asp Val Ser Asp Cys Ser Glu Leu Lys Asn Ile
1250                1255                1260

Pro Glu Asn Leu Gly Glu Val Glu Ser Leu Glu Glu Phe Asp Ala
1265                1270                1275

Ser Gly Thr Ser Ile Arg Gln Pro Pro Thr Ser Phe Phe Leu Leu
1280                1285                1290

Lys Asn Leu Lys Val Leu Ser Phe Lys Gly Cys Lys Arg Ile Ala
1295                1300                1305

Val Asn Leu Thr Asp Gln Ile Leu Pro Ser Leu Ser Gly Leu Cys
1310                1315                1320

Ser Leu Glu Glu Leu Asp Leu Cys Ala Cys Asn Leu Gly Glu Gly
```

```
               1325                1330                1335

Ala Val Pro Glu Asp Ile Gly Cys Leu Ser Ser Leu Arg Ser Leu
        1340                1345                1350

Asn Leu Ser Arg Asn Asn Phe Ile Ser Leu Pro Lys Ser Ile Asn
        1355                1360                1365

Gln Leu Ser Arg Leu Glu Lys Leu Ala Leu Lys Asp Cys Val Met
        1370                1375                1380

Leu Glu Ser Leu Pro Glu Val Pro Leu Lys Val Gln Lys Val Lys
        1385                1390                1395

Leu Asp Gly Cys Leu Lys Leu Lys Glu Ile Pro Asp Pro Ile Lys
        1400                1405                1410

Leu Cys Ser Leu Lys Arg Ser Glu Phe Lys Cys Leu Asn Cys Trp
        1415                1420                1425

Glu Leu Tyr Met His Asn Gly Gln Asn Asn Met Gly Leu Asn Met
        1430                1435                1440

Leu Glu Lys Tyr Leu Gln Gly Ser Ser Pro Arg Pro Gly Phe Gly
        1445                1450                1455

Ile Ala Val Pro Gly Asn Glu Ile Pro Gly Trp Phe Thr His Gln
        1460                1465                1470

Ser Lys Glu Ser Ser Ile Arg Val Gln Met Pro Ser Asn Tyr Leu
        1475                1480                1485

Asp Gly Asp Asp Asn Gly Trp Met Gly Phe Ala Ala Cys Ala Ala
        1490                1495                1500

Phe Ser Thr Tyr Glu Leu Lys Glu Arg Glu Asn Glu Ser Ser Ser
        1505                1510                1515

Glu Leu Glu Leu Ser Phe His Ser Tyr Asp Gln Gly Val Lys Val
        1520                1525                1530

Glu Asn Cys Gly Val Arg Met Val Asn Ser Gly His Leu Ile Val
        1535                1540                1545

Ala Ser Lys Glu Ala Ala Ser Ser Tyr Thr Pro Ser Trp Gln Ser
        1550                1555                1560

Pro Thr Gly His Leu Ile Ile Ala Ser Lys Glu Ala Ala Ser Ser
        1565                1570                1575

Tyr Ile Asp Ser Leu Ala Asn Ser Ser Ser Tyr Ser Gln Trp Met
        1580                1585                1590

His Asp Val Phe Phe Ser Phe Arg Gly Lys His Asn Ser Asn Asn
        1595                1600                1605

Phe Thr His Leu His Thr Ala Leu Phe Gln Arg Gly Ile Ile Arg
        1610                1615                1620

Tyr Lys Arg Gln Ile Lys Tyr Leu Lys Lys Ile Glu Ser Ser Leu
        1625                1630                1635

Val Ser Asp Ile Lys Glu Ser Gly Leu Ser Ile Ile Ile Phe Ala
        1640                1645                1650

Arg Asp Tyr Val Ser Thr Leu Gly Phe Gly Gly Phe Val Lys Ile
        1655                1660                1665

Asp Glu Phe Met Lys Lys Met Lys Ser Asp Thr Val Phe Pro Val
        1670                1675                1680

Ser Thr Val Ser Tyr Asn Val Glu Gln Ser Arg Val Asp Glu Gln
        1685                1690                1695

Thr Glu Ser Tyr Thr Ile Val Phe Asp Lys Asp Glu Glu Asp Phe
        1700                1705                1710

Ser Glu Asp Lys Glu Lys Val Gln Arg Trp Met Asp Ile Leu Thr
        1715                1720                1725
```

```
Glu Val Ala Ile Ser Ser Gly Ser Glu Ser Ser Lys Arg
    1730                1735            1740

<210> SEQ ID NO 43
<211> LENGTH: 896
<212> TYPE: PRT
<213> ORGANISM: Populus tricocarpa

<400> SEQUENCE: 43

Met Ala Glu Ala Ala Val Ser Phe Val Leu Glu Arg Leu Ala Asp Leu
1               5                   10                  15

Phe Asp Glu Leu Glu Phe His Thr Asp Val His Lys Glu Val Glu Arg
            20                  25                  30

Leu Gln Asp Glu Leu Arg Arg Ile Arg Cys Phe Leu Arg Asp Ala Asp
        35                  40                  45

Ala Lys Gln Asp Glu Asp Glu Arg Val Arg Asn Trp Val Ser Asp Ile
    50                  55                  60

Arg Asp Val Ala Tyr Asp Ala Gly Asp Leu Ile Asp Arg Phe Ile Met
65                  70                  75                  80

Asn Asn Asp Pro Leu Lys Lys Lys Lys Asn His Phe Ile Lys Lys
                85                  90                  95

Cys Thr Ser Tyr Val Lys Gly Trp Lys Gln Arg Ser Lys Ile Ala Glu
            100                 105                 110

Asp Leu Met Ala Ile Arg Ser Arg Leu Gln Asp Ile Ser Ala Ser Arg
        115                 120                 125

Glu Thr Tyr Gly Ile Gln Asn Val Gly Glu Gly Thr Thr Ala Ala Gly
    130                 135                 140

Glu Thr Leu Arg Lys Leu Arg Arg Ser Ser Pro Arg Asp Glu Glu Arg
145                 150                 155                 160

Asp Ile Val Gly Leu Glu Asp Asp Thr Ala Lys Leu Val Asp His Leu
                165                 170                 175

Leu Gln Met Gly Asp His Trp Ser Ala Val Ser Ile Val Gly Met Gly
            180                 185                 190

Gly Ile Gly Lys Thr Thr Leu Gly Ile Lys Ile Tyr Asn His Ser Ala
        195                 200                 205

Val Arg Ala Arg Phe Pro Ser Arg Ala Trp Ile Cys Val Ser Gln Glu
    210                 215                 220

Phe Ser Ala Arg Asp Ile Leu Gln Arg Val Ile Arg Gln Ile Ala Ser
225                 230                 235                 240

Pro Arg Glu Arg Leu Glu Ala Leu Thr Asp Glu Glu Leu Glu Asp Leu
                245                 250                 255

Val Tyr Glu Asn Leu Arg Arg Lys Arg Tyr Leu Val Val Leu Asp Asp
            260                 265                 270

Ile Trp Ser Thr Asn Ala Trp Asp Cys Leu Lys Lys Ala Phe Pro Val
        275                 280                 285

Asp Arg Ser Asn Gly Ser Arg Leu Leu Leu Thr Thr Arg Asn Lys Asn
    290                 295                 300

Val Ala Leu His Val Asp Pro Gln Thr Thr Pro Tyr Asp Leu Gly Phe
305                 310                 315                 320

Leu Ser Lys Gln Asn Ser Trp Glu Leu Phe Cys Lys Lys Thr Phe Ile
                325                 330                 335

Asp Gly Arg Asp Thr Ser Cys Ser Pro Ile Leu Glu Glu Ile Gly Arg
            340                 345                 350

Glu Ile Val Glu Arg Cys Ala Gly Leu Pro Leu Ala Ile Ile Val Ile
```

-continued

```
                355                 360                 365
Gly Gly Leu Leu Ser Arg Lys Lys Arg Leu Asn Glu Trp Glu Arg Ile
    370                 375                 380
Leu Asn Asn Met Asp Ser His Phe Ala Arg His Pro Asn Gly Val Ala
385                 390                 395                 400
Ala Ile Leu Ala Leu Ser Tyr Asn Asp Leu Pro Tyr Tyr Leu Lys Ser
                405                 410                 415
Cys Phe Leu Tyr Leu Gly Leu Phe Pro Glu Asp Cys Thr Ile Gln Ala
                420                 425                 430
His Lys Leu Phe Arg Leu Trp Val Ala Glu Gly Leu Ile Pro His Gln
                435                 440                 445
Glu Leu Arg Gly Glu Asp Val Ala Glu Asp Tyr Leu Asn Glu Leu Ile
                450                 455                 460
Glu Arg Asn Met Val Gln Met Glu Gly Met Ser Val Asn Gly Arg Val
465                 470                 475                 480
Lys Gln Cys Arg Leu His Asp Leu Leu Arg Asp Leu Ser Ile Ser Lys
                485                 490                 495
Ala Lys Thr Glu Asn Phe Leu Gln Ile Pro Gly Asn Glu Asn Ile Pro
                500                 505                 510
Ser Leu Thr Arg Cys Arg Arg His Pro Ile Tyr Ser Asp Ser His Leu
                515                 520                 525
Ser Cys Val Glu Arg Leu Ser Pro His Leu Arg Ser Leu Leu Phe Phe
                530                 535                 540
Arg Val Val Ser Arg Val Arg Tyr Arg Tyr Phe Ile Gly Arg Asn Val
545                 550                 555                 560
Tyr Gly Phe Cys Glu Leu Ser Gly Ala Lys Phe Asp Tyr Ile Thr Arg
                565                 570                 575
Asn Phe Asn Leu Leu Arg Ile Leu Glu Leu Glu Gly Ile Ser Cys Ser
                580                 585                 590
Ser Ile Pro Ser Thr Ile Gly Glu Leu Ile His Leu Ser Tyr Leu Gly
                595                 600                 605
Leu Lys Glu Thr Asn Ile Arg Val Leu Pro Ser Thr Leu Gly Ser Leu
                610                 615                 620
Cys Asn Leu Gln Thr Leu Asp Ile Ala Gly Asn Leu His Leu Arg Ile
625                 630                 635                 640
Ile Pro Asp Val Ile Cys Asn Met Lys Asn Leu Arg His Leu Tyr Met
                645                 650                 655
Cys Gly His Ser Gly Gly His Leu Arg Ile Asp Thr Leu Lys His Leu
                660                 665                 670
Gln Thr Leu Thr Glu Ile Asp Val Ser Arg Trp Lys Gln Asn Asn Thr
                675                 680                 685
Ala Asp Leu Val Ser Leu Arg Lys Leu Gly Ile Arg Gly Asn Leu Cys
                690                 695                 700
Ser Asp Thr Ile Lys Ile Phe Asp Ser Ile Ser Ala Leu Leu Gln Leu
705                 710                 715                 720
Arg Ser Leu Tyr Leu Arg Ala Glu Gly Ala Glu Phe Pro Ser Leu Val
                725                 730                 735
Gln Leu Gly Ser Leu Arg Ser Leu Ile Lys Leu His Leu Arg Gly Gly
                740                 745                 750
Ile Ser Gln Leu Pro Ser Gln Gln Asp Phe Pro Pro Asn Leu Ser Gln
                755                 760                 765
Leu Thr Leu Glu His Thr Gln Leu Glu Gln Glu Ser Ile Glu Ile Leu
                770                 775                 780
```

```
Glu Lys Leu Pro Lys Leu Ser Ile Leu Arg Phe Lys Ala Glu Ser Tyr
785                 790                 795                 800

Ser Lys Glu Lys Leu Thr Ile Ser Ala Asp Gly Phe Pro Gln Leu Glu
                805                 810                 815

Phe Leu Glu Phe Asn Ser Leu Glu Ser Leu His Glu Phe Asn Ile Glu
            820                 825                 830

Glu Asn Ala Val Pro Arg Leu Glu Ser Phe Leu Ile Val Asn Cys Lys
        835                 840                 845

Gly Leu Arg Met Leu Pro Glu Glu Met Arg Phe Val Ala Thr Leu His
    850                 855                 860

Lys Leu Val Ile Glu Glu Met Pro Lys Val Phe Val Asp Arg Leu Gln
865                 870                 875                 880

Gly Glu Asp Leu His Lys Val Gln His Ile Pro Leu Ile Lys Phe Ile
                885                 890                 895

<210> SEQ ID NO 44
<211> LENGTH: 1340
<212> TYPE: PRT
<213> ORGANISM: Populus tricocarpa

<400> SEQUENCE: 44

Met Glu Phe Val Ile Ser Ile Val Ala Thr Val Ala Glu Leu Leu Val
1               5                   10                  15

Val Pro Ile Lys Arg Gln Ile Gly Tyr Val Leu Asp Cys Asn Thr Asn
                20                  25                  30

Ile Gln Asn Leu Lys Asn Glu Val Glu Lys Leu Thr Asp Ala Lys Thr
            35                  40                  45

Arg Val Asn His Ser Ile Glu Glu Ala Arg Arg Asn Gly Glu Glu Ile
        50                  55                  60

Glu Val Asp Val Glu Asn Trp Leu Thr Ser Val Asn Gly Val Ile Gly
65                  70                  75                  80

Gly Gly Gly Gly Val Val Asp Glu Ser Ser Lys Lys Cys Phe Met
                85                  90                  95

Gly Leu Cys Pro Asp Leu Lys Leu Arg Tyr Arg Leu Gly Lys Ala Ala
            100                 105                 110

Lys Lys Glu Leu Thr Val Val Asn Leu Gln Glu Lys Gly Lys Phe
        115                 120                 125

Asp Arg Val Ser Tyr Arg Ala Ala Pro Ser Gly Ile Gly Pro Val Lys
    130                 135                 140

Asp Tyr Glu Ala Phe Glu Ser Arg Asn Ser Val Leu Asn Asp Ile Val
145                 150                 155                 160

Asp Ala Leu Lys Asp Cys Asp Val Asn Met Val Gly Val Tyr Gly Met
                165                 170                 175

Gly Gly Val Gly Lys Thr Thr Leu Ala Lys Lys Val Ala Glu Gln Val
            180                 185                 190

Lys Glu Gly Arg Leu Phe Asp Lys Val Val Leu Ala Val Val Ser His
        195                 200                 205

Thr Pro Asp Ile Arg Arg Ile Gln Gly Glu Ile Ala Asp Gly Leu Gly
    210                 215                 220

Leu Lys Leu Asn Ala Glu Thr Asp Lys Gly Arg Ala Asp Gln Leu Cys
225                 230                 235                 240

Glu Gly Leu Lys Lys Val Thr Arg Val Leu Val Ile Leu Asp Asp Ile
                245                 250                 255

Trp Lys Glu Leu Lys Leu Glu Asp Val Gly Ile Pro Ser Gly Ser Asp
```

```
                260                 265                 270
His Glu Gly Cys Lys Ile Leu Met Thr Ser Arg Asn Lys Asn Val Leu
            275                 280                 285

Ser Arg Glu Met Gly Ala Asn Arg Asn Phe Gln Val Gln Val Leu Pro
        290                 295                 300

Val Arg Glu Ala Trp Asn Phe Phe Glu Lys Met Val Gly Val Thr Val
305                 310                 315                 320

Lys Asn Pro Ser Val Gln Pro Val Ala Ala Glu Val Ala Lys Arg Cys
                325                 330                 335

Ala Gly Leu Pro Ile Leu Leu Ala Thr Val Ala Arg Ala Leu Lys Asn
            340                 345                 350

Glu Asp Leu Tyr Ala Trp Lys Asp Ala Leu Lys Gln Leu Thr Arg Phe
        355                 360                 365

Asp Lys Asp Glu Ile Asp Asn Gln Val Tyr Ser Cys Leu Glu Leu Ser
    370                 375                 380

Tyr Lys Ala Leu Arg Gly Asp Glu Ile Lys Ser Leu Phe Leu Leu Cys
385                 390                 395                 400

Gly Gln Phe Leu Thr Tyr Asp Ser Ser Ile Ser Asp Leu Leu Lys Tyr
                405                 410                 415

Ala Ile Gly Leu Asp Leu Phe Lys Gly Arg Ser Thr Leu Glu Glu Ala
            420                 425                 430

Arg Asn Arg Leu Arg Thr Leu Val Asp Glu Leu Lys Ala Ser Cys Leu
        435                 440                 445

Leu Leu Glu Gly Asp Lys Asp Gly Arg Val Lys Met His Asp Val Val
    450                 455                 460

Gln Ser Phe Ala Phe Ser Val Ala Ser Arg Asp His His Val Leu Ile
465                 470                 475                 480

Val Ala Asp Glu Phe Lys Glu Trp Pro Thr Ser Asp Val Leu Gln Gln
                485                 490                 495

Tyr Thr Ala Ile Ser Leu Pro Tyr Arg Lys Ile Pro Asp Leu Pro Ala
            500                 505                 510

Ile Leu Glu Cys Pro Asn Leu Asn Ser Phe Ile Leu Leu Asn Lys Asp
        515                 520                 525

Pro Ser Leu Gln Ile Pro Asp Asn Phe Phe Arg Glu Met Lys Glu Leu
    530                 535                 540

Lys Val Leu Asp Leu Thr Arg Val Asn Leu Ser Pro Leu Pro Ser Ser
545                 550                 555                 560

Leu Gln Phe Leu Glu Asn Leu Gln Thr Leu Cys Leu Asp Gly Cys Val
                565                 570                 575

Leu Glu Asp Ile Ser Ile Val Gly Glu Leu Lys Lys Leu Lys Val Leu
            580                 585                 590

Ser Leu Ile Ser Ser Asp Ile Val Cys Leu Pro Arg Glu Ile Gly Lys
        595                 600                 605

Leu Thr Arg Leu Leu Leu Leu Asp Leu Ser Asn Cys Glu Arg Leu Glu
    610                 615                 620

Val Ile Ser Pro Asn Val Leu Ser Ser Leu Thr Arg Leu Glu Glu Leu
625                 630                 635                 640

Tyr Met Gly Asn Ser Phe Val Lys Trp Glu Thr Glu Gly Ser Ser Ser
                645                 650                 655

Gln Arg Asn Asn Ala Cys Leu Ser Glu Leu Lys Arg Leu Ser Asn Leu
            660                 665                 670

Ile Thr Leu His Met Gln Ile Thr Asp Ala Asp Asn Met Leu Lys Asp
        675                 680                 685
```

-continued

```
Leu Ser Phe Leu Phe Gln Lys Leu Glu Arg Phe Arg Ile Phe Ile Gly
    690             695                 700

Asp Gly Trp Asp Trp Ser Val Lys Tyr Ala Thr Ser Arg Thr Leu Lys
705             710                 715                 720

Leu Lys Leu Asn Thr Val Ile Gln Leu Glu Glu Trp Val Asn Thr Leu
            725                 730                 735

Leu Lys Ser Thr Glu Glu Leu His Leu Gln Glu Leu Lys Gly Val Lys
            740                 745                 750

Ser Ile Leu Asn Asp Leu Asp Gly Glu Asp Phe Pro Arg Leu Lys His
        755                 760                 765

Leu His Val Gln Asn Cys Pro Gly Val Gln Tyr Ile Ile Asn Ser Ile
770                 775                 780

Arg Met Gly Pro Arg Thr Ala Phe Leu Asn Leu Asp Ser Leu Phe Leu
785                 790                 795                 800

Glu Asn Leu Asp Asn Leu Glu Lys Ile Cys His Gly Gln Leu Met Ala
                805                 810                 815

Glu Ser Leu Gly Lys Leu Arg Ile Leu Lys Val Glu Ser Cys His Arg
            820                 825                 830

Leu Lys Asn Leu Phe Ser Val Ser Met Ala Arg Arg Leu Val Arg Leu
            835                 840                 845

Glu Glu Ile Thr Ile Ile Asp Cys Lys Ile Met Glu Glu Val Val Ala
850                 855                 860

Glu Glu Ser Glu Asn Asp Thr Ala Asp Gly Glu Pro Ile Glu Phe Ala
865                 870                 875                 880

Gln Leu Arg Arg Leu Thr Leu Gln Cys Leu Pro Gln Phe Thr Ser Phe
                885                 890                 895

His Ser Asn Arg Arg Gln Lys Leu Leu Ala Ser Asp Val Arg Ser Lys
                900                 905                 910

Glu Ile Val Ala Gly Asn Glu Leu Gly Thr Ser Met Ser Leu Phe Asn
        915                 920                 925

Thr Lys Ile Leu Phe Pro Asn Leu Glu Asp Leu Lys Leu Ser Ser Ile
    930                 935                 940

Lys Val Glu Lys Ile Trp His Asp Gln Pro Ala Val Gln Pro Pro Cys
945                 950                 955                 960

Val Lys Asn Leu Ala Ser Met Val Val Glu Ser Cys Ser Asn Leu Asn
            965                 970                 975

Tyr Leu Leu Thr Ser Ser Met Val Gly Ser Leu Ala Gln Leu Glu Arg
            980                 985                 990

Leu Glu Ile Cys Asn Cys Glu Ser Met Glu Glu Ile Val Val Pro Glu
        995                 1000                1005

Gly Ile Gly Glu Gly Lys Met Met Ser Lys Met Leu Phe Pro Lys
    1010                1015                1020

Leu His Leu Leu Glu Leu Ser Gly Leu Pro Lys Leu Thr Arg Phe
    1025                1030                1035

Cys Thr Ser Asn Leu Leu Glu Cys His Ser Leu Lys Val Leu Met
    1040                1045                1050

Val Gly Asn Cys Pro Glu Leu Lys Glu Phe Ile Ser Ile Pro Ser
    1055                1060                1065

Ser Ala Asp Val Pro Val Met Ser Lys Pro Asp Asn Thr Lys Ser
    1070                1075                1080

Ala Phe Phe Asp Asp Lys Val Ala Phe Pro Asp Leu Glu Val Phe
    1085                1090                1095
```

-continued

```
Leu Ile Phe Glu Met Asp Asn Leu Lys Ala Ile Trp His Asn Glu
    1100                1105                1110

Leu His Ser Asp Ser Phe Cys Glu Leu Lys Ile Leu His Val Gly
    1115                1120                1125

His Gly Lys Asn Leu Leu Asn Ile Phe Pro Ser Ser Met Leu Gly
    1130                1135                1140

Arg Leu His Asn Leu Glu Asn Leu Ile Ile Asn Asp Cys Asp Ser
    1145                1150                1155

Val Glu Glu Ile Phe Asp Leu Gln Val Leu Ile Asn Val Glu Gln
    1160                1165                1170

Arg Leu Ala Asp Thr Ala Thr Gln Leu Arg Val Val Arg Leu Arg
    1175                1180                1185

Asn Leu Pro His Leu Lys His Val Trp Asn Arg Asp Pro Gln Gly
    1190                1195                1200

Ile Leu Ser Phe His Asn Leu Cys Thr Val His Val Arg Gly Cys
    1205                1210                1215

Pro Gly Leu Arg Ser Leu Phe Pro Ala Ser Ile Ala Leu Asn Leu
    1220                1225                1230

Leu Gln Leu Glu Glu Leu Leu Ile Glu Asn Cys Gly Val Glu Glu
    1235                1240                1245

Ile Val Ala Lys Asp Glu Gly Leu Glu Glu Gly Pro Ser Ser Phe
    1250                1255                1260

Arg Phe Ser Phe Pro Lys Val Thr Tyr Leu His Leu Val Glu Val
    1265                1270                1275

Pro Glu Leu Lys Arg Phe Tyr Pro Gly Val His Val Ser Glu Trp
    1280                1285                1290

Pro Arg Leu Lys Lys Phe Trp Val Tyr His Cys Lys Lys Ile Glu
    1295                1300                1305

Ile Phe Pro Ser Glu Ile Lys Cys Ser His Glu Pro Cys Trp Glu
    1310                1315                1320

Asp His Val Asp Ile Glu Gly Gln Gln Pro Leu Leu Ser Phe Arg
    1325                1330                1335

Lys Val
    1340

<210> SEQ ID NO 45
<211> LENGTH: 880
<212> TYPE: PRT
<213> ORGANISM: Populus tricocarpa

<400> SEQUENCE: 45

Met Ala Ile Gly Glu Ile Phe Leu Ala Ala Phe Leu Gly Met Leu Phe
1               5                   10                  15

Thr Arg Leu Thr Ser Pro Glu Phe Leu Lys Phe Ala Arg Arg Glu Gly
            20                  25                  30

Ile Trp Lys Lys Ala Asp Lys Trp Arg Gly Met Leu Leu Lys Val Gln
        35                  40                  45

Glu Val Leu Asp Asp Ala Glu Glu Lys Gln Leu Thr Glu Lys Ala Val
    50                  55                  60

Lys Ile Trp Leu Asp Asp Leu Arg Asp Leu Ala Tyr Asp Val Glu Asp
65                  70                  75                  80

Leu Leu Asp Glu Phe Ala Thr Glu Ser Leu Arg Arg Glu Leu Met Ala
                85                  90                  95

Ala Glu Glu Ala Ser Thr Ser Lys Val Arg Arg Ile Val Ser Thr Thr
            100                 105                 110
```

```
Leu Ser Phe Thr Lys Ile Ser Ala Ser Ala Ile Lys Phe Asn Pro Lys
            115                 120                 125

Met Arg Ser Lys Met Lys Glu Val Ser Ser Arg Leu Asp Gly Met Ala
130                 135                 140

Lys Gln Arg Ile Glu Leu Gly Leu Glu Lys Met Ser Gly Gly Arg Arg
145                 150                 155                 160

Thr Ser Thr Asp Val Trp Gln Lys Pro Ser Ala Ser Val Pro Asn
                165                 170                 175

Glu Pro Val Ile Tyr Gly Arg Asp Gly Asp Lys Lys Val Ile Asp
                180                 185                 190

Leu Leu Leu Thr Glu Glu Ala Asn His Gly Asp Thr Asn Phe His Val
            195                 200                 205

Val Pro Ile Val Gly Met Gly Gly Ile Gly Lys Thr Thr Leu Ala Gln
210                 215                 220

His Val Phe Gln Asp Glu Leu Val Lys Glu Trp Phe Ser Thr Lys Ala
225                 230                 235                 240

Trp Ala Cys Val Ser Asp Asp Phe Asp Val Met Arg Ile Ser Lys Ala
                245                 250                 255

Ile Leu Glu Ser Val Thr Pro His Pro Cys Asp Phe Lys Glu Tyr Asn
                260                 265                 270

Gln Val Gln Val Lys Leu Arg Glu Ala Leu Ala Gly Lys Lys Phe Leu
            275                 280                 285

Leu Val Leu Asp Asp Val Trp Asn Lys Asn Tyr Gly Leu Trp Val Ala
            290                 295                 300

Leu Lys Thr Pro Phe Ala Ala Gly Ala Pro Gly Ser Lys Ile Ile Leu
305                 310                 315                 320

Thr Thr Arg Asp Ala Asp Val Ala Leu Met Val Gly Pro Thr Glu Tyr
                325                 330                 335

His Cys Leu Lys Pro Leu Ser Asp Gln Asp Cys Trp Ser Val Phe Val
                340                 345                 350

Lys His Ala Phe Glu Asn Arg Asp Leu Gly Ala Gln Thr Asn Leu Gln
            355                 360                 365

Ser Val Cys Glu Arg Ile Val Thr Lys Cys Lys Gly Leu Pro Leu Ala
            370                 375                 380

Ala Arg Thr Leu Gly Gly Leu Leu Arg Thr Lys Gln Arg Glu Asp Glu
385                 390                 395                 400

Trp Glu Asp Ile Leu Asn Ser Lys Ile Trp Asp Leu Ser Asp Ser Gln
                405                 410                 415

Ser Asp Ile Leu Pro Val Leu Arg Leu Ser Tyr Tyr His Leu Pro Ser
                420                 425                 430

His Leu Lys Arg Cys Phe Thr Tyr Ser Ala Leu Ile Pro Lys Asp Phe
            435                 440                 445

Glu Phe Glu Glu Lys Asp Leu Val Leu Leu Trp Met Ala Glu Gly Leu
450                 455                 460

Val Pro Gln Gln Val Gln Asn Lys Gln Met Glu Asp Met Gly Ala Glu
465                 470                 475                 480

Tyr Phe Arg Asp Leu Val Ser Arg Ser Ile Phe Gln Val Ala Asn Cys
                485                 490                 495

Asp Glu Ser Arg Phe Val Met His Asp Leu Val Ser Asp Leu Ala Gln
            500                 505                 510

Trp Ala Ala Gly Asp Thr Cys Phe Gln Leu Gly Asn Asp Leu Asn Ala
            515                 520                 525
```

Ile Lys Gln Phe Lys Val Ser Lys Arg Ala Arg His Ser Ser Tyr Ile
    530                 535                 540

Arg Gly Trp Asp Gly Ile Arg Lys Phe Glu Val Phe His Thr Thr Lys
545                 550                 555                 560

Arg Leu Arg Thr Phe Leu Pro Leu Pro Ser Leu Leu Gly His Asn Thr
                565                 570                 575

Gly Tyr Leu Thr Ser His Val Pro Phe Asp Leu Leu Pro Glu Leu Glu
            580                 585                 590

Phe Leu Arg Val Leu Ser Leu Ser Gly Tyr Cys Ile Asp Thr Leu Pro
        595                 600                 605

Asn Ser Ile Gly Asp Leu Lys His Leu Arg Phe Leu Asn Leu Ser Phe
    610                 615                 620

Ser Ala Ile Arg Asn Leu Pro Gln Ser Val Cys Ser Leu Tyr Asn Leu
625                 630                 635                 640

Gln Thr Leu Leu Leu Lys Gly Cys Cys Leu Leu Glu Gly Leu Pro Ser
                645                 650                 655

Lys Leu Gly Ser Leu Ile Asn Leu Arg His Leu Asp Ile Thr Ser Ala
            660                 665                 670

Ser Ser Ile Lys Ala Met Pro Met Gly Ile Glu Lys Leu Thr Asn Leu
        675                 680                 685

Gln Thr Leu Ser Asp Phe Val Leu Gly Lys Asp Lys Gly Ser Arg Leu
    690                 695                 700

Ser Ser Leu Val Asn Leu Lys Ser Leu Arg Gly Thr Leu Cys Ile Thr
705                 710                 715                 720

Gly Leu Glu Asn Val Ile Asp Ala Arg Glu Ala Met Glu Ala Asn Ile
                725                 730                 735

Lys Asp Ile Asn Asn Leu Glu Val Leu Leu Leu Glu Trp Ser Pro Arg
            740                 745                 750

Thr Asp Asn Ser Arg Asn Glu Lys Val Asp Lys Asp Val Leu Asp Asp
        755                 760                 765

Leu Arg Pro His Gly Lys Val Lys Glu Leu Thr Ile Asn Cys Tyr Ala
    770                 775                 780

Gly Leu Thr Phe Pro Thr Trp Val Gly Asn Pro Ser Phe Ser Ser Ile
785                 790                 795                 800

Phe Leu Leu Arg Leu Glu Asn Cys Thr Lys Cys Thr Ser Leu Pro Pro
                805                 810                 815

Leu Gly Leu Leu Pro Ser Leu Lys Asn Leu Ser Ile Val Ser Leu Thr
            820                 825                 830

Ala Val Lys Lys Val Gly Pro Glu Phe Tyr Gly Gln Gly Cys Ser Lys
        835                 840                 845

Pro Phe Pro Val Leu Glu Thr Leu Leu Phe Lys Asn Met Gln Glu Trp
    850                 855                 860

Glu Glu Trp Met Ile Leu Val Gly Leu Val Leu Thr Asn Ser Leu Ser
865                 870                 875                 880

<210> SEQ ID NO 46
<211> LENGTH: 1417
<212> TYPE: PRT
<213> ORGANISM: Populus tricocarpa

<400> SEQUENCE: 46

Met Ala Leu Val Ile Gly Asp Ala Ile Leu Ser Ala Thr Ile Ser His
1               5                   10                  15

Ile Ile Asn Gln Leu Ala Ser Leu Glu Leu Leu Lys Phe Ala Arg Arg
            20                  25                  30

```
Gly Lys Ile His Ser Asp Ile Lys Lys Leu Glu Ala Asn Leu His Met
         35                  40                  45

Ile His Ala Val Leu Asp Asp Ala Glu Glu Lys Gln Met Gly Ser His
 50                  55                  60

Ala Val Lys Leu Trp Leu Asp Gln Ile Arg Glu Leu Ala Tyr Asp Met
 65                  70                  75                  80

Glu Asp Leu Leu Asp Gly Val Phe Ser Glu Leu Lys Glu Glu Gln Arg
                 85                  90                  95

Ala Ser Ser Ser Lys Ala Lys Ser Ala Ile Pro Gly Phe Leu Ser Ser
                100                 105                 110

Phe Tyr Pro Gly Asn Leu Leu Thr Tyr Lys Met Asp Ser Lys Ile
             115                 120                 125

Lys Arg Thr Thr Ala Arg Phe Gln Glu Ile Ala Gln Lys Lys Asn Asn
        130                 135                 140

Leu Glu Leu Arg Glu Asn Gly Ser Gly Gly Val Leu Lys Ser Lys Ser
145                 150                 155                 160

Leu Lys Arg Leu Pro Ser Thr Ser Leu Val Asp Leu Ser Tyr Val Ser
                165                 170                 175

Gly Arg Asp Lys Asp Lys Glu Glu Ile Leu Lys Leu Leu Phe Ser Asp
                180                 185                 190

Glu Gly Cys Asp Glu Tyr Gly Ile Gly Val Ile Pro Ile Val Gly Met
            195                 200                 205

Gly Gly Val Gly Lys Thr Thr Leu Ala Gln Leu Val Tyr Asn Asp Glu
210                 215                 220

Thr Val Asp Asn Phe Phe Asp Leu Lys Val Trp Cys Cys Val Ser Glu
225                 230                 235                 240

Asp Phe Asp Val Val Arg Val Thr Arg Thr Ile Leu Glu Ala Val Ser
                245                 250                 255

Gly Ser Tyr Asp Ala Lys Asp Leu Asn Leu Leu Gln Leu Arg Leu Arg
                260                 265                 270

Glu Lys Leu Ala Gly Lys Lys Phe Leu Ile Val Leu Asp Asp Val Trp
            275                 280                 285

Asn Glu Asn Tyr Asp Asp Trp Thr Val Leu Arg Arg Pro Phe Gln Val
        290                 295                 300

Thr Ser Pro Gly Ser Arg Ile Ile Leu Thr Thr Arg Asn Gln Asp Val
305                 310                 315                 320

Ala Leu Met Met Ser Ala Phe Pro Cys Tyr Leu Leu Lys Glu Leu Ser
                325                 330                 335

Phe Glu Asp Ser Leu Ser Leu Phe Ala Lys His Ala Leu Gly Arg Ser
            340                 345                 350

Asn Phe Ser Asp Leu Pro Asp Leu Gln Glu Ile Gly Gln Lys Ile Val
        355                 360                 365

Gln Arg Cys Gly Gly Leu Pro Leu Ala Val Lys Thr Leu Gly Gly Leu
    370                 375                 380

Leu Arg Thr Lys Pro Tyr Val Asp Glu Trp Glu Ser Val Leu Asn Ser
385                 390                 395                 400

Lys Met Trp Asp Ile Ser Glu His Lys Gly Gly Ile Val Pro Ala Leu
                405                 410                 415

Arg Leu Ser Tyr Tyr His Leu Pro Ser His Leu Lys Gln Leu Phe Val
            420                 425                 430

Phe Cys Ser Ile Leu Pro Lys Asp Tyr Glu Phe Tyr Lys Asp Glu Leu
        435                 440                 445
```

```
Val Leu Leu Trp Met Ala Gln Gly Phe Leu Pro Asp Ala Gly Gly Lys
    450                 455                 460
Lys Arg Met Glu Asp Phe Tyr Ser Cys Phe Asn Glu Leu Leu Ser Arg
465                 470                 475                 480
Ser Phe Phe Gln Arg Ser Ser Asn Glu Gln Arg Tyr Leu Met His
                485                 490                 495
His Leu Ile Ser Asp Leu Ala Gln Ser Ile Ala Gly Glu Thr Cys Val
            500                 505                 510
Asn Leu Asn Asp Lys Leu Glu Asn Lys Val Phe Pro Asp Pro Glu
            515                 520                 525
Lys Thr Arg His Met Ser Phe Thr Arg Thr Tyr Glu Val Leu Gln
530                 535                 540
Arg Phe Lys Asp Leu Gly Lys Leu Lys Arg Leu Arg Thr Phe Ile Ala
545                 550                 555                 560
Leu Arg Leu Tyr Ser Ser Pro Trp Ala Ala Tyr Cys Tyr Leu Ser Asn
                565                 570                 575
Asn Val Leu His Glu Ala Leu Ser Lys Leu Arg Arg Leu Arg Val Leu
            580                 585                 590
Ser Leu Ser Gly Tyr Cys Ile Thr Glu Leu Pro Asn Ser Ile Gly Asp
        595                 600                 605
Leu Lys Gln Leu Arg Tyr Leu Asn Phe Ser Gln Thr Lys Ile Lys Arg
    610                 615                 620
Leu Pro Glu Ser Val Ser Thr Leu Ile Asn Leu Gln Thr Leu Lys Leu
625                 630                 635                 640
Gly Cys Arg Lys Leu Asn Lys Leu Pro Gln Gly Thr Gly Asn Leu Ile
                645                 650                 655
Asp Leu Cys His Leu Asp Ile Thr Asp Thr Asp Asn Leu Phe Glu Met
            660                 665                 670
Pro Ser Trp Met Gly Asn Leu Thr Gly Leu Gln Lys Leu Ser Lys Phe
        675                 680                 685
Thr Val Gly Lys Lys Glu Gly Cys Gly Ile Glu Glu Leu Arg Gly Leu
    690                 695                 700
Gln Asn Leu Glu Gly Arg Leu Ser Ile Met Ala Leu His Asn Val Ile
705                 710                 715                 720
Asp Ala Arg His Ala Val His Ala Asn Leu Arg Gly Lys His Asn Leu
                725                 730                 735
Asp Glu Leu Glu Leu Glu Trp Ser Lys Ser Asp Ile Lys Asp Glu Asp
            740                 745                 750
Arg Gln His Gln Met Leu Val Leu Asp Ser Leu Gln Pro His Thr Asn
        755                 760                 765
Leu Lys Glu Leu Lys Ile Ser Phe Tyr Gly Gly Thr Glu Phe Pro Ser
    770                 775                 780
Trp Val Gly His Pro Ser Phe Ser Lys Ile Val His Leu Lys Leu Ser
785                 790                 795                 800
Cys Cys Arg Lys Cys Thr Val Leu Pro Pro Leu Gly Arg Leu Pro Leu
                805                 810                 815
Leu Arg Asp Leu Cys Ile Gln Gly Leu Asp Ala Val Glu Thr Val Gly
            820                 825                 830
His Glu Phe Tyr Gly Asp Cys Ser Ser Val Lys Pro Phe Pro Ser Leu
        835                 840                 845
Lys Thr Leu Thr Phe Glu Asp Met Gln Glu Trp Lys Ser Trp Ser Ala
    850                 855                 860
Val Gly Val Asp Gly Glu Ala Glu Glu Gln Phe Pro Ser Leu Ser Glu
```

-continued

```
            865                 870                 875                 880
Leu Thr Leu Trp Asn Cys Pro Lys Leu Leu Gly Arg Phe Pro Ser Cys
                    885                 890                 895
Leu Pro Ser Cys Val Lys Ile Thr Ile Ala Lys Cys Pro Met Leu Val
                    900                 905                 910
Asp Ser Asp Glu Lys Leu Pro Val Leu Gly Glu Leu Lys Leu Glu Glu
                    915                 920                 925
Cys Asp Glu Val Lys Pro Lys Cys Met Phe His Asn Ser Ser Leu Ile
                    930                 935                 940
Thr Leu Lys Leu Gly Ser Met Ser Arg Leu Tyr Leu Lys Gly Gln
945                 950                 955                 960
Leu Leu Gln Ser Leu Gly Ala Leu Lys Val Leu Met Ile Ser Asp Phe
                    965                 970                 975
Pro Lys Leu Thr Ser Leu Trp Gln Lys Gly Thr Gly Leu Glu Asn Phe
                    980                 985                 990
Glu His Pro Gln Phe Val Ser Leu Thr Glu Ile Gly Met Pro Ser Thr
                    995                 1000                1005
His Lys Ser Ser Lys Leu Ser Gly Cys Asp Lys Leu Asp Leu Leu
    1010                1015                1020
Pro Ile His Thr Val His Met Leu Leu Ser Leu Glu Asp Leu Cys
    1025                1030                1035
Ile Glu Ser Cys Pro Asn Leu Val Ser Ile Pro Glu Ala Gly Leu
    1040                1045                1050
Leu Ser Ser Leu Arg His Leu Val Leu Arg Asp Cys Lys Ala Leu
    1055                1060                1065
Arg Ser Leu Pro Asp Gly Met Ser Asn Cys Pro Leu Glu Asp Leu
    1070                1075                1080
Glu Ile Glu Glu Cys Pro Ser Leu Glu Cys Phe Pro Gly Arg Met
    1085                1090                1095
Leu Pro Ala Thr Leu Lys Gly Leu Lys Ile Arg Tyr Cys Thr Glu
    1100                1105                1110
Leu Lys Ser Leu Pro Glu Asp Leu Met His Asn Lys Asn Gly Pro
    1115                1120                1125
Gly Thr Leu Cys His Phe Glu His Leu Glu Ile Ile Gly Cys Pro
    1130                1135                1140
Ser Leu Lys Ser Phe Pro Asp Gly Lys Leu Pro Thr Arg Leu Lys
    1145                1150                1155
Thr Leu Lys Ile Trp Asp Cys Ser Gln Leu Lys Pro Leu Ser Glu
    1160                1165                1170
Met Met Leu His Asp Asp Met Ser Leu Glu Tyr Leu Ala Ile Ser
    1175                1180                1185
Asp Cys Glu Ala Leu Ser Ser Phe Pro Glu Cys Leu Ser Ser Phe
    1190                1195                1200
Lys His Leu Ser Glu Leu Asn Leu Ser Asn Cys Ser Ala Leu Lys
    1205                1210                1215
Leu Phe Pro Gly Val Gly Phe Pro Pro Ala Asn Leu Arg Thr Leu
    1220                1225                1230
Thr Ile Tyr Asn Cys Lys Asn Leu Lys Ser Leu Pro Asn Glu Met
    1235                1240                1245
Arg Lys Leu Thr Ser Leu Gln Glu Leu Thr Ile Cys Ser Cys Pro
    1250                1255                1260
Ala Leu Lys Ser Phe Pro Asn Gly Asp Met Pro Pro His Leu Thr
    1265                1270                1275
```

```
Ser Leu Glu Ile Trp Asp Cys Asp Asn Leu Asp Gly Cys Leu Ser
    1280            1285            1290

Glu Trp Asn Leu Gln Ser Leu Thr Cys Leu Arg Asp Phe Ser Ile
    1295            1300            1305

Ala Gly Gly Cys Phe Ser His Thr Val Ser Phe Pro Asp Glu Lys
    1310            1315            1320

Cys Leu Leu Pro Thr Asn Leu Thr Ser Val Trp Ile Gly Arg Leu
    1325            1330            1335

Pro Asn Leu Glu Ser Leu Ser Met Gln Leu Gln Ser Leu Ala Tyr
    1340            1345            1350

Leu Glu Glu Leu Glu Ile Val Asp Cys Pro Lys Leu Lys Ser Leu
    1355            1360            1365

Pro Arg Gly Cys Leu Pro His Ala Leu Gly Arg Phe Ser Ile Arg
    1370            1375            1380

Asp Cys Pro Leu Met Thr Gln Arg Cys Ser Lys Leu Lys Gly Val
    1385            1390            1395

Tyr Trp Pro Leu Ile Ser His Ile Pro Cys Val Glu Ile Asp Asp
    1400            1405            1410

Gly Asn Asp Met
    1415

<210> SEQ ID NO 47
<211> LENGTH: 1043
<212> TYPE: PRT
<213> ORGANISM: Populus tricocarpa

<400> SEQUENCE: 47

Met Glu Ala Leu Gln Val Ile Ser Ser Ala Thr Gln Ile Ile Ser Ser
1               5                   10                  15

Met Val Gly Ala Val Ser Ala Leu Asp Gln Ala Ser Arg Asn Leu Asp
                20                  25                  30

Glu Ala Pro Lys Arg Ile Arg Ser Leu Glu Glu Phe Val Tyr Asp Leu
            35                  40                  45

Glu Asn Leu Thr Arg Gly Ile Arg Gln Lys His Val Tyr Lys Leu His
        50                  55                  60

Asn Pro Gln Leu Asp His Gln Ile Gln Ser Leu Asn Ala Leu Ile Glu
65                  70                  75                  80

Arg Leu Arg Pro Asn Ile Thr Lys Ala Arg Arg Ile Val Ser Arg Ser
                85                  90                  95

Arg Ile Lys Asn Leu Ala Lys Val Val Trp Ser Ser Met Ala Gly Asp
            100                 105                 110

Pro Leu Ser Lys Leu Ile Asn Thr Ile Arg Asp Asp Leu Asn Trp Trp
        115                 120                 125

Leu Glu Ser Gln Arg Leu Thr Gln His Val Gln Lys Val Ile Glu Ser
    130                 135                 140

Thr Ala Gln Asp Val Pro Val Arg Leu Lys Ile Lys Ile Glu Gln Gly
145                 150                 155                 160

Trp Pro Leu Ser Ser Lys Cys His Phe Val Arg Asn Leu Leu Glu Gln
                165                 170                 175

Glu Asp Ser His Arg Val Ile Leu Ile Val Gly Leu Ser Gly Ile Gly
            180                 185                 190

Lys Ser Cys Leu Ala Arg Gln Val Ala Ser Asn Pro Pro Thr Lys Phe
        195                 200                 205

Val Gly Gly Ala Val Glu Leu Gly Phe Gly Gln Trp Cys Ser Arg Asn
```

```
                210                 215                 220
Ala Cys Asn Gly Asn Lys Asp Glu Tyr Gln Arg Arg Leu Ala Arg Lys
225                 230                 235                 240

Ile Ser Asn Phe Leu Val Gln Ile Gly Phe Trp Lys Lys Ile Lys Asp
                245                 250                 255

Glu Asn Ser Gly Asp Leu Glu Tyr Val Cys Cys Ile Leu Gln Glu Ala
                260                 265                 270

Leu Tyr Gly Lys Ser Ile Val Ile Leu Leu Asp Asp Val Trp Glu Gln
                275                 280                 285

Asp Ile Val Glu Arg Phe Ala Lys Leu Tyr Asp Asn Asp Cys Lys Tyr
                290                 295                 300

Leu Val Thr Thr Arg Asn Glu Ala Val Cys Glu Ile Thr Glu Ala Glu
305                 310                 315                 320

Lys Val Glu Leu Ser Lys Asp Asp Thr Arg Glu Ile Ser Lys Ala Ile
                325                 330                 335

Leu Gln Tyr His Ser Leu Leu Gly Met Glu Glu Leu Pro Gly Ile Ala
                340                 345                 350

Glu Thr Leu Leu Glu Arg Cys Gly His His Pro Leu Thr Val Ala Val
                355                 360                 365

Met Gly Lys Ala Leu Arg Lys Glu Val Arg Ala Glu Lys Trp Glu Lys
                370                 375                 380

Ala Ile Thr Asn Leu Ser Thr Phe Ala Thr Cys Ala Pro Gly Pro Val
385                 390                 395                 400

Ser Tyr Val Asn Glu Lys Glu Ala Glu Ser Thr Leu Thr Ile Phe Gly
                405                 410                 415

Ser Phe Glu Phe Ser Leu Glu Ala Met Pro Arg Asp Ser Lys Arg Leu
                420                 425                 430

Phe Ile Ala Leu Ala Ser Leu Ser Trp Ala Glu Pro Val Pro Glu Ala
                435                 440                 445

Cys Leu Glu Ala Val Trp Ser Val Ile Gly Asp Glu Ser Leu Phe Pro
                450                 455                 460

Leu Ile Val Cys Lys Leu Val Glu Gly Ser Leu Leu Ile Lys Thr Asp
465                 470                 475                 480

Met Asp Pro Leu Tyr Leu Val His Asp Met Val Ser Leu Tyr Leu Ala
                485                 490                 495

Ser Lys Ala Asp Asp Ser Thr Glu Ile Leu Leu Asn Glu Tyr Ser Pro
                500                 505                 510

Asp Glu Thr Ala Phe Ile Cys Pro Trp Leu Leu Ile Phe Gly Lys Glu
                515                 520                 525

Asn Val Lys Lys Ile Ala Glu Glu Arg Met Glu Phe Leu Phe Asn Val
                530                 535                 540

Leu Glu Gly Lys Gln Val Thr Thr Leu Glu Ala Leu Ile His Ala
545                 550                 555                 560

Leu Met Ala Ser Lys Ser Met Ser Glu Leu Glu Val Ser Arg Glu Lys
                565                 570                 575

Phe Ser Arg Ile Leu Gly Pro Arg Ile Ala Asp Leu Ile Ser Thr Asp
                580                 585                 590

Ser Leu Ser Leu Ile Ala Val Thr Thr Glu Ala Ile Thr Asn Ile Phe
                595                 600                 605

Ser Lys Ser Asp Tyr Cys Asn Tyr Phe Pro Ser Leu Glu Thr Thr Gly
                610                 615                 620

Ala Ile Asn Arg Leu Ala Thr Thr Leu Glu Tyr Cys Glu Glu Asn Pro
625                 630                 635                 640
```

```
Ile Thr Gln Ile His Ile Leu Ile Val Leu Ala Lys Leu Ala Glu Phe
            645                 650                 655

Gly Ser Pro Gly Thr Val Asp Lys Val Leu Asp Ser Ile Pro Phe Asn
        660                 665                 670

Gln Leu Ala Asp Leu Leu Ser Ser Ala Glu Lys Trp His Glu Ser
    675                 680                 685

Met Phe Thr Val Leu Asn Ser Leu Thr Lys Ala Gly Lys Ser Asn Ala
    690                 695                 700

Val Glu Arg Met Phe Ala Ser Gly Ile Glu Lys Lys Leu Ile Lys Leu
705                 710                 715                 720

Leu Glu Asn Gly Ser Glu Val Leu Gln His His Ala Ile Val Thr Leu
                725                 730                 735

Lys Gly Phe Tyr Glu Val Ala Arg Thr Pro Glu Asn Val Ser Leu Gln
            740                 745                 750

Pro Ser Asn Leu Asn Leu Leu Pro Trp Gln Val Arg His Arg Leu Glu
        755                 760                 765

Thr Phe Val Leu Ser Asp Arg Thr Val Pro His Ser Pro Lys Pro Leu
    770                 775                 780

Ser Phe Glu Asp Leu Val Tyr Lys Val Leu Asp Gly Asn Lys Arg Gln
785                 790                 795                 800

Val Leu Gln Ala Met Gln Asp Leu Ile Pro Ile Glu Lys Ser Ala
                805                 810                 815

Asp Ser Arg Val Arg Glu Met Ile Leu His Ser Pro Leu Val Asn Arg
            820                 825                 830

Leu Ser Glu Leu Leu Gln Ser Arg His Ser Glu His Asn Ser Ile Arg
        835                 840                 845

Ser Glu Ser Ala Phe Leu Leu Met Lys Leu Ala Phe Ser Gly Gly Glu
    850                 855                 860

Pro Cys Ile Lys Lys Phe Leu Asp His Asp Ile Val Pro Glu Leu Val
865                 870                 875                 880

Lys Met Met Gln Cys Asn Val Val Glu Leu Gln Asp Ser Ala Tyr Thr
                885                 890                 895

Ala Leu His Gln Met Leu Phe Ser Asn Gly Gly Ile Leu Val Leu Asn
            900                 905                 910

Asn Ile Phe Glu Thr Gly Phe Val Asp Arg Met Val Gln Ser Val Asp
        915                 920                 925

Ser Lys Ser Ile Lys Thr Gln Glu Val Asn Val His Cys Ile Leu Asp
    930                 935                 940

Leu Val Glu Leu Gly Asn Lys Ser Cys Leu Glu Gln Met Leu Ser Leu
945                 950                 955                 960

Gln Val Val Glu Lys Leu Val Lys Leu Glu Lys Asn Thr Gly Gly Ser
                965                 970                 975

Gly Glu Thr Ile Val Gly Phe Leu Lys Gly Met Asp Lys Cys Lys His
            980                 985                 990

Leu Ser Met Met Glu Arg Arg Val  Ile Lys Gln Gln Val  Val Arg Lys
        995                 1000                1005

Ile Arg Ala Cys Leu Lys Gly  His Lys Phe Glu Thr  Gln Ile Leu
    1010                1015                1020

Ala Ser  Val Asp Ala Cys Val  Ser Glu Gly Ser Lys  Gly Ser Ser
    1025                1030                1035

Ser Arg  Tyr Arg Lys
    1040
```

<210> SEQ ID NO 48
<211> LENGTH: 877
<212> TYPE: PRT
<213> ORGANISM: Ricinus communis

<400> SEQUENCE: 48

```
Met Glu Val Ile Gly Pro Leu Ile Gly Ile Leu Cys Ser Thr Cys Asp
1               5                   10                  15

Asn Met Ala Arg Lys Ile Ser Tyr Val Ile Asn Val Asn Arg Lys Val
            20                  25                  30

His Ser Leu Thr Thr Leu Leu Glu Glu Leu Lys Tyr Lys Arg Asp Asp
        35                  40                  45

Ile Gln Arg Gln Val Asp Cys Ala Glu Leu Lys Gly Leu Ile Cys Thr
    50                  55                  60

Cys Gln Val Gln Gly Trp Leu Glu Arg Val Lys Asp Val Glu Thr Lys
65                  70                  75                  80

Ala Ser Leu Ile Thr Gly Val Leu Gly Gln Arg Lys Gln Cys Phe Met
                85                  90                  95

Cys Cys Val Ala Asn Ser Cys Thr Arg Tyr Lys Leu Ser Lys Arg Val
            100                 105                 110

Ser Glu Leu Gln Met Glu Ile Asn Glu Leu Ile Gly Lys Gly Ala Phe
        115                 120                 125

Asp Ala Val Ile Ala Asp Gly Leu Val Ser Glu Thr Val Gln Glu Met
    130                 135                 140

Pro Ile Arg Pro Ser Val Gly Leu Asn Met Met Val Glu Lys Val Gln
145                 150                 155                 160

Gln Phe Leu Ala Glu Asp Glu Val Gly Ile Ile Gly Ile Tyr Gly Met
                165                 170                 175

Gly Gly Ile Gly Lys Thr Thr Leu Leu Lys Ser Ile Asn Asn Lys Phe
            180                 185                 190

Leu Thr Lys Ser His Glu Phe Glu Val Val Ile Trp Ala Val Val Ser
        195                 200                 205

Lys Asp Phe Ile Val Asp Asn Ile Gln Gln Ala Val Gly Ala Arg Leu
    210                 215                 220

Gly Leu Ser Trp Glu Glu Cys Glu Gly Arg Glu Gln Arg Val Trp Lys
225                 230                 235                 240

Ile Tyr Arg Val Met Lys Ser Lys Phe Leu Leu Leu Asp Asp
                245                 250                 255

Val Trp Glu Gly Ile Asp Leu Gln Gln Ile Gly Ile Pro Leu Pro Asn
                260                 265                 270

Lys Glu Asn Lys Cys Lys Val Ile Phe Thr Thr Arg Ser Leu Asp Val
        275                 280                 285

Cys Ser Asp Leu Asp Ala His Arg Lys Leu Lys Val Glu Ile Leu Gly
    290                 295                 300

Lys Glu Asp Ser Trp Lys Leu Phe Cys Asp Lys Met Ala Gly Arg Glu
305                 310                 315                 320

Ile Leu Glu Trp Glu Ser Ile Arg Pro Tyr Ala Glu Thr Ile Val Arg
                325                 330                 335

Lys Cys Gly Gly Leu Pro Leu Ala Leu Ile Thr Ile Gly Lys Ala Met
            340                 345                 350

Ala Asn Lys Glu Thr Glu Glu Glu Trp Arg Tyr Ala Val Glu Ile Leu
        355                 360                 365

Asn Arg Tyr Pro Ser Glu Ile Arg Gly Met Glu Asp Val Phe Thr Leu
    370                 375                 380
```

```
Leu Lys Phe Ser Tyr Asp Asn Leu Glu Thr Asp Thr Leu Arg Ser Cys
385                 390                 395                 400

Phe Leu Tyr Cys Ala Leu Tyr Pro Glu Asp Tyr Ser Ile Asp Lys Glu
            405                 410                 415

Gln Leu Ile Glu Tyr Trp Ile Gly Gly Phe Leu Asp Ser Asn Val
        420                 425                 430

His Asn Lys Gly His Ala Ile Ile Gly Ser Leu Lys Val Ala Cys Leu
            435                 440                 445

Leu Glu Thr Gly Glu Glu Lys Thr Gln Val Lys Met His Asp Val Val
            450                 455                 460

Arg Ser Phe Ala Leu Trp Ile Ala Thr Glu Cys Gly Leu Asn Lys Gly
465                 470                 475                 480

Leu Ile Leu Val Glu Ala Ser Met Gly Leu Thr Ala Val Pro Asp Ala
                485                 490                 495

Glu Arg Trp Asn Gly Ala Gln Arg Val Ser Leu Met Asp Asn Gly Ile
                500                 505                 510

Thr Thr Leu Ala Glu Val Pro Asp Cys Pro Asn Leu Leu Thr Leu Leu
            515                 520                 525

Leu Gln Tyr Asn Ser Gly Leu Ser Arg Ile Pro Asp Thr Tyr Phe Leu
            530                 535                 540

Leu Met Pro Ser Leu Arg Val Leu Asp Leu Ser Leu Thr Ser Leu Arg
545                 550                 555                 560

Glu Leu Pro Ala Ser Ile Asn Arg Leu Val Glu Leu Gln His Leu Asp
                565                 570                 575

Leu Ser Gly Thr Lys Ile Thr Ala Leu Pro Lys Glu Leu Gly His Leu
                580                 585                 590

Ser Lys Leu Lys His Leu Asp Leu Gln Arg Ala Thr Ser Leu Arg Thr
                595                 600                 605

Ile Pro Gln Gln Ala Leu Ser Gly Leu Leu Gln Leu Arg Val Leu Asn
            610                 615                 620

Phe Tyr Tyr Ser Tyr Ala Gly Trp Gly Gly Asn Asn Ser Glu Thr Ala
625                 630                 635                 640

Lys Glu Val Gly Phe Ala Asp Leu Glu Cys Leu Lys His Leu Thr Thr
                645                 650                 655

Leu Gly Ile Thr Ile Lys Glu Ser Lys Met Leu Lys Lys Leu Gly Ile
                660                 665                 670

Phe Ser Ser Leu Leu Asn Thr Ile Gln Tyr Leu Tyr Ile Lys Glu Cys
            675                 680                 685

Lys Arg Leu Phe Cys Leu Gln Ile Ser Ser Asn Thr Ser Tyr Gly Lys
            690                 695                 700

Asn Leu Arg Arg Leu Ser Ile Asn Asn Cys Tyr Asp Leu Lys Tyr Leu
705                 710                 715                 720

Glu Val Asp Glu Glu Ala Gly Asp Lys Trp Leu Leu Ser Leu Glu Val
                725                 730                 735

Leu Ala Leu His Gly Leu Pro Ser Leu Val Val Trp Lys Asn Pro
            740                 745                 750

Val Thr Arg Glu Cys Leu Gln Asn Leu Arg Ser Val Asn Ile Trp His
            755                 760                 765

Cys His Lys Leu Lys Glu Val Ser Trp Val Phe Gln Leu Gln Asn Leu
            770                 775                 780

Glu Phe Leu Tyr Leu Met Tyr Cys Asn Glu Met Glu Glu Val Val Ser
785                 790                 795                 800
```

-continued

```
Arg Glu Asn Met Pro Met Glu Ala Pro Lys Ala Phe Pro Ser Leu Lys
            805                 810                 815

Thr Leu Ser Ile Arg Asn Leu Pro Lys Leu Arg Ser Ile Ala Gln Arg
        820                 825                 830

Ala Leu Ala Phe Pro Thr Leu Glu Thr Ile Ala Val Ile Asp Cys Pro
        835                 840                 845

Lys Leu Lys Met Leu Pro Ile Lys Thr His Ser Thr Leu Thr Leu Pro
        850                 855                 860

Thr Val Tyr Gly Ser Lys Glu Trp Trp Asp Gly Leu Glu
865                 870                 875

<210> SEQ ID NO 49
<211> LENGTH: 1002
<212> TYPE: PRT
<213> ORGANISM: Corchorus olitorius

<400> SEQUENCE: 49

Met Gly Arg Ala Asp Phe Thr Thr Thr Pro Lys Leu Leu Leu Leu
1               5                   10                  15

Leu Val Phe Ile Ala Met Leu Trp Leu Ser Thr Phe Gly Phe Ala Ala
            20                  25                  30

Ala Thr Pro Leu Leu His Ser Glu Glu Val Lys Ala Leu Lys Ala Ile
        35                  40                  45

Gly Lys Lys Met Gly Lys Lys Asp Trp Asp Phe Gly Val Asp Pro Cys
50                  55                  60

Ser Gly Lys Gly Lys Trp Ile Glu Gly Asp Glu Thr Gly Phe Ala
65                  70                  75                  80

Ser Lys Val Thr Cys Asn Cys Ser Phe Asn Asn Thr Thr Cys His
            85                  90                  95

Val Val Thr Met Asp Leu Ser Arg Asn Tyr Phe Thr Gly Ser Ile Pro
            100                 105                 110

Lys Glu Trp Ala Thr Met Lys Leu Asp Met Leu Ser Phe Met Gly Asn
        115                 120                 125

Arg Leu Ser Gly Pro Phe Pro Lys Val Leu Thr Asn Ile Thr Ser Leu
130                 135                 140

Thr Asn Leu Ser Ile Glu Gly Asn Asn Phe Ser Gly Pro Ile Pro Pro
145                 150                 155                 160

Glu Ile Gly Lys Leu Ile Asn Leu Gln Lys Leu Val Leu Ser Ser Asn
            165                 170                 175

Ala Leu Ser Gly Glu Leu Pro Ala Glu Leu Ala Lys Leu Val Asn Leu
        180                 185                 190

Thr Asp Ile Arg Phe Ser Asp Asn Phe Ser Gly Lys Ile Pro Asp
        195                 200                 205

Phe Ile Ser Asn Trp Lys Gln Ile Gln Lys Leu Gln Phe Gln Gly Cys
        210                 215                 220

Ser Leu Glu Gly Pro Ile Pro Ser Ser Ile Ser Thr Leu Thr Ser Leu
225                 230                 235                 240

Ser Asp Leu Arg Ile Ser Asp Leu Lys Gly Lys Gly Ser Pro Phe Pro
            245                 250                 255

Leu Leu Arg Asn His Asp Ser Leu Lys Thr Leu Ile Leu Arg Asn Cys
        260                 265                 270

Lys Ile His Gly Glu Ile Pro Glu Tyr Ile Gly Asp Met Lys Lys Leu
        275                 280                 285

Lys Thr Leu Asp Leu Ser Tyr Asn Asn Leu Thr Gly Glu Ile Pro Ser
        290                 295                 300
```

```
Ser Phe Tyr Lys Leu Thr Lys Ala Asp Phe Leu Tyr Leu Thr Arg Asn
305                 310                 315                 320

Gln Leu Thr Gly Ser Val Pro Glu Trp Ile Leu Glu Arg Asn Lys Asn
            325                 330                 335

Ala Asp Ile Ser Phe Asn Asn Phe Thr Trp Asp Thr Ser Ser Pro Ile
            340                 345                 350

Glu Cys Pro Arg Gly Ser Val Asn Leu Val Glu Ser Tyr Ser Thr Pro
            355                 360                 365

Thr Asn Lys Leu Ser Lys Val His Ser Cys Leu Lys Gln Asn Phe Pro
370                 375                 380

Cys Ser Ala Ser Thr Ser Gln His Lys Tyr Ser Leu His Ile Asn Cys
385                 390                 395                 400

Gly Gly Gln Glu Leu Asn Val Asn Gly Asp Ala Lys Tyr Glu Ala Asp
            405                 410                 415

Met Glu Pro Arg Gly Ala Ser Met Phe Tyr Leu Gly His Asn Trp Ala
            420                 425                 430

Leu Ser Ser Thr Gly Asn Phe Met Asp Asn Asp Ile Asp Ala Asp Asp
            435                 440                 445

Tyr Ile Val Thr Asn Thr Ser Ala Leu Ser Asn Val Ser Ala Ala Thr
450                 455                 460

His Glu Leu Tyr Thr Thr Ala Arg Val Ser Pro Leu Ser Leu Thr Tyr
465                 470                 475                 480

Tyr Gly Leu Cys Leu Gly Asn Gly Asn Tyr Thr Val Asn Leu His Phe
            485                 490                 495

Ala Glu Ile Ile Tyr Ile Asn Asp Arg Ser Phe Tyr Ser Leu Gly Lys
            500                 505                 510

Arg Ile Phe Asp Val Tyr Ile Gln Gly Glu Leu Val Leu Lys Asp Phe
            515                 520                 525

Asn Ile Gln Asp Glu Ala Gly Gly Thr Gly Lys Pro Ile Val Lys Asn
530                 535                 540

Phe Thr Ala Val Val Thr Arg Asn Thr Leu Lys Ile His Leu Tyr Trp
545                 550                 555                 560

Ala Gly Arg Gly Thr Thr Gly Ile Pro Ala Arg Gly Met Tyr Gly Pro
            565                 570                 575

Leu Ile Ser Ala Ile Ser Val Val Ser Asn Phe Glu Pro Pro Thr Val
            580                 585                 590

Val Gly Lys Lys Asn Tyr Leu Ile Ile Ala Ala Gly Ala Ala Ser Ala
            595                 600                 605

Ala Ile Leu Ile Val Leu Met Val Leu Gly Ile Ile Trp Arg Lys Gly
            610                 615                 620

Trp Leu Gly Gly Lys Ile Ser Ala Glu Asn Glu Leu Lys Asp Leu Asp
625                 630                 635                 640

Leu Gln Thr Gly Ile Phe Ser Leu Arg Gln Ile Lys Ala Ala Thr Asn
            645                 650                 655

Asn Phe Asp Ala Glu Asn Lys Ile Gly Glu Gly Gly Phe Gly Ser Val
            660                 665                 670

Tyr Lys Gly Leu Leu Ser Asp Gly Thr Val Ile Ala Val Lys Gln Leu
            675                 680                 685

Ser Ser Lys Ser Lys Gln Gly Asn Arg Glu Phe Val Asn Glu Ile Gly
            690                 695                 700

Met Ile Ser Ala Leu Gln His Pro Asn Leu Val Lys Leu Tyr Gly Cys
705                 710                 715                 720
```

-continued

Cys Val Glu Gly Asn Gln Leu Leu Val Tyr Glu Tyr Met Glu His
                725                 730                 735

Asn Cys Val Ser Arg Ala Leu Phe Gly Lys Gly Ser Thr Pro Lys Leu
            740                 745                 750

Lys Leu Asp Trp Ser Thr Arg Lys Asn Ile Cys Leu Gly Ile Ala Arg
        755                 760                 765

Gly Leu Ala Tyr Leu His Glu Glu Ser Arg Ile Lys Ile Val His Arg
    770                 775                 780

Asp Ile Lys Thr Ser Asn Val Leu Leu Asp Lys Asn Leu Asn Ala Lys
785                 790                 795                 800

Ile Ser Asp Phe Gly Leu Ala Lys Leu Asn Asp Asp Lys Thr His
        805                 810                 815

Ile Ser Thr Arg Ile Ala Gly Thr Ile Gly Tyr Met Ala Pro Glu Tyr
        820                 825                 830

Ala Met Arg Gly Tyr Leu Thr Ser Lys Ala Asp Val Tyr Ser Phe Gly
    835                 840                 845

Val Val Ala Leu Glu Ile Val Ser Gly Lys Ser Asn Thr Asn Tyr Arg
    850                 855                 860

Pro Thr Glu Asp Phe Val Tyr Leu Leu Asp Trp Ala Tyr Val Leu Arg
865                 870                 875                 880

Glu Arg Gly Ser Leu Leu Glu Leu Val Asp Pro Glu Leu Gly Ser Glu
            885                 890                 895

Tyr Ser Ser Glu Glu Ala Met Val Met Leu Asn Val Ala Leu Leu Cys
        900                 905                 910

Thr Asn Ala Ala Pro Thr Leu Arg Pro Thr Met Ser Gln Val Val Ser
    915                 920                 925

Met Leu Glu Gly Gln Thr Ser Val Gln Asp Ile Leu Ser Asp Pro Gly
930                 935                 940

Phe Ser Ser Met Asn Ser Lys Phe Lys Ala Leu Val Asn His Phe Trp
945                 950                 955                 960

Gln Asn Pro Ser Gln Thr Met Ser Leu Ser Ser Asn Gly Pro Asn Thr
            965                 970                 975

Asp Ser Ser Ser Ser Asn Ile Glu Asp Ile Glu Glu Asn Ser His Leu
        980                 985                 990

Leu Arg Val Ser Ser Ile Gln Ser  Glu Ala
            995                 1000

<210> SEQ ID NO 50
<211> LENGTH: 1014
<212> TYPE: PRT
<213> ORGANISM: Arabidopsis thaliana

<400> SEQUENCE: 50

Met Ile Tyr Leu His Arg Ile Tyr Phe Ile Ile Val Leu Phe Thr Leu
1               5                   10                  15

Ile Phe His Gly Arg Leu Gly Phe Ser Asp Asn Asn Lys Leu His Glu
            20                  25                  30

Ala Glu Val Arg Ala Leu Lys Glu Ile Gly Lys Lys Leu Gly Lys Lys
        35                  40                  45

Asp Trp Asp Phe Asn Lys Asp Pro Cys Ser Gly Glu Gly Thr Trp Ile
    50                  55                  60

Val Thr Thr Tyr Thr Thr Lys Gly Phe Glu Ser Asn Ile Thr Cys Asp
65                  70                  75                  80

Cys Ser Phe Leu Pro Gln Asn Ser Ser Cys His Val Ile Arg Ile Ala
                85                  90                  95

```
Leu Lys Ser Gln Asn Leu Thr Gly Ile Val Pro Pro Glu Phe Ser Lys
            100                 105                 110

Leu Arg His Leu Lys Val Leu Asp Leu Ser Arg Asn Ser Leu Thr Gly
            115                 120                 125

Ser Ile Pro Lys Glu Trp Ala Ser Met Arg Leu Glu Asp Leu Ser Phe
130                 135                 140

Met Gly Asn Arg Leu Ser Gly Pro Phe Pro Lys Val Leu Thr Arg Leu
145                 150                 155                 160

Thr Met Leu Arg Asn Leu Ser Leu Glu Gly Asn Gln Phe Ser Gly Pro
                165                 170                 175

Ile Pro Pro Asp Ile Gly Gln Leu Val His Leu Glu Lys Leu His Leu
            180                 185                 190

Pro Ser Asn Ala Phe Thr Gly Pro Leu Thr Glu Lys Leu Gly Leu Leu
            195                 200                 205

Lys Asn Leu Thr Asp Met Arg Ile Ser Asp Asn Asn Phe Thr Gly Pro
            210                 215                 220

Ile Pro Asp Phe Ile Ser Asn Trp Thr Arg Ile Leu Lys Leu Gln Met
225                 230                 235                 240

His Gly Cys Gly Leu Asp Gly Pro Ile Pro Ser Ser Ile Ser Ser Leu
                245                 250                 255

Thr Ser Leu Thr Asp Leu Arg Ile Ser Asp Leu Gly Gly Lys Pro Ser
            260                 265                 270

Ser Phe Pro Pro Leu Lys Asn Leu Glu Ser Ile Lys Thr Leu Ile Leu
            275                 280                 285

Arg Lys Cys Lys Ile Ile Gly Pro Ile Pro Lys Tyr Ile Gly Asp Leu
            290                 295                 300

Lys Lys Leu Lys Thr Leu Asp Leu Ser Phe Asn Leu Leu Ser Gly Glu
305                 310                 315                 320

Ile Pro Ser Ser Phe Glu Asn Met Lys Lys Ala Asp Phe Ile Tyr Leu
                325                 330                 335

Thr Gly Asn Lys Leu Thr Gly Gly Val Pro Asn Tyr Phe Val Glu Arg
            340                 345                 350

Asn Lys Asn Val Asp Val Ser Phe Asn Phe Thr Asp Glu Ser Ser
            355                 360                 365

Ile Pro Ser His Asp Cys Asn Arg Val Thr Ser Asn Leu Val Glu Ser
370                 375                 380

Phe Ala Leu Gly Asn Lys Ser His Lys Gly Ser Thr Cys Phe Leu Gln
385                 390                 395                 400

Arg Met Pro Cys Val His Pro Lys Arg Tyr His Leu Tyr Lys Leu Tyr
                405                 410                 415

Ile Asn Cys Gly Gly Gly Glu Val Lys Val Asp Lys Glu Ile Thr Tyr
            420                 425                 430

Gln Ala Asp Asp Glu Pro Lys Gly Ala Ser Met Tyr Val Leu Gly Ala
            435                 440                 445

Asn Lys Arg Trp Ala Leu Ser Ser Thr Gly Asn Phe Met Asp Asn Asp
            450                 455                 460

Asp Asp Ala Asp Glu Tyr Thr Val Gln Asn Thr Ser Arg Leu Ser Val
465                 470                 475                 480

Asn Ala Ser Ser Pro Ser Phe Gly Leu Tyr Arg Thr Ala Arg Val Ser
                485                 490                 495

Pro Leu Ser Leu Thr Tyr Gly Ile Cys Leu Gly Asn Gly Asn Tyr
            500                 505                 510
```

-continued

```
Thr Val Asn Leu His Phe Ala Glu Ile Ile Phe Thr Asp Asn Thr
            515                 520                 525
Leu Tyr Ser Leu Gly Lys Arg Leu Phe Asp Ile Tyr Val Gln Asp Gln
530                 535                 540
Leu Val Ile Lys Asn Phe Asn Ile Gln Glu Ala Ala Arg Gly Ser Gly
545                 550                 555                 560
Lys Pro Ile Ile Lys Ser Phe Leu Val Asn Val Thr Asp His Thr Leu
                565                 570                 575
Lys Ile Gly Leu Arg Trp Ala Gly Lys Gly Thr Thr Gly Ile Pro Ile
                580                 585                 590
Arg Gly Val Tyr Gly Pro Met Ile Ser Ala Ile Ser Val Glu Pro Asn
            595                 600                 605
Phe Lys Pro Pro Val Tyr Tyr Asp Thr Lys Asp Ile Ile Leu Lys Val
            610                 615                 620
Gly Val Pro Val Ala Ala Thr Leu Leu Leu Phe Ile Ile Val Gly
625                 630                 635                 640
Val Phe Trp Lys Lys Arg Arg Asp Lys Asn Asp Ile Asp Lys Glu Leu
                645                 650                 655
Arg Gly Leu Asp Leu Gln Thr Gly Thr Phe Thr Leu Arg Gln Ile Lys
                660                 665                 670
Ala Ala Thr Asp Asn Phe Asp Val Thr Arg Lys Ile Gly Glu Gly Gly
                675                 680                 685
Phe Gly Ser Val Tyr Lys Gly Glu Leu Ser Glu Gly Lys Leu Ile Ala
            690                 695                 700
Val Lys Gln Leu Ser Ala Lys Ser Arg Gln Gly Asn Arg Glu Phe Val
705                 710                 715                 720
Asn Glu Ile Gly Met Ile Ser Ala Leu Gln His Pro Asn Leu Val Lys
                725                 730                 735
Leu Tyr Gly Cys Cys Val Glu Gly Asn Gln Leu Ile Leu Val Tyr Glu
                740                 745                 750
Tyr Leu Glu Asn Asn Cys Leu Ser Arg Ala Leu Phe Gly Lys Asp Glu
                755                 760                 765
Ser Ser Arg Leu Lys Leu Asp Trp Ser Thr Arg Lys Lys Ile Phe Leu
770                 775                 780
Gly Ile Ala Lys Gly Leu Thr Phe Leu His Glu Glu Ser Arg Ile Lys
785                 790                 795                 800
Ile Val His Arg Asp Ile Lys Ala Ser Asn Val Leu Leu Asp Lys Asp
                805                 810                 815
Leu Asn Ala Lys Ile Ser Asp Phe Gly Leu Ala Lys Leu Asn Asp Asp
                820                 825                 830
Gly Asn Thr His Ile Ser Thr Arg Ile Ala Gly Thr Ile Gly Tyr Met
                835                 840                 845
Ala Pro Glu Tyr Ala Met Arg Gly Tyr Leu Thr Glu Lys Ala Asp Val
850                 855                 860
Tyr Ser Phe Gly Val Val Ala Leu Glu Ile Val Ser Gly Lys Ser Asn
865                 870                 875                 880
Thr Asn Phe Arg Pro Thr Glu Asp Phe Val Tyr Leu Leu Asp Trp Ala
                885                 890                 895
Tyr Val Leu Gln Glu Arg Gly Ser Leu Leu Glu Leu Val Asp Pro Thr
                900                 905                 910
Leu Ala Ser Asp Tyr Ser Glu Glu Glu Ala Met Leu Met Leu Asn Val
                915                 920                 925
Ala Leu Met Cys Thr Asn Ala Ser Pro Thr Leu Arg Pro Thr Met Ser
```

-continued

```
    930                 935                 940

Gln Val Val Ser Leu Ile Glu Gly Lys Thr Ala Met Gln Glu Leu Leu
945                 950                 955                 960

Ser Asp Pro Ser Phe Ser Thr Val Asn Pro Lys Leu Lys Ala Leu Arg
                965                 970                 975

Asn His Phe Trp Gln Asn Glu Leu Ser Arg Ser Leu Ser Phe Ser Thr
            980                 985                 990

Ser Gly Pro Arg Thr Ala Ser Ala  Asn Ser Leu Val Asp  Ala Glu Glu
        995                 1000                1005

Lys Thr  Gly Leu Leu Asp
    1010

<210> SEQ ID NO 51
<211> LENGTH: 2037
<212> TYPE: PRT
<213> ORGANISM: Ricinus communis

<400> SEQUENCE: 51

Met Ala Ser Gly Gln Val Phe Ala Lys Glu Arg Leu His Arg Ile Lys
1               5                   10                  15

Asn His Lys His Tyr Arg Phe Arg Gln Glu Glu Trp Tyr Cys Thr Leu
            20                  25                  30

Pro Leu Leu Gly Ile Gly Arg Ala Arg Pro Leu Thr Met Val Leu Leu
        35                  40                  45

Gln Leu Met Ala Val Ala Gln Thr Asn Gly Arg Val Pro Thr Gly Ala
    50                  55                  60

Ser Ile Thr Ala Thr Asp Asp Ser Pro Ser Trp Pro Ser Ala Ser Gly
65                  70                  75                  80

Glu Phe Ala Phe Gly Phe Arg Gln Leu Glu Asn Lys Asp Tyr Phe Leu
                85                  90                  95

Leu Ser Ile Trp Tyr Glu Lys Ile Pro Glu Lys Thr Val Val Trp Tyr
            100                 105                 110

Ala Ile Gly Glu Asp Pro Thr Asp Asp Pro Ala Val Pro Arg Gly Ser
        115                 120                 125

Lys Leu Glu Leu Thr Asp Asp Arg Gly Leu Leu Leu Ala Asp Pro Gln
    130                 135                 140

Gly Asn Gln Ile Trp Ser Ser Gly Ile Pro Pro Gly Ala Ala Val Ser
145                 150                 155                 160

Ser Gly Val Met Asn Asp Thr Gly Asn Phe Val Leu Gln Asn Arg Asn
                165                 170                 175

Ser Phe Arg Leu Trp Glu Ser Phe Asn Asn Pro Thr Asp Thr Leu Leu
            180                 185                 190

Pro Thr Gln Ile Met Glu Val Gly Gly Val Val Ser Ser Arg Arg Thr
        195                 200                 205

Glu Thr Asn Phe Ser Leu Gly Arg Phe Gln Leu Arg Leu Leu Asp Asn
    210                 215                 220

Gly Asn Leu Val Leu Asn Tyr Met Asn Leu Pro Thr Lys Phe Val Tyr
225                 230                 235                 240

Asp Asp Tyr Tyr Ser Ser Glu Thr Ser Asp Ala Ser Asn Ser Ser Asn
                245                 250                 255

Ser Gly Tyr Arg Leu Ile Phe Asn Glu Ser Gly Tyr Met Tyr Ile Leu
            260                 265                 270

Arg Arg Asn Gly Leu Ile Glu Asp Leu Thr Lys Thr Ala Leu Pro Thr
        275                 280                 285

-continued

```
Ile Asp Phe Tyr His Arg Ala Thr Leu Asn Phe Asp Gly Val Phe Thr
    290                 295                 300
Gln Tyr Phe Tyr Pro Lys Ala Ser Ser Gly Asn Arg Ser Trp Ser Ser
305                 310                 315                 320
Val Trp Ser Lys Pro Asp Asp Ile Cys Val Asn Met Gly Ala Asp Leu
                325                 330                 335
Gly Ser Gly Ala Cys Gly Tyr Asn Ser Ile Cys Asn Leu Lys Ala Asp
                340                 345                 350
Lys Arg Pro Glu Cys Lys Cys Pro Gln Gly Phe Ser Leu Asp Gln
                355                 360                 365
Asn Asp Lys Tyr Gly Ser Cys Ile Pro Asp Phe Glu Leu Ser Cys Arg
370                 375                 380
Asp Asp Gly Leu Asn Ser Thr Glu Asp Gln Tyr Asp Phe Val Glu Leu
385                 390                 395                 400
Ile Asn Val Asp Trp Pro Thr Ser Asp Tyr Glu Arg Tyr Lys Pro Ile
                405                 410                 415
Asn Glu Asp Glu Cys Arg Lys Ser Cys Leu Asn Asp Cys Leu Cys Ser
                420                 425                 430
Val Ala Ile Phe Arg Asp Gly Cys Trp Lys Lys Leu Pro Leu Ser
            435                 440                 445
Asn Gly Arg Phe Asp Ile Gly Met Asn Gly Lys Ala Phe Leu Lys Phe
450                 455                 460
Pro Lys Gly Tyr Val Pro Leu Asp Arg Pro Pro Gln Leu Pro Gly
465                 470                 475                 480
Glu Lys Lys Lys Pro Asp Ile Lys Phe Ile Thr Gly Ser Val Val Leu
                485                 490                 495
Gly Thr Ser Val Phe Val Asn Phe Val Leu Val Gly Ala Phe Cys Leu
            500                 505                 510
Thr Ser Ser Phe Ile Tyr Arg Lys Thr Glu Lys Val Lys Glu Gly
            515                 520                 525
Gly Ser Gly Leu Glu Thr Asn Leu Arg Tyr Phe Thr Tyr Lys Glu Leu
            530                 535                 540
Ala Glu Ala Thr Asn Asp Phe Lys Asp Glu Val Gly Arg Gly Phe
545                 550                 555                 560
Gly Val Val Tyr Lys Gly Thr Ile Gln Ala Gly Ser Thr Arg Val Val
                565                 570                 575
Ala Val Lys Lys Leu Asp Lys Val Val Gln Asp Gly Glu Lys Glu Phe
                580                 585                 590
Lys Thr Glu Val Gln Val Ile Gly Gln Thr His His Lys Asn Leu Val
            595                 600                 605
Arg Leu Leu Gly Phe Cys Asp Glu Gly Gln Asn Arg Leu Leu Val Tyr
610                 615                 620
Glu Phe Leu Ser Asn Gly Thr Leu Ala Asn Phe Leu Phe Gly Cys Ser
625                 630                 635                 640
Lys Pro Asn Trp Lys Gln Arg Thr Gln Ile Ala Phe Gly Ile Ala Arg
                645                 650                 655
Gly Leu Leu Tyr Leu His Glu Glu Cys Gly Thr Gln Ile Ile His Cys
            660                 665                 670
Asp Ile Lys Pro Gln Asn Ile Leu Asp Asn Tyr Tyr Asn Ala Arg
            675                 680                 685
Ile Ser Asp Phe Gly Leu Ala Lys Leu Leu Val Met Asp Gln Ser Lys
690                 695                 700
Thr Gln Thr Ala Ile Arg Gly Thr Lys Gly Tyr Val Ala Pro Glu Trp
```

```
            705                 710                 715                 720
        Phe Arg Asn Arg Pro Ile Thr Val Lys Val Asp Val Tyr Ser Phe Gly
                        725                 730                 735

Val Met Leu Leu Glu Ile Ile Cys Cys Arg Arg Asn Val Asp Leu Glu
                        740                 745                 750

Ile Gly Glu Val Glu Asn Pro Val Leu Thr Asp Trp Ala Tyr Asp Cys
                        755                 760                 765

Tyr Met Asp Gly Ser Leu Asp Val Leu Ile Gly Asp Asp Thr Glu Ala
                        770                 775                 780

Lys Asn Asp Ile Ser Thr Leu Glu Arg Leu Leu Lys Pro Ala Arg Gln
        785                 790                 795                 800

Asn Arg Ile Arg Ala Ser Ser Asn Ser Pro Asn Ala Ala Thr Pro
                        805                 810                 815

Val Ala Leu Ala Pro Ala Ala Pro Pro Leu Gly Arg His Thr Phe
                        820                 825                 830

Ser Pro Leu Asp Leu Pro Pro Trp Ser Asn Pro Arg Ser Gln Gln Ile
                        835                 840                 845

Met Ala Thr Lys Val Thr Gly Ile Leu Thr Ala Gly Lys Lys Val Lys
                850                 855                 860

Arg Gly Gly Ser Arg Ser Arg Pro Pro Trp Phe Leu Arg Phe Ser Cys
        865                 870                 875                 880

Thr His Ala Pro Pro Val Ala Glu Ala Ala Thr Pro Asn Glu Pro Ile
                        885                 890                 895

Lys Ala Asn Asn Ile Thr Lys Lys Ser Pro Val Asp Ile Ala Arg Val
                        900                 905                 910

Thr Cys Asp Lys Ile Tyr Gly Val Gly Asn Thr Lys Thr Gly Met Gly
                        915                 920                 925

Gln Ala Ser Arg Glu Phe Glu Leu Met Lys Met Lys Asp Asn Glu Ser
                        930                 935                 940

Val Lys Asp Tyr Ser Gly Arg Leu Met Asp Val Val Asn Gln Met Arg
        945                 950                 955                 960

Leu Leu Gly Lys Ala Phe Thr Asp His Lys Val Val Glu Lys Ile Met
                        965                 970                 975

Val Ser Val Pro Gln Lys Phe Glu Ala Lys Ile Ser Ala Ile Glu Glu
                        980                 985                 990

Ser Cys Asp Met Asn Asn Leu Thr Ile Ala Glu Leu Thr Ser Lys Leu
                        995                 1000                1005

His Val Gln Glu Gln Arg Val Gln Met Arg Asp Glu Glu Ala Ile
                1010                1015                1020

Glu Gly Ala Phe Gln Ala Asn Thr Lys Glu Arg Ser Ser Gly Tyr
                1025                1030                1035

Leu Gln Arg Lys Lys Ser Phe Lys Phe Thr Lys Gly Lys Thr Glu
                1040                1045                1050

Met Ser Ser Arg Lys Gln Asn Tyr Ser Pro Cys Ser His Cys Lys
                1055                1060                1065

Arg Thr Asn His Ala Glu Lys Asp Cys Trp Tyr Lys Asp Lys Pro
                1070                1075                1080

Ser Phe Lys Cys Thr Phe Cys Asn Asn Leu Gly His Ser Glu Lys
                1085                1090                1095

Tyr Cys Arg Ala Lys Lys Lys Gln Ser Gln Gln His Ile His Gln
                1100                1105                1110

Asn Ala Asn Val Ser Glu Lys Glu Lys Glu Asp Asp Glu His Leu
                1115                1120                1125
```

```
Phe Met Ala Ser Gln Val Ile Ser Ser His Glu Gln Asn Ile Trp
    1130                1135                1140

Leu Ile Asp Ser Gly Cys Thr Ser Tyr Met Thr Lys His Leu Ala
    1145                1150                1155

Ile Phe Ser Ser Ile Asp Lys Ser Ile Gln Pro Lys Val Lys Leu
    1160                1165                1170

Gly Asn Gly Asp Val Val Gln Ala Lys Gly Arg Gly Thr Ile Ala
    1175                1180                1185

Val Ser Thr Lys Arg Gly Tyr Arg Ile Tyr Asn Leu Ser Ala Ala
    1190                1195                1200

Lys Val Gln Ile Ser Ile Asp Val His Phe Asn Glu Asn Ser Cys
    1205                1210                1215

Trp Lys Trp Asp Leu Lys Glu Val Asp Arg Thr Thr Ala Ala
    1220                1225                1230

Leu Glu Pro Ala Val Gly Gly Thr Gly Asp Gln Ser Asp Ile Glu
    1235                1240                1245

Gly Thr Ser Asp Thr Ser Ile Leu Lys Val Arg Pro Leu Ser Asp
    1250                1255                1260

Val Tyr Glu Arg Cys Asn Pro Val Tyr Ala Lys Pro Thr Ser Tyr
    1265                1270                1275

Thr Glu Ala Ala Arg Phe Pro Ala Trp Ile Asp Ala Ile Lys Ser
    1280                1285                1290

Glu Ile Asp Ser Ile Glu Arg Asn Gly Thr Trp Lys Leu Thr Glu
    1295                1300                1305

Leu Pro Gln Asn Lys Lys Glu Ile Gly Val Lys Trp Val Phe Lys
    1310                1315                1320

Thr Lys Phe Asn Pro Asp Gly Ser Ile Phe Arg His Lys Ala Arg
    1325                1330                1335

Leu Val Val Lys Gly Phe Ala Gln Val Ala Gly Val Asp Tyr Asp
    1340                1345                1350

Asp Thr Phe Ala Pro Val Ala Arg His Asp Thr Ile Arg Leu Leu
    1355                1360                1365

Leu Ala Leu Ala Gly Gln Lys Lys Trp Lys Val Tyr His Leu Asp
    1370                1375                1380

Val Lys Phe Ala Phe Leu Asn Gly Ile Leu Leu Glu Glu Ile Tyr
    1385                1390                1395

Val Gln Gln Pro Glu Gly Phe Val Val Thr Ser His Glu His Lys
    1400                1405                1410

Val Tyr Lys Leu His Lys Ala Leu Tyr Gly Leu Lys Gln Ala Pro
    1415                1420                1425

Arg Ala Trp Tyr Asn Arg Ile Asp Thr Tyr Leu Ile Gln Leu Gly
    1430                1435                1440

Phe Lys Arg Ser Glu Asn Glu Val Thr Leu Tyr Leu Lys Gln Asp
    1445                1450                1455

Gln Asp Gly Leu Gln Leu Val Ile Ser Leu Tyr Val Asp Asp Met
    1460                1465                1470

Leu Val Thr Gly Ser Asn Val Lys Leu Leu Ala Glu Phe Lys Arg
    1475                1480                1485

Glu Met Gln Asp Val Phe Glu Met Ser Asp Leu Gly Ile Ile Asn
    1490                1495                1500

Tyr Phe Leu Gly Met Glu Ile His Gln Cys Ser Ser Gly Ile Phe
    1505                1510                1515
```

-continued

```
Ile Ser Gln Arg Lys Tyr Ala Val Asp Ile Leu Lys Arg Phe Lys
1520                1525                1530

Leu Glu Ser Cys Lys Glu Val Thr Thr Leu Met Ala Gln Asn Glu
    1535                1540                1545

Lys Ile Ser Lys Asn Asp Gly Glu Lys Leu Glu Glu Pro Ser Ala
1550                1555                1560

Tyr Arg Ser Leu Val Gly Ser Leu Leu Tyr Leu Thr Ala Thr Lys
1565                1570                1575

Pro Asp Leu Met Phe Leu Ala Gly Leu Leu Ser Arg Phe Met Ser
1580                1585                1590

Ser Pro Ser Asn Phe His Met Gly Val Ala Lys Arg Val Leu Lys
1595                1600                1605

Tyr Ile Arg Gly Thr Thr Asn Leu Gly Ile Leu Tyr Ser Lys Ser
1610                1615                1620

Gly Gly Val Asn Leu Ser Gly Tyr Ala Asp Ser Asp Trp Ala Gly
1625                1630                1635

Ser Val Asp Asp Met Lys Ser Thr Phe Gly Tyr Val Phe Thr Ile
1640                1645                1650

Gly Ser Gly Thr Ile Cys Trp Asn Ala Lys Lys Gln Glu Val Val
1655                1660                1665

Ala Gln Ser Thr Ala Glu Ala Glu Tyr Ile Phe Leu Ala Ala Ala
1670                1675                1680

Ala Asn Gln Ala Ile Trp Leu Asn Lys Leu Leu Ala Lys Asn Lys
1685                1690                1695

Val His Gln Leu Ser Phe Ile Val Ile Thr Phe Ala Met Leu Leu
1700                1705                1710

Ser Ala Val Ala Phe Glu Ser Glu Ile Arg Ser Phe Leu Gly Leu
1715                1720                1725

Ala Gly Tyr Tyr Arg Arg Phe Val Glu Asn Phe Ser Arg Ile Ser
1730                1735                1740

Ala Pro Leu Thr Lys Leu Thr Gln Lys Asn Val Lys Phe Gln Trp
1745                1750                1755

Ser Glu Ala Cys Glu Lys Ser Phe Leu Glu Leu Lys Glu Arg Leu
1760                1765                1770

Thr Thr Ala Pro Val Leu Ala Val Pro Ser Gly Ser Gly Gly Tyr
1775                1780                1785

Thr Val Tyr Cys Asp Ala Ser Arg Val Gly Leu Gly Cys Val Leu
1790                1795                1800

Met Gln His Gly Lys Val Ile Ala Tyr Ala Ser Arg Gln Leu Lys
1805                1810                1815

Lys His Glu Gln Asn Tyr Pro Thr His Asp Leu Glu Met Thr Ala
1820                1825                1830

Val Ile Phe Ala Leu Lys Ile Trp Arg His Tyr Leu Tyr Gly Glu
1835                1840                1845

Thr Cys Glu Ile Phe Thr Asp His Lys Ser Leu Lys Tyr Ile Phe
1850                1855                1860

Gln Gln Arg Asp Leu Asn Leu Arg Gln Arg Arg Trp Met Glu Leu
1865                1870                1875

Leu Lys Asp Tyr Asp Cys Thr Ile His Tyr His Pro Gly Lys Ala
1880                1885                1890

Asn Val Val Ala Asp Ala Leu Ser Arg Lys Ser Ser Gly Ser Leu
1895                1900                1905

Ala His Ile Gln Glu Val Arg Arg Pro Leu Ile Arg Glu Leu His
```

```
              1910                1915                1920

Glu Leu Val Asp Glu Gly Val Arg Phe Asp Leu Ser Glu Ala Gly
    1925                1930                1935

Ala Met Ile Ala His Phe Gln Val Lys Ser Asp Leu Phe Asp Lys
    1940                1945                1950

Ile Lys Ala Ala Gln Lys Lys Asp Asp Ser Leu Leu Arg Ile Arg
    1955                1960                1965

Asn Glu Val Glu Gln Gly Lys Ala Ala Gly Phe Val Ile Gly Asp
    1970                1975                1980

Asp Asp Val Leu Arg Tyr Lys Asp Arg Leu Cys Val Pro Asp Val
    1985                1990                1995

Asp Asp Leu Arg Arg Glu Leu Met Val Glu Ala His Gln Thr Val
    2000                2005                2010

Tyr Thr Val His Pro Gly Ser Thr Lys Met Tyr Lys Asp Leu Lys
    2015                2020                2025

Val Phe Asp Leu Ser Glu Gly Lys Gly
    2030                2035

<210> SEQ ID NO 52
<211> LENGTH: 999
<212> TYPE: PRT
<213> ORGANISM: Ricinus communis

<400> SEQUENCE: 52

Met Asp Leu Arg Glu Asp Ser Ser Arg Phe Gly Ser Val Thr Ile Ser
1               5                   10                  15

Thr Leu Arg Asn Met Ser Ser Ser Ser Ala Phe Phe Ser Ala Asn
                20                  25                  30

Gln Ser Pro Phe Phe Ser Pro Arg Ser Pro Thr Cys Gln Ile Ser Glu
                35                  40                  45

Ser Thr Arg Ser Asp Ala Gln Cys Asp Ser Ile His Leu Ser Gly Glu
    50                  55                  60

His Leu Thr Ser Ser Ser Gly Asn Pro Leu Leu Thr Ser Pro Ala Asn
65                  70                  75                  80

Val Arg Asp Ala Val Ser Asp Met Ser Arg Asp Pro Val Ala Glu Ile
                85                  90                  95

Gly Thr Asp Phe Gln Lys Leu Asp Arg Ile Phe Ser Ser Thr Gly Ile
                100                 105                 110

Ser Asn Ser Ser Pro Tyr Ser Tyr Asn Asn Leu His Asp Ile Gly Tyr
                115                 120                 125

Ser Gly Phe Arg Glu Lys Gln Arg Lys His Glu Arg Ser Gln Val Thr
    130                 135                 140

Leu Tyr Thr Pro Val Ser Ile Ser Leu Pro Ser Tyr Arg Leu Arg Ser
145                 150                 155                 160

Cys Asp Val Phe Ile Gly Leu His Gly Arg Lys Pro Ser Leu Leu Arg
                165                 170                 175

Phe Ala Asn Trp Ile Arg Ala Glu Leu Glu Val Gln Gly Ile Ser Cys
                180                 185                 190

Phe Ile Ser Asp Arg Ala Arg Cys Arg Asn Ser Arg Lys His Gly Leu
                195                 200                 205

Val Glu Arg Ala Met Asp Val Ser Ser Phe Gly Ile Val Ile Leu Thr
    210                 215                 220

Lys Lys Ser Phe Arg Asn Pro Tyr Thr Ile Glu Glu Leu Arg Phe Phe
225                 230                 235                 240
```

Thr Ser Lys Lys Asn Leu Val Pro Leu Phe Asp Leu Ser Pro Asp
            245                 250                 255

Asp Cys Leu Val Arg Asp Ile Val Glu Asn Arg Gly Glu Leu Trp Glu
        260                 265                 270

Lys His Gly Gly Glu Leu Trp Leu Leu Tyr Gly Gly Leu Glu Asn Glu
            275                 280                 285

Trp Lys Glu Ala Val Asn Ser Leu Ser Arg Val Asp Glu Trp Lys Leu
290                 295                 300

Glu Ala Gln Glu Gly Asn Trp Arg Asp Cys Ile Leu Arg Ala Val Thr
305                 310                 315                 320

Leu Leu Ala Met Arg Leu Gly Arg Arg Ser Val Val Glu Arg Met Thr
                325                 330                 335

Lys Trp Lys Glu Lys Val Asp Lys Asp Glu Phe Pro Phe Pro Arg Asn
            340                 345                 350

Glu Asn Phe Ile Gly Arg Lys Lys Glu Leu Ser Glu Leu Glu Phe Ile
        355                 360                 365

Leu Phe Gly Asp Val Ser Gly Asp Ser Glu Arg Asp Tyr Phe Glu Leu
    370                 375                 380

Lys Thr Lys Pro Arg Arg Lys Asn Leu Thr Ile Gly Trp Ser Lys Ser
385                 390                 395                 400

Ser Ser Met Glu Glu Lys Arg Arg Asp Trp Lys Trp Glu Asn Arg Ala
                405                 410                 415

Lys Lys Gly Lys Glu Pro Val Val Trp Lys Ser Glu Lys Glu Ile
            420                 425                 430

Glu Met Gln Ser Thr Glu Ile Pro His Arg Gln His His Ala Arg Thr
        435                 440                 445

Lys Gly Ala Arg Arg Tyr Ala Lys Arg Lys Arg Ser Thr Lys Ile Val
    450                 455                 460

Tyr Gly Lys Gly Val Ala Cys Val Ser Gly Glu Ser Gly Ile Gly Lys
465                 470                 475                 480

Thr Glu Leu Leu Leu Glu Phe Ala Tyr Arg Tyr His Gln Arg Tyr Lys
                485                 490                 495

Met Val Leu Trp Ile Gly Gly Glu Ser Arg Tyr Ile Arg His Asn Tyr
        500                 505                 510

Leu Asn Leu Trp Ser Phe Leu Glu Val Asp Val Gly Val Gln Asn Cys
    515                 520                 525

Pro Gly Lys Ser Arg Ile Arg Asn Phe Glu Glu Gln Glu Glu Glu Ala
530                 535                 540

Ile Ser Arg Val Arg Lys Glu Leu Met Arg Asn Ile Pro Phe Leu Val
545                 550                 555                 560

Val Ile Asp Asn Leu Glu Ser Glu Lys Asp Trp Trp Asp His Lys Leu
                565                 570                 575

Val Met Asp Leu Leu Pro Arg Phe Gly Gly Glu Thr His Ile Ile Ile
        580                 585                 590

Ser Thr Arg Leu Pro Arg Val Met Asn Leu Glu Pro Leu Lys Leu Ser
    595                 600                 605

Tyr Leu Ser Gly Val Glu Ala Thr Cys Ile Met Gln Gly Ser Gly Lys
    610                 615                 620

Asp Tyr Ser Ile Ala Glu Ile Glu Ala Leu Arg Val Ile Glu Glu Lys
625                 630                 635                 640

Leu Gly Arg Leu Thr Leu Gly Leu Ala Ile Val Gly Ala Ile Leu Ser
                645                 650                 655

Glu Leu Pro Ile Asn Pro Ser Arg Leu Leu Asp Thr Ile Asn Arg Met

```
                    660                 665                 670
Pro Leu Arg Glu Ile Ser Trp Ser Gly Arg Glu Ala Asn Ser Leu Thr
                675                 680                 685

Lys Asn Ser Phe Leu Leu Gln Leu Phe Glu Val Cys Phe Ser Ile Phe
            690                 695                 700

Asp His Ala Asp Gly Pro Arg Ser Leu Ala Thr Arg Met Val Gln Ala
705                 710                 715                 720

Ser Gly Trp Phe Ala Pro Ala Ile Pro Val Ser Leu Leu Ala Leu
                725                 730                 735

Ala Ala Asn Lys Ile Pro Gln Lys His Arg Gly Thr Gln Leu Trp Arg
            740                 745                 750

Lys Leu Leu Arg Ser Leu Ser Cys Gly Leu Ser Ser Tyr Thr Lys
        755                 760                 765

Arg Ser Glu Ala Glu Ala Ser Ser Met Leu Leu Arg Phe Asn Ile Ala
        770                 775                 780

Lys Ser Ser Thr Lys Gln Gly Tyr Val His Val Asn Glu Leu Val Lys
785                 790                 795                 800

Ile Tyr Met Arg Lys Arg Gly Thr Ala Ile Val Ala Gln Ala Met Val
                805                 810                 815

Gln Ala Val Ile Ser Arg Gly Ser Ile Ser His Ser Glu His Ile
            820                 825                 830

Trp Ala Ala Leu Phe Leu Leu Phe Gly Phe Ser Asn Asp Pro Lys Ala
            835                 840                 845

Val Glu Leu Lys Val Ser Glu Leu Leu Tyr Leu Val Arg Glu Met Val
    850                 855                 860

Leu Pro Leu Ala Ile Arg Thr Phe Ile Ser Phe Ser Arg Cys Asn Ala
865                 870                 875                 880

Ala Leu Glu Leu Leu Arg Leu Cys Thr Asn Ala Leu Glu Ala Ala Asp
                885                 890                 895

Gln Ala Phe Val Thr Pro Val Glu Lys Trp Leu Asp Lys Ser Leu Cys
            900                 905                 910

Trp Arg Pro Ile Gln Thr Asn Ala Gln Leu Asn Pro Tyr Leu Trp Gln
        915                 920                 925

Glu Leu Ala Leu Ser Arg Ala Thr Val Leu Glu Thr Arg Ala Lys Leu
    930                 935                 940

Met Leu Arg Gly Gly Gln Phe Asp Ile Gly Asp Leu Ile Arg Lys
945                 950                 955                 960

Val Ile Phe Ile Arg Thr Ser Ile Cys Gly Asp His Pro Glu Thr
                965                 970                 975

Val Ser Ala Arg Glu Thr Leu Ser Lys Leu Thr Arg Leu Leu Ala Asn
            980                 985                 990

Val Gln Ile Tyr Thr Ser Pro
        995

<210> SEQ ID NO 53
<211> LENGTH: 1005
<212> TYPE: PRT
<213> ORGANISM: Populus tricocarpa

<400> SEQUENCE: 53

Met Leu Ser His Tyr Leu Leu Cys Arg Met Asp Leu Arg Glu Asp Ser
1               5                   10                  15

Ser Arg Phe Gly Leu Leu Pro Val Thr Thr Ser Arg Ile Ser Ser Ser
            20                  25                  30
```

-continued

```
Ser Ser Ala Phe Phe Ser Ala Asn Gln Ser Pro Phe Phe Ser Pro Arg
        35                  40                  45
Ser Pro Thr Cys Gln Val Ser Glu Ser Thr Arg Ser Asp Ala Gln Tyr
 50                  55                  60
Asp Ser Thr His Leu Ser Gly Asp Pro Leu Ser Ser Ser Gly Ile
 65                  70                  75                  80
Pro Glu Pro Gln Ser Leu Ala Asn Thr Arg Asp Ala Leu Ala Asp Met
                 85                  90                  95
Thr Arg Asp Pro Val Ser Gly Ile Ala Asn Asp Phe Gln Lys Phe Asn
                100                 105                 110
Arg Ile Ser Ser Ser Thr Gly Ile Ser Ser Ser Thr Leu Cys Ile Tyr
            115                 120                 125
Asn Tyr Ala Arg Asp Arg Gly Tyr Ser Gly Phe Arg Glu Lys Pro Arg
        130                 135                 140
Lys His Gly Arg Ser His Gly Met Ser Tyr Thr Pro Val Ser Val Ser
145                 150                 155                 160
Ser Cys Lys Leu Arg Ser Cys Asp Val Phe Ile Gly Leu His Gly Arg
                165                 170                 175
Lys Pro Ser Leu Met Arg Phe Ala Asn Trp Leu Arg Ala Glu Leu Glu
            180                 185                 190
Val Gln Gly Met Ser Cys Phe Val Ser Asp Arg Ala Arg Cys Arg Asn
        195                 200                 205
Ser Arg Lys Asn Gly Ile Val Asp Arg Ala Met Asp Val Ser Ser Phe
    210                 215                 220
Gly Ile Val Ile Leu Thr Lys Lys Ser Phe Arg Asn Pro Tyr Ala Ile
225                 230                 235                 240
Glu Glu Leu Gln Tyr Phe Glu Ser Lys Lys Asn Leu Val Pro Val Phe
                245                 250                 255
Phe Asp Leu Ser Pro Asp Asp Cys Leu Val Arg Asp Ile Ile Glu Lys
            260                 265                 270
Arg Gly Glu Leu Trp Glu Lys His Gly Gly Leu Trp His Leu Tyr
        275                 280                 285
Gly Gly Leu Glu Asn Glu Trp Lys Glu Ala Val Asn Gly Ile Ser Arg
    290                 295                 300
Val Asp Glu Trp Lys Leu Glu Ala Gln Glu Gly Asn Trp Arg Asp Cys
305                 310                 315                 320
Ile Leu Arg Ala Val Thr Leu Leu Ala Leu Arg Leu Gly Arg Arg Ser
                325                 330                 335
Val Val Glu Arg Leu Thr Lys Trp Arg Glu Val Val Glu Lys Glu Glu
            340                 345                 350
Phe Pro Phe Pro Arg Asn Glu Asn Phe Val Gly Arg Lys Lys Glu Leu
        355                 360                 365
Ser Glu Leu Glu Phe Ile Leu Phe Gly Asp Val Ser Gly Asn Ser Glu
    370                 375                 380
Arg Asp Tyr Phe Glu Leu Lys Ala Arg Pro Arg Arg Lys Asn Leu Thr
385                 390                 395                 400
Val Gly Trp Asn Lys Asn Ser Ser Val Glu Glu Lys Arg Arg Glu Gln
                405                 410                 415
Gln Gly Asp Asn Ser Ser Glu Lys Gly Lys Glu Pro Val Val Trp Lys
            420                 425                 430
Glu Ser Glu Arg Glu Ile Glu Met Gln Ser Gly Asp Phe Ser Gln Arg
        435                 440                 445
Gln His Leu Val Lys Pro Lys Ser Ser Gly Arg Tyr Gly Lys Arg Lys
```

```
            450                 455                 460
Arg Ser Thr Lys Ile Leu Tyr Gly Lys Gly Ile Ala Cys Val Ser Gly
465                 470                 475                 480

Glu Ser Gly Ile Gly Lys Thr Glu Leu Leu Leu Glu Phe Ala Tyr Arg
                485                 490                 495

Tyr His Gln Arg Tyr Lys Met Val Leu Trp Ile Gly Gly Glu Ser Arg
                500                 505                 510

Tyr Ile Arg Gln Asn Tyr Leu Asn Leu Arg Ser Phe Leu Asp Val Asp
                515                 520                 525

Ile Gly Val Glu Asn Tyr Ser Gly Lys Ser Arg Ile Arg Ser Phe Glu
530                 535                 540

Glu Gln Glu Glu Glu Ala Ile Ser Lys Val Arg Lys Glu Leu Leu Arg
545                 550                 555                 560

Asn Ile Pro Phe Leu Val Val Ile Asp Asn Leu Glu Ser Glu Lys Asp
                565                 570                 575

Trp Trp Asp His Lys Ile Val Met Asp Leu Leu Pro Arg Phe Gly Gly
                580                 585                 590

Glu Thr His Ile Ile Ile Ser Thr Arg Leu Pro Arg Val Met Asn Leu
                595                 600                 605

Glu Pro Leu Lys Leu Ser Tyr Leu Ser Ala Val Glu Ala Met Cys Leu
                610                 615                 620

Met Gln Gly Ser Asp Lys Asp Tyr Ser Ile Ala Glu Ile Asp Ala Leu
625                 630                 635                 640

Arg Val Ile Glu Glu Lys Val Gly Arg Leu Thr Leu Gly Leu Ala Ile
                645                 650                 655

Val Gly Ala Ile Leu Ser Glu Leu Pro Ile Asn Pro Ser Arg Leu Leu
                660                 665                 670

Asp Thr Ile Asn Arg Met Pro Leu Arg Glu Met Ser Trp Ser Gly Arg
                675                 680                 685

Glu Ala His Ser Met Arg Lys Asn Thr Phe Leu Leu Gln Leu Phe Glu
690                 695                 700

Val Cys Phe Ser Ile Phe Asp His Ala Asp Gly Pro Arg Ser Leu Ala
705                 710                 715                 720

Thr Arg Met Val Gln Ala Ser Ala Trp Phe Ala Pro Ala Ala Ile Pro
                725                 730                 735

Val Ser Leu Leu Ala Leu Ala Ala Lys Lys Ile Pro Glu Lys His Lys
                740                 745                 750

Gly Thr His Leu Trp Arg Lys Leu Leu Ser Ser Leu Ser Cys Gly Leu
                755                 760                 765

Ser Ser Ser Tyr Thr Lys Arg Ser Glu Ala Glu Ala Ser Ser Met Leu
770                 775                 780

Leu Arg Phe Asn Ile Ala Arg Ser Ser Thr Lys Gln Gly Tyr Val His
785                 790                 795                 800

Val Asn Glu Leu Ile Lys Leu Tyr Ala Arg Lys Arg Gly Val Thr Gly
                805                 810                 815

Val Ala Gln Ala Met Val His Ala Val Ile Ser Arg Gly Ser Val Ser
                820                 825                 830

His His Ser Glu His Ile Trp Ala Ala Cys Phe Leu Leu Phe Ala Phe
                835                 840                 845

Gly Thr Asp Pro Lys Ala Val Glu Leu Lys Val Ser Glu Leu Leu Tyr
850                 855                 860

Leu Val Lys Gln Val Val Leu Pro Leu Ala Ile Arg Thr Phe Ile Thr
865                 870                 875                 880
```

-continued

```
Phe Ser Arg Cys Ser Ala Ala Leu Glu Leu Arg Leu Cys Thr Asn
            885                 890                 895

Ala Leu Glu Ala Ala Asp Gln Ala Phe Val Thr Pro Val Glu Lys Trp
        900                 905                 910

Leu Asp Lys Ser Leu Cys Trp Arg Pro Ile Gln Thr Asn Ala Gln Leu
        915                 920                 925

Asn Pro Tyr Leu Trp Gln Glu Leu Ala Leu Ser Arg Ala Thr Val Leu
        930                 935                 940

Glu Thr Arg Ala Lys Leu Met Leu Arg Gly Gly Gln Phe Asp Ile Gly
945                 950                 955                 960

Asp Asp Leu Ile Arg Lys Ala Ile Phe Ile Arg Thr Ser Ile Cys Gly
            965                 970                 975

Asp Asp His Pro Asp Thr Val Ser Ala Arg Glu Thr Leu Ser Lys Leu
            980                 985                 990

Thr Arg Leu His Ala Asn Val Gln Ile Gln Asn Ser Ser
            995                1000                1005

<210> SEQ ID NO 54
<211> LENGTH: 1308
<212> TYPE: PRT
<213> ORGANISM: Ricinus communis

<400> SEQUENCE: 54

Met Ala Gly Ala Leu Ile Gly Gly Ser Phe Leu Ser Ala Phe Leu Gln
1               5                   10                  15

Val Leu Phe Asp Arg Met Ala Ser Arg Glu Val Leu Asp Phe Phe Lys
            20                  25                  30

Gly Gln Lys Leu Asn Asp Ala Leu Leu Asn Lys Leu Lys Thr Thr Met
        35                  40                  45

Ile Ser Val Asn Ala Val Leu Asp Asp Ala Glu Glu Lys Gln Ile Thr
    50                  55                  60

Lys Pro Ala Val Lys Glu Trp Leu Asp Glu Leu Lys Asp Ala Ala Tyr
65                  70                  75                  80

Glu Ala Asp Asp Leu Leu Asp Glu Ile Ala Tyr Glu Cys Leu Arg Ser
                85                  90                  95

Glu Val Glu Ala Thr Ser Gln Thr Asp Val Asp Gln Val Arg Asn Phe
            100                 105                 110

Phe Ser Asn Phe Ser Pro Phe Lys Lys Val Lys Glu Val Lys Leu Glu
        115                 120                 125

Glu Val Ser Lys Leu Glu Glu Ile Leu Glu Arg Leu Glu Leu Leu Val
    130                 135                 140

Lys Gln Lys Glu Ala Leu Gly Leu Arg Glu Gly Ile Glu Glu Arg His
145                 150                 155                 160

Ser His Lys Ile Pro Thr Thr Ser Leu Val Asp Glu Ser Val Gly Ile
                165                 170                 175

Tyr Gly Arg Asp Phe Asp Lys Lys Ala Ile Val Lys Gln Leu Phe Glu
            180                 185                 190

Ala Asn Gly Asn Asp Leu Ser Val Ile Pro Ile Val Gly Met Gly Gly
        195                 200                 205

Val Gly Lys Thr Thr Leu Ala Gln Tyr Val Tyr Asn Glu Pro Arg Val
    210                 215                 220

Gln Glu Ser Phe Asp Leu Lys Ala Trp Val Cys Val Ser Ala Val Phe
225                 230                 235                 240

Asp Val Phe Lys Val Thr Lys Asp Ile Leu Glu Asp Val Thr Arg Lys
```

-continued

```
              245                 250                 255
Lys Cys Asp Ile Thr Thr Leu Asn Leu Leu Gln Leu Glu Leu Lys Glu
              260                 265                 270

Lys Leu Lys Gly Lys Arg Phe Leu Val Leu Asp Asp Val Trp Asp
              275                 280             285

Asp Asn Tyr Ala Asn Trp Asp Val Leu Arg Lys Pro Leu Lys Ser Gly
              290                 295                 300

Ala Leu Gly Ser Lys Ile Ile Val Thr Thr Arg His Glu Thr Val Ala
305               310                 315                 320

Ser Ile Met Gly Asn Val Leu His His His Leu Thr Glu Leu Ser
              325                 330                 335

Asp His Asp Cys Trp Leu Leu Phe Ser Lys His Ala Phe Gly Glu Gly
              340                 345             350

Asn Ser Ala Ala His Pro Glu Leu Ala Ile Leu Gly Gln Glu Ile Val
              355                 360                 365

Arg Lys Cys Arg Gly Leu Pro Leu Ala Ala Lys Ala Leu Gly Gly Val
              370                 375             380

Leu Arg Ser Lys Arg Asp Thr Lys Glu Trp Glu Arg Ile Phe Lys Ser
385               390                 395                 400

Leu Leu Trp Glu Leu Ser Asn Asp Glu Ile Leu Pro Ala Leu Arg Leu
                  405                 410                 415

Ser Tyr His Tyr Leu Pro Pro His Leu Lys Arg Cys Phe Ala Tyr Cys
                  420                 425             430

Ala Val Phe Pro Lys Asp Tyr Asn Phe Ser Lys Glu Glu Leu Ile Leu
              435                 440                 445

Leu Trp Arg Ala Glu Gly Phe Ile Val Gln Pro Lys Gly Ser Arg Glu
              450                 455                 460

Lys Glu Asp Val Gly Ala Glu Tyr Phe Glu Asp Leu Val Ser Arg Ser
465               470                 475                 480

Phe Phe Gln Lys Ser His Leu Tyr Lys Ser Ala Phe Val Met His Asp
                  485                 490                 495

Leu Ile Asn Asp Leu Ala Lys Tyr Val Ser Gly Glu Phe Cys Phe Gln
              500                 505             510

Trp Glu Asn Gly Asp Ser Cys Glu Val Ala Lys Arg Thr Arg His Leu
              515                 520             525

Ser Tyr Leu Arg Thr Asn His Asp Thr Ser Val Lys Phe Glu Ser Ile
              530                 535                 540

Tyr Arg Ala Lys His Leu Arg Thr Leu Arg Val Lys Trp Ser Trp
545               550                 555                 560

Thr Asp Arg Lys Val Lys Tyr Asp Leu Leu Pro Ser Leu Arg Leu
                  565                 570             575

Arg Val Leu Ser Leu Phe Gln Cys Asp Asp Val Val Leu Leu Pro Asn
              580                 585                 590

Thr Ile Gly Asn Leu Lys His Leu Arg Tyr Leu Asp Leu Ser Gly Thr
              595                 600                 605

Ser Ile Lys Arg Leu Pro Asp Ser Ile Asn Ser Leu Tyr Asn Leu Glu
              610                 615             620

Thr Leu Leu Met Tyr Gly Cys Gln Asp Leu Ile Lys Leu Pro Ile Thr
625               630                 635                 640

Met Ser Ser Leu Ile Ser Leu Cys His Leu Asp Ile Arg Glu Thr Lys
                  645                 650             655

Leu Gln Glu Met Pro Leu Lys Met Ser Lys Leu Thr Lys Leu Glu Met
              660                 665                 670
```

```
Leu Thr Asp Phe Val Leu Gly Lys Glu Ser Gly Ser Ile Lys Glu
        675                 680                 685

Leu Gly Glu Leu Gln Asn Leu Arg Gly Ser Leu Cys Ile Trp Asn Leu
    690                 695                 700

Gln Asn Val Ala Asp Ala Gln Asp Ala Met Ala Ala Asn Leu Lys Asn
705                 710                 715                 720

Lys Lys His Leu Arg Met Leu Asp Leu Arg Trp Asp Gly Glu Thr Asp
                725                 730                 735

Asp Ser Leu His Glu Arg Ala Ile Val Glu Gln Leu Gln Pro His Met
                740                 745                 750

Asn Val Glu Ser Leu Cys Ile Val Gly Tyr Gly Thr Arg Phe Pro
            755                 760                 765

Asp Trp Ile Ala Asn Pro Thr Phe Ser His Met Val Thr Leu Glu Leu
    770                 775                 780

Ser Arg Cys Lys Tyr Cys Ser Phe Leu Pro Pro Leu Gly Gln Leu Val
785                 790                 795                 800

Ser Leu Lys Ser Leu Tyr Ile Ile Ala Leu Asp Ser Ile Val Ser Val
                805                 810                 815

Gly Leu Glu Phe Tyr Gly Ser Cys Thr His Pro Lys Lys Pro Phe Gly
                820                 825                 830

Ser Leu Glu Ile Leu His Phe Glu Arg Met Pro Gln Trp Arg Glu Trp
                835                 840                 845

Ile Cys His Val Asp Glu Gly Glu Asn Gly Ala Phe Pro Leu Leu Gln
    850                 855                 860

Gln Leu Tyr Ile Asn Glu Cys Pro Asn Leu Ile Gln Thr Leu Pro Gly
865                 870                 875                 880

Asn Leu Pro Ser Leu Thr Thr Ile Lys Ile Val Gly Cys Pro Gln Leu
                885                 890                 895

Ala Ala Ser Phe Pro Ser Ala Pro Ala Ile Gln Lys Leu Lys Leu Lys
                900                 905                 910

Asp Asp His Arg Asn Val Leu Leu Gln Asn Phe Asp Phe Ser Ser Leu
                915                 920                 925

Lys Val Val Lys Phe His Ser Val Asp Pro Leu Leu Gln Gly Met Glu
                930                 935                 940

Lys Ile Gly Val Leu Phe Ile Ser Glu Glu Ile Glu Val Gly Asn Cys
945                 950                 955                 960

Asp Ser Leu Lys Cys Phe Pro Leu Glu Leu Phe Pro Glu Leu Tyr Ser
                965                 970                 975

Leu Glu Ile Tyr Arg Cys Gln Asn Leu Glu Cys Ile Ser Glu Ala Glu
                980                 985                 990

Val Thr Ser Lys Gly Leu Asn Val Leu Glu Ser Ile Lys Ile Arg Glu
                995                 1000                1005

Cys Pro Lys Leu Ile Ser Phe Pro Lys Gly Gly Leu Asn Ala Pro
    1010                1015                1020

Asn Leu Thr Ser Leu His Leu Cys Asp Cys Ser Asn Leu Lys Ser
    1025                1030                1035

Leu Pro Glu Cys Met His Ser Leu Leu Pro Ser Leu Tyr Ala Leu
    1040                1045                1050

Ala Ile Asn Asn Cys Pro Lys Leu Glu Ser Phe Pro Glu Gly Gly
    1055                1060                1065

Leu Pro Pro Lys Leu Tyr Ser Leu Val Ile Glu Ser Cys Asp Lys
    1070                1075                1080
```

```
Leu Val Thr Gly Arg Met Lys Trp Asn Leu Gln Thr Ile Ser Leu
1085                1090                1095

Lys Tyr Phe Ser Ile Ser Lys Asn Glu Asp Val Glu Ser Phe Pro
1100                1105                1110

Glu Lys Met Leu Leu Pro Ser Thr Leu Thr Cys Leu Gln Ile Ser
1115                1120                1125

Asn Phe Gln Asn Leu Lys Ser Leu Asp Tyr Asp Gly Ile Gln His
1130                1135                1140

Leu Thr Ser Leu Thr Glu Leu Thr Ile Ser Asn Cys Pro Lys Leu
1145                1150                1155

Gln Ser Val Thr Glu Gln Glu Leu Pro Leu Thr Val Thr Tyr Leu
1160                1165                1170

Asp Ile Trp Asp Leu Gln Asn Leu Lys Ser Leu Asp Phe Arg Gly
1175                1180                1185

Leu Cys Tyr Leu Thr Ser Leu Lys Glu Leu Glu Ile Trp Asn Cys
1190                1195                1200

Pro Asn Leu Gln Ser Met Pro Glu Asp Gly Leu Pro Ser Ser Leu
1205                1210                1215

Val Cys Leu Thr Ile Ser Asn Leu Gln Asn Leu Gln Ser Leu Asn
1220                1225                1230

Phe Lys Gly Leu Gln Asp Leu Thr Phe Leu Ile Glu Leu Asp Ile
1235                1240                1245

Leu Asp Cys Pro Lys Leu Glu Ser Ile Pro Glu Glu Gly Leu Pro
1250                1255                1260

Thr Ser Leu Ser Ser Leu Ile Ile Tyr Asn Cys Pro Ser Leu Lys
1265                1270                1275

Gln Arg Cys Lys Gln Glu Lys Gly Glu Asp Trp Pro Lys Ile Ser
1280                1285                1290

His Ile Arg His Ile Glu Ile Asp Gly Asp Thr Met Asn Lys Cys
1295                1300                1305

<210> SEQ ID NO 55
<211> LENGTH: 848
<212> TYPE: PRT
<213> ORGANISM: Ricinus communis

<400> SEQUENCE: 55

Met Val Asp Ala Val Val Thr Val Phe Leu Glu Arg Leu Leu Asn Thr
1               5                   10                  15

Leu Val Glu Glu Gly Arg Val Val Asn Glu Phe Arg Asp Arg Phe Glu
                20                  25                  30

Asn Leu Gln Lys Glu Leu Glu Leu Met Gln Ser Val Leu Lys Asp Ala
        35                  40                  45

Asp Lys Arg Lys Arg Lys Asp Gly Thr Leu His Thr Ile Met Gly Asn
    50                  55                  60

Leu Arg Glu Leu Ile Tyr Glu Ala Glu Asp Ile Leu Ala Asp Cys Gln
65                  70                  75                  80

Leu Gln Ser Arg Glu Asp Asp Arg Leu Ser Asn Gly Trp Leu Thr Cys
                85                  90                  95

Ile His Pro Pro Asn Leu His Phe Gln Tyr Lys Thr Gly Lys Arg Leu
            100                 105                 110

Arg Glu Ile Asn Glu Lys Ile Thr Lys Ile Lys Gln Asp Ile Ser Tyr
        115                 120                 125

Leu Asp Leu Ser Asn Ser Asn Gln Met Gly Arg Arg Asp Ala His Asn
    130                 135                 140
```

```
Asp Gln Met Ser Arg Trp Ser Ser Pro Val Tyr Asp His Thr Gln Val
145                 150                 155                 160

Val Gly Leu Glu Gly Asp Thr Gln Lys Ile Lys Asn Trp Leu Phe Glu
            165                 170                 175

Ala Asp Asp Gly Ile Leu Ala Ile Gly Val Val Gly Met Gly Gly Leu
            180                 185                 190

Gly Lys Thr Thr Ile Ala Gln Lys Val Phe Asn Asp Arg Glu Ile Asp
        195                 200                 205

Asp His Phe Glu Arg Arg Met Trp Ile Ser Val Ser Gln Thr Leu Asp
        210                 215                 220

Glu Val Gln Ile Met Arg Ser Met Leu Arg Asn Leu Gly Asp Ala Ser
225                 230                 235                 240

Ile Gly Asp Asn Gln Gly Glu Leu Leu Lys Lys Ile Asn Gln Tyr Leu
            245                 250                 255

Leu Gly Lys Arg Phe Leu Ile Val Met Asp Asp Val Trp Gly Leu Asp
            260                 265                 270

Val Asn Trp Trp Arg Arg Ile Tyr Glu Gly Leu Pro Lys Gly Asn Gly
        275                 280                 285

Ser Ser Ile Ile Ile Thr Thr Arg Ile Glu Glu Val Ala Arg Lys Met
290                 295                 300

Gly Val Thr Glu Val Arg Ile His Arg Pro Lys Phe Leu Ser Lys Asp
305                 310                 315                 320

Asp Ser Trp Leu Leu Phe Arg Lys Ile Ala Phe Ala Ala Thr Gly Gly
            325                 330                 335

Glu Cys Arg His Pro Glu Leu Glu Asn Val Gly Thr Glu Ile Val Gln
            340                 345                 350

Lys Cys Lys Gly Leu Pro Leu Ala Ile Lys Ala Ile Gly Gly Leu Leu
        355                 360                 365

Leu Tyr Lys Ser His Tyr His Glu Trp Arg Gln Ile Ala Gly Asn Phe
        370                 375                 380

Arg Asp Glu Leu Ala Glu Asn Asp Asp Ser Val Met Ala Ser Leu Gln
385                 390                 395                 400

Leu Ser Tyr Asp Glu Leu Pro Pro Tyr Leu Lys Ser Cys Phe Leu Ser
            405                 410                 415

Phe Ser Leu Tyr Pro Glu Asp Cys Val Ile Lys Lys Glu Gln Leu Val
            420                 425                 430

His Trp Trp Ile Gly Glu Gly Phe Val Pro Leu Arg Ile Gly Arg Ser
        435                 440                 445

Ser Thr Glu Ala Gly Glu Gly Cys Phe Ser Gly Leu Thr Asn Arg Cys
        450                 455                 460

Leu Val Glu Val Val Asp Lys Thr Tyr Asn Gly Thr Ile Ala Thr Cys
465                 470                 475                 480

Lys Ile His Asp Met Val Arg Asp Leu Val Ile Lys Met Ala Gly Asp
            485                 490                 495

Asp Ala Phe Phe Lys Leu Asn Gly Ile Gly Cys Arg His Leu Ala Ile
            500                 505                 510

Cys Ser Asn Met Asp Gln Lys Lys Leu Thr Ala Asn Gln Lys Leu Arg
            515                 520                 525
```

-continued

```
Ala Leu Leu Ser Thr Thr Lys Thr Gly Glu Val Asn Arg Ile Val Ser
    530             535             540
Ser Ile Ala Asn Lys Phe Ser Glu Cys Lys Tyr Leu Arg Val Leu Asp
545             550             555             560
Leu Cys Lys Ser Ile Phe Glu Val Pro Leu Thr Asn Leu Leu Tyr Gln
            565             570             575
Ile Gly Asp Leu Gln His Leu Thr Tyr Leu Ser Leu Ser Asn Thr His
            580             585             590
Pro Leu Ile Glu Leu Pro Pro Ser Leu Glu Lys Leu Lys Asn Leu Gln
        595             600             605
Ile Leu Asp Met Ser Tyr Cys Gln Asn Leu Lys Met Leu Pro Pro Tyr
    610             615             620
Leu Ile Thr Phe Lys Lys Leu Arg Val Leu Asp Val Ser His Cys Gly
625             630             635             640
Ser Leu Glu Tyr Leu Pro Lys Gly Leu Gly Arg Leu Ser Asn Leu Glu
            645             650             655
Val Leu Met Gly Phe Arg Pro Ser Arg Leu Gly Gln Leu Gly Gly Cys
            660             665             670
Arg Ile Ala Glu Leu Arg Asn Leu Thr Arg Leu Arg Thr Leu Ser Leu
            675             680             685
His Leu Thr Gln Gly Asp Glu Ile Glu Asp Asn Glu Val Asn Ala Leu
        690             695             700
Val Asn Leu Gln Glu Leu Glu His Leu Thr Ile Ser Cys Phe Asp Ser
705             710             715             720
Gln Gly Asn Asp Leu Ile Gly Lys Leu Asp Arg Leu Tyr Pro Pro Pro
            725             730             735
Glu Ile Tyr Glu Leu Ser Leu Ala Phe Tyr Pro Gly Lys Met Ser Pro
            740             745             750
Val Trp Leu Asn Pro Ile Ser Leu Pro Met Leu Arg Tyr Leu Ser Ile
        755             760             765
Ser Ser Gly Asn Leu Ala Gln Met His Gln Ser Phe Trp Gly Glu Asp
    770             775             780
Asn Ser Val Trp Lys Ile Glu Ala Leu Leu Leu Glu Ser Leu Ser Glu
785             790             795             800
Leu Gly Met Asp Trp Ser Met Ile Gln Asn Val Met Pro Ser Leu Arg
            805             810             815
Ile Val Asn Ser Ser Trp Cys Pro Asp Leu Ser Ala Phe Pro Ile Glu
            820             825             830
Glu Ile Gly Phe Arg Gly Gly Val Trp Thr Lys Glu Glu Gln Arg Asn
            835             840             845
```

What is claimed is:

1. A nucleic acid molecule comprising a cDNA sequence having at least 95% sequence identity to a nucleic acid sequence selected from the group consisting of: SEQ ID NO: 1, 3, and 5, wherein said nucleic acid molecule encodes a *Corchorus olitorius* Toll and Interleukin-1 Receptor domain at their N-terminus Nucleotide-Binding Site-Leucine-Rich Repeat (ColTIR-NBS-LRR) resistance protein.

2. An expression vector, comprising the nucleic acid molecule of claim 1.

3. A transgenic plant, comprising the expression vector of claim 2.

4. A material obtained from the transgenic plant of claim 3, wherein said material comprises the expression vector.

5. A seed from the transgenic plant of claim 3, wherein said seed comprises the expression vector.

6. A method for making a transgenic plant, comprising the steps of: transfecting at least one plant cell with the expression vector of claim 2; and growing said at least one plant cell into the transgenic plant.

7. A method of improving disease resistance in a jute plant, comprising the step of incorporating into the jute plant the nucleic acid molecule of claim 1.

8. The nucleic acid molecule of claim 1, wherein said cDNA has at least 98% sequence identity to the nucleotide sequence selected from the group consisting of SEQ ID NO: 1, 3, and 5.

9. The nucleic acid molecule of claim 1, wherein said cDNA has at least 99% sequence identity to the nucleotide sequence selected from the group consisting of SEQ ID NO: 1, 3, and 5.

10. The nucleic acid molecule of claim 1, wherein said cDNA has 100% sequence identity to the nucleotide sequence selected from the group consisting of SEQ ID NO: 1, 3, and 5.

11. The nucleic acid molecule of claim 10, wherein said cDNA is SEQ ID NO: 1.

12. The nucleic acid molecule of claim 10, wherein said cDNA is SEQ ID NO: 3.

13. The nucleic acid molecule of claim 10, wherein said cDNA is SEQ ID NO: 5.

* * * * *